(12) United States Patent
Milhausen

(10) Patent No.: US 6,514,694 B2
(45) Date of Patent: Feb. 4, 2003

(54) METHODS FOR THE DETECTION OF ENCYSTED PARASITES

(75) Inventor: Michael James Milhausen, Boulder, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/216,393

(22) Filed: Dec. 18, 1998

(65) Prior Publication Data

US 2001/0014447 A1 Aug. 16, 2001

Related U.S. Application Data

(63) Continuation-in-part of application No. 08/994,825, filed on Dec. 19, 1997, now abandoned.

(51) Int. Cl.$^7$ ................................................ C12Q 1/68
(52) U.S. Cl. ........................ 435/6; 435/91.2; 435/91.32; 436/63; 436/94
(58) Field of Search .................... 435/6, 91.2, 91.32; 436/63, 94

(56) References Cited

U.S. PATENT DOCUMENTS 5,266,689 A * 11/1993 Chakraborty et al. .......... 435/6
5,770,368 A * 6/1998 DeLeon et al. ................ 435/6
5,888,748 A * 3/1999 Crabb et al. ................. 435/7.3

OTHER PUBLICATIONS

Bukhari et al., 1998, *Applied and Environmental Microbiology*, vol. 64, No. 11, pp. 4495–4499.

Burg et al., 1989, *Journal of Clinical Microbiology*, vol. 27, No. 8, pp. 1787–1792.

Caggana et al., 1998, *Human Mutation*, vol. 11, pp. 404–409.

Gibbons et al., 1998, *Protist*, vol. 149, pp. 127–134.

Hock, B., 1996, *Ann. Biol. Clin.*, vol. 54, pp. 243–252.

Morgan et al., 1998, *Parasitology Today*, vol. 14, No. 6, pp. 241–245.

Rochelle et al., 1997, *Applied and Environmental Microbiology*, vol. 63, No. 1, pp. 106–114.

Roy et al., 1997, *BioTechniques*, vol. 23, No. 5, pp. 942–945.

Cox–Singh et al., 1997 *International Journal for Parasitology*, vol. 27, No. 12, pp. 1575–1577.

* cited by examiner

Primary Examiner—James Martinell
(74) Attorney, Agent, or Firm—Heska Corporation

(57) ABSTRACT

The present invention relates to immunogenic *Toxoplasma gondii* proteins, to *T. gondii* nucleic acid molecules, including those that encode such proteins and to antibodies raised against such proteins. The present invention also includes methods to obtain such proteins, nucleic acid molecules and antibodies. Also included in the present invention are compositions comprising such proteins, nucleic acid molecules and/or antibodies, as well as the use of such compositions to inhibit oocyst shedding by cats due to infection with *T. gondii*. The present invention also includes the use of certain *T. gondii*-based antisera to identify such nucleic acid molecules and proteins, as well as nucleic acid molecules and proteins identified by such methods. The present invention also relates to novel methods for the detection of cysts and oocysts.

18 Claims, No Drawings

SEQUENCE LISTING

```
<160> NUMBER OF SEQ ID NOS: 366

<210> SEQ ID NO 1
<211> LENGTH: 357
<212> TYPE: DNA
<213> ORGANISM: Toxoplasma gondii
<220> FEATURE:
<221> NAME/KEY: CDS
<222> LOCATION: (1)..(357)
<223> OTHER INFORMATION:

<400> SEQUENCE: 1 cgc ttc ttg tgt cac ctg cgg cga cgg ggg gac tct cag cag ggc tcg        48
Arg Phe Leu Cys His Leu Arg Arg Arg Gly Asp Ser Gln Gln Gly Ser
1               5                   10                  15
```

-continued

| | | |
|---|---|---|
| tgg att cca agc ggc tct gtt ctt ctc tct tct tcg ccg gcg cat tcc<br>Trp Ile Pro Ser Gly Ser Val Leu Leu Ser Ser Ser Pro Ala His Ser<br>               20                           25                     30 | | 96 |
| gcc ggt cct cgg aat act cga acg tct cga gtt gcg cgc gtt ggc ctg<br>Ala Gly Pro Arg Asn Thr Arg Thr Ser Arg Val Ala Arg Val Gly Leu<br>         35                          40                     45 | | 144 |
| gaa gcc ggg cct gcg aaa ggc gag aca gaa agc aga cga agc aga cag<br>Glu Ala Gly Pro Ala Lys Gly Glu Thr Glu Ser Arg Arg Ser Arg Gln<br>50                         55                          60 | | 192 |
| gac gaa ggg agc gac gtc cgt ggg cgc ttt ttt cga ggc aga caa acc<br>Asp Glu Gly Ser Asp Val Arg Gly Arg Phe Phe Arg Gly Arg Gln Thr<br>65                       70                       75                     80 | | 240 |
| gga gac tct cgc atc cac atg ggg gtc tac gag ggt cac gat ggc aac<br>Gly Asp Ser Arg Ile His Met Gly Val Tyr Glu Gly His Asp Gly Asn<br>                     85                           90                     95 | | 288 |
| gag ttc ggc gaa gag aga gaa caa ggt gca tgc gat ttt tcc gca tct<br>Glu Phe Gly Glu Glu Arg Glu Gln Gly Ala Cys Asp Phe Ser Ala Ser<br>               100                        105                     110 | | 336 |
| cct cgc tcg gaa ggc gga tcg<br>Pro Arg Ser Glu Gly Gly Ser<br>        115 | | 357 |

<210> SEQ ID NO 2
<211> LENGTH: 119
<212> TYPE: PRT
<213> ORGANISM: Toxoplasma gondii

<400> SEQUENCE: 2

Arg Phe Leu Cys His Leu Arg Arg Gly Asp Ser Gln Gln Gly Ser
1               5                   10                  15

Trp Ile Pro Ser Gly Ser Val Leu Leu Ser Ser Ser Pro Ala His Ser
            20                  25                  30

Ala Gly Pro Arg Asn Thr Arg Thr Ser Arg Val Ala Arg Val Gly Leu
        35                  40                  45

Glu Ala Gly Pro Ala Lys Gly Glu Thr Glu Ser Arg Arg Ser Arg Gln
    50                  55                  60

Asp Glu Gly Ser Asp Val Arg Gly Arg Phe Phe Arg Gly Arg Gln Thr
65                  70                  75                  80

Gly Asp Ser Arg Ile His Met Gly Val Tyr Glu Gly His Asp Gly Asn
                85                  90                  95

Glu Phe Gly Glu Glu Arg Glu Gln Gly Ala Cys Asp Phe Ser Ala Ser
            100                 105                 110

Pro Arg Ser Glu Gly Gly Ser
        115

<210> SEQ ID NO 3
<211> LENGTH: 339
<212> TYPE: DNA
<213> ORGANISM: Toxoplasma gondii
<220> FEATURE:
<221> NAME/KEY: CDS
<222> LOCATION: (1)..(324)
<223> OTHER INFORMATION:

<400> SEQUENCE: 3

| | | |
|---|---|---|
| cga gga gac ggt ggg agc gca ctg gcc cga ggc gcg gca ctg gga ctt<br>Arg Gly Asp Gly Gly Ser Ala Leu Ala Arg Gly Ala Ala Leu Gly Leu<br>1                       5                         10                     15 | | 48 |
| ggg ggc gcg aca gcc gcc gaa aca gct gct gcg cga ata gct gct ctc<br>Gly Gly Ala Thr Ala Ala Glu Thr Ala Ala Ala Arg Ile Ala Ala Leu<br>                 20                           25                     30 | | 96 |

-continued

```
aaa cca tcg ctc ttc gcg gcc tcc gaa ctc cct ccc gat gag aca gca      144
Lys Pro Ser Leu Phe Ala Ala Ser Glu Leu Pro Pro Asp Glu Thr Ala
         35                  40                  45 gac agt gga gac aca ggg ccg ttc cgg cga gac cgg gac ttc ttc gcc      192
Asp Ser Gly Asp Thr Gly Pro Phe Arg Arg Asp Arg Asp Phe Phe Ala
 50                  55                  60 ggc acc gcg ggc gaa cac gat gcg tcg gcg atg cga gac aaa gag gcc      240
Gly Thr Ala Gly Glu His Asp Ala Ser Ala Met Arg Asp Lys Glu Ala
 65                  70                  75                  80 gca ggc tcc tca ggc gaa gag aca ccc gca gag atc ggc atc ttg ggc      288
Ala Gly Ser Ser Gly Glu Glu Thr Pro Ala Glu Ile Gly Ile Leu Gly
                 85                  90                  95 agc cgc gga aac agt tgg ccg gga gac caa ggc tgc tgaagcgtcg ctcgc     339
Ser Arg Gly Asn Ser Trp Pro Gly Asp Gln Gly Cys
             100                 105
```

<210> SEQ ID NO 4
<211> LENGTH: 108
<212> TYPE: PRT
<213> ORGANISM: Toxoplasma gondii

<400> SEQUENCE: 4

```
Arg Gly Asp Gly Gly Ser Ala Leu Ala Arg Gly Ala Ala Leu Gly Leu
 1               5                  10                  15

Gly Gly Ala Thr Ala Ala Glu Thr Ala Ala Arg Ile Ala Ala Leu
                 20                  25                  30

Lys Pro Ser Leu Phe Ala Ala Ser Glu Leu Pro Pro Asp Glu Thr Ala
         35                  40                  45

Asp Ser Gly Asp Thr Gly Pro Phe Arg Arg Asp Arg Asp Phe Phe Ala
 50                  55                  60

Gly Thr Ala Gly Glu His Asp Ala Ser Ala Met Arg Asp Lys Glu Ala
 65                  70                  75                  80

Ala Gly Ser Ser Gly Glu Glu Thr Pro Ala Glu Ile Gly Ile Leu Gly
                 85                  90                  95

Ser Arg Gly Asn Ser Trp Pro Gly Asp Gln Gly Cys
             100                 105
```

<210> SEQ ID NO 5
<211> LENGTH: 526
<212> TYPE: DNA
<213> ORGANISM: Toxoplasma gondii
<220> FEATURE:
<221> NAME/KEY: CDS
<222> LOCATION: (1)..(525)
<223> OTHER INFORMATION:

<400> SEQUENCE: 5

```
cgg aca aaa aag ttt tcc tac gct ccg aac gga gcg gat tct aac aac       48
Arg Thr Lys Lys Phe Ser Tyr Ala Pro Asn Gly Ala Asp Ser Asn Asn
 1               5                  10                  15 tcc tct ctt ccg cac ttt cca tct gtg ttt cca gcg agc gcc gta gtc       96
Ser Ser Leu Pro His Phe Pro Ser Val Phe Pro Ala Ser Ala Val Val
                 20                  25                  30 tcc ccc atc gac gaa aac cct gca gag atg gaa agc acc atc tcc gag      144
Ser Pro Ile Asp Glu Asn Pro Ala Glu Met Glu Ser Thr Ile Ser Glu
         35                  40                  45 ggc gaa gca ggt tct gcg gtg gcg gct cct gaa caa ggt atc cag cca      192
Gly Glu Ala Gly Ser Ala Val Ala Ala Pro Glu Gln Gly Ile Gln Pro
 50                  55                  60 gag gca gaa ttt gct acc gcc agc gaa gaa cca cgt ccc ctg gaa cct      240
Glu Ala Glu Phe Ala Thr Ala Ser Glu Glu Pro Arg Pro Leu Glu Pro
```

```
Glu Ala Glu Phe Ala Thr Ala Ser Glu Glu Pro Arg Pro Leu Glu Pro
 65                  70                  75                  80 gtc gac ccc gaa atg gca gct cag cag ccg caa ctg cct caa gaa gct     288
Val Asp Pro Glu Met Ala Ala Gln Gln Pro Gln Leu Pro Gln Glu Ala
                 85                  90                  95 atg cca act gag aat gcg gac ctt ctt gga aac cag ccc aga atg cgc     336
Met Pro Thr Glu Asn Ala Asp Leu Leu Gly Asn Gln Pro Arg Met Arg
            100                 105                 110 aat gct ctc gaa ccc tct gcc aag gtc ctc gaa ccg gaa acc ctg gaa     384
Asn Ala Leu Glu Pro Ser Ala Lys Val Leu Glu Pro Glu Thr Leu Glu
        115                 120                 125 ggg tca cct gct ctc gtc ccg ccg gca gag act gaa gag ggg aca gcc     432
Gly Ser Pro Ala Leu Val Pro Pro Ala Glu Thr Glu Glu Gly Thr Ala
130                 135                 140 gcc caa att gcg gag gaa atg agc aag cag gat cag ggc atg cag gaa     480
Ala Gln Ile Ala Glu Glu Met Ser Lys Gln Asp Gln Gly Met Gln Glu
145                 150                 155                 160 gcc agg cct caa gaa gtt ctc agt aag caa tgg gtt ctt cga tat t       526
Ala Arg Pro Gln Glu Val Leu Ser Lys Gln Trp Val Leu Arg Tyr
                165                 170                 175
```

<210> SEQ ID NO 6
<211> LENGTH: 175
<212> TYPE: PRT
<213> ORGANISM: Toxoplasma gondii

<400> SEQUENCE: 6

```
Arg Thr Lys Lys Phe Ser Tyr Ala Pro Asn Gly Ala Asp Ser Asn Asn
 1               5                  10                  15

Ser Ser Leu Pro His Phe Pro Ser Val Phe Pro Ala Ser Ala Val Val
            20                  25                  30

Ser Pro Ile Asp Glu Asn Pro Ala Glu Met Glu Ser Thr Ile Ser Glu
        35                  40                  45

Gly Glu Ala Gly Ser Ala Val Ala Pro Glu Gln Gly Ile Gln Pro
    50                  55                  60

Glu Ala Glu Phe Ala Thr Ala Ser Glu Glu Pro Arg Pro Leu Glu Pro
 65                  70                  75                  80

Val Asp Pro Glu Met Ala Ala Gln Gln Pro Gln Leu Pro Gln Glu Ala
                 85                  90                  95

Met Pro Thr Glu Asn Ala Asp Leu Leu Gly Asn Gln Pro Arg Met Arg
            100                 105                 110

Asn Ala Leu Glu Pro Ser Ala Lys Val Leu Glu Pro Glu Thr Leu Glu
        115                 120                 125

Gly Ser Pro Ala Leu Val Pro Pro Ala Glu Thr Glu Glu Gly Thr Ala
130                 135                 140

Ala Gln Ile Ala Glu Glu Met Ser Lys Gln Asp Gln Gly Met Gln Glu
145                 150                 155                 160

Ala Arg Pro Gln Glu Val Leu Ser Lys Gln Trp Val Leu Arg Tyr
                165                 170                 175
```

<210> SEQ ID NO 7
<211> LENGTH: 1478
<212> TYPE: DNA
<213> ORGANISM: Toxoplasma gondii
<220> FEATURE:
<221> NAME/KEY: CDS
<222> LOCATION: (19)..(1161)
<223> OTHER INFORMATION:

<400> SEQUENCE: 7

```
gaggacgcag acgtgagt atg ctc cag agg gat cac gga atc cac gga gag      51
                    Met Leu Gln Arg Asp His Gly Ile His Gly Glu
                     1               5                  10 gaa gcc ggt ttg ttc cgc aag gct gtt ccg ggc ttg gac gac cca gct      99
Glu Ala Gly Leu Phe Arg Lys Ala Val Pro Gly Leu Asp Asp Pro Ala
            15                  20                  25 gaa gac gat gaa gcc gac ggc gaa agt gcc tcg gat gag gca gaa gcc     147
Glu Asp Asp Glu Ala Asp Gly Glu Ser Ala Ser Asp Glu Ala Glu Ala
                30                  35                  40 gac tct gac gtc ttg gcg gac gac gaa gaa ggg aca tcc ctc atc gaa     195
Asp Ser Asp Val Leu Ala Asp Asp Glu Glu Gly Thr Ser Leu Ile Glu
        45                  50                  55 aat gcg agt gag gaa gac aca gac aac tcc gag gca gac agt caa cag     243
Asn Ala Ser Glu Glu Asp Thr Asp Asn Ser Glu Ala Asp Ser Gln Gln
 60                  65                  70                  75 gag gat gac agt gtg gga gag gat tcc ttt ctc cag cag gag ggc gag     291
Glu Asp Asp Ser Val Gly Glu Asp Ser Phe Leu Gln Gln Glu Gly Glu
                80                  85                  90 gac tcc gag gaa gaa aga gca gtc gag gac ccg tat gct gcc gcc gaa     339
Asp Ser Glu Glu Glu Arg Ala Val Glu Asp Pro Tyr Ala Ala Ala Glu
            95                 100                 105 ccc tct tat ctt gaa gag gac aac act gtt gac gac agc gcg gcg gag     387
Pro Ser Tyr Leu Glu Glu Asp Asn Thr Val Asp Asp Ser Ala Ala Glu
           110                 115                 120 gat tat gcc cct gct tcg ttt gtc cag atc ggc agt gga gag aga aaa     435
Asp Tyr Ala Pro Ala Ser Phe Val Gln Ile Gly Ser Gly Glu Arg Lys
       125                 130                 135 atc cgg gcg cac atg cat ctt gac agc cgc caa gtt gcc ccc gaa aga     483
Ile Arg Ala His Met His Leu Asp Ser Arg Gln Val Ala Pro Glu Arg
140                 145                 150                 155 ttc gcg cat gcg ttc aac cag gat cat gtc aga ctt ctg gac cag acc     531
Phe Ala His Ala Phe Asn Gln Asp His Val Arg Leu Leu Asp Gln Thr
                160                 165                 170 gcc gtc gag gac gaa ctt ctc gat gag gcc gcc ccg ggc gga ggc gcg     579
Ala Val Glu Asp Glu Leu Leu Asp Glu Ala Ala Pro Gly Gly Gly Ala
            175                 180                 185 agc gcc gta gtc tcc ccc atc gac gaa aac cct gca gag atg gaa agc     627
Ser Ala Val Val Ser Pro Ile Asp Glu Asn Pro Ala Glu Met Glu Ser
        190                 195                 200 acc atc tcc gag ggc gaa gca ggt tct gcg gtg gcg gct cct gaa caa     675
Thr Ile Ser Glu Gly Glu Ala Gly Ser Ala Val Ala Ala Pro Glu Gln
    205                 210                 215 ggt atc cag cca gag gca gaa ttt gct acc gcc agc gaa gaa cca cgt     723
Gly Ile Gln Pro Glu Ala Glu Phe Ala Thr Ala Ser Glu Glu Pro Arg
220                 225                 230                 235 ccc ctg gaa cct gtc gac ccc gaa atg gca gct cag cag ccg caa ctg     771
Pro Leu Glu Pro Val Asp Pro Glu Met Ala Ala Gln Gln Pro Gln Leu
                240                 245                 250 cct caa gaa gct atg cca act gag aat gcg gac ctt ctt gga aac cag     819
Pro Gln Glu Ala Met Pro Thr Glu Asn Ala Asp Leu Leu Gly Asn Gln
            255                 260                 265 ccc aga atg cgc aat gct ctc gaa ccc tct gcc aag gtc ctc gaa ccg     867
Pro Arg Met Arg Asn Ala Leu Glu Pro Ser Ala Lys Val Leu Glu Pro
        270                 275                 280 gaa acc ctg gaa ggg tca cct gct ctc gtc ccg ccg gca gag act gaa     915
Glu Thr Leu Glu Gly Ser Pro Ala Leu Val Pro Pro Ala Glu Thr Glu
    285                 290                 295 gag ggg aca gcc gcc caa att gcg gag gaa atg agc aag cag gat cag     963
Glu Gly Thr Ala Ala Gln Ile Ala Glu Glu Met Ser Lys Gln Asp Gln
```

-continued

```
              300                 305                 310                 315
ggc atg cag gaa gcc agg cct caa gaa gtt ctc aca cga cac acc tgg           1011
Gly Met Gln Glu Ala Arg Pro Gln Glu Val Leu Thr Arg His Thr Trp
            320                 325                 330 caa gat atg gag aga act gag gac cta cga aag aac gac gtc ccg gct           1059
Gln Asp Met Glu Arg Thr Glu Asp Leu Arg Lys Asn Asp Val Pro Ala
            335                 340                 345 gca gtg gcg aat tcc ggc agc cag atc atc acg gct gcg tcg tcc gtc           1107
Ala Val Ala Asn Ser Gly Ser Gln Ile Ile Thr Ala Ala Ser Ser Val
            350                 355                 360 gcc ctt gct ggt cta ctg gtc gca gga cag ctt ttg ttc agc gtg ggc           1155
Ala Leu Ala Gly Leu Leu Val Ala Gly Gln Leu Leu Phe Ser Val Gly
            365                 370                 375 atg tac tgagaataat attcttgctt cgtggaatat tgttgctacc tgaaagttaa           1211
Met Tyr
380 actattttcg ctgtgaatgt ggggggggtt cgccgactgt gttcccgccc aacattcgtg         1271 gttaatgagt tttgtcccat cgtgcattgc gacgctcaac cacacttcta ttttgggggg         1331 gcatcttagg taatatgcta aggttatttt ctgcgtcgct gaactctggt cttgcaaaag         1391 aagctaactc ttttccggca taacttcgtt tttggtgtca aaaaaaaaaa aaaaaaaaa          1451 aaaaaaaaaa aaaaaaaaaa aaaaaaa                                             1478
```

<210> SEQ ID NO 8
<211> LENGTH: 381
<212> TYPE: PRT
<213> ORGANISM: Toxoplasma gondii

<400> SEQUENCE: 8

```
Met Leu Gln Arg Asp His Gly Ile His Gly Glu Glu Ala Gly Leu Phe
1               5                  10                  15

Arg Lys Ala Val Pro Gly Leu Asp Asp Pro Ala Glu Asp Glu Ala
            20                  25                  30

Asp Gly Glu Ser Ala Ser Asp Glu Ala Glu Ala Asp Ser Asp Val Leu
        35                  40                  45

Ala Asp Asp Glu Glu Gly Thr Ser Leu Ile Glu Asn Ala Ser Glu Glu
    50                  55                  60

Asp Thr Asp Asn Ser Glu Ala Asp Ser Gln Gln Glu Asp Asp Ser Val
65                  70                  75                  80

Gly Glu Asp Ser Phe Leu Gln Gln Glu Gly Glu Asp Ser Glu Glu
                85                  90                  95

Arg Ala Val Glu Asp Pro Tyr Ala Ala Ala Glu Pro Ser Tyr Leu Glu
            100                 105                 110

Glu Asp Asn Thr Val Asp Asp Ser Ala Ala Glu Asp Tyr Ala Pro Ala
        115                 120                 125

Ser Phe Val Gln Ile Gly Ser Gly Arg Lys Ile Arg Ala His Met
    130                 135                 140

His Leu Asp Ser Arg Gln Val Ala Pro Glu Arg Phe Ala His Ala Phe
145                 150                 155                 160

Asn Gln Asp His Val Arg Leu Leu Asp Gln Thr Ala Val Glu Asp Glu
                165                 170                 175

Leu Leu Asp Glu Ala Ala Pro Gly Gly Gly Ala Ser Ala Val Val Ser
            180                 185                 190

Pro Ile Asp Glu Asn Pro Ala Glu Met Glu Ser Thr Ile Ser Glu Gly
        195                 200                 205
```

```
Glu Ala Gly Ser Ala Val Ala Ala Pro Glu Gln Gly Ile Gln Pro Glu
        210                 215                 220

Ala Glu Phe Ala Thr Ala Ser Glu Glu Pro Arg Pro Leu Glu Pro Val
225                 230                 235                 240

Asp Pro Glu Met Ala Ala Gln Gln Pro Gln Leu Pro Gln Glu Ala Met
                245                 250                 255

Pro Thr Glu Asn Ala Asp Leu Leu Gly Asn Gln Pro Arg Met Arg Asn
            260                 265                 270

Ala Leu Glu Pro Ser Ala Lys Val Leu Glu Pro Glu Thr Leu Glu Gly
        275                 280                 285

Ser Pro Ala Leu Val Pro Pro Ala Glu Thr Glu Glu Gly Thr Ala Ala
    290                 295                 300

Gln Ile Ala Glu Glu Met Ser Lys Gln Asp Gln Gly Met Gln Glu Ala
305                 310                 315                 320

Arg Pro Gln Glu Val Leu Thr Arg His Thr Trp Gln Asp Met Glu Arg
                325                 330                 335

Thr Glu Asp Leu Arg Lys Asn Asp Val Pro Ala Ala Val Ala Asn Ser
            340                 345                 350

Gly Ser Gln Ile Ile Thr Ala Ala Ser Ser Val Ala Leu Ala Gly Leu
        355                 360                 365

Leu Val Ala Gly Gln Leu Leu Phe Ser Val Gly Met Tyr
    370                 375                 380

<210> SEQ ID NO 9
<211> LENGTH: 657
<212> TYPE: DNA
<213> ORGANISM: Toxoplasma gondii
<220> FEATURE:
<221> NAME/KEY: CDS
<222> LOCATION: (1)..(657)
<223> OTHER INFORMATION:

<400> SEQUENCE: 9 gag atg agc gcc cca gat agg caa aca gga aag ctt tcc gat tta ccg    48
Glu Met Ser Ala Pro Asp Arg Gln Thr Gly Lys Leu Ser Asp Leu Pro
1               5                   10                  15 cca ttt gct gag ctg cca cag ctg gca gaa ata cca aag ctc tcc gaa    96
Pro Phe Ala Glu Leu Pro Gln Leu Ala Glu Ile Pro Lys Leu Ser Glu
            20                  25                  30 ctt ccg aaa atc gcg gac atg ccg aaa ttt tcg gat atg ccc aag atg   144
Leu Pro Lys Ile Ala Asp Met Pro Lys Phe Ser Asp Met Pro Lys Met
        35                  40                  45 gcc gag atg ccc aag tta tca gat ata ccc aag atg gct gag atg ccc   192
Ala Glu Met Pro Lys Leu Ser Asp Ile Pro Lys Met Ala Glu Met Pro
50                  55                  60 aag tta tca gat ata ccc aag atg gct gag atg ccc aag tta tca gat   240
Lys Leu Ser Asp Ile Pro Lys Met Ala Glu Met Pro Lys Leu Ser Asp
65                  70                  75                  80 ata ccc aag atg gct gag atg ccc aag ttt tca gat ata ccc aag atg   288
Ile Pro Lys Met Ala Glu Met Pro Lys Phe Ser Asp Ile Pro Lys Met
                85                  90                  95 gct gag atg cca aag tta tca gat atg ccc aga atg gct gac att cca   336
Ala Glu Met Pro Lys Leu Ser Asp Met Pro Arg Met Ala Asp Ile Pro
            100                 105                 110 cag ttt cca gag atg cct agg atg gtt gac atg cct cag ttt cca gaa   384
Gln Phe Pro Glu Met Pro Arg Met Val Asp Met Pro Gln Phe Pro Glu
        115                 120                 125 atc ccc agg atg gct gat atg cgg aga ttt ccg gag atg tcc aag ata   432
Ile Pro Arg Met Ala Asp Met Arg Arg Phe Pro Glu Met Ser Lys Ile
```

```
                       130                 135                 140
gct gac atg cca aag ttt cca gac atg cca aac gtc act gag atg cca       480
Ala Asp Met Pro Lys Phe Pro Asp Met Pro Asn Val Thr Glu Met Pro
145                 150                 155                 160 aag ctt gca gat ttg cca agg ctt gct gac atg ccc agt att gcc gac       528
Lys Leu Ala Asp Leu Pro Arg Leu Ala Asp Met Pro Ser Ile Ala Asp
                165                 170                 175 atg ccc cgg ctc tca gac atg ccc agt att gca gac atg ccc cgg ctc       576
Met Pro Arg Leu Ser Asp Met Pro Ser Ile Ala Asp Met Pro Arg Leu
            180                 185                 190 tca gac ata ccc agt att gcc gac atg ccc cgg ctc tca gac atg ccc       624
Ser Asp Ile Pro Ser Ile Ala Asp Met Pro Arg Leu Ser Asp Met Pro
        195                 200                 205 agt att gcc gac atg ccg aaa ttc tct agc cgg                           657
Ser Ile Ala Asp Met Pro Lys Phe Ser Ser Arg
    210                 215
```

<210> SEQ ID NO 10
<211> LENGTH: 219
<212> TYPE: PRT
<213> ORGANISM: Toxoplasma gondii

<400> SEQUENCE: 10

```
Glu Met Ser Ala Pro Asp Arg Gln Thr Gly Lys Leu Ser Asp Leu Pro
1               5                   10                  15

Pro Phe Ala Glu Leu Pro Gln Leu Ala Glu Ile Pro Lys Leu Ser Glu
            20                  25                  30

Leu Pro Lys Ile Ala Asp Met Pro Lys Phe Ser Asp Met Pro Lys Met
        35                  40                  45

Ala Glu Met Pro Lys Leu Ser Asp Ile Pro Lys Met Ala Glu Met Pro
50                  55                  60

Lys Leu Ser Asp Ile Pro Lys Met Ala Glu Met Pro Lys Leu Ser Asp
65                  70                  75                  80

Ile Pro Lys Met Ala Glu Met Pro Lys Phe Ser Asp Ile Pro Lys Met
                85                  90                  95

Ala Glu Met Pro Lys Leu Ser Asp Met Pro Arg Met Ala Asp Ile Pro
            100                 105                 110

Gln Phe Pro Glu Met Pro Arg Met Val Asp Met Pro Gln Phe Pro Glu
        115                 120                 125

Ile Pro Arg Met Ala Asp Met Arg Arg Phe Pro Glu Met Ser Lys Ile
    130                 135                 140

Ala Asp Met Pro Lys Phe Pro Asp Met Pro Asn Val Thr Glu Met Pro
145                 150                 155                 160

Lys Leu Ala Asp Leu Pro Arg Leu Ala Asp Met Pro Ser Ile Ala Asp
                165                 170                 175

Met Pro Arg Leu Ser Asp Met Pro Ser Ile Ala Asp Met Pro Arg Leu
            180                 185                 190

Ser Asp Ile Pro Ser Ile Ala Asp Met Pro Arg Leu Ser Asp Met Pro
        195                 200                 205

Ser Ile Ala Asp Met Pro Lys Phe Ser Ser Arg
    210                 215
```

<210> SEQ ID NO 11
<211> LENGTH: 1029
<212> TYPE: DNA
<213> ORGANISM: Toxoplasma gondii
<220> FEATURE:
<221> NAME/KEY: CDS

<222> LOCATION: (1)..(819)
<223> OTHER INFORMATION:

<400> SEQUENCE: 11

| | | | | | | | | | | | | | | | | |
|---|---|---|---|---|---|---|---|---|---|---|---|---|---|---|---|---|
| gag | atg | agc | gcc | cca | gat | agg | caa | aca | gga | aag | ctt | tcc | gat | tta | ccg | 48 |
| Glu | Met | Ser | Ala | Pro | Asp | Arg | Gln | Thr | Gly | Lys | Leu | Ser | Asp | Leu | Pro | |
| 1 | | | | 5 | | | | | 10 | | | | | 15 | | |

| cca | ttt | gct | gag | ctg | cca | cag | ctg | gca | gaa | ata | cca | aag | ctc | tcc | gaa | 96 |
|---|---|---|---|---|---|---|---|---|---|---|---|---|---|---|---|---|
| Pro | Phe | Ala | Glu | Leu | Pro | Gln | Leu | Ala | Glu | Ile | Pro | Lys | Leu | Ser | Glu | |
| | | | 20 | | | | | 25 | | | | | 30 | | | |

| ctt | ccg | aaa | atc | gcg | gac | atg | ccg | aaa | ttt | tcg | gat | atg | ccc | aag | atg | 144 |
|---|---|---|---|---|---|---|---|---|---|---|---|---|---|---|---|---|
| Leu | Pro | Lys | Ile | Ala | Asp | Met | Pro | Lys | Phe | Ser | Asp | Met | Pro | Lys | Met | |
| | | 35 | | | | | 40 | | | | | 45 | | | | |

| gcc | gag | atg | ccc | aag | tta | tca | gat | ata | ccc | aag | atg | gct | gag | atg | ccc | 192 |
|---|---|---|---|---|---|---|---|---|---|---|---|---|---|---|---|---|
| Ala | Glu | Met | Pro | Lys | Leu | Ser | Asp | Ile | Pro | Lys | Met | Ala | Glu | Met | Pro | |
| 50 | | | | | 55 | | | | | 60 | | | | | | |

| aag | tta | tca | gat | ata | ccc | aag | atg | gct | gag | atg | ccc | aag | tta | tca | gat | 240 |
|---|---|---|---|---|---|---|---|---|---|---|---|---|---|---|---|---|
| Lys | Leu | Ser | Asp | Ile | Pro | Lys | Met | Ala | Glu | Met | Pro | Lys | Leu | Ser | Asp | |
| 65 | | | | | 70 | | | | | 75 | | | | | 80 | |

| ata | ccc | aag | atg | gct | gag | atg | ccc | aag | ttt | tca | gat | ata | ccc | aag | atg | 288 |
|---|---|---|---|---|---|---|---|---|---|---|---|---|---|---|---|---|
| Ile | Pro | Lys | Met | Ala | Glu | Met | Pro | Lys | Phe | Ser | Asp | Ile | Pro | Lys | Met | |
| | | | | 85 | | | | | 90 | | | | | 95 | | |

| gct | gag | atg | cca | aag | tta | tca | gat | atg | ccc | aga | atg | gct | gac | att | cca | 336 |
|---|---|---|---|---|---|---|---|---|---|---|---|---|---|---|---|---|
| Ala | Glu | Met | Pro | Lys | Leu | Ser | Asp | Met | Pro | Arg | Met | Ala | Asp | Ile | Pro | |
| | | 100 | | | | | 105 | | | | | 110 | | | | |

| cag | ttt | cca | gag | atg | cct | agg | atg | gtt | gac | atg | cct | cag | ttt | cca | gaa | 384 |
|---|---|---|---|---|---|---|---|---|---|---|---|---|---|---|---|---|
| Gln | Phe | Pro | Glu | Met | Pro | Arg | Met | Val | Asp | Met | Pro | Gln | Phe | Pro | Glu | |
| | | 115 | | | | | 120 | | | | | 125 | | | | |

| atc | ccc | agg | atg | gct | gat | atg | cgg | aga | ttt | ccg | gag | atg | tcc | aag | ata | 432 |
|---|---|---|---|---|---|---|---|---|---|---|---|---|---|---|---|---|
| Ile | Pro | Arg | Met | Ala | Asp | Met | Arg | Arg | Phe | Pro | Glu | Met | Ser | Lys | Ile | |
| | 130 | | | | | 135 | | | | | 140 | | | | | |

| gct | gac | atg | cca | aag | ttt | cca | gac | atg | cca | aac | gtc | act | gag | atg | cca | 480 |
|---|---|---|---|---|---|---|---|---|---|---|---|---|---|---|---|---|
| Ala | Asp | Met | Pro | Lys | Phe | Pro | Asp | Met | Pro | Asn | Val | Thr | Glu | Met | Pro | |
| 145 | | | | | 150 | | | | | 155 | | | | | 160 | |

| aag | ctt | gca | gat | ttg | cca | agg | ctt | gct | gac | atg | ccc | agt | att | gcc | gac | 528 |
|---|---|---|---|---|---|---|---|---|---|---|---|---|---|---|---|---|
| Lys | Leu | Ala | Asp | Leu | Pro | Arg | Leu | Ala | Asp | Met | Pro | Ser | Ile | Ala | Asp | |
| | | | | 165 | | | | | 170 | | | | | 175 | | |

| atg | ccc | cgg | ctc | tca | gac | atg | ccc | agt | att | gca | gac | atg | ccc | cgg | ctc | 576 |
|---|---|---|---|---|---|---|---|---|---|---|---|---|---|---|---|---|
| Met | Pro | Arg | Leu | Ser | Asp | Met | Pro | Ser | Ile | Ala | Asp | Met | Pro | Arg | Leu | |
| | | 180 | | | | | 185 | | | | | 190 | | | | |

| tca | gac | ata | ccc | agt | att | gcc | gac | atg | ccc | cgg | ctc | tca | gac | atg | ccc | 624 |
|---|---|---|---|---|---|---|---|---|---|---|---|---|---|---|---|---|
| Ser | Asp | Ile | Pro | Ser | Ile | Ala | Asp | Met | Pro | Arg | Leu | Ser | Asp | Met | Pro | |
| | | 195 | | | | | 200 | | | | | 205 | | | | |

| agt | att | gcc | gac | atg | ccg | aaa | ttc | tct | agt | aac | cga | gtt | cat | ggg | caa | 672 |
|---|---|---|---|---|---|---|---|---|---|---|---|---|---|---|---|---|
| Ser | Ile | Ala | Asp | Met | Pro | Lys | Phe | Ser | Ser | Asn | Arg | Val | His | Gly | Gln | |
| 210 | | | | | 215 | | | | | 220 | | | | | | |

| agt | tac | cat | att | ctg | gcg | ata | tgg | aca | ccg | tcc | ctt | tcc | gga | ctc | aag | 720 |
|---|---|---|---|---|---|---|---|---|---|---|---|---|---|---|---|---|
| Ser | Tyr | His | Ile | Leu | Ala | Ile | Trp | Thr | Pro | Ser | Leu | Ser | Gly | Leu | Lys | |
| 225 | | | | | 230 | | | | | 235 | | | | | 240 | |

| gag | ttt | ttt | acc | ccg | ctc | tct | gac | cta | atc | aag | cca | gaa | gct | gct | tcc | 768 |
|---|---|---|---|---|---|---|---|---|---|---|---|---|---|---|---|---|
| Glu | Phe | Phe | Thr | Pro | Leu | Ser | Asp | Leu | Ile | Lys | Pro | Glu | Ala | Ala | Ser | |
| | | | | 245 | | | | | 250 | | | | | 255 | | |

| ctg | aca | agc | ctg | gcc | aag | cca | tct | gga | gtt | ttt | ctg | aga | acc | ctg | ctg | 816 |
|---|---|---|---|---|---|---|---|---|---|---|---|---|---|---|---|---|
| Leu | Thr | Ser | Leu | Ala | Lys | Pro | Ser | Gly | Val | Phe | Leu | Arg | Thr | Leu | Leu | |
| | | | | 260 | | | | | 265 | | | | | 270 | | |

| gct | | | | | | | | | | | | | | | | 869 |
|---|---|---|---|---|---|---|---|---|---|---|---|---|---|---|---|---|
| Ala | tgatgagaaa atgtatattg acaaatggct gtatctccat agttatagtg | | | | | | | | | | | | | | | | aggaatgtat tgacttattc cgaggactct atactgaacc cgcggcatac gaggaaactg    929 acaagttggt gatgtgcgtt tctgatcttc cccgaaaaga aaaaaaaatg accgtcttaa    989 aaaaaaaaaa aaaaaaaaaa aaaaaaaaaa aaaaaaaaaa                1029

<210> SEQ ID NO 12
<211> LENGTH: 273
<212> TYPE: PRT
<213> ORGANISM: Toxoplasma gondii

<400> SEQUENCE: 12

Glu Met Ser Ala Pro Asp Arg Gln Thr Gly Lys Leu Ser Asp Leu Pro
1               5                   10                  15

Pro Phe Ala Glu Leu Pro Gln Leu Ala Glu Ile Pro Lys Leu Ser Glu
            20                  25                  30

Leu Pro Lys Ile Ala Asp Met Pro Lys Phe Ser Asp Met Pro Lys Met
        35                  40                  45

Ala Glu Met Pro Lys Leu Ser Asp Ile Pro Lys Met Ala Glu Met Pro
    50                  55                  60

Lys Leu Ser Asp Ile Pro Lys Met Ala Glu Met Pro Lys Leu Ser Asp
65                  70                  75                  80

Ile Pro Lys Met Ala Glu Met Pro Lys Phe Ser Asp Ile Pro Lys Met
                85                  90                  95

Ala Glu Met Pro Lys Leu Ser Asp Met Pro Arg Met Ala Asp Ile Pro
            100                 105                 110

Gln Phe Pro Glu Met Pro Arg Met Val Asp Met Pro Gln Phe Pro Glu
        115                 120                 125

Ile Pro Arg Met Ala Asp Met Arg Arg Phe Pro Glu Met Ser Lys Ile
    130                 135                 140

Ala Asp Met Pro Lys Phe Pro Asp Met Pro Asn Val Thr Glu Met Pro
145                 150                 155                 160

Lys Leu Ala Asp Leu Pro Arg Leu Ala Asp Met Pro Ser Ile Ala Asp
                165                 170                 175

Met Pro Arg Leu Ser Asp Met Pro Ser Ile Ala Asp Met Pro Arg Leu
            180                 185                 190

Ser Asp Ile Pro Ser Ile Ala Asp Met Pro Arg Leu Ser Asp Met Pro
        195                 200                 205

Ser Ile Ala Asp Met Pro Lys Phe Ser Ser Asn Arg Val His Gly Gln
    210                 215                 220

Ser Tyr His Ile Leu Ala Ile Trp Thr Pro Ser Leu Ser Gly Leu Lys
225                 230                 235                 240

Glu Phe Phe Thr Pro Leu Ser Asp Leu Ile Lys Pro Glu Ala Ala Ser
                245                 250                 255

Leu Thr Ser Leu Ala Lys Pro Ser Gly Val Phe Leu Arg Thr Leu Leu
            260                 265                 270

Ala

<210> SEQ ID NO 13
<211> LENGTH: 425
<212> TYPE: DNA
<213> ORGANISM: Toxoplasma gondii
<220> FEATURE:
<221> NAME/KEY: CDS
<222> LOCATION: (1)..(423)
<223> OTHER INFORMATION:

<400> SEQUENCE: 13 cgc gga att ccg gat cag cgt agc agt cgc agc cac act gga gtg gaa        48
Arg Gly Ile Pro Asp Gln Arg Ser Ser Arg Ser His Thr Gly Val Glu
1               5                   10                  15

```
agt ctg gtt ttg ccc tcc aga ggg gag gaa gag gcg aga gag gag acg      96
Ser Leu Val Leu Pro Ser Arg Gly Glu Glu Ala Arg Glu Glu Thr
        20                  25                  30 tct gca acg cgc cag atg ccg acg ctt ctc tct tcg ccg agg cct cca     144
Ser Ala Thr Arg Gln Met Pro Thr Leu Leu Ser Ser Pro Arg Pro Pro
            35                  40                  45 ctc gcg ctg ggg ttg gga gac aag tct ccc tgc gga gag tgg gtg tcg     192
Leu Ala Leu Gly Leu Gly Asp Lys Ser Pro Cys Gly Glu Trp Val Ser
    50                  55                  60 ccg aat gac atg gtt tct gcg ttg tcc ctc tgg gaa gca ggc gag gct     240
Pro Asn Asp Met Val Ser Ala Leu Ser Leu Trp Glu Ala Gly Glu Ala
65                  70                  75                  80 tgg cag ttc aag aca gcg aaa att ctt gac tct ttc gaa ggg gag acc     288
Trp Gln Phe Lys Thr Ala Lys Ile Leu Asp Ser Phe Glu Gly Glu Thr
                85                  90                  95 cca gaa ggg gag gga tgc ggc gca cag gaa aga agg aca gcc gca tgc     336
Pro Glu Gly Glu Gly Cys Gly Ala Gln Glu Arg Arg Thr Ala Ala Cys
            100                 105                 110 aag ctg gtg cga ctc ccg gtg aac gtg gag ggg cgg tcg aca aag gtg     384
Lys Leu Val Arg Leu Pro Val Asn Val Glu Gly Arg Ser Thr Lys Val
    115                 120                 125 tgg agc ttg gct ctt ctt tct tct ctg cgt ctg aag atc cg              425
Trp Ser Leu Ala Leu Leu Ser Ser Leu Arg Leu Lys Ile
130                 135                 140

<210> SEQ ID NO 14
<211> LENGTH: 141
<212> TYPE: PRT
<213> ORGANISM: Toxoplasma gondii

<400> SEQUENCE: 14

Arg Gly Ile Pro Asp Gln Arg Ser Ser Arg Ser His Thr Gly Val Glu
1               5                   10                  15

Ser Leu Val Leu Pro Ser Arg Gly Glu Glu Ala Arg Glu Glu Thr
            20                  25                  30

Ser Ala Thr Arg Gln Met Pro Thr Leu Leu Ser Ser Pro Arg Pro Pro
            35                  40                  45

Leu Ala Leu Gly Leu Gly Asp Lys Ser Pro Cys Gly Glu Trp Val Ser
    50                  55                  60

Pro Asn Asp Met Val Ser Ala Leu Ser Leu Trp Glu Ala Gly Glu Ala
65                  70                  75                  80

Trp Gln Phe Lys Thr Ala Lys Ile Leu Asp Ser Phe Glu Gly Glu Thr
                85                  90                  95

Pro Glu Gly Glu Gly Cys Gly Ala Gln Glu Arg Arg Thr Ala Ala Cys
            100                 105                 110

Lys Leu Val Arg Leu Pro Val Asn Val Glu Gly Arg Ser Thr Lys Val
    115                 120                 125

Trp Ser Leu Ala Leu Leu Ser Ser Leu Arg Leu Lys Ile
130                 135                 140

<210> SEQ ID NO 15
<211> LENGTH: 417
<212> TYPE: DNA
<213> ORGANISM: Toxoplasma gondii
<220> FEATURE:
<221> NAME/KEY: CDS
<222> LOCATION: (1)..(417)
<223> OTHER INFORMATION:

<400> SEQUENCE: 15
```

-continued

```
cgc ggc ctt tcc gat gac gcc tct cac gcg gag acc cct tca ccg ctc      48
Arg Gly Leu Ser Asp Asp Ala Ser His Ala Glu Thr Pro Ser Pro Leu
 1               5                  10                  15 acg ccc tcg agg gtg gac agc ttc tca gac gga gtt gag aga aca cgc      96
Thr Pro Ser Arg Val Asp Ser Phe Ser Asp Gly Val Glu Arg Thr Arg
             20                  25                  30 aga agc tct ccg cga gtc gag gag cac cag acg agc tcg aga gag gaa     144
Arg Ser Ser Pro Arg Val Glu Glu His Gln Thr Ser Ser Arg Glu Glu
         35                  40                  45 aaa gct gcg aca gag cgc gtt cca aaa ctg tct cgt ctc ccc tcg ctc     192
Lys Ala Ala Thr Glu Arg Val Pro Lys Leu Ser Arg Leu Pro Ser Leu
 50                  55                  60 cga gct cct cta cgc agc acg gac cga cgc gcc tcg ccg cct cgt cgg     240
Arg Ala Pro Leu Arg Ser Thr Asp Arg Arg Ala Ser Pro Pro Arg Arg
 65                  70                  75                  80 ctg tcg caa ctt ctt cgc tgc tgc aca acc tcg aga ttc gcg agc aaa     288
Leu Ser Gln Leu Leu Arg Cys Cys Thr Thr Ser Arg Phe Ala Ser Lys
                 85                  90                  95 gga acg gcg tat cca gac gag gag tgg ggg cat aga gtc cga gca cag     336
Gly Thr Ala Tyr Pro Asp Glu Glu Trp Gly His Arg Val Arg Ala Gln
             100                 105                 110 aga aca gaa gag act gtc tcc tct ctg acg acg aag cgc ctt ctc act     384
Arg Thr Glu Glu Thr Val Ser Ser Leu Thr Thr Lys Arg Leu Leu Thr
         115                 120                 125 cga agt cct aat tcg cag act gcc ttc ccg cgg                         417
Arg Ser Pro Asn Ser Gln Thr Ala Phe Pro Arg
 130                 135
```

<210> SEQ ID NO 16
<211> LENGTH: 139
<212> TYPE: PRT
<213> ORGANISM: Toxoplasma gondii

<400> SEQUENCE: 16

```
Arg Gly Leu Ser Asp Asp Ala Ser His Ala Glu Thr Pro Ser Pro Leu
 1               5                  10                  15

Thr Pro Ser Arg Val Asp Ser Phe Ser Asp Gly Val Glu Arg Thr Arg
             20                  25                  30

Arg Ser Ser Pro Arg Val Glu Glu His Gln Thr Ser Ser Arg Glu Glu
         35                  40                  45

Lys Ala Ala Thr Glu Arg Val Pro Lys Leu Ser Arg Leu Pro Ser Leu
 50                  55                  60

Arg Ala Pro Leu Arg Ser Thr Asp Arg Arg Ala Ser Pro Pro Arg Arg
 65                  70                  75                  80

Leu Ser Gln Leu Leu Arg Cys Cys Thr Thr Ser Arg Phe Ala Ser Lys
                 85                  90                  95

Gly Thr Ala Tyr Pro Asp Glu Glu Trp Gly His Arg Val Arg Ala Gln
             100                 105                 110

Arg Thr Glu Glu Thr Val Ser Ser Leu Thr Thr Lys Arg Leu Leu Thr
         115                 120                 125

Arg Ser Pro Asn Ser Gln Thr Ala Phe Pro Arg
 130                 135
```

<210> SEQ ID NO 17
<211> LENGTH: 507
<212> TYPE: DNA
<213> ORGANISM: Toxoplasma gondii
<220> FEATURE:
<221> NAME/KEY: CDS

```
<222> LOCATION: (1)..(153)
<223> OTHER INFORMATION:

<400> SEQUENCE: 17 ggc agg gga agt gga cga cac ccg tcg ctg agc ttt cgc ctg gag tgg      48
Gly Arg Gly Ser Gly Arg His Pro Ser Leu Ser Phe Arg Leu Glu Trp
1               5                   10                  15 aga cat cta cct gtg agt gaa cca ggc gtt ctg ctt tcg ccg ctc ctt      96
Arg His Leu Pro Val Ser Glu Pro Gly Val Leu Leu Ser Pro Leu Leu
            20                  25                  30 tgc agg cca gag gac aat gat aca aat ata agt gac act ctt ctc ttc     144
Cys Arg Pro Glu Asp Asn Asp Thr Asn Ile Ser Asp Thr Leu Leu Phe
        35                  40                  45 gat atc ggt taactgacaa agaaccacag cggagttaaa atagcagcgt              193
Asp Ile Gly
    50 ttgcagttca acgcatgcac aaactgctta actcccacat gcttgccttt gagagacgcg    253 acagcacatc gttcgagctt gcacgcagcg aagacatcta gacagcaatt aggagatgcc    313 tgccgaattt gtatgtaagg cgcaaacgtc tcctcggtgc gaatcacaat tacgcacatt    373 tgcccggact tacatctgtc ttctactggg gtctttcctt gtcaaaccgt gccgctgcaa    433 ctccaaacta gctcgttagt gagatgctgg caaggttttg acaagaatcg agttctgcga    493 ctgcatcgtg gtcg                                                      507

<210> SEQ ID NO 18
<211> LENGTH: 51
<212> TYPE: PRT
<213> ORGANISM: Toxoplasma gondii

<400> SEQUENCE: 18

Gly Arg Gly Ser Gly Arg His Pro Ser Leu Ser Phe Arg Leu Glu Trp
1               5                   10                  15

Arg His Leu Pro Val Ser Glu Pro Gly Val Leu Leu Ser Pro Leu Leu
            20                  25                  30

Cys Arg Pro Glu Asp Asn Asp Thr Asn Ile Ser Asp Thr Leu Leu Phe
        35                  40                  45

Asp Ile Gly
    50

<210> SEQ ID NO 19
<211> LENGTH: 718
<212> TYPE: DNA
<213> ORGANISM: Toxoplasma gondii
<220> FEATURE:
<221> NAME/KEY: CDS
<222> LOCATION: (1)..(297)
<223> OTHER INFORMATION:

<400> SEQUENCE: 19 gaa ttc cga ctg aat gac tac ctc ttt cag gtg cca gag ggt ccc ccc      48
Glu Phe Arg Leu Asn Asp Tyr Leu Phe Gln Val Pro Glu Gly Pro Pro
1               5                   10                  15 gcg aga agc cat ggg ttc gac aga aga cga gca gca gcg agc aaa aac      96
Ala Arg Ser His Gly Phe Asp Arg Arg Arg Ala Ala Ala Ser Lys Asn
            20                  25                  30 gca aca gaa gaa acg cgg agg ctg gcg ggc aaa gaa acg ccg ccg cac     144
Ala Thr Glu Glu Thr Arg Arg Leu Ala Gly Lys Glu Thr Pro Pro His
        35                  40                  45 aga gag gcc ccg gaa aag aca acg cga ggc gaa gaa gac aga caa gag     192
Arg Glu Ala Pro Glu Lys Thr Thr Arg Gly Glu Glu Asp Arg Gln Glu
```

-continued

```
           50                  55                  60
agc gag agg gaa aga agg cga gcc ggc gtg atg gac aaa aag aac cag    240
Ser Glu Arg Glu Arg Arg Ala Gly Val Met Asp Lys Lys Asn Gln
65                  70                  75                  80 gac ctt gac gat gaa acc cgg aga agg ggg acg gcg gag gag gag agg    288
Asp Leu Asp Asp Glu Thr Arg Arg Arg Gly Thr Ala Glu Glu Glu Arg
                85                  90                  95 aat gga gac tgaaaaaagc gaagatgac aggccagagt aagacgagga             337
Asn Gly Asp ggtgcaggac aaggatgtct cttattcacc gagtctcgtt aaccagcgtt ggtcttatca    397
agaggtgcag gacacagatg agacatccgg ttcgtccaaa gaccagttgg agcactcgag    457
agaggcaaga cagaagctga gggttcgcga cagacatcca gctgcctccg cgggcgttgt    517
tcactgagga cttggtcgga aaggggagag aaacatagaa acgaagaaca ccaagacctg    577
gaagaggtgc agattcctct tgggcactcg caggagacgc cttcgtcagt tttttttgtt    637
cactcaacgg actctgtcgt cacgagggaa ctcagacaga gacctcaagg agacagagga    697
acgcaacgca cgtcggaatt c                                             718
```

<210> SEQ ID NO 20
<211> LENGTH: 99
<212> TYPE: PRT
<213> ORGANISM: Toxoplasma gondii

<400> SEQUENCE: 20

```
Glu Phe Arg Leu Asn Asp Tyr Leu Phe Gln Val Pro Glu Gly Pro Pro
1               5                   10                  15

Ala Arg Ser His Gly Phe Asp Arg Arg Arg Ala Ala Ser Lys Asn
            20                  25                  30

Ala Thr Glu Glu Thr Arg Arg Leu Ala Gly Lys Glu Thr Pro Pro His
        35                  40                  45

Arg Glu Ala Pro Glu Lys Thr Thr Arg Gly Glu Glu Asp Arg Gln Glu
    50                  55                  60

Ser Glu Arg Glu Arg Arg Ala Gly Val Met Asp Lys Lys Asn Gln
65                  70                  75                  80

Asp Leu Asp Asp Glu Thr Arg Arg Arg Gly Thr Ala Glu Glu Glu Arg
                85                  90                  95

Asn Gly Asp
```

<210> SEQ ID NO 21
<211> LENGTH: 441
<212> TYPE: DNA
<213> ORGANISM: Toxoplasma gondii
<220> FEATURE:
<221> NAME/KEY: CDS
<222> LOCATION: (1)..(441)
<223> OTHER INFORMATION:

<400> SEQUENCE: 21

```
cgg atc gcc tcg gca ctt cct cat tat ccg tcg cat ggg cat ttc ctg     48
Arg Ile Ala Ser Ala Leu Pro His Tyr Pro Ser His Gly His Phe Leu
1               5                   10                  15 gaa gag gaa caa att ttg ctg ttg gat tgg cag tat caa ctt ggg caa     96
Glu Glu Glu Gln Ile Leu Leu Leu Asp Trp Gln Tyr Gln Leu Gly Gln
            20                  25                  30 cga ggc atg gag tcc ggt gta ccc ccc tgc gtg cag cat ggg gat gcg    144
Arg Gly Met Glu Ser Gly Val Pro Pro Cys Val Gln His Gly Asp Ala
        35                  40                  45
```

```
acg aga agt ttg act tca ccg aaa agg gat gtc agt cat gac ggt cac      192
Thr Arg Ser Leu Thr Ser Pro Lys Arg Asp Val Ser His Asp Gly His
    50                  55                  60 caa gga aac agc gga aca aac gca gat gaa gcc ggc caa ggg gcc atg      240
Gln Gly Asn Ser Gly Thr Asn Ala Asp Glu Ala Gly Gln Gly Ala Met
 65                  70                  75                  80 gca ggc cga gga aag tgc gag tgg agc cgc acc acc ggt gcc aac gta      288
Ala Gly Arg Gly Lys Cys Glu Trp Ser Arg Thr Thr Gly Ala Asn Val
                 85                  90                  95 ggg tcg tcg tca tgt gtg gtt gat gcg tgt ttg gcg tct gcg ggt aga      336
Gly Ser Ser Ser Cys Val Val Asp Ala Cys Leu Ala Ser Ala Gly Arg
            100                 105                 110 cat cag gcg gcg agc atg cgt ccg ttt gca cga gat gga ttc ggc gag      384
His Gln Ala Ala Ser Met Arg Pro Phe Ala Arg Asp Gly Phe Gly Glu
        115                 120                 125 tct act gcg gag aac aga ccc cgt cgg gac ggc gga ctg cca cgt tct      432
Ser Thr Ala Glu Asn Arg Pro Arg Arg Asp Gly Gly Leu Pro Arg Ser
130                 135                 140 ctt gga tcg                                                          441
Leu Gly Ser
145
```

<210> SEQ ID NO 22
<211> LENGTH: 147
<212> TYPE: PRT
<213> ORGANISM: Toxoplasma gondii

<400> SEQUENCE: 22

```
Arg Ile Ala Ser Ala Leu Pro His Tyr Pro Ser His Gly His Phe Leu
 1               5                  10                  15

Glu Glu Glu Gln Ile Leu Leu Asp Trp Gln Tyr Gln Leu Gly Gln
            20                  25                  30

Arg Gly Met Glu Ser Gly Val Pro Pro Cys Val Gln His Gly Asp Ala
        35                  40                  45

Thr Arg Ser Leu Thr Ser Pro Lys Arg Asp Val Ser His Asp Gly His
    50                  55                  60

Gln Gly Asn Ser Gly Thr Asn Ala Asp Glu Ala Gly Gln Gly Ala Met
 65                  70                  75                  80

Ala Gly Arg Gly Lys Cys Glu Trp Ser Arg Thr Thr Gly Ala Asn Val
                 85                  90                  95

Gly Ser Ser Ser Cys Val Val Asp Ala Cys Leu Ala Ser Ala Gly Arg
            100                 105                 110

His Gln Ala Ala Ser Met Arg Pro Phe Ala Arg Asp Gly Phe Gly Glu
        115                 120                 125

Ser Thr Ala Glu Asn Arg Pro Arg Arg Asp Gly Gly Leu Pro Arg Ser
    130                 135                 140

Leu Gly Ser
145
```

<210> SEQ ID NO 23
<211> LENGTH: 428
<212> TYPE: DNA
<213> ORGANISM: Toxoplasma gondii
<220> FEATURE:
<221> NAME/KEY: CDS
<222> LOCATION: (1)..(426)
<223> OTHER INFORMATION:

<400> SEQUENCE: 23 cgg cgg cgt cag cgt gca gac cct tca gac tgg aaa gga tgt gag aat      48

```
Arg Arg Arg Gln Arg Ala Asp Pro Ser Asp Trp Glu Gly Cys Glu Asn
  1               5                  10                  15 gtg gaa aag gat cat ttc ggg agt cgc gag agg cac tcg aat ggg gaa      96
Val Glu Lys Asp His Phe Gly Ser Arg Glu Arg His Ser Asn Gly Glu
             20                  25                  30 gag ttc aag aca cag gga aac gtt ggt cga ggt tca ctg agg cag gaa     144
Glu Phe Lys Thr Gln Gly Asn Val Gly Arg Gly Ser Leu Arg Gln Glu
             35                  40                  45 ccc ttt acc gat gga gtg tac cac gac agg cag cag cgc ttc tcg gag     192
Pro Phe Thr Asp Gly Val Tyr His Asp Arg Gln Gln Arg Phe Ser Glu
     50                  55                  60 aaa gaa cct gcg aag ccg atg ttc act tcc ctc gcg gat ccg agc gtg     240
Lys Glu Pro Ala Lys Pro Met Phe Thr Ser Leu Ala Asp Pro Ser Val
 65                  70                  75                  80 agg aga cat ttt aag gag gaa gaa cga cgg aaa ttc cag gaa aag         288
Arg Arg His Phe Lys Glu Glu Glu Arg Arg Lys Phe Gln Glu Lys
                 85                  90                  95 gca gaa gag gag atc ttg cgc ctt ctc aaa cgc gca gct gag tgc agc     336
Ala Glu Glu Glu Ile Leu Arg Leu Leu Lys Arg Ala Ala Glu Cys Ser
                100                 105                 110 gag gaa gat ttg aaa agg gaa gaa cgc tcc gaa aag gct acc gaa aag     384
Glu Glu Asp Leu Lys Arg Glu Glu Arg Ser Glu Lys Ala Thr Glu Lys
            115                 120                 125 ggg tcc cgt ctc ttc tct gga gag gag gtg cga ttc ttt ccg cc         428
Gly Ser Arg Leu Phe Ser Gly Glu Glu Val Arg Phe Phe Pro
        130                 135                 140

<210> SEQ ID NO 24
<211> LENGTH: 142
<212> TYPE: PRT
<213> ORGANISM: Toxoplasma gondii

<400> SEQUENCE: 24

Arg Arg Arg Gln Arg Ala Asp Pro Ser Asp Trp Glu Gly Cys Glu Asn
  1               5                  10                  15

Val Glu Lys Asp His Phe Gly Ser Arg Glu Arg His Ser Asn Gly Glu
             20                  25                  30

Glu Phe Lys Thr Gln Gly Asn Val Gly Arg Gly Ser Leu Arg Gln Glu
             35                  40                  45

Pro Phe Thr Asp Gly Val Tyr His Asp Arg Gln Gln Arg Phe Ser Glu
     50                  55                  60

Lys Glu Pro Ala Lys Pro Met Phe Thr Ser Leu Ala Asp Pro Ser Val
 65                  70                  75                  80

Arg Arg His Phe Lys Glu Glu Glu Arg Arg Lys Phe Gln Glu Lys
                 85                  90                  95

Ala Glu Glu Glu Ile Leu Arg Leu Leu Lys Arg Ala Ala Glu Cys Ser
                100                 105                 110

Glu Glu Asp Leu Lys Arg Glu Glu Arg Ser Glu Lys Ala Thr Glu Lys
            115                 120                 125

Gly Ser Arg Leu Phe Ser Gly Glu Glu Val Arg Phe Phe Pro
        130                 135                 140

<210> SEQ ID NO 25
<211> LENGTH: 282
<212> TYPE: DNA
<213> ORGANISM: Toxoplasma gondii

<400> SEQUENCE: 25
cgcgacccgc tgccagtgtt ttgagtctaa ccgccgtatg tcgcggattc cacgtggaaa      60
```

```
acgacggacc gtcaagacgc ccgagagtgc cgcaatttca cggaccgttc gttcgattcc      120
accaacacct tacgctagcg cttgctagga aacacacatg cgacggcggc tggggcctgg      180
tcgcggatct atccgtacaa tgggagaatc gtctgatgtc tccactgtcc cgctaccgca      240
caggtcctct acaggccaca ccggtagaca gtgagcggcg gc                         282
```

<210> SEQ ID NO 26
<211> LENGTH: 304
<212> TYPE: DNA
<213> ORGANISM: Toxoplasma gondii
<220> FEATURE:
<221> NAME/KEY: CDS
<222> LOCATION: (1)..(303)
<223> OTHER INFORMATION:

<400> SEQUENCE: 26

```
cgg act ggc aca gga ccg aag cgc agt tcc tcg aaa ccg acg tcg act       48
Arg Thr Gly Thr Gly Pro Lys Arg Ser Ser Ser Lys Pro Thr Ser Thr
1               5                   10                  15 tgg gtc cga ttg tta gtc cat act gaa aca aca atg gaa aac gaa ttg       96
Trp Val Arg Leu Leu Val His Thr Glu Thr Thr Met Glu Asn Glu Leu
                20                  25                  30 atg aac caa gta agc gac ctc tcg aat gag gct tgg caa aag aaa gaa      144
Met Asn Gln Val Ser Asp Leu Ser Asn Glu Ala Trp Gln Lys Lys Glu
            35                  40                  45 ctt ccc gtc cta cac aag tgg aca aac agc cct gaa cac tcc ctc ttg      192
Leu Pro Val Leu His Lys Trp Thr Asn Ser Pro Glu His Ser Leu Leu
        50                  55                  60 aca tcg gaa gac aga gaa aat agt ctt tca aag cca acc gcg gac tca      240
Thr Ser Glu Asp Arg Glu Asn Ser Leu Ser Lys Pro Thr Ala Asp Ser
65                  70                  75                  80 cca gac agc ttc cgg tat ggc aca cgc aga caa agt cac gca aaa gat      288
Pro Asp Ser Phe Arg Tyr Gly Thr Arg Arg Gln Ser His Ala Lys Asp
                85                  90                  95 ctg ttc tcc gat ccc g                                                 304
Leu Phe Ser Asp Pro
                100
```

<210> SEQ ID NO 27
<211> LENGTH: 101
<212> TYPE: PRT
<213> ORGANISM: Toxoplasma gondii

<400> SEQUENCE: 27

```
Arg Thr Gly Thr Gly Pro Lys Arg Ser Ser Ser Lys Pro Thr Ser Thr
1               5                   10                  15

Trp Val Arg Leu Leu Val His Thr Glu Thr Thr Met Glu Asn Glu Leu
                20                  25                  30

Met Asn Gln Val Ser Asp Leu Ser Asn Glu Ala Trp Gln Lys Lys Glu
            35                  40                  45

Leu Pro Val Leu His Lys Trp Thr Asn Ser Pro Glu His Ser Leu Leu
        50                  55                  60

Thr Ser Glu Asp Arg Glu Asn Ser Leu Ser Lys Pro Thr Ala Asp Ser
65                  70                  75                  80

Pro Asp Ser Phe Arg Tyr Gly Thr Arg Arg Gln Ser His Ala Lys Asp
                85                  90                  95

Leu Phe Ser Asp Pro
                100
```

```
<210> SEQ ID NO 28
<211> LENGTH: 284
<212> TYPE: DNA
<213> ORGANISM: Toxoplasma gondii
<220> FEATURE:
<221> NAME/KEY: CDS
<222> LOCATION: (1)..(282)
<223> OTHER INFORMATION:

<400> SEQUENCE: 28 ccg gac ttc ctc atg tct gaa gat gct tgt ctt gtt cgg ttc gtg cga        48
Pro Asp Phe Leu Met Ser Glu Asp Ala Cys Leu Val Arg Phe Val Arg
1               5                   10                  15 cac gcg tcg gcc aca cac gcg tat aca cgc agg gca agt gcg agg acg        96
His Ala Ser Ala Thr His Ala Tyr Thr Arg Arg Ala Ser Ala Arg Thr
            20                  25                  30 gta aag ccg ctc aaa ggc caa gga gac aaa gaa cag ggt gcg aca gga       144
Val Lys Pro Leu Lys Gly Gln Gly Asp Lys Glu Gln Gly Ala Thr Gly
        35                  40                  45 aga aat gtt gag gca ata aag aag gaa acc cct ctg aga cgg gaa gcg       192
Arg Asn Val Glu Ala Ile Lys Lys Glu Thr Pro Leu Arg Arg Glu Ala
50                  55                  60 aga gaa aac gcg ttt ttt tcg acg ttt tcc ccc gac aga gcg agc gcc       240
Arg Glu Asn Ala Phe Phe Ser Thr Phe Ser Pro Asp Arg Ala Ser Ala
65                  70                  75                  80 tcc tgt ctc cgc att cac gcg tgt gcc gcg gca gag gaa ccc gg            284
Ser Cys Leu Arg Ile His Ala Cys Ala Ala Glu Glu Pro
                85                  90

<210> SEQ ID NO 29
<211> LENGTH: 94
<212> TYPE: PRT
<213> ORGANISM: Toxoplasma gondii

<400> SEQUENCE: 29

Pro Asp Phe Leu Met Ser Glu Asp Ala Cys Leu Val Arg Phe Val Arg
1               5                   10                  15

His Ala Ser Ala Thr His Ala Tyr Thr Arg Arg Ala Ser Ala Arg Thr
            20                  25                  30

Val Lys Pro Leu Lys Gly Gln Gly Asp Lys Glu Gln Gly Ala Thr Gly
        35                  40                  45

Arg Asn Val Glu Ala Ile Lys Lys Glu Thr Pro Leu Arg Arg Glu Ala
    50                  55                  60

Arg Glu Asn Ala Phe Phe Ser Thr Phe Ser Pro Asp Arg Ala Ser Ala
65                  70                  75                  80

Ser Cys Leu Arg Ile His Ala Cys Ala Ala Glu Glu Pro
                85                  90

<210> SEQ ID NO 30
<211> LENGTH: 690
<212> TYPE: DNA
<213> ORGANISM: Toxoplasma gondii
<220> FEATURE:
<221> NAME/KEY: CDS
<222> LOCATION: (1)..(690)
<223> OTHER INFORMATION:

<400> SEQUENCE: 30 cga cgt ccc tac cac tat gaa atg ttg gac atc ccg agc atc cgg cgt        48
Arg Arg Pro Tyr His Tyr Glu Met Leu Asp Ile Pro Ser Ile Arg Arg
1               5                   10                  15 gtg gag ttg cca ggt gcg cag gtc cgt atg cca atg gcc aaa gag ctc        96
Val Glu Leu Pro Gly Ala Gln Val Arg Met Pro Met Ala Lys Glu Leu
```

-continued

```
          20                  25                  30
gta cgc gat tgg ggt tct gtc gtc cag cag cag acg act tct gat tct    144
Val Arg Asp Trp Gly Ser Val Val Gln Gln Gln Thr Thr Ser Asp Ser
         35                  40                  45 tct agt gac aca cca gct acc cgc agt cgc tct gct gaa gca ctc tgt    192
Ser Ser Asp Thr Pro Ala Thr Arg Ser Arg Ser Ala Glu Ala Leu Cys
 50                  55                  60 gtc ttt tcg acg cct tgt aca gca gac agc gac caa cgt atg aaa ggc    240
Val Phe Ser Thr Pro Cys Thr Ala Asp Ser Asp Gln Arg Met Lys Gly
 65                  70                  75                  80 cgc cat tac cca cag tca tat cat acg ccg agg gac agc gcc acc aaa    288
Arg His Tyr Pro Gln Ser Tyr His Thr Pro Arg Asp Ser Ala Thr Lys
                 85                  90                  95 aga gaa aaa cct ctc aaa agt aca ttt atc tgg ggc act aca gtg gaa    336
Arg Glu Lys Pro Leu Lys Ser Thr Phe Ile Trp Gly Thr Thr Val Glu
            100                 105                 110 gac aga aac cac ccc atc agc cca gac ccg ttc tca agg ctg cag gga    384
Asp Arg Asn His Pro Ile Ser Pro Asp Pro Phe Ser Arg Leu Gln Gly
        115                 120                 125 tgt ggc cag acc ctc cag gac gag ctc cca tca gct cgc act aga ccg    432
Cys Gly Gln Thr Leu Gln Asp Glu Leu Pro Ser Ala Arg Thr Arg Pro
130                 135                 140 gga tgg gcc gca ttg gac tcc cgc ctg aaa aac aag gac ccg cag att    480
Gly Trp Ala Ala Leu Asp Ser Arg Leu Lys Asn Lys Asp Pro Gln Ile
145                 150                 155                 160 agc gca gga gac gaa gcc gcg aag gtc gac gac acg tca gcg gaa cct    528
Ser Ala Gly Asp Glu Ala Ala Lys Val Asp Asp Thr Ser Ala Glu Pro
                165                 170                 175 tgc ctg gga acg gta ccg tcc ttt tgt cgg ctt gta aca agt cac gac    576
Cys Leu Gly Thr Val Pro Ser Phe Cys Arg Leu Val Thr Ser His Asp
            180                 185                 190 ttg cta gag gct gga gcg cag gtt cgt gtg ctt ggg cca acg aca gac    624
Leu Leu Glu Ala Gly Ala Gln Val Arg Val Leu Gly Pro Thr Thr Asp
        195                 200                 205 ccg gag aca gag acc gct tct cag ctc cag aca act gag ctt gcc acg    672
Pro Glu Thr Glu Thr Ala Ser Gln Leu Gln Thr Thr Glu Leu Ala Thr
    210                 215                 220 ctg aca act gtg gat ccg                                             690
Leu Thr Thr Val Asp Pro
225                 230

<210> SEQ ID NO 31
<211> LENGTH: 230
<212> TYPE: PRT
<213> ORGANISM: Toxoplasma gondii

<400> SEQUENCE: 31

Arg Arg Pro Tyr His Tyr Glu Met Leu Asp Ile Pro Ser Ile Arg Arg
 1               5                  10                  15

Val Glu Leu Pro Gly Ala Gln Val Arg Met Pro Met Ala Lys Glu Leu
                20                  25                  30

Val Arg Asp Trp Gly Ser Val Val Gln Gln Gln Thr Thr Ser Asp Ser
            35                  40                  45

Ser Ser Asp Thr Pro Ala Thr Arg Ser Arg Ser Ala Glu Ala Leu Cys
    50                  55                  60

Val Phe Ser Thr Pro Cys Thr Ala Asp Ser Asp Gln Arg Met Lys Gly
65                  70                  75                  80

Arg His Tyr Pro Gln Ser Tyr His Thr Pro Arg Asp Ser Ala Thr Lys
                85                  90                  95
```

```
Arg Glu Lys Pro Leu Lys Ser Thr Phe Ile Trp Gly Thr Thr Val Glu
            100                 105                 110

Asp Arg Asn His Pro Ile Ser Pro Asp Pro Phe Ser Arg Leu Gln Gly
        115                 120                 125

Cys Gly Gln Thr Leu Gln Asp Glu Leu Pro Ser Ala Arg Thr Arg Pro
    130                 135                 140

Gly Trp Ala Ala Leu Asp Ser Arg Leu Lys Asn Lys Asp Pro Gln Ile
145                 150                 155                 160

Ser Ala Gly Asp Glu Ala Ala Lys Val Asp Asp Thr Ser Ala Glu Pro
                165                 170                 175

Cys Leu Gly Thr Val Pro Ser Phe Cys Arg Leu Val Thr Ser His Asp
            180                 185                 190

Leu Leu Glu Ala Gly Ala Gln Val Arg Val Leu Gly Pro Thr Thr Asp
        195                 200                 205

Pro Glu Thr Glu Thr Ala Ser Gln Leu Gln Thr Glu Leu Ala Thr
    210                 215                 220

Leu Thr Thr Val Asp Pro
225                 230
```

<210> SEQ ID NO 32
<211> LENGTH: 313
<212> TYPE: DNA
<213> ORGANISM: Toxoplasma gondii
<220> FEATURE:
<221> NAME/KEY: CDS
<222> LOCATION: (1)..(162)
<223> OTHER INFORMATION:

<400> SEQUENCE: 32

```
cgc agg aat aat cct gac ggt cag acg cag cgg ttc gtg cag aca gtg    48
Arg Arg Asn Asn Pro Asp Gly Gln Thr Gln Arg Phe Val Gln Thr Val
1               5                   10                  15 aag caa tgg cag agt gta aaa agc aga acc aga gcg tgt ctg tcg gcc    96
Lys Gln Trp Gln Ser Val Lys Ser Arg Thr Arg Ala Cys Leu Ser Ala
            20                  25                  30 aaa gga aag aga agg caa atc aca cag cga ata aac ctc acc tct gtc   144
Lys Gly Lys Arg Arg Gln Ile Thr Gln Arg Ile Asn Leu Thr Ser Val
        35                  40                  45 tcg cac ccc gaa gca acg taggagagcc actggtgccg ccactctgtg           192
Ser His Pro Glu Ala Thr
    50 ctgacaaaaa agaaccggcc cttcttcggc aggggcgtag ccagtctgca gacatttcaa  252 tttcgaagcg accggaagca gtgaaatttc cagggaagac gcccaggaga cgtcaacagc  312 g                                                                  313
```

<210> SEQ ID NO 33
<211> LENGTH: 54
<212> TYPE: PRT
<213> ORGANISM: Toxoplasma gondii

<400> SEQUENCE: 33

```
Arg Arg Asn Asn Pro Asp Gly Gln Thr Gln Arg Phe Val Gln Thr Val
1               5                   10                  15

Lys Gln Trp Gln Ser Val Lys Ser Arg Thr Arg Ala Cys Leu Ser Ala
            20                  25                  30

Lys Gly Lys Arg Arg Gln Ile Thr Gln Arg Ile Asn Leu Thr Ser Val
        35                  40                  45
```

Ser His Pro Glu Ala Thr
    50

<210> SEQ ID NO 34
<211> LENGTH: 389
<212> TYPE: DNA
<213> ORGANISM: Toxoplasma gondii
<220> FEATURE:
<221> NAME/KEY: CDS
<222> LOCATION: (1)..(195)
<223> OTHER INFORMATION:

<400> SEQUENCE: 34

| cgc tct cac gga ggc gca agt gag ttt tgg ctt tac ctc ttg aga aaa | 48 |
|---|---|
| Arg Ser His Gly Gly Ala Ser Glu Phe Trp Leu Tyr Leu Leu Arg Lys | |
| 1               5                   10                  15 | |

| cgg aac tct cca gaa gat cct cgt tcc gtc cgt cct cca cgt ccg tgt | 96 |
|---|---|
| Arg Asn Ser Pro Glu Asp Pro Arg Ser Val Arg Pro Pro Arg Pro Cys | |
|         20                  25                  30 | |

| gtc ttt cga gag atg gac aaa cag aga agc aga atc aag aaa gga ttc | 144 |
|---|---|
| Val Phe Arg Glu Met Asp Lys Gln Arg Ser Arg Ile Lys Lys Gly Phe | |
|     35                  40                  45 | |

| gca ttt gca ctt ggg tct gtc ttt tac ttc caa ggt cgt gaa ttt cat | 192 |
|---|---|
| Ala Phe Ala Leu Gly Ser Val Phe Tyr Phe Gln Gly Arg Glu Phe His | |
|  50                  55                  60 | |

| gcg tgacgaataa gagagacagg agtaggccgc aacttctcgt ctcttggcag | 245 |
|---|---|
| Ala | |
| 65 | | tttccgattt ctcttccttc cgaagccctt gctgccaagc actccatccg gtccggttgg     305 tctctctcag gttcttcgag caatcgacgc gatgttctct gctgtcgatg cgggggcttg     365 gcgtgtctgc atatctcttc cagg     389

<210> SEQ ID NO 35
<211> LENGTH: 65
<212> TYPE: PRT
<213> ORGANISM: Toxoplasma gondii

<400> SEQUENCE: 35

Arg Ser His Gly Gly Ala Ser Glu Phe Trp Leu Tyr Leu Leu Arg Lys
1               5                   10                  15

Arg Asn Ser Pro Glu Asp Pro Arg Ser Val Arg Pro Pro Arg Pro Cys
            20                  25                  30

Val Phe Arg Glu Met Asp Lys Gln Arg Ser Arg Ile Lys Lys Gly Phe
        35                  40                  45

Ala Phe Ala Leu Gly Ser Val Phe Tyr Phe Gln Gly Arg Glu Phe His
    50                  55                  60

Ala
65

<210> SEQ ID NO 36
<211> LENGTH: 548
<212> TYPE: DNA
<213> ORGANISM: Toxoplasma gondii
<220> FEATURE:
<221> NAME/KEY: CDS
<222> LOCATION: (1)..(546)
<223> OTHER INFORMATION:

<400> SEQUENCE: 36

| cga tct tct tct cac cgt tcg ctc ttc ttt ctc tcc gtt gtc tgc gtc | 48 |
|---|---|
| Arg Ser Ser Ser His Arg Ser Leu Phe Phe Leu Ser Val Val Cys Val | |
| 1               5                   10                  15 | |

```
ctc tcc cca ctg cct ctc gcc gtc cgc gtc gtt cgc ctc cgg ggg agc      96
Leu Ser Pro Leu Pro Leu Ala Val Arg Val Val Arg Leu Arg Gly Ser
            20                  25                  30 cgg cag tgt ggc gag cac ggc ggc ttc gct cga aga gca gcg cct cgc     144
Arg Gln Cys Gly Glu His Gly Gly Phe Ala Arg Arg Ala Ala Pro Arg
        35                  40                  45 gcg ttc ctt cgg gga cgc ccg aca agc ctg cgt tca tcc cag aga acg     192
Ala Phe Leu Arg Gly Arg Pro Thr Ser Leu Arg Ser Ser Gln Arg Thr
    50                  55                  60 cct cgg tct gcg caa atg cgc cgt cgc tcc cca cac atg aga tgc ttt     240
Pro Arg Ser Ala Gln Met Arg Arg Arg Ser Pro His Met Arg Cys Phe
65                  70                  75                  80 tgc gag act ggc agc agc gcc tgt tgc gag cga agg aag agg agc gcg     288
Cys Glu Thr Gly Ser Ser Ala Cys Cys Glu Arg Arg Lys Arg Ser Ala
                85                  90                  95 agg gat ggc aac ctc cag gag agc gcg aag aag gcc cgt ccc tcg aat     336
Arg Asp Gly Asn Leu Gln Glu Ser Ala Lys Lys Ala Arg Pro Ser Asn
            100                 105                 110 ccg atg agc aag gca atc cat gct tca gtc gac cga gtc cag tgc ggt     384
Pro Met Ser Lys Ala Ile His Ala Ser Val Asp Arg Val Gln Cys Gly
        115                 120                 125 caa cag gac tcg aaa agg tcg agg aga tgg ccg gcg gct tcg act tct     432
Gln Gln Asp Ser Lys Arg Ser Arg Arg Trp Pro Ala Ala Ser Thr Ser
    130                 135                 140 gcg ggg gtg cag gcg att cgt gga aga aac agc gaa gtc ccg agg gtg     480
Ala Gly Val Gln Ala Ile Arg Gly Arg Asn Ser Glu Val Pro Arg Val
145                 150                 155                 160 gac agg tcc gcc aag tcg cct acg cca ctc tcg aag aag ccg aaa atg     528
Asp Arg Ser Ala Lys Ser Pro Thr Pro Leu Ser Lys Lys Pro Lys Met
                165                 170                 175 cgg tct ctg ccg cat acg gc                                           548
Arg Ser Leu Pro His Thr
            180
```

<210> SEQ ID NO 37
<211> LENGTH: 182
<212> TYPE: PRT
<213> ORGANISM: Toxoplasma gondii

<400> SEQUENCE: 37

```
Arg Ser Ser His Arg Ser Leu Phe Phe Leu Ser Val Val Cys Val
1               5                   10                  15

Leu Ser Pro Leu Pro Leu Ala Val Arg Val Val Arg Leu Arg Gly Ser
            20                  25                  30

Arg Gln Cys Gly Glu His Gly Gly Phe Ala Arg Arg Ala Ala Pro Arg
        35                  40                  45

Ala Phe Leu Arg Gly Arg Pro Thr Ser Leu Arg Ser Ser Gln Arg Thr
    50                  55                  60

Pro Arg Ser Ala Gln Met Arg Arg Arg Ser Pro His Met Arg Cys Phe
65                  70                  75                  80

Cys Glu Thr Gly Ser Ser Ala Cys Cys Glu Arg Arg Lys Arg Ser Ala
                85                  90                  95

Arg Asp Gly Asn Leu Gln Glu Ser Ala Lys Lys Ala Arg Pro Ser Asn
            100                 105                 110

Pro Met Ser Lys Ala Ile His Ala Ser Val Asp Arg Val Gln Cys Gly
        115                 120                 125

Gln Gln Asp Ser Lys Arg Ser Arg Arg Trp Pro Ala Ala Ser Thr Ser
    130                 135                 140
```

```
Ala Gly Val Gln Ala Ile Arg Gly Arg Asn Ser Glu Val Pro Arg Val
145                 150                 155                 160

Asp Arg Ser Ala Lys Ser Pro Thr Pro Leu Ser Lys Lys Pro Lys Met
                165                 170                 175

Arg Ser Leu Pro His Thr
            180

<210> SEQ ID NO 38
<211> LENGTH: 310
<212> TYPE: DNA
<213> ORGANISM: Toxoplasma gondii
<220> FEATURE:
<221> NAME/KEY: CDS
<222> LOCATION: (1)..(285)
<223> OTHER INFORMATION:
<220> FEATURE:
<221> NAME/KEY: misc_feature
<222> LOCATION: (46)..(46)
<223> OTHER INFORMATION: At nucleotide 46, y = c or t/u
      At amino acid residue 16, Xaa = Arg or Cys
<220> FEATURE:
<221> NAME/KEY: misc_feature
<222> LOCATION: (69)..(69)
<223> OTHER INFORMATION: At nucleotide 69, m = a or c
      At amino acid residue 23, Xaa = Thr
<220> FEATURE:
<221> NAME/KEY: misc_feature
<222> LOCATION: (72)..(72)
<223> OTHER INFORMATION: At nucleotide 72, m = a or c
      At amino acid residue 24, Xaa = Glu or Asp
<220> FEATURE:
<221> NAME/KEY: misc_feature
<222> LOCATION: (74)..(75)
<223> OTHER INFORMATION: At nucleotide 74, m = a or c
      At nucleotide 75, w = a or t/u
      At amino acid residue 25, Xaa = Glu, Asp or Ala
<220> FEATURE:
<221> NAME/KEY: misc_feature
<222> LOCATION: (94)..(94)
<223> OTHER INFORMATION: At nucleotide 94, s = c or g
      At amino acid residue 32, Xaa = Val or Leu
<220> FEATURE:
<221> NAME/KEY: misc_feature
<222> LOCATION: (112)..(112)
<223> OTHER INFORMATION: At nucleotide 112, s = c or g
      At amino acid residue 38, Xaa = Gly or Arg
<220> FEATURE:
<221> NAME/KEY: misc_feature
<222> LOCATION: (135)..(135)
<223> OTHER INFORMATION: At nucleotide 135, w = a or t/u
      At amino acid residue 45, Xaa = Gln or His
<220> FEATURE:
<221> NAME/KEY: misc_feature
<222> LOCATION: (169)..(169)
<223> OTHER INFORMATION: At nucleotide 169, s = c or g
      At amino acid residue 57, Xaa = Gly, Glu, Arg or Gln
<220> FEATURE:
<221> NAME/KEY: misc_feature
<222> LOCATION: (238)..(238)
<223> OTHER INFORMATION: At nucleotide 238, m = a or c
      At amino acid residue 80, Xaa = Arg

<400> SEQUENCE: 38 cgg gat cca gct gca cct aac agc aca cag gct gtg gca gcc gct ygt    48
Arg Asp Pro Ala Ala Pro Asn Ser Thr Gln Ala Val Ala Ala Ala Xaa
1               5                   10                  15 acc gtg gta gtg atg aaa acm gam gmw gaa gtg tcc ggt gac aac stc    96
Thr Val Val Val Met Lys Xaa Xaa Xaa Glu Val Ser Gly Asp Asn Xaa
            20                  25                  30 agt caa ccg ggt agg sgt ccg ccg tcg cca aag ccg caw acg acg aag   144
Ser Gln Pro Gly Arg Xaa Pro Pro Ser Pro Lys Pro Xaa Thr Thr Lys
        35                  40                  45
```

```
ttt ccg cgg aga gag tca cca gac srg cag ggg acg agg cgg aga act   192
Phe Pro Arg Arg Glu Ser Pro Asp Xaa Gln Gly Thr Arg Arg Arg Thr
    50                  55                  60 gaa agc cga ggc gct gtt agc agg gta tgg cca ggg gaa aac cag mga   240
Glu Ser Arg Gly Ala Val Ser Arg Val Trp Pro Gly Glu Asn Gln Xaa
65                  70                  75                  80 aga ctg tct gcc gtc gac gat tcg ata ccg gct aac cca tcg ctt       285
Arg Leu Ser Ala Val Asp Asp Ser Ile Pro Ala Asn Pro Ser Leu
                85                  90                  95 tgaacgggtg cgccctgcg atccg                                        310
```

<210> SEQ ID NO 39
<211> LENGTH: 95
<212> TYPE: PRT
<213> ORGANISM: Toxoplasma gondii
<220> FEATURE:
<221> NAME/KEY: misc_feature
<222> LOCATION: (16)..(16)
<223> OTHER INFORMATION: The 'Xaa' at location 16 stands for Arg, or
      Cys.
<220> FEATURE:
<221> NAME/KEY: misc_feature
<222> LOCATION: (23)..(23)
<223> OTHER INFORMATION: The 'Xaa' at location 23 stands for Thr.
<220> FEATURE:
<221> NAME/KEY: misc_feature
<222> LOCATION: (24)..(24)
<223> OTHER INFORMATION: The 'Xaa' at location 24 stands for Glu, or
      Asp.
<220> FEATURE:
<221> NAME/KEY: misc_feature
<222> LOCATION: (25)..(25)
<223> OTHER INFORMATION: The 'Xaa' at location 25 stands for Glu, Asp,
      or Ala.
<220> FEATURE:
<221> NAME/KEY: misc_feature
<222> LOCATION: (32)..(32)
<223> OTHER INFORMATION: The 'Xaa' at location 32 stands for Val, or
      Leu.
<220> FEATURE:
<221> NAME/KEY: misc_feature
<222> LOCATION: (38)..(38)
<223> OTHER INFORMATION: The 'Xaa' at location 38 stands for Gly, or
      Arg.
<220> FEATURE:
<221> NAME/KEY: misc_feature
<222> LOCATION: (45)..(45)
<223> OTHER INFORMATION: The 'Xaa' at location 45 stands for Gln, or
      His.
<220> FEATURE:
<221> NAME/KEY: misc_feature
<222> LOCATION: (57)..(57)
<223> OTHER INFORMATION: The 'Xaa' at location 57 stands for Gly, Glu,
      Arg, or Gln.
<220> FEATURE:
<221> NAME/KEY: misc_feature
<222> LOCATION: (80)..(80)
<223> OTHER INFORMATION: The 'Xaa' at location 80 stands for Arg.

<400> SEQUENCE: 39

Arg Asp Pro Ala Ala Pro Asn Ser Thr Gln Ala Val Ala Ala Ala Xaa
1               5                   10                  15

Thr Val Val Val Met Lys Xaa Xaa Xaa Glu Val Ser Gly Asp Asn Xaa
                20                  25                  30

Ser Gln Pro Gly Arg Xaa Pro Ser Pro Lys Pro Xaa Thr Thr Lys
            35                  40                  45

Phe Pro Arg Arg Glu Ser Pro Asp Xaa Gln Gly Thr Arg Arg Arg Thr
    50                  55                  60

Glu Ser Arg Gly Ala Val Ser Arg Val Trp Pro Gly Glu Asn Gln Xaa

```
                    65                  70                  75                  80
                Arg Leu Ser Ala Val Asp Asp Ser Ile Pro Ala Asn Pro Ser Leu
                                    85                  90                  95

<210> SEQ ID NO 40
<211> LENGTH: 220
<212> TYPE: DNA
<213> ORGANISM: Toxoplasma gondii
<220> FEATURE:
<221> NAME/KEY: CDS
<222> LOCATION: (1)..(219)
<223> OTHER INFORMATION:

<400> SEQUENCE: 40 cgg gat cct tgc ctc agt gtc agg gac atc gag cgt atg ttc cgt ata      48
Arg Asp Pro Cys Leu Ser Val Arg Asp Ile Glu Arg Met Phe Arg Ile
1               5                   10                  15 tgt cac cat cgt tct ctg tct cgc ctc ctt ggc gcc tct gtt gct tgg      96
Cys His His Arg Ser Leu Ser Arg Leu Leu Gly Ala Ser Val Ala Trp
            20                  25                  30 gat gca gtt gac tgc tct tcg gct tcg tcg cgc aca cac tgg tcc ttg     144
Asp Ala Val Asp Cys Ser Ser Ala Ser Ser Arg Thr His Trp Ser Leu
        35                  40                  45 ctt gcg tct gag ctc cct tcc gaa cgg gtt ctt ttt cga ctg cag gtt     192
Leu Ala Ser Glu Leu Pro Ser Glu Arg Val Leu Phe Arg Leu Gln Val
    50                  55                  60 ctt cta aaa ttg cca gtt ccc gat ccc g                                220
Leu Leu Lys Leu Pro Val Pro Asp Pro
65                  70

<210> SEQ ID NO 41
<211> LENGTH: 73
<212> TYPE: PRT
<213> ORGANISM: Toxoplasma gondii

<400> SEQUENCE: 41

Arg Asp Pro Cys Leu Ser Val Arg Asp Ile Glu Arg Met Phe Arg Ile
1               5                   10                  15

Cys His His Arg Ser Leu Ser Arg Leu Leu Gly Ala Ser Val Ala Trp
            20                  25                  30

Asp Ala Val Asp Cys Ser Ser Ala Ser Ser Arg Thr His Trp Ser Leu
        35                  40                  45

Leu Ala Ser Glu Leu Pro Ser Glu Arg Val Leu Phe Arg Leu Gln Val
    50                  55                  60

Leu Leu Lys Leu Pro Val Pro Asp Pro
65                  70

<210> SEQ ID NO 42
<211> LENGTH: 642
<212> TYPE: DNA
<213> ORGANISM: Toxoplasma gondii
<220> FEATURE:
<221> NAME/KEY: CDS
<222> LOCATION: (1)..(102)
<223> OTHER INFORMATION:
<220> FEATURE:
<221> NAME/KEY: misc_feature
<222> LOCATION: (19)..(19)
<223> OTHER INFORMATION: At nucleotide 19, n = unknown
      At amino acid residue 7, Xaa = Ile, Val, Leu or Phe
<220> FEATURE:
<221> NAME/KEY: misc_feature
<222> LOCATION: (23)..(23)
<223> OTHER INFORMATION: At nucleotide 23, n = unknown
      At amino acid residue 8, Xaa = Ser or Leu
```

-continued

```
<220> FEATURE:
<221> NAME/KEY: misc_feature
<222> LOCATION: (27)..(27)
<223> OTHER INFORMATION: At nucleotide 27, n = unknown
      At amino acid residue 9, Xaa = Tyr
<220> FEATURE:
<221> NAME/KEY: misc_feature
<222> LOCATION: (28)..(29)
<223> OTHER INFORMATION: At nucleotides 28 and 29, n = unknown
      At amino acid residue 10, Xaa = Asn, Ser, Thr, Ile, Asp, Gly, Ala
      , Val, His, Arg, Pro, Leu, Tyr, Cys or Phe
<220> FEATURE:
<221> NAME/KEY: misc_feature
<222> LOCATION: (41)..(41)
<223> OTHER INFORMATION: At nucleotide 41, n = unknown
      At amino acid residue 14, Xaa = Lys, Arg, Thr or ILE
<220> FEATURE:
<221> NAME/KEY: misc_feature
<222> LOCATION: (86)..(86)
<223> OTHER INFORMATION: At nucleotide 86, n = unknown
      At amino acid residue 29, Xaa = Lys, Arg, Thr or Met
<220> FEATURE:
<221> NAME/KEY: misc_feature
<222> LOCATION: (88)..(88)
<223> OTHER INFORMATION: At nucleotide 88, n = unknown
      At amino acid residue 30, Xaa = Lys, Glu or Gln
<220> FEATURE:
<221> NAME/KEY: misc_feature
<222> LOCATION: (96)..(96)
<223> OTHER INFORMATION: At nucleotide 96, n = unknown
      At amino acid residue 32, Xaa = Thr
<220> FEATURE:
<221> NAME/KEY: misc_feature
<222> LOCATION: (110)..(111)
<223> OTHER INFORMATION: n = unknown
<220> FEATURE:
<221> NAME/KEY: misc_feature
<222> LOCATION: (113)..(113)
<223> OTHER INFORMATION: n = unknown
<220> FEATURE:
<221> NAME/KEY: misc_feature
<222> LOCATION: (119)..(119)
<223> OTHER INFORMATION: n = unknown
<220> FEATURE:
<221> NAME/KEY: misc_feature
<222> LOCATION: (122)..(122)
<223> OTHER INFORMATION: n = unknown
<220> FEATURE:
<221> NAME/KEY: misc_feature
<222> LOCATION: (132)..(132)
<223> OTHER INFORMATION: n = unknown
<220> FEATURE:
<221> NAME/KEY: misc_feature
<222> LOCATION: (137)..(137)
<223> OTHER INFORMATION: n = unknown
<220> FEATURE:
<221> NAME/KEY: misc_feature
<222> LOCATION: (149)..(149)
<223> OTHER INFORMATION: n = unknown
<220> FEATURE:
<221> NAME/KEY: misc_feature
<222> LOCATION: (164)..(164)
<223> OTHER INFORMATION: n = unknown
<220> FEATURE:
<221> NAME/KEY: misc_feature
<222> LOCATION: (169)..(169)
<223> OTHER INFORMATION: n = unknown
<220> FEATURE:
<221> NAME/KEY: misc_feature
<222> LOCATION: (172)..(173)
<223> OTHER INFORMATION: n = unknown
<220> FEATURE:
<221> NAME/KEY: misc_feature
<222> LOCATION: (209)..(209)
<223> OTHER INFORMATION: n = unknown
<220> FEATURE:
<221> NAME/KEY: misc_feature
<222> LOCATION: (217)..(217)
<223> OTHER INFORMATION: n = unknown
```

```
<220> FEATURE:
<221> NAME/KEY: misc_feature
<222> LOCATION: (220)..(220)
<223> OTHER INFORMATION: n = unknown
<220> FEATURE:
<221> NAME/KEY: misc_feature
<222> LOCATION: (234)..(234)
<223> OTHER INFORMATION: n = unknown
<220> FEATURE:
<221> NAME/KEY: misc_feature
<222> LOCATION: (236)..(236)
<223> OTHER INFORMATION: n = unknown
<220> FEATURE:
<221> NAME/KEY: misc_feature
<222> LOCATION: (250)..(250)
<223> OTHER INFORMATION: n = unknown
<220> FEATURE:
<221> NAME/KEY: misc_feature
<222> LOCATION: (257)..(257)
<223> OTHER INFORMATION: n = unknown
<220> FEATURE:
<221> NAME/KEY: misc_feature
<222> LOCATION: (492)..(492)
<223> OTHER INFORMATION: n = unknown
<220> FEATURE:
<221> NAME/KEY: misc_feature
<222> LOCATION: (505)..(505)
<223> OTHER INFORMATION: n = unknown
<220> FEATURE:
<221> NAME/KEY: misc_feature
<222> LOCATION: (512)..(512)
<223> OTHER INFORMATION: n = unknown
<220> FEATURE:
<221> NAME/KEY: misc_feature
<222> LOCATION: (524)..(524)
<223> OTHER INFORMATION: n = unknown
<220> FEATURE:
<221> NAME/KEY: misc_feature
<222> LOCATION: (527)..(527)
<223> OTHER INFORMATION: n = unknown
<220> FEATURE:
<221> NAME/KEY: misc_feature
<222> LOCATION: (533)..(533)
<223> OTHER INFORMATION: n = unknown

<400> SEQUENCE: 42 cgg cgg gaa acc atg gag ntt tna tan nnt aca act tcc ana tgc atg         48
Arg Arg Glu Thr Met Glu Xaa Xaa Xaa Xaa Thr Thr Ser Xaa Cys Met
1               5                   10                  15 gta ggt acc caa aat gca aac tat aga cac aaa caa ang naa aat acn         96
Val Gly Thr Gln Asn Ala Asn Tyr Arg His Lys Gln Xaa Xaa Asn Xaa
            20                  25                  30 tgg ggg tgatgcanna ngggggangtn ggggacagan aaatngtcct tcagttntca        152
Trp Gly tctttgcccg cngcgtngan nacgcaatac agcgggcgca gcggctcatc acaccantac      212
acganttntg caaagaagca cntntcttct ctcttcangt ctctntacca cttctaccac      272
ctgcaccccc gcttcgtcca caaaacacat ttgaacgatg tgaccaaaat gatccacaaa      332
aacacgattg tttcgtcaca tgaaacctca gcaaattcag gcgccaggac ggctccttca      392
aacgtctaat ccagagtcct ctccgctcaa aaacacgatt gtttcgtcac atggaacctc      452
agcaaattca ggcgccagga cggcctccct tcaaacgtcn taatccagag tcntttccgn      512
tccatcccca cnttntgccc nttcacgttt ccagtggtgg catgtcatcg tctcccctg       572 tcaacgtccc atcacctgag tacaggcgcg aagcagcgga cagctgttct tccatctccc      632
tgtattccgg                                                             642

<210> SEQ ID NO 43
<211> LENGTH: 34
```

```
<212> TYPE: PRT
<213> ORGANISM: Toxoplasma gondii
<220> FEATURE:
<221> NAME/KEY: misc_feature
<222> LOCATION: (7)..(7)
<223> OTHER INFORMATION: The 'Xaa' at location 7 stands for Ile, Val,
      Leu, or Phe.
<220> FEATURE:
<221> NAME/KEY: misc_feature
<222> LOCATION: (8)..(8)
<223> OTHER INFORMATION: The 'Xaa' at location 8 stands for Ser, or Leu.
<220> FEATURE:
<221> NAME/KEY: misc_feature
<222> LOCATION: (9)..(9)
<223> OTHER INFORMATION: The 'Xaa' at location 9 stands for Tyr.
<220> FEATURE:
<221> NAME/KEY: misc_feature
<222> LOCATION: (10)..(10)
<223> OTHER INFORMATION: The 'Xaa' at location 10 stands for Asn, Ser,
      Thr, Ile, Asp, Gly, Ala, Val, His, Arg, Pro, Leu, Tyr, Cys, or
      Phe.
<220> FEATURE:
<221> NAME/KEY: misc_feature
<222> LOCATION: (14)..(14)
<223> OTHER INFORMATION: The 'Xaa' at location 14 stands for Lys, Arg,
      Thr, or Ile.
<220> FEATURE:
<221> NAME/KEY: misc_feature
<222> LOCATION: (29)..(29)
<223> OTHER INFORMATION: The 'Xaa' at location 29 stands for Lys, Arg,
      Thr, or Met.
<220> FEATURE:
<221> NAME/KEY: misc_feature
<222> LOCATION: (30)..(30)
<223> OTHER INFORMATION: The 'Xaa' at location 30 stands for Lys, Glu,
      Gln.
<220> FEATURE:
<221> NAME/KEY: misc_feature
<222> LOCATION: (32)..(32)
<223> OTHER INFORMATION: The 'Xaa' at location 32 stands for Thr.

<400> SEQUENCE: 43

Arg Arg Glu Thr Met Glu Xaa Xaa Xaa Xaa Thr Thr Ser Xaa Cys Met
1               5                   10                  15

Val Gly Thr Gln Asn Ala Asn Tyr Arg His Lys Gln Xaa Xaa Asn Xaa
            20                  25                  30

Trp Gly

<210> SEQ ID NO 44
<211> LENGTH: 381
<212> TYPE: DNA
<213> ORGANISM: Toxoplasma gondii
<220> FEATURE:
<221> NAME/KEY: CDS
<222> LOCATION: (1)..(81)
<223> OTHER INFORMATION:

<400> SEQUENCE: 44 cgg atc cac aaa aac acg att gtt tcg tca cat gga acc tca gca aat     48
Arg Ile His Lys Asn Thr Ile Val Ser Ser His Gly Thr Ser Ala Asn
1               5                   10                  15 tca ggc gcc agg acg gcc tcc ctt caa acg tcc taatccagag tcctctccgc  101
Ser Gly Ala Arg Thr Ala Ser Leu Gln Thr Ser
            20                  25 tccatcccca ccttctgccc cttcacgttt ccagtggtgg catgtcatcg tctcccctg   161 tcaacgtccc atcacctgag tacaggcgcg aagcagcgga cagctgttct tccatctccc  221
tgtattccgg agtctctatc gcttgcaagg cgagcaggcg ggcctcgaca gaagggttaa  281
tcaacttgta aaccagaagt ttcacgttct ctggcacccg ccggcacctc gaaaaaaga   341
```

```
attcgacact gtattcgtac cccgattttg tatcgggagg                              381
```

<210> SEQ ID NO 45
<211> LENGTH: 27
<212> TYPE: PRT
<213> ORGANISM: Toxoplasma gondii

<400> SEQUENCE: 45

```
Arg Ile His Lys Asn Thr Ile Val Ser Ser His Gly Thr Ser Ala Asn
1               5                   10                  15

Ser Gly Ala Arg Thr Ala Ser Leu Gln Thr Ser
            20                  25
```

<210> SEQ ID NO 46
<211> LENGTH: 432
<212> TYPE: DNA
<213> ORGANISM: Toxoplasma gondii
<220> FEATURE:
<221> NAME/KEY: CDS
<222> LOCATION: (1)..(255)
<223> OTHER INFORMATION:

<400> SEQUENCE: 46

```
ttt ttt tcg agg tgc cgg cgg gtg cca gag aac gtg aaa ctt ctg gtt        48
Phe Phe Ser Arg Cys Arg Arg Val Pro Glu Asn Val Lys Leu Leu Val
1               5                   10                  15 tac aag ttg att aac cct tct gtc gag gcc cgc ctg ctc gcc ttg caa        96
Tyr Lys Leu Ile Asn Pro Ser Val Glu Ala Arg Leu Leu Ala Leu Gln
            20                  25                  30 gcg ata gag act ccg gaa tac agg gag atg gaa gaa cag ctg tcc gct       144
Ala Ile Glu Thr Pro Glu Tyr Arg Glu Met Glu Glu Gln Leu Ser Ala
        35                  40                  45 gct tcg cgc ctg tac tca ggt gat ggg acg ttg aca ggg gga gac gat       192
Ala Ser Arg Leu Tyr Ser Gly Asp Gly Thr Leu Thr Gly Gly Asp Asp
    50                  55                  60 gac atg cca cca ctg aaa cgt gaa ggg gca gaa ggt ggg gat gga gcg       240
Asp Met Pro Pro Leu Lys Arg Glu Gly Ala Glu Gly Gly Asp Gly Ala
65                  70                  75                  80 gag agg act ctg gat taggacgttt gaagggaggc cgtcctggcg cctgaatttg       295
Glu Arg Thr Leu Asp
                85 ctgaggttcc atgtgacgaa acaatcgtgt ttttgagcgg agaggactct ggattaggac     355 gtttgaaggg aggccgtcct ggcgcctgaa tttgctgagg tttcatgtga cgaaacaatc     415 gtgttttttgt ggatccg                                                    432
```

<210> SEQ ID NO 47
<211> LENGTH: 85
<212> TYPE: PRT
<213> ORGANISM: Toxoplasma gondii

<400> SEQUENCE: 47

```
Phe Phe Ser Arg Cys Arg Arg Val Pro Glu Asn Val Lys Leu Leu Val
1               5                   10                  15

Tyr Lys Leu Ile Asn Pro Ser Val Glu Ala Arg Leu Leu Ala Leu Gln
            20                  25                  30

Ala Ile Glu Thr Pro Glu Tyr Arg Glu Met Glu Glu Gln Leu Ser Ala
        35                  40                  45

Ala Ser Arg Leu Tyr Ser Gly Asp Gly Thr Leu Thr Gly Gly Asp Asp
    50                  55                  60

Asp Met Pro Pro Leu Lys Arg Glu Gly Ala Glu Gly Gly Asp Gly Ala
```

```
                65                  70                  75                  80
Glu Arg Thr Leu Asp
                85
```

<210> SEQ ID NO 48
<211> LENGTH: 282
<212> TYPE: DNA
<213> ORGANISM: Toxoplasma gondii
<220> FEATURE:
<221> NAME/KEY: CDS
<222> LOCATION: (1)..(105)
<223> OTHER INFORMATION:

<400> SEQUENCE: 48

```
cgg cgg gct gct tcc cag gaa cgt ttc gcg gct gcg tgt gga cag caa      48
Arg Arg Ala Ala Ser Gln Glu Arg Phe Ala Ala Ala Cys Gly Gln Gln
1               5                   10                  15 agc ctt acc ctc gag ttt tct ctc gtg gct gcc gac gtc ggc gac gcc      96
Ser Leu Thr Leu Glu Phe Ser Leu Val Ala Ala Asp Val Gly Asp Ala
            20                  25                  30 gcg aac tcc tgagatcaaa cacacaaaaa ggccctcgtt gaaacatccc              145
Ala Asn Ser
        35 cacgcacgag cagaaggacg cgagcaagaa aacgtctcca gccttctctt gcggtcgctt    205 gcaagcggga gtgtcgtctc cctctgtctt tctctgtgta ctcgaagccc agcgacttcc    265 ttgtcgagtt tctccgg                                                   282
```

<210> SEQ ID NO 49
<211> LENGTH: 35
<212> TYPE: PRT
<213> ORGANISM: Toxoplasma gondii

<400> SEQUENCE: 49

```
Arg Arg Ala Ala Ser Gln Glu Arg Phe Ala Ala Ala Cys Gly Gln Gln
1               5                   10                  15

Ser Leu Thr Leu Glu Phe Ser Leu Val Ala Ala Asp Val Gly Asp Ala
            20                  25                  30

Ala Asn Ser
        35
```

<210> SEQ ID NO 50
<211> LENGTH: 466
<212> TYPE: DNA
<213> ORGANISM: Toxoplasma gondii
<220> FEATURE:
<221> NAME/KEY: CDS
<222> LOCATION: (1)..(213)
<223> OTHER INFORMATION:
<220> FEATURE:
<221> NAME/KEY: misc_feature
<222> LOCATION: (8)..(8)
<223> OTHER INFORMATION: At nucleotide 8, s = c or g
      At amino acid residue 3, Xaa = Trp or Ser
<220> FEATURE:
<221> NAME/KEY: misc_feature
<222> LOCATION: (33)..(33)
<223> OTHER INFORMATION: At nucleotide 33, m = a or c
      At amino acid residue 11, Xaa = Lys or Asn
<220> FEATURE:
<221> NAME/KEY: misc_feature
<222> LOCATION: (107)..(107)
<223> OTHER INFORMATION: At nucleotide 107, y = c or t/u
      At amino acid residue 36, Xaa = Thr or Ile

<400> SEQUENCE: 50

```
ttt ttt tsg agg tgc cgg cgg gtg cca gag aam gtg aaa ttc tgg ttt      48
Phe Phe Xaa Arg Cys Arg Arg Val Pro Glu Xaa Val Lys Phe Trp Phe
1               5                   10                  15 aac aag ttg att aac cct tct gtc gag gcc cgc ctg ttc gcc ttg caa      96
Asn Lys Leu Ile Asn Pro Ser Val Glu Ala Arg Leu Phe Ala Leu Gln
                20                  25                  30 gcg ata gag ayt ccg gaa tac agg gag atg gaa gaa cag ctg tcc gct     144
Ala Ile Glu Xaa Pro Glu Tyr Arg Glu Met Glu Glu Gln Leu Ser Ala
            35                  40                  45 gct tcg cgc ctg tac tca ggt gat ggg acg ttg aca ggg gga gac gat     192
Ala Ser Arg Leu Tyr Ser Gly Asp Gly Thr Leu Thr Gly Gly Asp Asp
        50                  55                  60 gac atg cca cca ctg gaa acg tgaaggggca aaggtgggg atggagcgga         243
Asp Met Pro Pro Leu Glu Thr
65                  70 gaggactctg gattaggacg tttgaaggga ggccgtcctg gcgcctgaat ttgctgaggt   303
tccatgtgac gaaacaatcg tgtttttgag cggagaggac tctggattag gacgtttgaa   363
gggaggccgt cctggcgcct gaatttgctg aggtttcatg tgacgaaaca atcgtgtttt   423
tgtggatcct cccgatacaa aatcggggta cgaatacagt gtc                    466
```

\<210\> SEQ ID NO 51
\<211\> LENGTH: 71
\<212\> TYPE: PRT
\<213\> ORGANISM: Toxoplasma gondii
\<220\> FEATURE:
\<221\> NAME/KEY: misc_feature
\<222\> LOCATION: (3)..(3)
\<223\> OTHER INFORMATION: The 'Xaa' at location 3 stands for Trp, or Ser.
\<220\> FEATURE:
\<221\> NAME/KEY: misc_feature
\<222\> LOCATION: (11)..(11)
\<223\> OTHER INFORMATION: The 'Xaa' at location 11 stands for Lys, or Asn.
\<220\> FEATURE:
\<221\> NAME/KEY: misc_feature
\<222\> LOCATION: (36)..(36)
\<223\> OTHER INFORMATION: The 'Xaa' at location 36 stands for Thr, or Ile.

\<400\> SEQUENCE: 51

```
Phe Phe Xaa Arg Cys Arg Arg Val Pro Glu Xaa Val Lys Phe Trp Phe
1               5                   10                  15

Asn Lys Leu Ile Asn Pro Ser Val Glu Ala Arg Leu Phe Ala Leu Gln
                20                  25                  30

Ala Ile Glu Xaa Pro Glu Tyr Arg Glu Met Glu Glu Gln Leu Ser Ala
            35                  40                  45

Ala Ser Arg Leu Tyr Ser Gly Asp Gly Thr Leu Thr Gly Gly Asp Asp
        50                  55                  60

Asp Met Pro Pro Leu Glu Thr
65                  70
```

\<210\> SEQ ID NO 52
\<211\> LENGTH: 539
\<212\> TYPE: DNA
\<213\> ORGANISM: Toxoplasma gondii
\<220\> FEATURE:
\<221\> NAME/KEY: CDS
\<222\> LOCATION: (1)..(60)
\<223\> OTHER INFORMATION:
\<220\> FEATURE:
\<221\> NAME/KEY: misc_feature
\<222\> LOCATION: (22)..(22)
\<223\> OTHER INFORMATION: At nucleotide 22, n = unknown
       At amino acid residue 8, Xaa = Met, Val or Leu
\<220\> FEATURE:
\<221\> NAME/KEY: misc_feature

```
<222> LOCATION: (26)..(26)
<223> OTHER INFORMATION: At nucleotide 26, r = a or g
      At amino acid residue 9, Xaa = Gly or Glu
<220> FEATURE:
<221> NAME/KEY: misc_feature
<222> LOCATION: (47)..(47)
<223> OTHER INFORMATION: At nucleotide 47, n = unknown
      At amino acid residue 16, Xaa = Tyr, Cys, Ser or Phe

<400> SEQUENCE: 52 gat agc aca cgg aat gga tgc ntg grg gtt ggg agc gac tat att tnt     48
Asp Ser Thr Arg Asn Gly Cys Xaa Xaa Val Gly Ser Asp Tyr Ile Xaa
1               5                   10                  15 tat ttg gtg ctt taaagctcca actacaggac ctgaagagga atactccatc         100
Tyr Leu Val Leu
            20 gaattcttgt tctcattgtg ccggcgggca ccagagaacg tgaaactact ggtttacaag   160 ttgattaacc cttctgtcga ggcccgcctg tcgccttgca agctacggag actccggaat   220 acagggagat ggaagaacag ctgtccgctg cttcgcgcct gtactcaggt gatgggacgt   280 tgacaggggg agacgatgac atgccaccac cggaaacgtg aagggcagaa ggtggggat    340 ggagcggaga ggactctgga ttaggacgtt tgaagggagg ccgtcctggc gcctgaattt   400 tgctgaggtt tcatgtgacg aaacaatcgt gtttttgtgg atccggaatt ccggatcggg   460 gaatttcctc tcacaccgct tggggccgag acacgcgcag agacgttgtt gggcctccac   520 aacacagggg ggattaagg                                                539

<210> SEQ ID NO 53
<211> LENGTH: 20
<212> TYPE: PRT
<213> ORGANISM: Toxoplasma gondii
<220> FEATURE:
<221> NAME/KEY: misc_feature
<222> LOCATION: (8)..(8)
<223> OTHER INFORMATION: The 'Xaa' at location 8 stands for Met, Val,
      or Leu.
<220> FEATURE:
<221> NAME/KEY: misc_feature
<222> LOCATION: (9)..(9)
<223> OTHER INFORMATION: The 'Xaa' at location 9 stands for Gly, or Glu.
<220> FEATURE:
<221> NAME/KEY: misc_feature
<222> LOCATION: (16)..(16)
<223> OTHER INFORMATION: The 'Xaa' at location 16 stands for Tyr, Cys,
      Ser, or Phe.

<400> SEQUENCE: 53

Asp Ser Thr Arg Asn Gly Cys Xaa Xaa Val Gly Ser Asp Tyr Ile Xaa
1               5                   10                  15

Tyr Leu Val Leu
            20

<210> SEQ ID NO 54
<211> LENGTH: 1233
<212> TYPE: DNA
<213> ORGANISM: Toxoplasma gondii

<400> SEQUENCE: 54
cgggatccct gaaggagagc atattcctga agagttccca gaaggcgagc atgttcctga   60
ggaggaaatc cctgaaggag aacatattcc tgaggaggag ttccctgaag gagagcatgt   120
tcctgaggag gagatccctg aaggcgagca tgttcctgag gaggagctcc ctggaggaga   180
acttattcct gaggaggaga tccctgaagg agagcatgtt cctgaagagc tccctgaagg   240
```

-continued

```
cgagcatgtt cctgaggagg agatccctga aggagagcat gttcctgaag aggaaatccc      300
tgaaggcgag catgttcctg aggaggagat ccctgaagga aacatgctc cagaggaaga       360 gactcctgca cctgaggaga ccgaaaagga ggaggaagaa ggcgtgccag tcgcagcgat      420
tgccggtggt gtcgtcggag gtgtgttgct cattgctggt ggtgcaggtg ctgccgtgta      480
cacaaaccaa ggtggcgttg aagcagctga agacgaagtg atgtttgaga gcgaagaaga     540
cggaacccag gctggcgaga accgcgagag gagacggtca ttgagatcga agatgacgca     600
tgggcagaca ttggactaaa ggagactagg aggtctgtgt gggcacatgc aggcgtgcga    660
caaaaccgtg atcgcgaggt attctgtgtt acgggcggag cgtctgcggc tgtccttcga    720 agggaggcg gagtgacact ctgagctagg taccagacga acgcagccat ttgtgtccgt      780
ccgctgtttc ttgatcctgg acacagacca gacccgacac gggtgctgaa cggtaatgca    840
aactgtcggg aaaacctctc cggcgcgaaa acagagattt acaccgtt gagatctgag       900 tagcggaagt gcatgcgcat gtgtgtccac gagaaggaa gattttcttt cgagaacgtt      960 tcccttgtt cgcacattcc tacgcgggc tcgtgccgca tgcatgtcga gggactgcg     1020 ttcgagtgct ctttcgccgt tgcagtgctg gacattgcgg cgtgggcaaa ggatagaagt   1080
gacgacctct gacatggcag tgaaggtggc agagactcgc ggaaaatcca aaaactctct 1140
gccgtttcgg tcgaggaatc acctttcttt ttttcgtctc tggacccgcc tccgtggtgt  1200
tcccttgccc ttgcaagccg ctgctatgta gcg                                 1233
```

<210> SEQ ID NO 55
<211> LENGTH: 411
<212> TYPE: DNA
<213> ORGANISM: Toxoplasma gondii
<220> FEATURE:
<221> NAME/KEY: CDS
<222> LOCATION: (1)..(180)
<223> OTHER INFORMATION:

<400> SEQUENCE: 55

```
cga cga cct cgg ctt ctc cac ata caa gga atg tct tcc tgt ttt gga       48
Arg Arg Pro Arg Leu Leu His Ile Gln Gly Met Ser Ser Cys Phe Gly
1               5                   10                  15 cct aag caa ccc gac ctt tat ctt ttg cac cag ctg tgc ttc ttt tac      96
Pro Lys Gln Pro Asp Leu Tyr Leu Leu His Gln Leu Cys Phe Phe Tyr
            20                  25                  30 ttg tgt gaa tca ctg tgt aaa caa act gag aag cgt gta tgc atg gtc     144
Leu Cys Glu Ser Leu Cys Lys Gln Thr Glu Lys Arg Val Cys Met Val
        35                  40                  45 gcc ttt gca tgt gga cga ggc cgc cgt cgc aca gcg tgattctcat          190
Ala Phe Ala Cys Gly Arg Gly Arg Arg Arg Thr Ala
    50                  55                  60 ctctgttgcg tgggggcgcg gatgagaatc aactccttag tgtcacagca tcagtgcagt   250
gcgtggagca acaattcttt tcgtgcacag acaagacaca ccagatatga agaacacta    310 acgggcactt accgttgtcc gtctatatat ttatatttag tcaatgctga gattagacct   370
agacttgtga gagagagtgt gaaacccaaa tgcctagatc c                       411
```

<210> SEQ ID NO 56
<211> LENGTH: 60
<212> TYPE: PRT
<213> ORGANISM: Toxoplasma gondii

<400> SEQUENCE: 56

Arg Arg Pro Arg Leu Leu His Ile Gln Gly Met Ser Ser Cys Phe Gly

```
1               5                   10                  15
Pro Lys Gln Pro Asp Leu Tyr Leu Leu His Gln Leu Cys Phe Phe Tyr
                20                  25                  30

Leu Cys Glu Ser Leu Cys Lys Gln Thr Glu Lys Arg Val Cys Met Val
        35                  40                  45

Ala Phe Ala Cys Gly Arg Gly Arg Arg Arg Thr Ala
    50                  55                  60

<210> SEQ ID NO 57
<211> LENGTH: 441
<212> TYPE: DNA
<213> ORGANISM: Toxoplasma gondii
<220> FEATURE:
<221> NAME/KEY: CDS
<222> LOCATION: (1)..(354)
<223> OTHER INFORMATION:
<220> FEATURE:
<221> NAME/KEY: misc_feature
<222> LOCATION: (152)..(152)
<223> OTHER INFORMATION: At nucleotide 152, k = g or t/u
      At amino acid residue 51, Xaa = Trp or Leu
<220> FEATURE:
<221> NAME/KEY: misc_feature
<222> LOCATION: (238)..(238)
<223> OTHER INFORMATION: At nucleotide 238, k = g or t/u
      At amino acid residue 80, Xaa = Aal or Ser
<220> FEATURE:
<221> NAME/KEY: misc_feature
<222> LOCATION: (226)..(226)
<223> OTHER INFORMATION: At nucleotide 226, k = s = c or g
      At amino acid residue 109, Xaa = Arg or Pro

<400> SEQUENCE: 57 cgg atc gaa gaa gct gaa gcg gag aca cga atc gcc gag aca ggc aaa      48
Arg Ile Glu Glu Ala Glu Ala Glu Thr Arg Ile Ala Glu Thr Gly Lys
1               5                   10                  15 cac agc ggg aat gag aat cga ctc tgc gat aga agt ggg cgc cat gga      96
His Ser Gly Asn Glu Asn Arg Leu Cys Asp Arg Ser Gly Arg His Gly
                20                  25                  30 atc aag gaa ccg agg cga agg agg ccc atg ctg ttg gcc gag gtg ccc     144
Ile Lys Glu Pro Arg Arg Arg Arg Pro Met Leu Leu Ala Glu Val Pro
            35                  40                  45 tgc ttg tkg gag ggc gcc cga cga aca ggg ttt cgt cag aga caa gca     192
Cys Leu Xaa Glu Gly Ala Arg Arg Thr Gly Phe Arg Gln Arg Gln Ala
        50                  55                  60 ctt cgc tcg cgt ttg tgg ccc ctt gcc gtg cgg cac gcg tgc gta kcc     240
Leu Arg Ser Arg Leu Trp Pro Leu Ala Val Arg His Ala Cys Val Xaa
65                  70                  75                  80 ttc aag aga gac tgc gga agc aga gag agg cca ttg agg ctg tcc gag     288
Phe Lys Arg Asp Cys Gly Ser Arg Glu Arg Pro Leu Arg Leu Ser Glu
                85                  90                  95 gtc ggc tcc agc cga gct gga tcc gaa tcc tgc agc csg gga tcc act     336
Val Gly Ser Ser Arg Ala Gly Ser Glu Ser Cys Ser Xaa Gly Ser Thr
            100                 105                 110 agt cta gac gcg cac ccg tgacccactt caggaygcgg vmatwatrcm            384
Ser Leu Asp Ala His Pro
            115 ggggcagatt tttwmggyta actatcattt ccccstwgtt gattmttcca gcaattg      441

<210> SEQ ID NO 58
<211> LENGTH: 118
<212> TYPE: PRT
<213> ORGANISM: Toxoplasma gondii
<220> FEATURE:
<221> NAME/KEY: misc_feature
```

```
<222> LOCATION: (51)..(51)
<223> OTHER INFORMATION: The 'Xaa' at location 51 stands for Trp, or
      Leu.
<220> FEATURE:
<221> NAME/KEY: misc_feature
<222> LOCATION: (80)..(80)
<223> OTHER INFORMATION: The 'Xaa' at location 80 stands for Ala, or
      Ser.
<220> FEATURE:
<221> NAME/KEY: misc_feature
<222> LOCATION: (109)..(109)
<223> OTHER INFORMATION: The 'Xaa' at location 109 stands for Arg, or
      Pro.

<400> SEQUENCE: 58

Arg Ile Glu Glu Ala Glu Ala Glu Thr Arg Ile Ala Glu Thr Gly Lys
1               5                   10                  15

His Ser Gly Asn Glu Asn Arg Leu Cys Asp Arg Ser Gly Arg His Gly
            20                  25                  30

Ile Lys Glu Pro Arg Arg Arg Pro Met Leu Leu Ala Glu Val Pro
        35                  40                  45

Cys Leu Xaa Glu Gly Ala Arg Arg Thr Gly Phe Arg Gln Arg Gln Ala
50                  55                  60

Leu Arg Ser Arg Leu Trp Pro Leu Ala Val Arg His Ala Cys Val Xaa
65                  70                  75                  80

Phe Lys Arg Asp Cys Gly Ser Arg Glu Arg Pro Leu Arg Leu Ser Glu
                85                  90                  95

Val Gly Ser Ser Arg Ala Gly Ser Glu Ser Cys Ser Xaa Gly Ser Thr
            100                 105                 110

Ser Leu Asp Ala His Pro
        115

<210> SEQ ID NO 59
<211> LENGTH: 491
<212> TYPE: DNA
<213> ORGANISM: Toxoplasma gondii
<220> FEATURE:
<221> NAME/KEY: CDS
<222> LOCATION: (1)..(102)
<223> OTHER INFORMATION:

<400> SEQUENCE: 59 cgg cgg tat tat agg aca cgg ccg cct gct ggt aac atc tgt aat tta      48
Arg Arg Tyr Tyr Arg Thr Arg Pro Pro Ala Gly Asn Ile Cys Asn Leu
1               5                   10                  15 tca ttg tat ccc gtc gtc ccg tgt tcc aaa ctg gga atc ttt tct ttc      96
Ser Leu Tyr Pro Val Val Pro Cys Ser Lys Leu Gly Ile Phe Ser Phe
            20                  25                  30 ctg agc tgacggtttg gcccgcaagc tcagccgagt acgaaaccat gattaggttg      152
Leu Ser gaggcctaat gtgcttttc gccagctgtc aaacgggcag ccaaggttga tttctctatg     212
agttgtcctc cgcgctctcg aattggtatt tcgtggtttc agattgaaag cgtcactcga    272
gctattacga ggcgtttcag caaaaaggaa gaatcactca gacacctgac cgacgcttga    332
tgtgctggcg gttgtgcaaa tccaggcatc actcaacgcc gatgctcagc aggacccatg    392
gatcttaaga ggtctgttc cactacatca gtgagagttt caaaaagaat cctgataact     452
acgcgcttct acaggtgccg cctttatggc aacgatccg                           491

<210> SEQ ID NO 60
<211> LENGTH: 34
<212> TYPE: PRT
```

```
<213> ORGANISM: Toxoplasma gondii

<400> SEQUENCE: 60

Arg Arg Tyr Tyr Arg Thr Arg Pro Pro Ala Gly Asn Ile Cys Asn Leu
1               5                   10                  15

Ser Leu Tyr Pro Val Val Pro Cys Ser Lys Leu Gly Ile Phe Ser Phe
            20                  25                  30

Leu Ser

<210> SEQ ID NO 61
<211> LENGTH: 387
<212> TYPE: DNA
<213> ORGANISM: Toxoplasma gondii
<220> FEATURE:
<221> NAME/KEY: CDS
<222> LOCATION: (1)..(387)
<223> OTHER INFORMATION:

<400> SEQUENCE: 61
```

| | | |
|---|---|---|
| cgg atc gct ctg agt ctc ttt ggg ctc cct gcc gca tgc agg cat gaa<br>Arg Ile Ala Leu Ser Leu Phe Gly Leu Pro Ala Ala Cys Arg His Glu<br>1               5                   10              15 | | 48 |
| agt gtc tcg ccg cga gag aca gag aag gaa gtg cag agc gag cgt ggg<br>Ser Val Ser Pro Arg Glu Thr Glu Lys Glu Val Gln Ser Glu Arg Gly<br>              20                   25                   30 | | 96 |
| cga gaa cgg acg cag aaa ggc gca ggc gag aag gag acc ggc gta gac<br>Arg Glu Arg Thr Gln Lys Gly Ala Gly Glu Lys Glu Thr Gly Val Asp<br>              35                   40                   45 | | 144 |
| gga gtg act gga gag cag gtc tta gcg ctc act aag ggt gaa cct gaa<br>Gly Val Thr Gly Glu Gln Val Leu Ala Leu Thr Lys Gly Glu Pro Glu<br>50              55                   60 | | 192 |
| gcg gca gaa gaa gcg aga gaa gag gac gag gga aag gga gaa gac aga<br>Ala Ala Glu Glu Ala Arg Glu Glu Asp Glu Gly Lys Gly Glu Asp Arg<br>65                  70                   75                   80 | | 240 |
| tgg tac gag gaa ggc gcg agg cga gag aaa gag gcg gct cga gtc atg<br>Trp Tyr Glu Glu Gly Ala Arg Arg Glu Lys Glu Ala Ala Arg Val Met<br>                    85                   90                   95 | | 288 |
| tcc act ccg cag acg tat gcc gaa gcc acc gac aca aca gct gca tgc<br>Ser Thr Pro Gln Thr Tyr Ala Glu Ala Thr Asp Thr Thr Ala Ala Cys<br>              100                  105               110 | | 336 |
| aga gac gaa agg gag ctc gcc tcg ggg gtc gaa gag aag aca cag gat<br>Arg Asp Glu Arg Glu Leu Ala Ser Gly Val Glu Glu Lys Thr Gln Asp<br>             115                  120               125 | | 384 |
| ccg<br>Pro | | 387 |

```
<210> SEQ ID NO 62
<211> LENGTH: 129
<212> TYPE: PRT
<213> ORGANISM: Toxoplasma gondii

<400> SEQUENCE: 62

Arg Ile Ala Leu Ser Leu Phe Gly Leu Pro Ala Ala Cys Arg His Glu
1               5                   10                  15

Ser Val Ser Pro Arg Glu Thr Glu Lys Glu Val Gln Ser Glu Arg Gly
            20                  25                  30

Arg Glu Arg Thr Gln Lys Gly Ala Gly Glu Lys Glu Thr Gly Val Asp
        35                  40                  45

Gly Val Thr Gly Glu Gln Val Leu Ala Leu Thr Lys Gly Glu Pro Glu
    50                  55                  60
```

-continued

```
Ala Ala Glu Glu Ala Arg Glu Glu Asp Glu Gly Lys Gly Glu Asp Arg
 65                  70                  75                  80

Trp Tyr Glu Glu Gly Ala Arg Arg Glu Lys Glu Ala Ala Arg Val Met
                 85                  90                  95

Ser Thr Pro Gln Thr Tyr Ala Glu Ala Thr Asp Thr Ala Ala Cys
            100                 105                 110

Arg Asp Glu Arg Glu Leu Ala Ser Gly Val Glu Lys Thr Gln Asp
        115                 120                 125

Pro
```

<210> SEQ ID NO 63
<211> LENGTH: 417
<212> TYPE: DNA
<213> ORGANISM: Toxoplasma gondii
<220> FEATURE:
<221> NAME/KEY: CDS
<222> LOCATION: (1)..(417)
<223> OTHER INFORMATION:
<220> FEATURE:
<221> NAME/KEY: misc_feature
<222> LOCATION: (72)..(72)
<223> OTHER INFORMATION: At nucleotide 72, n = unknown
<220> FEATURE:
<221> NAME/KEY: misc_feature
<222> LOCATION: (74)..(74)
<223> OTHER INFORMATION: At nucleotide 74, n = unknown
    At amino acid residue 25, Xaa = Tyr, Cys, Ser or Phe
<220> FEATURE:
<221> NAME/KEY: misc_feature
<222> LOCATION: (139)..(139)
<223> OTHER INFORMATION: At nucleotide 139, n = unknown
    At amino acid residue 47, Xaa = Ile, Met, Val, Leu or Phe
<220> FEATURE:
<221> NAME/KEY: misc_feature
<222> LOCATION: (141)..(141)
<223> OTHER INFORMATION: At nucleotide 141, n = unknown
    At amino acid residue 47, Xaa = Ile, Met, Val, Leu or Phe

<400> SEQUENCE: 63

```
ctt gca tgc gct gtg gca atg gaa gaa gca ccc gcg cca ggg caa cca        48
Leu Ala Cys Ala Val Ala Met Glu Glu Ala Pro Ala Pro Gly Gln Pro
 1               5                  10                  15 ccc gaa gaa ggg gac gat ggc ggn tnt cag cag cgc ctg gag atc gct        96
Pro Glu Glu Gly Asp Asp Gly Gly Xaa Gln Gln Arg Leu Glu Ile Ala
            20                  25                  30 ctg agt ctc ttt ggg ctc cct gcc gca tgc agg cat gaa agt ntn tcg       144
Leu Ser Leu Phe Gly Leu Pro Ala Ala Cys Arg His Glu Ser Xaa Ser
         35                  40                  45 ccg cga gag aca gag aag gaa gtg cag agc gag cgt ggg cga gaa cgg       192
Pro Arg Glu Thr Glu Lys Glu Val Gln Ser Glu Arg Gly Arg Glu Arg
 50                  55                  60 acg cag aaa ggc gca ggc gag aag gag acc ggc gta gac gga gtg act       240
Thr Gln Lys Gly Ala Gly Glu Lys Glu Thr Gly Val Asp Gly Val Thr
 65                  70                  75                  80 gga gag cag ctc tta gcg ctc act aag ggt gaa cct gaa gcg gca gaa       288
Gly Glu Gln Leu Leu Ala Leu Thr Lys Gly Glu Pro Glu Ala Ala Glu
                 85                  90                  95 gaa gcg aga gaa gag gac gag gga aag gga gaa gac aga tgg aac gag       336
Glu Ala Arg Glu Glu Asp Glu Gly Lys Gly Glu Asp Arg Trp Asn Glu
            100                 105                 110 gaa ggc gcg agg cga gag aaa gag gcg gct cga gtc atg tcc act ccg       384
Glu Gly Ala Arg Arg Glu Lys Glu Ala Ala Arg Val Met Ser Thr Pro
        115                 120                 125 cag acg tat gcc gaa gcc acc gac aca aca gcg                           417
Gln Thr Tyr Ala Glu Ala Thr Asp Thr Thr Ala
```

```
                130                 135

<210> SEQ ID NO 64
<211> LENGTH: 139
<212> TYPE: PRT
<213> ORGANISM: Toxoplasma gondii
<220> FEATURE:
<221> NAME/KEY: misc_feature
<222> LOCATION: (25)..(25)
<223> OTHER INFORMATION: The 'Xaa' at location 25 stands for Tyr, Cys,
      Ser, or Phe.
<220> FEATURE:
<221> NAME/KEY: misc_feature
<222> LOCATION: (47)..(47)
<223> OTHER INFORMATION: The 'Xaa' at location 47 stands for Ile, Met,
      Val, Leu, or Phe.

<400> SEQUENCE: 64

Leu Ala Cys Ala Val Ala Met Glu Glu Ala Pro Ala Pro Gly Gln Pro
1               5                  10                  15

Pro Glu Glu Gly Asp Asp Gly Gly Xaa Gln Gln Arg Leu Glu Ile Ala
            20                  25                  30

Leu Ser Leu Phe Gly Leu Pro Ala Ala Cys Arg His Glu Ser Xaa Ser
        35                  40                  45

Pro Arg Glu Thr Glu Lys Glu Val Gln Ser Glu Arg Gly Arg Glu Arg
    50                  55                  60

Thr Gln Lys Gly Ala Gly Glu Lys Glu Thr Gly Val Asp Gly Val Thr
65                  70                  75                  80

Gly Glu Gln Leu Leu Ala Leu Thr Lys Gly Glu Pro Ala Ala Glu
                85                  90                  95

Glu Ala Arg Glu Glu Asp Glu Gly Lys Gly Glu Asp Arg Trp Asn Glu
            100                 105                 110

Glu Gly Ala Arg Arg Glu Lys Glu Ala Ala Arg Val Met Ser Thr Pro
        115                 120                 125

Gln Thr Tyr Ala Glu Ala Thr Asp Thr Thr Ala
    130                 135

<210> SEQ ID NO 65
<211> LENGTH: 416
<212> TYPE: DNA
<213> ORGANISM: Toxoplasma gondii
<220> FEATURE:
<221> NAME/KEY: CDS
<222> LOCATION: (1)..(414)
<223> OTHER INFORMATION:
<220> FEATURE:
<221> NAME/KEY: misc_feature
<222> LOCATION: (174)..(174)
<223> OTHER INFORMATION: At nucleotide 174, n = unknown
<220> FEATURE:
<221> NAME/KEY: misc_feature
<222> LOCATION: (207)..(207)
<223> OTHER INFORMATION: At nucleotide 207, n = unknown

<400> SEQUENCE: 65 ccg gat cgc ggg aga gaa gaa cgt gag gga gaa gaa gag agt gcc gag      48
Pro Asp Arg Gly Arg Glu Glu Arg Glu Gly Glu Glu Glu Ser Ala Glu
1               5                  10                  15 gct ttg cca gac cat aag cgg ggg cca gga aaa gag ctg gag gaa ggc      96
Ala Leu Pro Asp His Lys Arg Gly Pro Gly Lys Glu Leu Glu Glu Gly
            20                  25                  30 cga gac tcg cag gtc cgt ggt gag gag agc ggg cgc agc tcg ctt tcg     144
Arg Asp Ser Gln Val Arg Gly Glu Glu Ser Gly Arg Ser Ser Leu Ser
        35                  40                  45
```

```
cag gag agg gaa agt ttt cgt tct cag cgn gtc tcg gct gag ggt cag      192
Gln Glu Arg Glu Ser Phe Arg Ser Gln Arg Val Ser Ala Glu Gly Gln
         50                  55                  60 gag gtg gag gca gcn tct gtc aag gcg ctt gaa gag gca aag tcg aac      240
Glu Val Glu Ala Ala Ser Val Lys Ala Leu Glu Glu Ala Lys Ser Asn
 65                  70                  75                  80 gac aga ccc gac ggc gag agc aac gag ctg cgt cgc ttg tca ccc acc      288
Asp Arg Pro Asp Gly Glu Ser Asn Glu Leu Arg Arg Leu Ser Pro Thr
                     85                  90                  95 agc cag aca gag caa gaa ggc tcc gtc gag aaa gaa ggg aca tca gag      336
Ser Gln Thr Glu Gln Glu Gly Ser Val Glu Lys Glu Gly Thr Ser Glu
                100                 105                 110 gcg acg atg aac gac caa gac gag aca ggg aag gaa aaa caa gac caa      384
Ala Thr Met Asn Asp Gln Asp Glu Thr Gly Lys Glu Lys Gln Asp Gln
            115                 120                 125 cga gag gtg cct gtg ccc cgc gct ctt cgc tt                           416
Arg Glu Val Pro Val Pro Arg Ala Leu Arg
        130                 135
```

<210> SEQ ID NO 66
<211> LENGTH: 138
<212> TYPE: PRT
<213> ORGANISM: Toxoplasma gondii

<400> SEQUENCE: 66

```
Pro Asp Arg Gly Arg Glu Glu Arg Gly Glu Glu Ser Ala Glu
 1               5                  10                  15

Ala Leu Pro Asp His Lys Arg Gly Pro Gly Lys Glu Leu Glu Gly
             20                  25                  30

Arg Asp Ser Gln Val Arg Gly Glu Glu Ser Gly Arg Ser Ser Leu Ser
             35                  40                  45

Gln Glu Arg Glu Ser Phe Arg Ser Gln Arg Val Ser Ala Glu Gly Gln
         50                  55                  60

Glu Val Glu Ala Ala Ser Val Lys Ala Leu Glu Glu Ala Lys Ser Asn
 65                  70                  75                  80

Asp Arg Pro Asp Gly Glu Ser Asn Glu Leu Arg Arg Leu Ser Pro Thr
                     85                  90                  95

Ser Gln Thr Glu Gln Glu Gly Ser Val Glu Lys Glu Gly Thr Ser Glu
                100                 105                 110

Ala Thr Met Asn Asp Gln Asp Glu Thr Gly Lys Glu Lys Gln Asp Gln
            115                 120                 125

Arg Glu Val Pro Val Pro Arg Ala Leu Arg
        130                 135
```

<210> SEQ ID NO 67
<211> LENGTH: 500
<212> TYPE: DNA
<213> ORGANISM: Toxoplasma gondii

<400> SEQUENCE: 67

```
ccgagaatca tgttacgcca gtagacagc gtttagggag tgcagacatt ttaatctgga     60
cggagtccaa gtggacgcgg atgtagatat ctgtcgcagc acctccgcag ttgcgctagg    120
gattctgatg ctgctagttt taacatccaa aactctgact tcgcttggtg atctccaggt    180
gcatatacat gcgaaggcaa tcgtgtttgt gagaggcgaa tgtacgaatt tcagtgtctt    240
tgtgtggaag tcaagttccc ctgaaccagc tgcttgtttt attctaccgc taatgtatga    300
agcttagcct cgtgtcctct tcgcccgtac acgagacacg atccaagagt catacaaatt    360
```

-continued

```
cttgcggcgg tgaggtaatt gtcaacagaa acaaaagtcg cggtatctg tggtgtctct      420 gcttctgcac ttccaaggac cgccgcaagt tcggcccgat cggctggaac attcagtacg      480
agttcacgac ggaggatccg                                                  500
```

<210> SEQ ID NO 68
<211> LENGTH: 321
<212> TYPE: DNA
<213> ORGANISM: Toxoplasma gondii
<220> FEATURE:
<221> NAME/KEY: CDS
<222> LOCATION: (1)..(219)
<223> OTHER INFORMATION:

<400> SEQUENCE: 68

```
cgg cgg gac ttg cgg act tcg gtc tgg gac gct cgg gtg tac gta cac        48
Arg Arg Asp Leu Arg Thr Ser Val Trp Asp Ala Arg Val Tyr Val His
1               5                   10                  15 ctg gcg ggg ggc cag agg cgc tgc aac gag tcg cgg ggg atg gag gaa        96
Leu Ala Gly Gly Gln Arg Arg Cys Asn Glu Ser Arg Gly Met Glu Glu
            20                  25                  30 gcg agg aaa agg agg tgt ctc gcg atg cgg tgc cag tgg act tcg tct        144
Ala Arg Lys Arg Arg Cys Leu Ala Met Arg Cys Gln Trp Thr Ser Ser
        35                  40                  45 gcg cta gat tgg agg gag agc tgg aaa aat gcc gag aca gct tcg cac        192
Ala Leu Asp Trp Arg Glu Ser Trp Lys Asn Ala Glu Thr Ala Ser His
    50                  55                  60 gtc aca ttc ccg acg aaa cgc ccg cca tgaaggaaat cacagacatc              239
Val Thr Phe Pro Thr Lys Arg Pro Pro
65                  70 accaaccttc ccgccgtggc taaaggaccg tcctgtgtat gtacagtttt tccaggcgaa      299
agccgagaga cagcgaaacc gg                                               321
```

<210> SEQ ID NO 69
<211> LENGTH: 73
<212> TYPE: PRT
<213> ORGANISM: Toxoplasma gondii

<400> SEQUENCE: 69

```
Arg Arg Asp Leu Arg Thr Ser Val Trp Asp Ala Arg Val Tyr Val His
1               5                   10                  15

Leu Ala Gly Gly Gln Arg Arg Cys Asn Glu Ser Arg Gly Met Glu Glu
            20                  25                  30

Ala Arg Lys Arg Arg Cys Leu Ala Met Arg Cys Gln Trp Thr Ser Ser
        35                  40                  45

Ala Leu Asp Trp Arg Glu Ser Trp Lys Asn Ala Glu Thr Ala Ser His
    50                  55                  60

Val Thr Phe Pro Thr Lys Arg Pro Pro
65                  70
```

<210> SEQ ID NO 70
<211> LENGTH: 513
<212> TYPE: DNA
<213> ORGANISM: Toxoplasma gondii
<220> FEATURE:
<221> NAME/KEY: CDS
<222> LOCATION: (1)..(513)
<223> OTHER INFORMATION:

<400> SEQUENCE: 70

```
cgg gat cag gct tct atg cca ctg ccc ccg gcc ccc gaa gac ttt gac        48
Arg Asp Gln Ala Ser Met Pro Leu Pro Pro Ala Pro Glu Asp Phe Asp
```

```
                1               5                  10                 15
ctg cct cct atg cca ctg ccc gaa gca ccc gaa gac ttt gac cag gct                96
Leu Pro Pro Met Pro Leu Pro Glu Ala Pro Glu Asp Phe Asp Gln Ala
                 20                  25                  30 cct atg cca ctg ccc gag gca ccc gaa gac ttt gac cag gct cct atg               144
Pro Met Pro Leu Pro Glu Ala Pro Glu Asp Phe Asp Gln Ala Pro Met
             35                  40                  45 cca ctg ccc gag gca ccc gaa gac ttt gac cag cct cct atg cca ctg               192
Pro Leu Pro Glu Ala Pro Glu Asp Phe Asp Gln Pro Pro Met Pro Leu
         50                  55                  60 ccc gaa gca ccc gaa gac ttt gac cag gct cct atg cca ctg ccc gaa               240
Pro Glu Ala Pro Glu Asp Phe Asp Gln Ala Pro Met Pro Leu Pro Glu
 65                  70                  75                  80 gca ccc gaa gtc ttt gac cag gct cct atg cca ctg ccc gag gca ccc               288
Ala Pro Glu Val Phe Asp Gln Ala Pro Met Pro Leu Pro Glu Ala Pro
                 85                  90                  95 gaa gtc ttt gac cag gct cct atg cca ctg ccc gaa gca ccc gaa gac               336
Glu Val Phe Asp Gln Ala Pro Met Pro Leu Pro Glu Ala Pro Glu Asp
             100                 105                 110 ttt gac cag gct cct atg cca ctg ccc gaa gca ccc gaa gtc ttt gac               384
Phe Asp Gln Ala Pro Met Pro Leu Pro Glu Ala Pro Glu Val Phe Asp
         115                 120                 125 cag gct cct atg cca ctg ccc gag gca ccc gaa gac ttt gac cag gct               432
Gln Ala Pro Met Pro Leu Pro Glu Ala Pro Glu Asp Phe Asp Gln Ala
     130                 135                 140 cct atg cca gtg ccc gag gca ccc gaa gac ttt gac cag gct cct gag               480
Pro Met Pro Val Pro Glu Ala Pro Glu Asp Phe Asp Gln Ala Pro Glu
145                 150                 155                 160 cca ctg ccc gag gca gcc gaa gaa ttt gat ccc                                   513
Pro Leu Pro Glu Ala Ala Glu Glu Phe Asp Pro
                165                 170

<210> SEQ ID NO 71
<211> LENGTH: 171
<212> TYPE: PRT
<213> ORGANISM: Toxoplasma gondii

<400> SEQUENCE: 71

Arg Asp Gln Ala Ser Met Pro Leu Pro Ala Pro Glu Asp Phe Asp
 1               5                  10                  15

Leu Pro Pro Met Pro Leu Pro Glu Ala Pro Glu Asp Phe Asp Gln Ala
                 20                  25                  30

Pro Met Pro Leu Pro Glu Ala Pro Glu Asp Phe Asp Gln Ala Pro Met
             35                  40                  45

Pro Leu Pro Glu Ala Pro Glu Asp Phe Asp Gln Pro Pro Met Pro Leu
         50                  55                  60

Pro Glu Ala Pro Glu Asp Phe Asp Gln Ala Pro Met Pro Leu Pro Glu
 65                  70                  75                  80

Ala Pro Glu Val Phe Asp Gln Ala Pro Met Pro Leu Pro Glu Ala Pro
                 85                  90                  95

Glu Val Phe Asp Gln Ala Pro Met Pro Leu Pro Glu Ala Pro Glu Asp
             100                 105                 110

Phe Asp Gln Ala Pro Met Pro Leu Pro Glu Ala Pro Glu Val Phe Asp
         115                 120                 125

Gln Ala Pro Met Pro Leu Pro Glu Ala Pro Glu Asp Phe Asp Gln Ala
     130                 135                 140

Pro Met Pro Val Pro Glu Ala Pro Glu Asp Phe Asp Gln Ala Pro Glu
145                 150                 155                 160
```

```
Pro Leu Pro Glu Ala Ala Glu Glu Phe Asp Pro
            165                 170

<210> SEQ ID NO 72
<211> LENGTH: 528
<212> TYPE: DNA
<213> ORGANISM: Toxoplasma gondii
<220> FEATURE:
<221> NAME/KEY: CDS
<222> LOCATION: (1)..(528)
<223> OTHER INFORMATION:

<400> SEQUENCE: 72 cga tct gaa cgt tgt gca acc gtt ggg gac cca ggt aca ggc gtc tcc      48
Arg Ser Glu Arg Cys Ala Thr Val Gly Asp Pro Gly Thr Gly Val Ser
1               5                   10                  15 aac act gag gcg ggg gga aag cgc cca cac tgg cgt ctc agg cac ctt      96
Asn Thr Glu Ala Gly Gly Lys Arg Pro His Trp Arg Leu Arg His Leu
            20                  25                  30 caa tgc cac agg tat ccg gca tcc ttg gag aca gag ctt gag acg gag     144
Gln Cys His Arg Tyr Pro Ala Ser Leu Glu Thr Glu Leu Glu Thr Glu
        35                  40                  45 aca ctc gca cac aca ccc aga gag ctt gtg gtg aca aat cga agc ttg     192
Thr Leu Ala His Thr Pro Arg Glu Leu Val Val Thr Asn Arg Ser Leu
    50                  55                  60 ggg ttt gtc tcg ctt ctt cgc cag tcg ttc gcg tcg cag tca gaa gca     240
Gly Phe Val Ser Leu Leu Arg Gln Ser Phe Ala Ser Gln Ser Glu Ala
65                  70                  75                  80 gtc aag gcg acc gcg gag acg ccg aca gag aca gag aca gtc ctt gtg     288
Val Lys Ala Thr Ala Glu Thr Pro Thr Glu Thr Glu Thr Val Leu Val
                85                  90                  95 gcg ggc gag cgc aac acc gcg aaa gaa aga gag aga aaa ggg cag gac     336
Ala Gly Glu Arg Asn Thr Ala Lys Glu Arg Glu Arg Lys Gly Gln Asp
            100                 105                 110 gaa gag gtt tcg cag aga gca gcg gag aac aag aga gga cga gtg gag     384
Glu Glu Val Ser Gln Arg Ala Ala Glu Asn Lys Arg Gly Arg Val Glu
        115                 120                 125 gac aca gac tac cgg gag acg gat aag aaa gcc gag aaa gat gag cga     432
Asp Thr Asp Tyr Arg Glu Thr Asp Lys Lys Ala Glu Lys Asp Glu Arg
    130                 135                 140 gaa gag aac ccc cga gga gac aca ggg gag cag aga agc gag aag cac     480
Glu Glu Asn Pro Arg Gly Asp Thr Gly Glu Gln Arg Ser Glu Lys His
145                 150                 155                 160 acg aga gat tta ttg gga cag gag aga gag aac gca tgg gag atc ccg     528
Thr Arg Asp Leu Leu Gly Gln Glu Arg Glu Asn Ala Trp Glu Ile Pro
                165                 170                 175

<210> SEQ ID NO 73
<211> LENGTH: 176
<212> TYPE: PRT
<213> ORGANISM: Toxoplasma gondii

<400> SEQUENCE: 73

Arg Ser Glu Arg Cys Ala Thr Val Gly Asp Pro Gly Thr Gly Val Ser
1               5                   10                  15

Asn Thr Glu Ala Gly Gly Lys Arg Pro His Trp Arg Leu Arg His Leu
            20                  25                  30

Gln Cys His Arg Tyr Pro Ala Ser Leu Glu Thr Glu Leu Glu Thr Glu
        35                  40                  45

Thr Leu Ala His Thr Pro Arg Glu Leu Val Val Thr Asn Arg Ser Leu
    50                  55                  60
```

-continued

Gly Phe Val Ser Leu Leu Arg Gln Ser Phe Ala Ser Gln Ser Glu Ala
65                  70                  75                  80

Val Lys Ala Thr Ala Glu Thr Pro Thr Glu Thr Glu Thr Val Leu Val
                85                  90                  95

Ala Gly Glu Arg Asn Thr Ala Lys Glu Arg Glu Arg Lys Gly Gln Asp
            100                 105                 110

Glu Glu Val Ser Gln Arg Ala Ala Glu Asn Lys Arg Gly Arg Val Glu
        115                 120                 125

Asp Thr Asp Tyr Arg Glu Thr Asp Lys Lys Ala Glu Lys Asp Glu Arg
    130                 135                 140

Glu Glu Asn Pro Arg Gly Asp Thr Gly Glu Gln Arg Ser Glu Lys His
145                 150                 155                 160

Thr Arg Asp Leu Leu Gly Gln Glu Arg Glu Asn Ala Trp Glu Ile Pro
                165                 170                 175

<210> SEQ ID NO 74
<211> LENGTH: 375
<212> TYPE: DNA
<213> ORGANISM: Toxoplasma gondii
<220> FEATURE:
<221> NAME/KEY: CDS
<222> LOCATION: (1)..(375)
<223> OTHER INFORMATION:

<400> SEQUENCE: 74 ccg gag gag tac aag tgc agc aaa acc acg tac gaa gac agc tgc acc      48
Pro Glu Glu Tyr Lys Cys Ser Lys Thr Thr Tyr Glu Asp Ser Cys Thr
1               5                   10                  15 gat gtc gct gtc cag gtc ccc gac acc tgc tac cgc act gtc gat cag      96
Asp Val Ala Val Gln Val Pro Asp Thr Cys Tyr Arg Thr Val Asp Gln
            20                  25                  30 aag aag gct tac aag tgc aag aaa acg ctg acg aaa aac caa tgc acg     144
Lys Lys Ala Tyr Lys Cys Lys Lys Thr Leu Thr Lys Asn Gln Cys Thr
        35                  40                  45 aag gtt cca gtc cag gtt cca agc aca tgc acg aag acg gcg atg tca     192
Lys Val Pro Val Gln Val Pro Ser Thr Cys Thr Lys Thr Ala Met Ser
    50                  55                  60 aag gag gcg tac gac tgc tcg aag acc gag ttc cgc acc gag tgc acc     240
Lys Glu Ala Tyr Asp Cys Ser Lys Thr Glu Phe Arg Thr Glu Cys Thr
65                  70                  75                  80 gac gaa gtc gag caa gtc ccg tgc atg ggc aaa gag tgc aag ctg cgc     288
Asp Glu Val Glu Gln Val Pro Cys Met Gly Lys Glu Cys Lys Leu Arg
                85                  90                  95 cag ctg aag aag aag cgc gtc tgc agg cag gtc ccg ttc acc agc aag     336
Gln Leu Lys Lys Lys Arg Val Cys Arg Gln Val Pro Phe Thr Ser Lys
            100                 105                 110 aac gtc tgc tac aaa aat gtg ccc acg gag cag acg tcg               375
Asn Val Cys Tyr Lys Asn Val Pro Thr Glu Gln Thr Ser
        115                 120                 125

<210> SEQ ID NO 75
<211> LENGTH: 125
<212> TYPE: PRT
<213> ORGANISM: Toxoplasma gondii

<400> SEQUENCE: 75

Pro Glu Glu Tyr Lys Cys Ser Lys Thr Thr Tyr Glu Asp Ser Cys Thr
1               5                   10                  15

Asp Val Ala Val Gln Val Pro Asp Thr Cys Tyr Arg Thr Val Asp Gln
            20                  25                  30

```
Lys Lys Ala Tyr Lys Cys Lys Lys Thr Leu Thr Lys Asn Gln Cys Thr
             35                  40                  45

Lys Val Pro Val Gln Val Pro Ser Thr Cys Thr Lys Thr Ala Met Ser
 50                  55                  60

Lys Glu Ala Tyr Asp Cys Ser Lys Thr Glu Phe Arg Thr Glu Cys Thr
 65                  70                  75                  80

Asp Glu Val Glu Gln Val Pro Cys Met Gly Lys Glu Cys Lys Leu Arg
                 85                  90                  95

Gln Leu Lys Lys Lys Arg Val Cys Arg Gln Val Pro Phe Thr Ser Lys
             100                 105                 110

Asn Val Cys Tyr Lys Asn Val Pro Thr Glu Gln Thr Ser
             115                 120                 125

<210> SEQ ID NO 76
<211> LENGTH: 543
<212> TYPE: DNA
<213> ORGANISM: Toxoplasma gondii
<220> FEATURE:
<221> NAME/KEY: CDS
<222> LOCATION: (1)..(267)
<223> OTHER INFORMATION:

<400> SEQUENCE: 76 cga tcc aac agt tta cga ggt aca agg caa cag ccg aac ctc tac gag      48
Arg Ser Asn Ser Leu Arg Gly Thr Arg Gln Gln Pro Asn Leu Tyr Glu
 1               5                  10                  15 cac gtg tcc cca cgg ttc acg ctc tcc cat gga aaa gca aag cga ttc      96
His Val Ser Pro Arg Phe Thr Leu Ser His Gly Lys Ala Lys Arg Phe
             20                  25                  30 ctc cat tat cac cac tgc cac tgc cat tcc agc cta aga atc cta cac    144
Leu His Tyr His His Cys His Cys His Ser Ser Leu Arg Ile Leu His
         35                  40                  45 ttc aaa gac gaa ctt ttg cat cgt ccg tgc gtc tcc cgt ggc caa cac    192
Phe Lys Asp Glu Leu Leu His Arg Pro Cys Val Ser Arg Gly Gln His
 50                  55                  60 cct caa gcc aaa aga gag ggc acc ttc tac act gcc cac gca atc acc    240
Pro Gln Ala Lys Arg Glu Gly Thr Phe Tyr Thr Ala His Ala Ile Thr
 65                  70                  75                  80 ctg tgc ggc ggc aca caa aag cga aac tgacacacgc tactgccgtt          287
Leu Cys Gly Gly Thr Gln Lys Arg Asn
                 85 ccggaaagtg gtctgaaaga aactgacaac agccgcaaag agacatttac ccggtgcctg    347 gcgtggtcaa aaatccggca taatggtttc tgcgcatcct ccattcagcc gcccaacatc    407 tgcggtcgtt cttccgtcga aactatgaca caacgagcct gtggaacaa aacgttcgt     467 actgacgaca ttgcctgggt cggattcact gcatgtttgc agggtgcat ttccacggtg    527 ctctgcgtcg atcccg                                                   543

<210> SEQ ID NO 77
<211> LENGTH: 89
<212> TYPE: PRT
<213> ORGANISM: Toxoplasma gondii

<400> SEQUENCE: 77

Arg Ser Asn Ser Leu Arg Gly Thr Arg Gln Gln Pro Asn Leu Tyr Glu
 1               5                  10                  15

His Val Ser Pro Arg Phe Thr Leu Ser His Gly Lys Ala Lys Arg Phe
             20                  25                  30
```

```
Leu His Tyr His His Cys His Cys His Ser Ser Leu Arg Ile Leu His
                35                  40                  45

Phe Lys Asp Glu Leu Leu His Arg Pro Cys Val Ser Arg Gly Gln His
 50                  55                  60

Pro Gln Ala Lys Arg Glu Gly Thr Phe Tyr Thr Ala His Ala Ile Thr
 65                  70                  75                  80

Leu Cys Gly Gly Thr Gln Lys Arg Asn
                85

<210> SEQ ID NO 78
<211> LENGTH: 573
<212> TYPE: DNA
<213> ORGANISM: Toxoplasma gondii
<220> FEATURE:
<221> NAME/KEY: CDS
<222> LOCATION: (1)..(573)
<223> OTHER INFORMATION:

<400> SEQUENCE: 78 ccg gcg tcg tcg agc tcg agg ctg ggc aag ctg gct tac gac gat gca      48
Pro Ala Ser Ser Ser Ser Arg Leu Gly Lys Leu Ala Tyr Asp Asp Ala
 1               5                  10                  15 gga ggt gga cga gga gcg agc tcg cca cca tct tct aag ttg ttt gtt      96
Gly Gly Gly Arg Gly Ala Ser Ser Pro Pro Ser Ser Lys Leu Phe Val
                20                  25                  30 tcc cca gtc aac gac agg tca cgg atg gca gat caa cga aaa cct gca     144
Ser Pro Val Asn Asp Arg Ser Arg Met Ala Asp Gln Arg Lys Pro Ala
             35                  40                  45 ccc gaa caa tcg tcc aat cac gat tcg gaa tgc tgt tgc cta cgc tgt     192
Pro Glu Gln Ser Ser Asn His Asp Ser Glu Cys Cys Cys Leu Arg Cys
 50                  55                  60 ctg agt gag aag acg ctg atg atg gca cag ctc tgc agg cct gca cct     240
Leu Ser Glu Lys Thr Leu Met Met Ala Gln Leu Cys Arg Pro Ala Pro
 65                  70                  75                  80 gta acc ctg tct gta aca gag agg aac cta ttt gga gat aat ggc aga     288
Val Thr Leu Ser Val Thr Glu Arg Asn Leu Phe Gly Asp Asn Gly Arg
                 85                  90                  95 gac gtc gtt gaa tgg gag ggt tca tgc gga ttt ttt tct gga aat gca     336
Asp Val Val Glu Trp Glu Gly Ser Cys Gly Phe Phe Ser Gly Asn Ala
            100                 105                 110 tcg act agg cca tct ctg cag ttc tcc cct cac cgt gtc atc gat gcc     384
Ser Thr Arg Pro Ser Leu Gln Phe Ser Pro His Arg Val Ile Asp Ala
        115                 120                 125 cca aca gcc aat gac gat atg aga gat tgc aga gca gcc cct gaa gac     432
Pro Thr Ala Asn Asp Asp Met Arg Asp Cys Arg Ala Ala Pro Glu Asp
    130                 135                 140 ggg aca ggt acc tca aag gca aat att cac cgc agt agc aac ata aca     480
Gly Thr Gly Thr Ser Lys Ala Asn Ile His Arg Ser Ser Asn Ile Thr
145                 150                 155                 160 aaa acg aag gaa gag aat ggt aga gat gtg tgt gag gga ctc agg aaa     528
Lys Thr Lys Glu Glu Asn Gly Arg Asp Val Cys Glu Gly Leu Arg Lys
                165                 170                 175 ccg ttg cag gac gat tct gaa gga gtc caa caa cct ctt ccg ccg         573
Pro Leu Gln Asp Asp Ser Glu Gly Val Gln Gln Pro Leu Pro Pro
            180                 185                 190

<210> SEQ ID NO 79
<211> LENGTH: 191
<212> TYPE: PRT
<213> ORGANISM: Toxoplasma gondii

<400> SEQUENCE: 79
```

```
Pro Ala Ser Ser Ser Arg Leu Gly Lys Leu Ala Tyr Asp Asp Ala
1               5                   10                  15

Gly Gly Gly Arg Gly Ala Ser Ser Pro Pro Ser Ser Lys Leu Phe Val
                20                  25                  30

Ser Pro Val Asn Asp Arg Ser Arg Met Ala Asp Gln Arg Lys Pro Ala
            35                  40                  45

Pro Glu Gln Ser Ser Asn His Asp Ser Glu Cys Cys Cys Leu Arg Cys
        50                  55                  60

Leu Ser Glu Lys Thr Leu Met Met Ala Gln Leu Cys Arg Pro Ala Pro
65                  70                  75                  80

Val Thr Leu Ser Val Thr Glu Arg Asn Leu Phe Gly Asp Asn Gly Arg
                85                  90                  95

Asp Val Val Glu Trp Glu Gly Ser Cys Gly Phe Phe Ser Gly Asn Ala
            100                 105                 110

Ser Thr Arg Pro Ser Leu Gln Phe Ser Pro His Arg Val Ile Asp Ala
        115                 120                 125

Pro Thr Ala Asn Asp Asp Met Arg Asp Cys Arg Ala Ala Pro Glu Asp
130                 135                 140

Gly Thr Gly Thr Ser Lys Ala Asn Ile His Arg Ser Ser Asn Ile Thr
145                 150                 155                 160

Lys Thr Lys Glu Glu Asn Gly Arg Asp Val Cys Glu Gly Leu Arg Lys
                165                 170                 175

Pro Leu Gln Asp Asp Ser Glu Gly Val Gln Gln Pro Leu Pro Pro
            180                 185                 190

<210> SEQ ID NO 80
<211> LENGTH: 1835
<212> TYPE: DNA
<213> ORGANISM: Toxoplasma gondii
<220> FEATURE:
<221> NAME/KEY: CDS
<222> LOCATION: (1)..(1833)
<223> OTHER INFORMATION:

<400> SEQUENCE: 80 cgg atc agt ggg gac cag tac tct tgt ctt caa cga gga gcg gga gga      48
Arg Ile Ser Gly Asp Gln Tyr Ser Cys Leu Gln Arg Gly Ala Gly Gly
1               5                   10                  15 gac aag gag aca gca acc gag aga gaa gag agg aac aga gaa gat gcg      96
Asp Lys Glu Thr Ala Thr Glu Arg Glu Glu Arg Asn Arg Glu Asp Ala
                20                  25                  30 ccc tcc ttt ctt gaa gga gga ctc gga gat gac gag aca gag aga gcg     144
Pro Ser Phe Leu Glu Gly Gly Leu Gly Asp Asp Glu Thr Glu Arg Ala
            35                  40                  45 aag caa gcg agt gag ttg ccc gcg tct ctt tgc tct ttc gcc gca gca     192
Lys Gln Ala Ser Glu Leu Pro Ala Ser Leu Cys Ser Phe Ala Ala Ala
        50                  55                  60 cgc agg ggc gcg agc cgc gca gag aag aca ggc gca aag ggg gag gaa     240
Arg Arg Gly Ala Ser Arg Ala Glu Lys Thr Gly Ala Lys Gly Glu Glu
65                  70                  75                  80 gcc aga gag aaa gaa gtc agt ttc ggt gaa gac agt ggg cta tcc aga     288
Ala Arg Glu Lys Glu Val Ser Phe Gly Glu Asp Ser Gly Leu Ser Arg
                85                  90                  95 cag gtg gac atg gac agt tcg cag gaa tct gtc aac gaa gga gag ccg     336
Gln Val Asp Met Asp Ser Ser Gln Glu Ser Val Asn Glu Gly Glu Pro
            100                 105                 110 cta cac gac aga gcc gca ggg gag gac gca gaa ggc ggg gga gca gag     384
Leu His Asp Arg Ala Ala Gly Glu Asp Ala Glu Gly Gly Gly Ala Glu
```

|  |  |  |  |  |  |  |  |  |  |  |  |  |  |  |  |
|---|---|---|---|---|---|---|---|---|---|---|---|---|---|---|---|
|  |  | 115 |  |  |  | 120 |  |  |  |  | 125 |  |  |  |  |
| gcg | aac | gac | gga | gac | aga | gag | gga | gac | gag | aag | gag | act | cga | gac | gtc | 432 |
| Ala | Asn | Asp | Gly | Asp | Arg | Glu | Gly | Asp | Glu | Lys | Glu | Thr | Arg | Asp | Val |
|  | 130 |  |  |  | 135 |  |  |  | 140 |  |  |  |  |  |  |
| gag | gac | gaa | gga | gag | acg | cgt | cgt | tct | tcc | tct | ttc | gct | gaa | caa | act | 480 |
| Glu | Asp | Glu | Gly | Glu | Thr | Arg | Arg | Ser | Ser | Ser | Phe | Ala | Glu | Gln | Thr |
| 145 |  |  |  |  | 150 |  |  |  | 155 |  |  |  |  | 160 |
| gga | aat | gaa | aga | acc | gag | atg | aga | acc | aga | cat | ggg | ggt | gac | gag | ggc | 528 |
| Gly | Asn | Glu | Arg | Thr | Glu | Met | Arg | Thr | Arg | His | Gly | Gly | Asp | Glu | Gly |
|  |  |  |  | 165 |  |  |  |  | 170 |  |  |  | 175 |  |  |
| tgg | acc | tcg | aag | tcg | aat | cgg | ttc | gct | ttt | gcc | tgc | cct | cgg | ttt | tcc | 576 |
| Trp | Thr | Ser | Lys | Ser | Asn | Arg | Phe | Ala | Phe | Ala | Cys | Pro | Arg | Phe | Ser |
|  |  |  | 180 |  |  |  |  | 185 |  |  |  |  | 190 |  |  |
| aaa | tct | gat | gtc | tgc | tgt | tct | ccc | cag | gct | cgg | ctg | tct | ttg | cct | gaa | 624 |
| Lys | Ser | Asp | Val | Cys | Cys | Ser | Pro | Gln | Ala | Arg | Leu | Ser | Leu | Pro | Glu |
|  |  | 195 |  |  |  |  | 200 |  |  |  |  | 205 |  |  |  |
| cag | tcc | cta | ggc | tcc | tct | ccg | tcg | tcg | ccc | att | tct | gtc | aca | aat | gat | 672 |
| Gln | Ser | Leu | Gly | Ser | Ser | Pro | Ser | Ser | Pro | Ile | Ser | Val | Thr | Asn | Asp |
|  | 210 |  |  |  |  | 215 |  |  |  |  | 220 |  |  |  |  |
| gtc | tat | gct | ctc | ttc | gat | tcg | tct | gca | tct | cct | ctg | cat | gcg | gga | gag | 720 |
| Val | Tyr | Ala | Leu | Phe | Asp | Ser | Ser | Ala | Ser | Pro | Leu | His | Ala | Gly | Glu |
| 225 |  |  |  |  | 230 |  |  |  | 235 |  |  |  |  | 240 |  |
| tta | tct | tct | ctt | ccc | ggc | gcg | gtc | tcg | gcc | tca | gag | cgc | cta | ttg | act | 768 |
| Leu | Ser | Ser | Leu | Pro | Gly | Ala | Val | Ser | Ala | Ser | Glu | Arg | Leu | Leu | Thr |
|  |  |  |  | 245 |  |  |  |  | 250 |  |  |  | 255 |  |  |
| gct | ccg | gca | gaa | ata | ggt | ccc | tcg | gcc | tcc | tca | gcc | tgc | ctc | tcc | gtt | 816 |
| Ala | Pro | Ala | Glu | Ile | Gly | Pro | Ser | Ala | Ser | Ser | Ala | Cys | Leu | Ser | Val |
|  |  | 260 |  |  |  |  | 265 |  |  |  |  | 270 |  |  |  |
| tct | tgt | ggt | cca | ggc | gaa | atg | tct | ccg | aca | gcg | gat | acg | acg | aga | cac | 864 |
| Ser | Cys | Gly | Pro | Gly | Glu | Met | Ser | Pro | Thr | Ala | Asp | Thr | Thr | Arg | His |
|  | 275 |  |  |  |  | 280 |  |  |  |  | 285 |  |  |  |  |
| gac | gcg | gaa | gag | aga | gaa | cgc | agg | aga | gcg | gag | gaa | gag | aag | gag | aga | 912 |
| Asp | Ala | Glu | Glu | Arg | Glu | Arg | Arg | Ala | Glu | Glu | Glu | Lys | Glu | Arg |
|  | 290 |  |  |  |  | 295 |  |  |  |  | 300 |  |  |  |  |
| gag | aga | cag | gaa | gaa | gaa | gag | aga | gaa | cgc | agg | aga | gtg | gag | gaa | gag | 960 |
| Glu | Arg | Gln | Glu | Glu | Glu | Glu | Arg | Glu | Arg | Arg | Arg | Val | Glu | Glu | Glu |
| 305 |  |  |  |  | 310 |  |  |  |  | 315 |  |  |  |  | 320 |
| aag | gag | aga | gag | aga | cag | gaa | gaa | gaa | gag | aga | gaa | cgc | agg | aga | gtg | 1008 |
| Lys | Glu | Arg | Glu | Arg | Gln | Glu | Glu | Glu | Arg | Glu | Arg | Arg | Arg | Val |
|  |  |  |  | 325 |  |  |  |  | 330 |  |  |  |  | 335 |  |
| gag | gaa | gag | aag | gcg | aga | cag | aga | gag | gaa | gat | gag | aga | gaa | cgc | agg | 1056 |
| Glu | Glu | Glu | Lys | Ala | Arg | Gln | Arg | Glu | Glu | Asp | Glu | Arg | Glu | Arg | Arg |
|  |  |  | 340 |  |  |  |  | 345 |  |  |  |  | 350 |  |  |
| aga | gtg | gag | gaa | gag | aag | gcg | aga | cag | aga | gag | gaa | gaa | gag | aga | gaa | 1104 |
| Arg | Val | Glu | Glu | Glu | Lys | Ala | Arg | Gln | Arg | Glu | Glu | Glu | Arg | Glu |
|  |  | 355 |  |  |  |  | 360 |  |  |  |  | 365 |  |  |  |
| cgc | agg | aga | gtg | gag | gaa | gag | aag | gcg | aga | cag | aga | gag | gaa | gaa | gaa | 1152 |
| Arg | Arg | Arg | Val | Glu | Glu | Glu | Lys | Ala | Arg | Gln | Arg | Glu | Glu | Glu | Glu |
|  | 370 |  |  |  |  | 375 |  |  |  |  | 380 |  |  |  |  |
| gag | aga | gaa | cgc | agg | aga | gtg | gag | gaa | gag | aag | gcg | aga | cag | aga | gag | 1200 |
| Glu | Arg | Glu | Arg | Arg | Arg | Val | Glu | Glu | Glu | Lys | Ala | Arg | Gln | Arg | Glu |
| 385 |  |  |  |  | 390 |  |  |  |  | 395 |  |  |  |  | 400 |
| gaa | gaa | gaa | gag | aga | gaa | cgc | agg | aga | gtg | gag | gaa | gag | aag | gcg | aga | 1248 |
| Glu | Glu | Glu | Glu | Arg | Glu | Arg | Arg | Arg | Val | Glu | Glu | Glu | Lys | Ala | Arg |
|  |  |  |  | 405 |  |  |  |  | 410 |  |  |  |  | 415 |  |
| cag | aga | gag | gaa | gaa | gaa | gag | aga | gaa | ggc | agg | aga | gtg | gag | gaa | gag | 1296 |
| Gln | Arg | Glu | Glu | Glu | Glu | Glu | Arg | Glu | Gly | Arg | Arg | Val | Glu | Glu | Glu |
|  |  |  | 420 |  |  |  |  | 425 |  |  |  |  | 430 |  |  |
| aag | gcg | aga | cag | aga | gag | gaa | gaa | gaa | gag | aga | gaa | ggc | agg | aga | gtg | 1344 |

```
                                                                         -continued Lys Ala Arg Gln Arg Glu Glu Glu Glu Arg Glu Gly Arg Arg Val
            435                 440                 445 gag gaa gag aag gcg aga cag aga gag gaa gaa gag aga gaa cgc agg      1392
Glu Glu Glu Lys Ala Arg Gln Arg Glu Glu Glu Arg Glu Arg Arg
    450                 455                 460 aga gta gag gaa gag aag gag aga gag aga cag gag gaa gag aga gaa      1440
Arg Val Glu Glu Glu Lys Glu Arg Glu Arg Gln Glu Glu Glu Arg Glu
465                 470                 475                 480 cgc agg aga gta gag gaa gag aag gag aga gag aga cag gag gaa gaa      1488
Arg Arg Arg Val Glu Glu Glu Lys Glu Arg Glu Arg Gln Glu Glu Glu
                485                 490                 495 gag aga gaa cgc agg aga gtg gag gaa gag aag gag aga gag aga cag      1536
Glu Arg Glu Arg Arg Arg Val Glu Glu Glu Lys Glu Arg Glu Arg Gln
            500                 505                 510 gaa gaa gaa aag aga gaa cgc agg aga gtg gag gaa gag aag gcg aga      1584
Glu Glu Glu Lys Arg Glu Arg Arg Arg Val Glu Glu Glu Lys Ala Arg
        515                 520                 525 cag aga cag gaa gaa gaa ggg aga gaa aga caa aga gga gag gag aga      1632
Gln Arg Gln Glu Glu Glu Gly Arg Glu Arg Gln Arg Gly Glu Glu Arg
    530                 535                 540 gaa gag aga gag aga gaa ttt caa cag cgc gag cgg gag ctg aag aca      1680
Glu Glu Arg Glu Arg Glu Phe Gln Gln Arg Glu Arg Glu Leu Lys Thr
545                 550                 555                 560 cgg cta gta gag ctt cag aga gag cac gca gag tct gtt gaa acg tgg      1728
Arg Leu Val Glu Leu Gln Arg Glu His Ala Glu Ser Val Glu Thr Trp
                565                 570                 575 atg aag gag caa gga gaa cga gaa agg cac ttg act cag gat tgg gag      1776
Met Lys Glu Gln Gly Glu Arg Glu Arg His Leu Thr Gln Asp Trp Glu
            580                 585                 590 agg aaa ttg cat gcg ttt gaa gag cag agt cgg act gtg ttg ctc caa      1824
Arg Lys Leu His Ala Phe Glu Glu Gln Ser Arg Thr Val Leu Leu Gln
        595                 600                 605 gag aga tcc cg                                                       1835
Glu Arg Ser
    610

<210> SEQ ID NO 81
<211> LENGTH: 611
<212> TYPE: PRT
<213> ORGANISM: Toxoplasma gondii

<400> SEQUENCE: 81

Arg Ile Ser Gly Asp Gln Tyr Ser Cys Leu Gln Arg Gly Ala Gly Gly
1               5                   10                  15

Asp Lys Glu Thr Ala Thr Glu Arg Glu Glu Arg Asn Arg Glu Asp Ala
            20                  25                  30

Pro Ser Phe Leu Glu Gly Gly Leu Gly Asp Asp Glu Thr Glu Arg Ala
        35                  40                  45

Lys Gln Ala Ser Glu Leu Pro Ala Ser Leu Cys Ser Phe Ala Ala Ala
    50                  55                  60

Arg Arg Gly Ala Ser Arg Ala Glu Lys Thr Gly Ala Lys Gly Glu Glu
65                  70                  75                  80

Ala Arg Glu Lys Glu Val Ser Phe Gly Glu Asp Ser Gly Leu Ser Arg
                85                  90                  95

Gln Val Asp Met Asp Ser Ser Gln Glu Ser Val Asn Glu Gly Glu Pro
            100                 105                 110

Leu His Asp Arg Ala Ala Gly Glu Asp Ala Glu Gly Gly Gly Ala Glu
        115                 120                 125
```

-continued

```
Ala Asn Asp Gly Asp Arg Glu Gly Asp Glu Lys Glu Thr Arg Asp Val
    130                 135                 140
Glu Asp Glu Gly Glu Thr Arg Arg Ser Ser Phe Ala Glu Gln Thr
145                 150                 155                 160
Gly Asn Glu Arg Thr Glu Met Arg Thr Arg His Gly Gly Asp Glu Gly
                165                 170                 175
Trp Thr Ser Lys Ser Asn Arg Phe Ala Phe Ala Cys Pro Arg Phe Ser
            180                 185                 190
Lys Ser Asp Val Cys Cys Ser Pro Gln Ala Arg Leu Ser Leu Pro Glu
            195                 200                 205
Gln Ser Leu Gly Ser Ser Pro Ser Ser Pro Ile Ser Val Thr Asn Asp
    210                 215                 220
Val Tyr Ala Leu Phe Asp Ser Ser Ala Ser Pro Leu His Ala Gly Glu
225                 230                 235                 240
Leu Ser Ser Leu Pro Gly Ala Val Ser Ala Ser Glu Arg Leu Leu Thr
                245                 250                 255
Ala Pro Ala Glu Ile Gly Pro Ser Ala Ser Ser Ala Cys Leu Ser Val
            260                 265                 270
Ser Cys Gly Pro Gly Glu Met Ser Pro Thr Ala Asp Thr Thr Arg His
    275                 280                 285
Asp Ala Glu Glu Arg Glu Arg Arg Ala Glu Glu Lys Glu Arg
    290                 295                 300
Glu Arg Gln Glu Glu Glu Arg Glu Arg Arg Val Glu Glu
305                 310                 315                 320
Lys Glu Arg Glu Arg Gln Glu Glu Glu Arg Glu Arg Arg Val
                325                 330                 335
Glu Glu Glu Lys Ala Arg Gln Arg Glu Glu Asp Glu Arg Glu Arg Arg
            340                 345                 350
Arg Val Glu Glu Lys Ala Arg Gln Arg Glu Glu Glu Arg Glu
            355                 360                 365
Arg Arg Arg Val Glu Glu Glu Lys Ala Arg Gln Arg Glu Glu Glu Glu
    370                 375                 380
Glu Arg Glu Arg Arg Val Glu Glu Glu Lys Ala Arg Gln Arg Glu
385                 390                 395                 400
Glu Glu Glu Glu Arg Glu Arg Arg Val Glu Glu Glu Lys Ala Arg
                405                 410                 415
Gln Arg Glu Glu Glu Glu Arg Glu Gly Arg Arg Val Glu Glu Glu
            420                 425                 430
Lys Ala Arg Gln Arg Glu Glu Glu Glu Arg Glu Gly Arg Arg Val
            435                 440                 445
Glu Glu Glu Lys Ala Arg Gln Arg Glu Glu Glu Glu Arg Glu Arg Arg
    450                 455                 460
Arg Val Glu Glu Glu Lys Glu Arg Glu Arg Gln Glu Glu Glu Arg Glu
465                 470                 475                 480
Arg Arg Arg Val Glu Glu Glu Lys Glu Arg Glu Arg Gln Glu Glu Glu
                485                 490                 495
Glu Arg Glu Arg Arg Arg Val Glu Glu Glu Lys Glu Arg Glu Arg Gln
            500                 505                 510
Glu Glu Glu Lys Arg Glu Arg Arg Val Glu Glu Glu Lys Ala Arg
            515                 520                 525
Gln Arg Gln Glu Glu Glu Gly Arg Glu Arg Gln Arg Gly Glu Glu Arg
    530                 535                 540
Glu Glu Arg Glu Arg Glu Phe Gln Gln Arg Glu Arg Glu Leu Lys Thr
```

-continued

```
545                 550                 555                 560
Arg Leu Val Glu Leu Gln Arg Glu His Ala Glu Ser Val Glu Thr Trp
                565                 570                 575
Met Lys Glu Gln Gly Glu Arg Glu Arg His Leu Thr Gln Asp Trp Glu
                580                 585                 590
Arg Lys Leu His Ala Phe Glu Glu Gln Ser Arg Thr Val Leu Leu Gln
                595                 600                 605
Glu Arg Ser
    610

<210> SEQ ID NO 82
<211> LENGTH: 604
<212> TYPE: DNA
<213> ORGANISM: Toxoplasma gondii
<220> FEATURE:
<221> NAME/KEY: CDS
<222> LOCATION: (1)..(336)
<223> OTHER INFORMATION:

<400> SEQUENCE: 82 ccg atg caa ttt gtc tct cct tcc cct ttt gtg caa tcc gac tcc ccc      48
Pro Met Gln Phe Val Ser Pro Ser Pro Phe Val Gln Ser Asp Ser Pro
1               5                   10                  15 tct tcg ccc ttc gca caa tcg gct tca cct cct cct tcc gag tac caa      96
Ser Ser Pro Phe Ala Gln Ser Ala Ser Pro Pro Pro Ser Glu Tyr Gln
            20                  25                  30 gac tct ctt tcc ctt cct ttg gca gaa tcc gtc tcg tcg ctt cct ttg     144
Asp Ser Leu Ser Leu Pro Leu Ala Glu Ser Val Ser Ser Leu Pro Leu
        35                  40                  45 gcg aaa cag gct tct cct ctt cac ttg aca caa cac cct tct ccc ctt     192
Ala Lys Gln Ala Ser Pro Leu His Leu Thr Gln His Pro Ser Pro Leu
    50                  55                  60 cta tgg aca cag cgg gcc tct cca tct cct ttc ttg gtt caa cgg gat     240
Leu Trp Thr Gln Arg Ala Ser Pro Ser Pro Phe Leu Val Gln Arg Asp
65                  70                  75                  80 tcg tca cct cct tct gcg tca atg cgg ctt tct gct cgt cct ttg gca     288
Ser Ser Pro Pro Ser Ala Ser Met Arg Leu Ser Ala Arg Pro Leu Ala
                85                  90                  95 aaa cat gtc tct ccc ctt ctc cgg gca aaa cag gct tct cct ttt cca     336
Lys His Val Ser Pro Leu Leu Arg Ala Lys Gln Ala Ser Pro Phe Pro
            100                 105                 110 tagaaccagc agcgggcctc tccatctcct tcttggtcc accgggtttc gttcctttt     396 catccgtcaa tgcaggtttc atctcgtcct ttggggaaac atgtccctcc ccttctccgg     456
gcaaaacagg cttctccttt tccatagaac agcagcggg cctctccatc tccgttggtg     516
gtccaccggg tttcgttctc ttttcatctg tcaatgcagg tttcgtctcg tgctttggca     576
aaacatgtcc ctccccttct ccggggtg                                       604

<210> SEQ ID NO 83
<211> LENGTH: 112
<212> TYPE: PRT
<213> ORGANISM: Toxoplasma gondii

<400> SEQUENCE: 83

Pro Met Gln Phe Val Ser Pro Ser Pro Phe Val Gln Ser Asp Ser Pro
1               5                   10                  15

Ser Ser Pro Phe Ala Gln Ser Ala Ser Pro Pro Pro Ser Glu Tyr Gln
            20                  25                  30

Asp Ser Leu Ser Leu Pro Leu Ala Glu Ser Val Ser Ser Leu Pro Leu
```

|    |     |     |     |     |     |     |     |     |     |     |     |
|----|-----|-----|-----|-----|-----|-----|-----|-----|-----|-----|-----|
|    |     |     | 35  |     |     |     | 40  |     |     |     | 45  |
| Ala | Lys | Gln | Ala | Ser | Pro | Leu | His | Leu | Thr | Gln | His | Pro | Ser | Pro | Leu |
|     | 50  |     |     |     | 55  |     |     |     | 60  |     |     |

Ala Lys Gln Ala Ser Pro Leu His Leu Thr Gln His Pro Ser Pro Leu
    50                  55                  60

Leu Trp Thr Gln Arg Ala Ser Pro Ser Pro Phe Leu Val Gln Arg Asp
65              70                  75                  80

Ser Ser Pro Pro Ser Ala Ser Met Arg Leu Ser Ala Arg Pro Leu Ala
                85                  90                  95

Lys His Val Ser Pro Leu Leu Arg Ala Lys Gln Ala Ser Pro Phe Pro
            100                 105                 110

<210> SEQ ID NO 84
<211> LENGTH: 549
<212> TYPE: DNA
<213> ORGANISM: Toxoplasma gondii

<400> SEQUENCE: 84

```
ggcctttcca tcgccattct tggtccaccg ggttccgtca tctcttcctc cgtcaaggca      60
ggtttgtctc ggccttgggc aaaaaatgtc cttcccttc tccgggcaac acaagcttgt     120
ccttttccat agaaccagca gcgggctttt catctcccgt tggtggtcca ccgggtttcg    180
ttctcttttc atccgtcaat gcaggtttcg tctcgtcctt aggcaaaaca tgtctctccc    240
cttctccggg caaaacaagc ttgtcctttc ccatagaacc agcagcgggc ctctccatcg    300
ccattcttgg tccaccgggt ttcgttctct tttcatccgt caatgcaggt ttcgtctcgt    360
cctttggcaa acatgtctc tcccttctc cgggcaaaac aggcttctcc ttttccatag      420
aaccagcagc gggcctctcc atctcctttc ttggtccacc gggtttcgtt ctcttttcat    480
ccgtcaatgc aggtttcgtc tcgtccttag gcaaaacatg tctctcccct tctccgggca    540
acacaagcg                                                            549
```

<210> SEQ ID NO 85
<211> LENGTH: 270
<212> TYPE: DNA
<213> ORGANISM: Toxoplasma gondii
<220> FEATURE:
<221> NAME/KEY: CDS
<222> LOCATION: (1)..(270)
<223> OTHER INFORMATION:

<400> SEQUENCE: 85 cgg acg gat gaa cac tgg tgc atc atg aag gat att ggc tac aag ggc     48
Arg Thr Asp Glu His Trp Cys Ile Met Lys Asp Ile Gly Tyr Lys Gly
1               5                   10                  15 aca gac tcg aag tca aca aaa gca aac tca gcg gca gag tgc cag cag     96
Thr Asp Ser Lys Ser Thr Lys Ala Asn Ser Ala Ala Glu Cys Gln Gln
            20                  25                  30 atg tgc ctc aac gat gag agg tgt gac ttt ttc acg tgg caa cag gcg    144
Met Cys Leu Asn Asp Glu Arg Cys Asp Phe Phe Thr Trp Gln Gln Ala
        35                  40                  45 ggc aag cat tgt tgg ttt aag gct ggg gcg tcc act gcc tca aca aaa    192
Gly Lys His Cys Trp Phe Lys Ala Gly Ala Ser Thr Ala Ser Thr Lys
    50                  55                  60 tac aat cgg gct ggc gac tat tct gca cca aaa cac tgc ggc ctg ccg    240
Tyr Asn Arg Ala Gly Asp Tyr Ser Ala Pro Lys His Cys Gly Leu Pro
65                  70                  75                  80 acc aca tgt gtc aag gag cgg acc aag tcg                            270
Thr Thr Cys Val Lys Glu Arg Thr Lys Ser
                85                  90

```
<210> SEQ ID NO 86
<211> LENGTH: 90
<212> TYPE: PRT
<213> ORGANISM: Toxoplasma gondii

<400> SEQUENCE: 86

Arg Thr Asp Glu His Trp Cys Ile Met Lys Asp Ile Gly Tyr Lys Gly
1               5                   10                  15

Thr Asp Ser Lys Ser Thr Lys Ala Asn Ser Ala Ala Glu Cys Gln Gln
            20                  25                  30

Met Cys Leu Asn Asp Glu Arg Cys Asp Phe Phe Thr Trp Gln Gln Ala
        35                  40                  45

Gly Lys His Cys Trp Phe Lys Ala Gly Ala Ser Thr Ala Ser Thr Lys
    50                  55                  60

Tyr Asn Arg Ala Gly Asp Tyr Ser Ala Pro Lys His Cys Gly Leu Pro
65                  70                  75                  80

Thr Thr Cys Val Lys Glu Arg Thr Lys Ser
                85                  90

<210> SEQ ID NO 87
<211> LENGTH: 306
<212> TYPE: DNA
<213> ORGANISM: Toxoplasma gondii
<220> FEATURE:
<221> NAME/KEY: CDS
<222> LOCATION: (1)..(306)
<223> OTHER INFORMATION:

<400> SEQUENCE: 87 cgg cgg caa caa atg ggc cct gtt cga gcc cct gac ctc caa ttc aac      48
Arg Arg Gln Gln Met Gly Pro Val Arg Ala Pro Asp Leu Gln Phe Asn
1               5                   10                  15 cag tcg cca ctg ctc ccc cac aac ctc ggc cct gcc cac gtt ccc atg      96
Gln Ser Pro Leu Leu Pro His Asn Leu Gly Pro Ala His Val Pro Met
            20                  25                  30 gga ggt ctc ccg tcg cat cct cat atc tcg gac ttt cat aac tca tcg     144
Gly Gly Leu Pro Ser His Pro His Ile Ser Asp Phe His Asn Ser Ser
        35                  40                  45 gag tcg cgc ccg caa cat ccg ctg ctt gcc agc ggg ctc gca tcg aga     192
Glu Ser Arg Pro Gln His Pro Leu Leu Ala Ser Gly Leu Ala Ser Arg
    50                  55                  60 ctc gga cag ggc ctg acg ccc cag gag aga cag ttc gtg ctc tct caa     240
Leu Gly Gln Gly Leu Thr Pro Gln Glu Arg Gln Phe Val Leu Ser Gln
65                  70                  75                  80 cag tct ggc gga tcg acc tcg ttc ctg ctg cct gcg ttg ccg tct ctc     288
Gln Ser Gly Gly Ser Thr Ser Phe Leu Leu Pro Ala Leu Pro Ser Leu
                85                  90                  95 tca gag aac ctc tcc gcg                                              306
Ser Glu Asn Leu Ser Ala
            100

<210> SEQ ID NO 88
<211> LENGTH: 102
<212> TYPE: PRT
<213> ORGANISM: Toxoplasma gondii

<400> SEQUENCE: 88

Arg Arg Gln Gln Met Gly Pro Val Arg Ala Pro Asp Leu Gln Phe Asn
1               5                   10                  15

Gln Ser Pro Leu Leu Pro His Asn Leu Gly Pro Ala His Val Pro Met
            20                  25                  30
```

```
Gly Gly Leu Pro Ser His Pro His Ile Ser Asp Phe His Asn Ser Ser
            35                  40                  45

Glu Ser Arg Pro Gln His Pro Leu Leu Ala Ser Gly Leu Ala Ser Arg
        50                  55                  60

Leu Gly Gln Gly Leu Thr Pro Gln Glu Arg Gln Phe Val Leu Ser Gln
 65                  70                  75                  80

Gln Ser Gly Gly Ser Thr Ser Phe Leu Leu Pro Ala Leu Pro Ser Leu
                85                  90                  95

Ser Glu Asn Leu Ser Ala
            100

<210> SEQ ID NO 89
<211> LENGTH: 804
<212> TYPE: DNA
<213> ORGANISM: Toxoplasma gondii
<220> FEATURE:
<221> NAME/KEY: CDS
<222> LOCATION: (1)..(804)
<223> OTHER INFORMATION:

<400> SEQUENCE: 89 cgc gga ggc att tca gtt ccc aca ctt tcc atc atg aat cag agc acc     48
Arg Gly Gly Ile Ser Val Pro Thr Leu Ser Ile Met Asn Gln Ser Thr
 1               5                  10                  15 att gtt gcg acg tct gtg gtc gct ccg cag agc gca gtc tca ctt tcg     96
Ile Val Ala Thr Ser Val Val Ala Pro Gln Ser Ala Val Ser Leu Ser
                20                  25                  30 agg gcc cct agc cga cca ggg cct agc gag agt ttc ggt aaa cag caa    144
Arg Ala Pro Ser Arg Pro Gly Pro Ser Glu Ser Phe Gly Lys Gln Gln
            35                  40                  45 gaa agt cgt cca ggt gtt tcg ggt gct ggc ctc gct gaa agc aaa cgc    192
Glu Ser Arg Pro Gly Val Ser Gly Ala Gly Leu Ala Glu Ser Lys Arg
        50                  55                  60 gtg ccc agc ctt act cag ccg tct ctg gaa cgg tcc gta acc ata tca    240
Val Pro Ser Leu Thr Gln Pro Ser Leu Glu Arg Ser Val Thr Ile Ser
 65                  70                  75                  80 cga cgc aaa att gat gcg gtg ggc atg tca ctc gtg ccg aag tta gac    288
Arg Arg Lys Ile Asp Ala Val Gly Met Ser Leu Val Pro Lys Leu Asp
                85                  90                  95 agg aca acg act tct ctt gca gcg aag gag gag aaa ttc agt tct atc    336
Arg Thr Thr Thr Ser Leu Ala Ala Lys Glu Glu Lys Phe Ser Ser Ile
            100                 105                 110 gac aag ata gtc tca aag cca acc cat tct ttt ggg gag agt tcc aaa    384
Asp Lys Ile Val Ser Lys Pro Thr His Ser Phe Gly Glu Ser Ser Lys
        115                 120                 125 tta cca gcg ggt ata atg aaa gcg aaa tca atg ttt ccg tca caa acc    432
Leu Pro Ala Gly Ile Met Lys Ala Lys Ser Met Phe Pro Ser Gln Thr
130                 135                 140 ctt tcc gca ccg tgg aac gct cct gct cgt tgc gct cgg aaa gac agc    480
Leu Ser Ala Pro Trp Asn Ala Pro Ala Arg Cys Ala Arg Lys Asp Ser
145                 150                 155                 160 ttc ggg acg aag gcc tgg atc gaa aaa ctg caa aga gaa acc aca gac    528
Phe Gly Thr Lys Ala Trp Ile Glu Lys Leu Gln Arg Glu Thr Thr Asp
                165                 170                 175 acc tcg cag cct cca ctt gag cgt caa aag tcg cag cgc ctc gcg caa    576
Thr Ser Gln Pro Pro Leu Glu Arg Gln Lys Ser Gln Arg Leu Ala Gln
            180                 185                 190 acc gag cct gtg cag aaa ctc aag aca tcc tgg ttg gag cct cct caa    624
Thr Glu Pro Val Gln Lys Leu Lys Thr Ser Trp Leu Glu Pro Pro Gln
        195                 200                 205
```

```
gag gtc gaa agt gga cat gga gtc gct gaa ggc gac gat ctc agc gtt    672
Glu Val Glu Ser Gly His Gly Val Ala Glu Gly Asp Asp Leu Ser Val
    210                 215                 220 gca gca gcc gag tat cac gtc cca gaa acg gaa gat gga aaa ccc agc    720
Ala Ala Ala Glu Tyr His Val Pro Glu Thr Glu Asp Gly Lys Pro Ser
225                 230                 235                 240 ttc aaa cct agc gac ccc cgc gtg tgg aat cgc gag tgg atc cac cga    768
Phe Lys Pro Ser Asp Pro Arg Val Trp Asn Arg Glu Trp Ile His Arg
                245                 250                 255 agg ata cat aac ccc gtc ctc agt cgc tcg aac cgg                    804
Arg Ile His Asn Pro Val Leu Ser Arg Ser Asn Arg
                260                 265
```

<210> SEQ ID NO 90
<211> LENGTH: 268
<212> TYPE: PRT
<213> ORGANISM: Toxoplasma gondii

<400> SEQUENCE: 90

```
Arg Gly Gly Ile Ser Val Pro Thr Leu Ser Ile Met Asn Gln Ser Thr
1               5                   10                  15

Ile Val Ala Thr Ser Val Val Ala Pro Gln Ser Ala Val Ser Leu Ser
            20                  25                  30

Arg Ala Pro Ser Arg Pro Gly Pro Ser Glu Ser Phe Gly Lys Gln Gln
        35                  40                  45

Glu Ser Arg Pro Gly Val Ser Gly Ala Gly Leu Ala Glu Ser Lys Arg
    50                  55                  60

Val Pro Ser Leu Thr Gln Pro Ser Leu Glu Arg Ser Val Thr Ile Ser
65                  70                  75                  80

Arg Arg Lys Ile Asp Ala Val Gly Met Ser Leu Val Pro Lys Leu Asp
                85                  90                  95

Arg Thr Thr Thr Ser Leu Ala Ala Lys Glu Glu Lys Phe Ser Ser Ile
            100                 105                 110

Asp Lys Ile Val Ser Lys Pro Thr His Ser Phe Gly Glu Ser Ser Lys
        115                 120                 125

Leu Pro Ala Gly Ile Met Lys Ala Lys Ser Met Phe Pro Ser Gln Thr
    130                 135                 140

Leu Ser Ala Pro Trp Asn Ala Pro Ala Arg Cys Ala Arg Lys Asp Ser
145                 150                 155                 160

Phe Gly Thr Lys Ala Trp Ile Glu Lys Leu Gln Arg Glu Thr Thr Asp
                165                 170                 175

Thr Ser Gln Pro Pro Leu Glu Arg Gln Lys Ser Gln Arg Leu Ala Gln
            180                 185                 190

Thr Glu Pro Val Gln Lys Leu Lys Thr Ser Trp Leu Glu Pro Pro Gln
        195                 200                 205

Glu Val Glu Ser Gly His Gly Val Ala Glu Gly Asp Asp Leu Ser Val
    210                 215                 220

Ala Ala Ala Glu Tyr His Val Pro Glu Thr Glu Asp Gly Lys Pro Ser
225                 230                 235                 240

Phe Lys Pro Ser Asp Pro Arg Val Trp Asn Arg Glu Trp Ile His Arg
                245                 250                 255

Arg Ile His Asn Pro Val Leu Ser Arg Ser Asn Arg
            260                 265
```

<210> SEQ ID NO 91
<211> LENGTH: 867
<212> TYPE: DNA

<213> ORGANISM: Toxoplasma gondii
<220> FEATURE:
<221> NAME/KEY: CDS
<222> LOCATION: (1)..(867)
<223> OTHER INFORMATION:

<400> SEQUENCE: 91

| | | | | | | | | | | | | | | | | |
|---|---|---|---|---|---|---|---|---|---|---|---|---|---|---|---|---|
| cgg | gat | cca | gct | ggc | aag | gca | gta | aag | aag | gca | gcc | aca | ggg | ata | cca | 48 |
| Arg | Asp | Pro | Ala | Gly | Lys | Ala | Val | Lys | Lys | Ala | Ala | Thr | Gly | Ile | Pro | |
| 1 | | | | 5 | | | | | 10 | | | | | 15 | | |
| aag | cct | gca | gct | cca | ggt | ggc | aag | gca | gtc | aag | gtg | act | cct | gtc | gcg | 96 |
| Lys | Pro | Ala | Ala | Pro | Gly | Gly | Lys | Ala | Val | Lys | Val | Thr | Pro | Val | Ala | |
| | | | | 20 | | | | | 25 | | | | | 30 | | |
| cga | aaa | cct | gtt | gca | cca | aag | gca | gca | gct | cca | gac | ggc | aag | gcg | gtc | 144 |
| Arg | Lys | Pro | Val | Ala | Pro | Lys | Ala | Ala | Ala | Pro | Asp | Gly | Lys | Ala | Val | |
| | | 35 | | | | | 40 | | | | | 45 | | | | |
| aag | aag | gca | acc | gta | gtc | gtg | cca | aag | cct | gca | gct | ccc | agt | ggc | aag | 192 |
| Lys | Lys | Ala | Thr | Val | Val | Val | Pro | Lys | Pro | Ala | Ala | Pro | Ser | Gly | Lys | |
| | 50 | | | | | 55 | | | | | 60 | | | | | |
| gca | gtg | aag | aag | ccg | gtt | gtc | agc | gtg | cca | aag | cct | gca | aca | ctc | ggt | 240 |
| Ala | Val | Lys | Lys | Pro | Val | Val | Ser | Val | Pro | Lys | Pro | Ala | Thr | Leu | Gly | |
| 65 | | | | | 70 | | | | | 75 | | | | | 80 | |
| ggc | aag | gca | gtg | aag | aag | cca | gct | gcc | ggc | gtg | cca | aag | ccc | gca | gct | 288 |
| Gly | Lys | Ala | Val | Lys | Lys | Pro | Ala | Ala | Gly | Val | Pro | Lys | Pro | Ala | Ala | |
| | | | | 85 | | | | | 90 | | | | | 95 | | |
| ccc | gat | ggc | aag | gcg | gtg | aga | aag | cca | gtt | gtc | ggc | gtg | cca | aag | ccc | 336 |
| Pro | Asp | Gly | Lys | Ala | Val | Arg | Lys | Pro | Val | Val | Gly | Val | Pro | Lys | Pro | |
| | | | 100 | | | | | 105 | | | | | 110 | | | |
| gca | gct | ccc | gat | ggt | aag | gcg | gcg | aaa | aag | cca | gcg | tcc | ggc | gtg | cca | 384 |
| Ala | Ala | Pro | Asp | Gly | Lys | Ala | Ala | Lys | Lys | Pro | Ala | Ser | Gly | Val | Pro | |
| | | 115 | | | | | 120 | | | | | 125 | | | | |
| aag | cct | gcg | gat | cca | gct | ggc | aag | gca | gta | aag | aag | gca | gcc | aca | ggg | 432 |
| Lys | Pro | Ala | Asp | Pro | Ala | Gly | Lys | Ala | Val | Lys | Lys | Ala | Ala | Thr | Gly | |
| | 130 | | | | | 135 | | | | | 140 | | | | | |
| ata | cca | aag | cct | gca | gct | cca | ggt | ggc | aag | gca | atc | aag | gtg | act | cct | 480 |
| Ile | Pro | Lys | Pro | Ala | Ala | Pro | Gly | Gly | Lys | Ala | Ile | Lys | Val | Thr | Pro | |
| 145 | | | | | 150 | | | | | 155 | | | | | 160 | |
| gtc | gcg | cga | aaa | cct | gtt | gca | cca | aag | gca | gca | gct | cca | gac | ggc | aag | 528 |
| Val | Ala | Arg | Lys | Pro | Val | Ala | Pro | Lys | Ala | Ala | Ala | Pro | Asp | Gly | Lys | |
| | | | | 165 | | | | | 170 | | | | | 175 | | |
| gca | gtc | aag | aag | gca | acc | gta | gtc | gtg | cca | aag | cct | gca | gct | ccc | agt | 576 |
| Ala | Val | Lys | Lys | Ala | Thr | Val | Val | Val | Pro | Lys | Pro | Ala | Ala | Pro | Ser | |
| | | | 180 | | | | | 185 | | | | | 190 | | | |
| ggc | aag | gca | gtg | aag | aag | cca | gtt | gtc | agc | gtg | cca | aag | cct | gca | acg | 624 |
| Gly | Lys | Ala | Val | Lys | Lys | Pro | Val | Val | Ser | Val | Pro | Lys | Pro | Ala | Thr | |
| | | 195 | | | | | 200 | | | | | 205 | | | | |
| ctc | gat | ggc | aag | gcg | gtg | aga | aag | cca | gtt | gtc | ggc | gtg | cca | aag | ccc | 672 |
| Leu | Asp | Gly | Lys | Ala | Val | Arg | Lys | Pro | Val | Val | Gly | Val | Pro | Lys | Pro | |
| | 210 | | | | | 215 | | | | | 220 | | | | | |
| gca | gct | ccc | gat | ggt | aag | gcg | gtg | aaa | aag | cca | gtt | gtc | ggc | gtg | cca | 720 |
| Ala | Ala | Pro | Asp | Gly | Lys | Ala | Val | Lys | Lys | Pro | Val | Val | Gly | Val | Pro | |
| 225 | | | | | 230 | | | | | 235 | | | | | 240 | |
| aag | cct | gca | gct | cca | gat | gac | acg | gga | atc | aac | aag | gcg | acc | ctt | gtc | 768 |
| Lys | Pro | Ala | Ala | Pro | Asp | Asp | Thr | Gly | Ile | Asn | Lys | Ala | Thr | Leu | Val | |
| | | | | 245 | | | | | 250 | | | | | 255 | | |
| acg | cgg | aaa | cct | gag | gct | cca | gac | gtg | aag | gta | gtc | aag | aag | gca | acc | 816 |
| Thr | Arg | Lys | Pro | Glu | Ala | Pro | Asp | Val | Lys | Val | Val | Lys | Lys | Ala | Thr | |
| | | | 260 | | | | | 265 | | | | | 270 | | | |
| gta | gtt | gtg | cca | aaa | cct | gaa | gcg | cca | gat | ata | aag | gta | atg | acg | gat | 864 |
| Val | Val | Val | Pro | Lys | Pro | Glu | Ala | Pro | Asp | Ile | Lys | Val | Met | Thr | Asp | |
| | | 275 | | | | | 280 | | | | | 285 | | | | | ccg                                                                                 867
Pro <210> SEQ ID NO 92
<211> LENGTH: 289
<212> TYPE: PRT
<213> ORGANISM: Toxoplasma gondii

<400> SEQUENCE: 92

Arg Asp Pro Ala Gly Lys Ala Val Lys Ala Ala Thr Gly Ile Pro
1               5                   10                  15

Lys Pro Ala Ala Pro Gly Gly Lys Ala Val Lys Val Thr Pro Val Ala
            20                  25                  30

Arg Lys Pro Val Ala Pro Lys Ala Ala Pro Asp Gly Lys Ala Val
        35                  40                  45

Lys Lys Ala Thr Val Val Pro Lys Pro Ala Ala Pro Ser Gly Lys
    50                  55                  60

Ala Val Lys Lys Pro Val Val Ser Val Pro Lys Pro Ala Thr Leu Gly
65                  70                  75                  80

Gly Lys Ala Val Lys Pro Ala Ala Gly Val Pro Lys Pro Ala Ala
                85                  90                  95

Pro Asp Gly Lys Ala Val Arg Lys Pro Val Val Gly Val Pro Lys Pro
                100                 105                 110

Ala Ala Pro Asp Gly Lys Ala Ala Lys Lys Pro Ala Ser Gly Val Pro
            115                 120                 125

Lys Pro Ala Asp Pro Ala Gly Lys Ala Val Lys Lys Ala Thr Gly
    130                 135                 140

Ile Pro Lys Pro Ala Ala Pro Gly Gly Lys Ala Ile Lys Val Thr Pro
145                 150                 155                 160

Val Ala Arg Lys Pro Val Ala Pro Lys Ala Ala Pro Asp Gly Lys
                165                 170                 175

Ala Val Lys Lys Ala Thr Val Val Pro Lys Pro Ala Ala Pro Ser
            180                 185                 190

Gly Lys Ala Val Lys Lys Pro Val Val Ser Val Pro Lys Pro Ala Thr
            195                 200                 205

Leu Asp Gly Lys Ala Val Arg Lys Pro Val Val Gly Val Pro Lys Pro
    210                 215                 220

Ala Ala Pro Asp Gly Lys Ala Val Lys Lys Pro Val Val Gly Val Pro
225                 230                 235                 240

Lys Pro Ala Ala Pro Asp Asp Thr Gly Ile Asn Lys Ala Thr Leu Val
                245                 250                 255

Thr Arg Lys Pro Glu Ala Pro Asp Val Lys Val Val Lys Lys Ala Thr
            260                 265                 270

Val Val Val Pro Lys Pro Glu Ala Pro Asp Ile Lys Val Met Thr Asp
            275                 280                 285

Pro

<210> SEQ ID NO 93
<211> LENGTH: 1434
<212> TYPE: DNA
<213> ORGANISM: Toxoplasma gondii
<220> FEATURE:
<221> NAME/KEY: CDS
<222> LOCATION: (1)..(492)
<223> OTHER INFORMATION:

<400> SEQUENCE: 93

```
cgg ctt gtg ttg ccc gga gaa ggg gag aga cat gtt ttg cca aag gac        48
Arg Leu Val Leu Pro Gly Glu Gly Glu Arg His Val Leu Pro Lys Asp
 1               5                  10                  15 gag acg aaa cct gca ttg acg gat gaa aag aga acg aaa ccc ggt gga        96
Glu Thr Lys Pro Ala Leu Thr Asp Glu Lys Arg Thr Lys Pro Gly Gly
             20                  25                  30 cca agg aag gag atg gag agg ccc gct gct ggt tct atg gaa aag gac       144
Pro Arg Lys Glu Met Glu Arg Pro Ala Ala Gly Ser Met Glu Lys Asp
         35                  40                  45 aag ctt gtt ttg ccc gga gaa ggg gag aga cat gtt ttg cca aag gac       192
Lys Leu Val Leu Pro Gly Glu Gly Glu Arg His Val Leu Pro Lys Asp
     50                  55                  60 gag acg aaa cct gca ttg acg gag gaa aag aga acg aaa ccc ggt gga       240
Glu Thr Lys Pro Ala Leu Thr Glu Glu Lys Arg Thr Lys Pro Gly Gly
65                  70                  75                  80 cca cga acg gag atg gag agg ccc gct gct ggt tct atg gaa aag gac       288
Pro Arg Thr Glu Met Glu Arg Pro Ala Ala Gly Ser Met Glu Lys Asp
                 85                  90                  95 aag cct ggt ttg ccc gga gaa ggg gag aga cat gtt ttg cca aag gac       336
Lys Pro Gly Leu Pro Gly Glu Gly Glu Arg His Val Leu Pro Lys Asp
             100                 105                 110 gag acg aaa cct gca ttg acg gag gaa aag aga acg aac ctg gcg gac       384
Glu Thr Lys Pro Ala Leu Thr Glu Glu Lys Arg Thr Asn Leu Ala Asp
         115                 120                 125 caa gaa agg aga tgg aga gcc cgc tgc tgg ttc ttg gaa aag gag aac       432
Gln Glu Arg Arg Trp Arg Ala Arg Cys Trp Phe Leu Glu Lys Glu Asn
     130                 135                 140 ctg ttt ggc ccg gag aag ggg aga gac acg ctt cgc caa agg acg aga       480
Leu Phe Gly Pro Glu Lys Gly Arg Asp Thr Leu Arg Gln Arg Thr Arg
145                 150                 155                 160 cga aag ccg cat tgacgcaaaa ggaggtgacg aatcccgttg aaccaagaaa           532
Arg Lys Pro His ggcgatggag aggcccgctg ctggttctat ggaaaaggaa aacctgtttc cccggagaag     592
gggagggaca tgttttgcca agcacagac gaaacctgca ttgacagatg aaagagaac       652 gaaacccggt ggaccaccaa cggagatgga gaggcccgct gctggttta tggaaaagga     712 gaagcctgtt ttgcccggag aaggggaggg acatgtttcc ccaaaggacg agatgaaacc    772
tgcattgacg gatgaaaaga gaacgaaacc cggtggacca agaaaggaga tggagaggcc    832
cgctgctggt tttatggaaa aggagaagcc tgttttgccc ggagaagggg agagacatgt    892
tttgccaaag gacgagcaga aagccgcatt gacgcagaag gaggtgacga atcccgttga    952
accaagaaag gagatggaga ggcccgctgt gcccatagaa ggggagaagg gtgttgtgtc   1012
aagtgaagag gagaagcctg tttcgccaaa ggaagcgacg agacggattt tgccaaagga   1072
agggaaagag atttggtact cggaaggagg aggtgaagcc gattgtgcga agggcaaaga   1132
gggggagacg gattgcacaa aaggggaagg agaaacaaat tgcatcgaag gagggagaga   1192
aacccgctgt accaaaggaa ggtgaggaaa gacccgctga accaacggaa ggcgaggaaa   1252
ggcccgttgg gccaaaggaa ggcgaggaaa gacccgttgt gccggacgta gacaaggaga   1312
aacctgttgt gcctgaagga gacaaggaga aacctgttgt gccggaagga gacaaggatc   1372
accctgcttc tgccagagca ggatgaggag aaacacgcta catgggagaa agaaatgatc   1432
cg                                                                  1434

<210> SEQ ID NO 94
<211> LENGTH: 164
```

```
<212> TYPE: PRT
<213> ORGANISM: Toxoplasma gondii

<400> SEQUENCE: 94

Arg Leu Val Leu Pro Gly Glu Gly Glu Arg His Val Leu Pro Lys Asp
  1               5                  10                  15

Glu Thr Lys Pro Ala Leu Thr Asp Glu Lys Arg Thr Lys Pro Gly Gly
             20                  25                  30

Pro Arg Lys Glu Met Glu Arg Pro Ala Ala Gly Ser Met Glu Lys Asp
         35                  40                  45

Lys Leu Val Leu Pro Gly Gly Glu Arg His Val Leu Pro Lys Asp
     50                  55                  60

Glu Thr Lys Pro Ala Leu Thr Glu Glu Lys Arg Thr Lys Pro Gly Gly
 65                  70                  75                  80

Pro Arg Thr Glu Met Glu Arg Pro Ala Ala Gly Ser Met Glu Lys Asp
                 85                  90                  95

Lys Pro Gly Leu Pro Gly Gly Glu Arg His Val Leu Pro Lys Asp
                100                 105                 110

Glu Thr Lys Pro Ala Leu Thr Glu Glu Lys Arg Thr Asn Leu Ala Asp
            115                 120                 125

Gln Glu Arg Arg Trp Arg Ala Arg Cys Trp Phe Leu Glu Lys Glu Asn
        130                 135                 140

Leu Phe Gly Pro Glu Lys Gly Arg Asp Thr Leu Arg Gln Arg Thr Arg
145                 150                 155                 160

Arg Lys Pro His

<210> SEQ ID NO 95
<211> LENGTH: 680
<212> TYPE: DNA
<213> ORGANISM: Toxoplasma gondii
<220> FEATURE:
<221> NAME/KEY: CDS
<222> LOCATION: (1)..(678)
<223> OTHER INFORMATION:

<400> SEQUENCE: 95 cga cca aga gca ggg agg gag cag cct gct gtt ccg cgg cag gaa gaa      48
Arg Pro Arg Ala Gly Arg Glu Gln Pro Ala Val Pro Arg Gln Glu Glu
  1               5                  10                  15 cag aaa ctt gtt ttg caa aag aca gag agg aaa cca gtt ttg cca gag      96
Gln Lys Leu Val Leu Gln Lys Thr Glu Arg Lys Pro Val Leu Pro Glu
             20                  25                  30 gaa gac cag aaa ccg gtt tta cca gaa aca ggg gcg aaa cat gtt tta     144
Glu Asp Gln Lys Pro Val Leu Pro Glu Thr Gly Ala Lys His Val Leu
         35                  40                  45 ccg gaa ata gcg acc gaa tcc act ttg acg cag aaa gag ctg aca aaa     192
Pro Glu Ile Ala Thr Glu Ser Thr Leu Thr Gln Lys Glu Leu Thr Lys
     50                  55                  60 ccc gtt gaa aca aga cag gac atg agg ggg acc gct ggt tct atg gac     240
Pro Val Glu Thr Arg Gln Asp Met Arg Gly Thr Ala Gly Ser Met Asp
 65                  70                  75                  80 gag aag aag cct gtt ttg ccc gga gaa tgg gag aga cat gtc ttg cca     288
Glu Lys Lys Pro Val Leu Pro Gly Glu Trp Glu Arg His Val Leu Pro
                 85                  90                  95 aaa gac gag acg aaa cct gca ttg acg gag gaa aag aga acg aaa ccc     336
Lys Asp Glu Thr Lys Pro Ala Leu Thr Glu Glu Lys Arg Thr Lys Pro
                100                 105                 110 gtt gaa cca aga aag gag atg gag agg ccc gct cgc ccc atg gaa gag     384
Val Glu Pro Arg Lys Glu Met Glu Arg Pro Ala Arg Pro Met Glu Glu
```

-continued

```
             115                 120                 125
gag aag cct gtt tta ccc gga gaa ggg gag aga cat gtt ttg cca aag      432
Glu Lys Pro Val Leu Pro Gly Glu Gly Glu Arg His Val Leu Pro Lys
        130                 135                 140 gac ggg atg aaa cct gca ttg acg gat gaa aag aga acg aaa ccc ggt      480
Asp Gly Met Lys Pro Ala Leu Thr Asp Glu Lys Arg Thr Lys Pro Gly
145                 150                 155                 160 gga cca agg aag gag atg gag agg ccc gct gct ggt tct atg gaa aag      528
Gly Pro Arg Lys Glu Met Glu Arg Pro Ala Ala Gly Ser Met Glu Lys
                165                 170                 175 gac aag ctt gtg ttg ccc gga gaa ggg gag aga cat gtt ttg cct aag      576
Asp Lys Leu Val Leu Pro Gly Glu Gly Glu Arg His Val Leu Pro Lys
        180                 185                 190 gac gag acg aaa cct gca ttg acg gat gaa aag aga acg aaa ccc ggt      624
Asp Glu Thr Lys Pro Ala Leu Thr Asp Glu Lys Arg Thr Lys Pro Gly
195                 200                 205 gga cca aga aag gcg atg gag agg ccc gct gct ggt tct atg gaa aag      672
Gly Pro Arg Lys Ala Met Glu Arg Pro Ala Ala Gly Ser Met Glu Lys
        210                 215                 220 gac aag cg                                                           680
Asp Lys
225
```

<210> SEQ ID NO 96
<211> LENGTH: 226
<212> TYPE: PRT
<213> ORGANISM: Toxoplasma gondii

<400> SEQUENCE: 96

```
Arg Pro Arg Ala Gly Arg Glu Gln Pro Ala Val Pro Arg Gln Glu Glu
1               5                   10                  15

Gln Lys Leu Val Leu Gln Lys Thr Glu Arg Lys Pro Val Leu Pro Glu
            20                  25                  30

Glu Asp Gln Lys Pro Val Leu Pro Glu Thr Gly Ala Lys His Val Leu
        35                  40                  45

Pro Glu Ile Ala Thr Glu Ser Thr Leu Thr Gln Lys Glu Leu Thr Lys
    50                  55                  60

Pro Val Glu Thr Arg Gln Asp Met Arg Gly Thr Ala Gly Ser Met Asp
65                  70                  75                  80

Glu Lys Lys Pro Val Leu Pro Gly Glu Trp Glu Arg His Val Leu Pro
                85                  90                  95

Lys Asp Glu Thr Lys Pro Ala Leu Thr Glu Lys Arg Thr Lys Pro
            100                 105                 110

Val Glu Pro Arg Lys Glu Met Glu Arg Pro Ala Arg Pro Met Glu Glu
        115                 120                 125

Glu Lys Pro Val Leu Pro Gly Glu Gly Glu Arg His Val Leu Pro Lys
    130                 135                 140

Asp Gly Met Lys Pro Ala Leu Thr Asp Glu Lys Arg Thr Lys Pro Gly
145                 150                 155                 160

Gly Pro Arg Lys Glu Met Glu Arg Pro Ala Ala Gly Ser Met Glu Lys
                165                 170                 175

Asp Lys Leu Val Leu Pro Gly Glu Gly Glu Arg His Val Leu Pro Lys
            180                 185                 190

Asp Glu Thr Lys Pro Ala Leu Thr Asp Glu Lys Arg Thr Lys Pro Gly
        195                 200                 205

Gly Pro Arg Lys Ala Met Glu Arg Pro Ala Ala Gly Ser Met Glu Lys
    210                 215                 220
```

Asp Lys
225

<210> SEQ ID NO 97
<211> LENGTH: 296
<212> TYPE: DNA
<213> ORGANISM: Toxoplasma gondii
<220> FEATURE:
<221> NAME/KEY: CDS
<222> LOCATION: (1)..(294)
<223> OTHER INFORMATION:

<400> SEQUENCE: 97

| ccg gtc gac gtg gac gac ccc cgt ggc tgt tcg cag caa agc gga gac | 48 |
| Pro Val Asp Val Asp Asp Pro Arg Gly Cys Ser Gln Gln Ser Gly Asp | |
| 1               5                   10                  15     | |

| acc aga gac agc agc agt ccc gcc aca cct ggt ggt cgg ccg gct ggt | 96 |
| Thr Arg Asp Ser Ser Ser Pro Ala Thr Pro Gly Gly Arg Pro Ala Gly | |
|             20                  25                  30         | |

| ggg gca gga ggt gca gcg aca agc ccg aag gga cag gcc ttt gcc ccg | 144 |
| Gly Ala Gly Gly Ala Ala Thr Ser Pro Lys Gly Gln Ala Phe Ala Pro | |
|         35                  40                  45             | |

| cgg ggc ggt gaa ggg gag ata aag ccc cag gag aca gga aac agt gga | 192 |
| Arg Gly Gly Glu Gly Glu Ile Lys Pro Gln Glu Thr Gly Asn Ser Gly | |
|     50                  55                  60                 | |

| gac agc aag gcg gag gga aag gaa gca agt gga gac gcg aac act tcg | 240 |
| Asp Ser Lys Ala Glu Gly Lys Glu Ala Ser Gly Asp Ala Asn Thr Ser | |
| 65                  70                  75                  80 | |

| gaa gga aag cga ttg tcg ggc gaa gtg gac aag aca gcc gag gtg gag | 288 |
| Glu Gly Lys Arg Leu Ser Gly Glu Val Asp Lys Thr Ala Glu Val Glu | |
|                 85                  90                  95     | |

| aca gcc gg                                                      | 296 |
| Thr Ala                                                         | |

<210> SEQ ID NO 98
<211> LENGTH: 98
<212> TYPE: PRT
<213> ORGANISM: Toxoplasma gondii

<400> SEQUENCE: 98

Pro Val Asp Val Asp Asp Pro Arg Gly Cys Ser Gln Gln Ser Gly Asp
1               5                   10                  15

Thr Arg Asp Ser Ser Ser Pro Ala Thr Pro Gly Gly Arg Pro Ala Gly
            20                  25                  30

Gly Ala Gly Gly Ala Ala Thr Ser Pro Lys Gly Gln Ala Phe Ala Pro
        35                  40                  45

Arg Gly Gly Glu Gly Glu Ile Lys Pro Gln Glu Thr Gly Asn Ser Gly
    50                  55                  60

Asp Ser Lys Ala Glu Gly Lys Glu Ala Ser Gly Asp Ala Asn Thr Ser
65                  70                  75                  80

Glu Gly Lys Arg Leu Ser Gly Glu Val Asp Lys Thr Ala Glu Val Glu
                85                  90                  95

Thr Ala

<210> SEQ ID NO 99
<211> LENGTH: 723
<212> TYPE: DNA
<213> ORGANISM: Toxoplasma gondii
<220> FEATURE:
<221> NAME/KEY: CDS
<222> LOCATION: (1)..(159)

<223> OTHER INFORMATION:

<400> SEQUENCE: 99

| cga tcc tcc cga ggg acc gca gga agg ctc gcg tcc gaa gaa gac gac | 48 |
| Arg Ser Ser Arg Gly Thr Ala Gly Arg Leu Ala Ser Glu Glu Asp Asp | |
| 1               5                   10                  15 | |

| gga gac aac gaa gaa gag gaa cga gaa gaa gaa agg gag aga cgc gaa | 96 |
| Gly Asp Asn Glu Glu Glu Glu Arg Glu Glu Glu Arg Glu Arg Arg Glu | |
|             20                  25                  30 | |

| aga gaa gac ggg gaa gac gca ggc tct agg cgt cga gag aag gac ttc | 144 |
| Arg Glu Asp Gly Glu Asp Ala Gly Ser Arg Arg Arg Glu Lys Asp Phe | |
|         35                  40                  45 | |

| ttc cca gac acg act tgaatgcgta aaggcgtatt tttgtttccg atgaaaactc | 199 |
| Phe Pro Asp Thr Thr | |
|     50 | |

| gccaggggag gcgacttctc gcctctgagg aatccgacag tgacgagagg aagagggaag | 259 |
| gagacgcaga gaaggacgcg tcaggaggat ccggaattcc ggatcgggcg atggccccgg | 319 |
| agcgcgtgag ggcggtacac tgaagaacca acggaagaac actggggtc gaaaatgtgt | 379 |
| ttcctttccg atgtggtctt cccagctttc ctgcagacat gtgtacagaa cagctgagaa | 439 |
| aaaacgacga aagctccaat tgtctcttcg ttctcgagca gagaaaaccc ccgaggcct | 499 |
| tcgcttggtc agggcgaaac ctcaaggtg catgcagagt cggccgtgcc cagagtagcc | 559 |
| tagtcatgca gcccatcagt agcttaattt gacgcaatgg ctattttttac attgtgaaga | 619 |
| gggttttcca atcaacaaac gccagagaag cctgtgttct ggaaaacctg aacgacggcc | 679 |
| gtcgttcccc tgtctgcttt accccctgac agtgcgtggt gagg | 723 |

<210> SEQ ID NO 100
<211> LENGTH: 53
<212> TYPE: PRT
<213> ORGANISM: Toxoplasma gondii

<400> SEQUENCE: 100

Arg Ser Ser Arg Gly Thr Ala Gly Arg Leu Ala Ser Glu Glu Asp Asp
1               5                   10                  15

Gly Asp Asn Glu Glu Glu Glu Arg Glu Glu Glu Arg Glu Arg Arg Glu
            20                  25                  30

Arg Glu Asp Gly Glu Asp Ala Gly Ser Arg Arg Arg Glu Lys Asp Phe
        35                  40                  45

Phe Pro Asp Thr Thr
    50

<210> SEQ ID NO 101
<211> LENGTH: 270
<212> TYPE: DNA
<213> ORGANISM: Toxoplasma gondii
<220> FEATURE:
<221> NAME/KEY: CDS
<222> LOCATION: (1)..(270)
<223> OTHER INFORMATION:

<400> SEQUENCE: 101

| cgg aag ccg att gtg cga agg gca aag agg ggg aga cgg att gca caa | 48 |
| Arg Lys Pro Ile Val Arg Arg Ala Lys Arg Gly Arg Arg Ile Ala Gln | |
| 1               5                   10                  15 | |

| aag ggg aag gag aaa caa att gca tcg aag gag ggg aag aaa ccc gct | 96 |
| Lys Gly Lys Glu Lys Gln Ile Ala Ser Lys Glu Gly Lys Lys Pro Ala | |
|             20                  25                  30 | |

| gta cca aag gaa ggt gag gaa aga ccc gct gaa cca acg gaa ggc gag | 144 |

```
Val Pro Lys Glu Gly Glu Arg Pro Ala Glu Pro Thr Glu Gly Glu
            35                  40                  45 gaa agg ccc gtt ggg cca aag gaa ggc gag gaa aga ccc gtt gtg ccg        192
Glu Arg Pro Val Gly Pro Lys Glu Gly Glu Arg Pro Val Val Pro
 50                  55                  60 gac gta gac aag gag aaa cct gtt gtg cct gaa gga gac aag gag aaa        240
Asp Val Asp Lys Glu Lys Pro Val Val Pro Glu Gly Asp Lys Glu Lys
65                  70                  75                  80 cct gtt gtg ccg gaa gga gac aag gat ccg                                270
Pro Val Val Pro Glu Gly Asp Lys Asp Pro
                85                  90

<210> SEQ ID NO 102
<211> LENGTH: 90
<212> TYPE: PRT
<213> ORGANISM: Toxoplasma gondii

<400> SEQUENCE: 102

Arg Lys Pro Ile Val Arg Arg Ala Lys Arg Gly Arg Ile Ala Gln
1               5                   10                  15

Lys Gly Lys Glu Lys Gln Ile Ala Ser Lys Gly Lys Lys Pro Ala
            20                  25                  30

Val Pro Lys Glu Gly Glu Arg Pro Ala Glu Pro Thr Glu Gly Glu
            35                  40                  45

Glu Arg Pro Val Gly Pro Lys Glu Gly Glu Arg Pro Val Val Pro
 50                  55                  60

Asp Val Asp Lys Glu Lys Pro Val Val Pro Glu Gly Asp Lys Glu Lys
65                  70                  75                  80

Pro Val Val Pro Glu Gly Asp Lys Asp Pro
                85                  90

<210> SEQ ID NO 103
<211> LENGTH: 503
<212> TYPE: DNA
<213> ORGANISM: Toxoplasma gondii
<220> FEATURE:
<221> NAME/KEY: CDS
<222> LOCATION: (1)..(186)
<223> OTHER INFORMATION:
<220> FEATURE:
<221> NAME/KEY: misc_feature
<222> LOCATION: (433)..(433)
<223> OTHER INFORMATION: n = unknown
<220> FEATURE:
<221> NAME/KEY: misc_feature
<222> LOCATION: (489)..(489)
<223> OTHER INFORMATION: n = unknown

<400> SEQUENCE: 103 cgg cat ctc tgg tgc gtg cgc gag aga tcc ccg caa cga gaa aga tgg        48
Arg His Leu Trp Cys Val Arg Glu Arg Ser Pro Gln Arg Glu Arg Trp
1               5                   10                  15 agc ttc gtc tcg ttc tcg ctt ttc ttc tct ttc cag ttc ttt ttc agc        96
Ser Phe Val Ser Phe Ser Leu Phe Phe Ser Phe Gln Phe Phe Phe Ser
            20                  25                  30 aag caa gtc tcg cgc ctc cct cgt ccg agc agc gtc act gca ctg tgg        144
Lys Gln Val Ser Arg Leu Pro Arg Pro Ser Ser Val Thr Ala Leu Trp
        35                  40                  45 gcc atc agc aga aag aag gcg aag aaa aga gac gac ggc aga                186
Ala Ile Ser Arg Lys Lys Ala Lys Lys Arg Asp Asp Gly Arg
 50                  55                  60 taatggcgcg aaaatctatc ccaaaaacac atatatgcct tatggcagtg agcgaagaga      246
```

```
gggaactgcc aacgccttgg cggaagcccg ttctccaaac gaggttgagg taccaaacct      306
gcatgcggag agaccaaggc aggttttgtc ttccgtcgct tccgtggatg cttttcgcac      366
gtatgcaaaa gagagaacgg gaccaagtgc aagaagttat agagcagtcc cgacgacaga      426
gacgcancta gaggccgagc aagaatcgtt ttttcttct cgtaagggaa acgcagtgca       486
tanaagcaaa agaccgg                                                     503
```

<210> SEQ ID NO 104
<211> LENGTH: 62
<212> TYPE: PRT
<213> ORGANISM: Toxoplasma gondii

<400> SEQUENCE: 104

```
Arg His Leu Trp Cys Val Arg Glu Arg Ser Pro Gln Arg Glu Arg Trp
1               5                   10                  15

Ser Phe Val Ser Phe Ser Leu Phe Phe Ser Phe Gln Phe Phe Phe Ser
            20                  25                  30

Lys Gln Val Ser Arg Leu Pro Arg Pro Ser Ser Val Thr Ala Leu Trp
        35                  40                  45

Ala Ile Ser Arg Lys Lys Ala Lys Lys Arg Asp Asp Gly Arg
    50                  55                  60
```

<210> SEQ ID NO 105
<211> LENGTH: 322
<212> TYPE: DNA
<213> ORGANISM: Toxoplasma gondii
<220> FEATURE:
<221> NAME/KEY: CDS
<222> LOCATION: (1)..(219)
<223> OTHER INFORMATION:
<220> FEATURE:
<221> NAME/KEY: misc_feature
<222> LOCATION: (141)..(141)
<223> OTHER INFORMATION: At nucleotide 141, n = unknown
     At amino acid residue 47, Xaa = Ser

<400> SEQUENCE: 105

```
cgg cgg gac ttg cgg act tcg gtc tgg gac gct cgg gtg tac gta cac       48
Arg Arg Asp Leu Arg Thr Ser Val Trp Asp Ala Arg Val Tyr Val His
1               5                   10                  15 ctg gcg ggg ggc cag agg cgc tgc aac gag tcg cgg ggg atg gag gaa       96
Leu Ala Gly Gly Gln Arg Arg Cys Asn Glu Ser Arg Gly Met Glu Glu
            20                  25                  30 gcg agg aaa agg agg tgt ctc gcg atg cgg tgc cag tgg act tcn tct      144
Ala Arg Lys Arg Arg Cys Leu Ala Met Arg Cys Gln Trp Thr Xaa Ser
        35                  40                  45 gcg cta gat tgg agg gag agc tgg aaa aat gcc gag aca gct tcg cac      192
Ala Leu Asp Trp Arg Glu Ser Trp Lys Asn Ala Glu Thr Ala Ser His
    50                  55                  60 gtc aca ttc ccg acg aaa cgc ccg cca tgaaggaaat cacagacatc             239
Val Thr Phe Pro Thr Lys Arg Pro Pro
65                  70 accaaccttc ccgccgtggc taaaggaccg tcctgtgtat gtacagtttt tccaggcgaa     299
agccgaagag acagcgaaac cgg                                             322
```

<210> SEQ ID NO 106
<211> LENGTH: 73
<212> TYPE: PRT
<213> ORGANISM: Toxoplasma gondii
<220> FEATURE:
<221> NAME/KEY: misc_feature
<222> LOCATION: (47)..(47)

-continued

<223> OTHER INFORMATION: The 'Xaa' at location 47 stands for Ser.

<400> SEQUENCE: 106

Arg Arg Asp Leu Arg Thr Ser Val Trp Asp Ala Arg Val Tyr Val His
1               5                   10                  15

Leu Ala Gly Gly Gln Arg Arg Cys Asn Glu Ser Arg Gly Met Glu Glu
            20                  25                  30

Ala Arg Lys Arg Cys Leu Ala Met Arg Cys Gln Trp Thr Xaa Ser
        35                  40                  45

Ala Leu Asp Trp Arg Glu Ser Trp Lys Asn Ala Glu Thr Ala Ser His
    50                  55                  60

Val Thr Phe Pro Thr Lys Arg Pro Pro
65                  70

<210> SEQ ID NO 107
<211> LENGTH: 390
<212> TYPE: DNA
<213> ORGANISM: Toxoplasma gondii
<220> FEATURE:
<221> NAME/KEY: CDS
<222> LOCATION: (1)..(201)
<223> OTHER INFORMATION:
<220> FEATURE:
<221> NAME/KEY: misc_feature
<222> LOCATION: (104)..(104)
<223> OTHER INFORMATION: At nucleotide 104, n = unknown
      At amino acid residue 35, Xaa = Lys, Arg, Thr or Ile

<400> SEQUENCE: 107 cgg cga atc ccc cag gaa ttg ttg aaa cag agt ctc aga ttc tac gga       48
Arg Arg Ile Pro Gln Glu Leu Leu Lys Gln Ser Leu Arg Phe Tyr Gly
1               5                   10                  15 ctc cga ggg cct ctg ctt gcc cgc cct gtg cac agg cgt cag cac gtg       96
Leu Arg Gly Pro Leu Leu Ala Arg Pro Val His Arg Arg Gln His Val
            20                  25                  30 gtt ctc ana gaa aaa gtt ggt aag tgg aag tgg tgg agc caa gaa aaa      144
Val Leu Xaa Glu Lys Val Gly Lys Trp Lys Trp Trp Ser Gln Glu Lys
        35                  40                  45 ctc aac tct tct tgt ttt ccg gag aat ttt cct ggt gtt caa ttc cac      192
Leu Asn Ser Ser Cys Phe Pro Glu Asn Phe Pro Gly Val Gln Phe His
    50                  55                  60 ggt tct gga tagtctttgt tgtattaaaa cacatctaga aggactgaga              241
Gly Ser Gly
65 cgttgtcggt agttgaatta cagacacttc gttttccagc gtcagcttgc atgcccgtcc    301 cctgtttctg gaacacaagc tttgagaagg aaacgagaca gagaacgacg aaggaagtga    361 agcaaatcct ctgacggatt tccattcgg                                      390

<210> SEQ ID NO 108
<211> LENGTH: 67
<212> TYPE: PRT
<213> ORGANISM: Toxoplasma gondii
<220> FEATURE:
<221> NAME/KEY: misc_feature
<222> LOCATION: (35)..(35)
<223> OTHER INFORMATION: The 'Xaa' at location 35 stands for Lys,
      Arg, Thr, or Ile.

<400> SEQUENCE: 108

Arg Arg Ile Pro Gln Glu Leu Leu Lys Gln Ser Leu Arg Phe Tyr Gly
1               5                   10                  15

Leu Arg Gly Pro Leu Leu Ala Arg Pro Val His Arg Arg Gln His Val

```
                    20                  25                  30
Val Leu Xaa Glu Lys Val Gly Lys Trp Lys Trp Trp Ser Gln Glu Lys
         35                  40                  45

Leu Asn Ser Ser Cys Phe Pro Glu Asn Phe Pro Gly Val Gln Phe His
     50                  55                  60

Gly Ser Gly
 65

<210> SEQ ID NO 109
<211> LENGTH: 699
<212> TYPE: DNA
<213> ORGANISM: Toxoplasma gondii
<220> FEATURE:
<221> NAME/KEY: CDS
<222> LOCATION: (1)..(699)
<223> OTHER INFORMATION:

<400> SEQUENCE: 109 ccg tgc gtc tgt gag gaa aag tgc aag aca ggg ccg aac tgt gac cag        48
Pro Cys Val Cys Glu Glu Lys Cys Lys Thr Gly Pro Asn Cys Asp Gln
 1               5                  10                  15 cat aaa ccg gag tgc tgt ggg tcg aac gac gac tgc cat cag cct cag        96
His Lys Pro Glu Cys Cys Gly Ser Asn Asp Asp Cys His Gln Pro Gln
             20                  25                  30 ggg tac tgc aag atg gac atg tcc aca tgc atc tgc cgt cca ggc ttc       144
Gly Tyr Cys Lys Met Asp Met Ser Thr Cys Ile Cys Arg Pro Gly Phe
         35                  40                  45 acg ggc gag aac tgc gga aca cgg gaa gat ctg tgc gca ggt gtg acg       192
Thr Gly Glu Asn Cys Gly Thr Arg Glu Asp Leu Cys Ala Gly Val Thr
     50                  55                  60 tgc aag aac ggc ggg aca tgc gac tcc gtc act ggc ctg tgc cag tgc       240
Cys Lys Asn Gly Gly Thr Cys Asp Ser Val Thr Gly Leu Cys Gln Cys
 65                  70                  75                  80 gat gcc tgc cac ggc ggg aag acc tgc gag att acg aag gaa cac tgc       288
Asp Ala Cys His Gly Gly Lys Thr Cys Glu Ile Thr Lys Glu His Cys
                 85                  90                  95 tgc atc aat gac agt gac tgc aac ggc cac ggc acc tgc aac acg agc       336
Cys Ile Asn Asp Ser Asp Cys Asn Gly His Gly Thr Cys Asn Thr Ser
            100                 105                 110 aac aat acc tgc aac tgc gag gca ggc ttc gct ggc acc aac tgc tcg       384
Asn Asn Thr Cys Asn Cys Glu Ala Gly Phe Ala Gly Thr Asn Cys Ser
        115                 120                 125 agc agc gaa ggc aag tgc agc ggc aag acc tgc ttg agt gga cac tgc       432
Ser Ser Glu Gly Lys Cys Ser Gly Lys Thr Cys Leu Ser Gly His Cys
    130                 135                 140 aat ccg gcg act ggc gca tgc gtc tgc gac ccg tgc cac acc ggc gag       480
Asn Pro Ala Thr Gly Ala Cys Val Cys Asp Pro Cys His Thr Gly Glu
145                 150                 155                 160 aga tgc gaa acg ctc gtc aag gac tgc tgt gtt gtg aac gac acg tgc       528
Arg Cys Glu Thr Leu Val Lys Asp Cys Cys Val Val Asn Asp Thr Cys
                165                 170                 175 aag ttc ccc aac ggc gtc tgc act gac agc aac agg tgt gag tgc cag       576
Lys Phe Pro Asn Gly Val Cys Thr Asp Ser Asn Arg Cys Glu Cys Gln
            180                 185                 190 agc ggc tgg ggc cag ggc gac tgc agc aaa cca gtc gac aag tgc gaa       624
Ser Gly Trp Gly Gln Gly Asp Cys Ser Lys Pro Val Asp Lys Cys Glu
        195                 200                 205 gac gtc agt tgc aac aac ggt tca tca tgc gac gcg gac tcc ggc aca       672
Asp Val Ser Cys Asn Asn Gly Ser Ser Cys Asp Ala Asp Ser Gly Thr
    210                 215                 220
```

```
tgc att tgc ccc cca ggc ttt gga gac                                    699
Cys Ile Cys Pro Pro Gly Phe Gly Asp
225                 230
```

<210> SEQ ID NO 110
<211> LENGTH: 233
<212> TYPE: PRT
<213> ORGANISM: Toxoplasma gondii

<400> SEQUENCE: 110

```
Pro Cys Val Cys Glu Glu Lys Cys Lys Thr Gly Pro Asn Cys Asp Gln
1               5                   10                  15

His Lys Pro Glu Cys Cys Gly Ser Asn Asp Asp Cys His Gln Pro Gln
            20                  25                  30

Gly Tyr Cys Lys Met Asp Met Ser Thr Cys Ile Cys Arg Pro Gly Phe
        35                  40                  45

Thr Gly Glu Asn Cys Gly Thr Arg Glu Asp Leu Cys Ala Gly Val Thr
    50                  55                  60

Cys Lys Asn Gly Gly Thr Cys Asp Ser Val Thr Gly Leu Cys Gln Cys
65                  70                  75                  80

Asp Ala Cys His Gly Lys Thr Cys Glu Ile Thr Lys Glu His Cys
                85                  90                  95

Cys Ile Asn Asp Ser Asp Cys Asn Gly His Gly Thr Cys Asn Thr Ser
            100                 105                 110

Asn Asn Thr Cys Asn Cys Glu Ala Gly Phe Ala Gly Thr Asn Cys Ser
        115                 120                 125

Ser Ser Glu Gly Lys Cys Ser Gly Lys Thr Cys Leu Ser Gly His Cys
    130                 135                 140

Asn Pro Ala Thr Gly Ala Cys Val Cys Asp Pro Cys His Thr Gly Glu
145                 150                 155                 160

Arg Cys Glu Thr Leu Val Lys Asp Cys Cys Val Val Asn Asp Thr Cys
                165                 170                 175

Lys Phe Pro Asn Gly Val Cys Thr Asp Ser Asn Arg Cys Glu Cys Gln
            180                 185                 190

Ser Gly Trp Gly Gln Gly Asp Cys Ser Lys Pro Val Asp Lys Cys Glu
        195                 200                 205

Asp Val Ser Cys Asn Asn Gly Ser Ser Cys Asp Ala Asp Ser Gly Thr
    210                 215                 220

Cys Ile Cys Pro Pro Gly Phe Gly Asp
225                 230
```

<210> SEQ ID NO 111
<211> LENGTH: 419
<212> TYPE: DNA
<213> ORGANISM: Toxoplasma gondii
<220> FEATURE:
<221> NAME/KEY: CDS
<222> LOCATION: (1)..(417)
<223> OTHER INFORMATION:

<400> SEQUENCE: 111

```
gag atg agc gcc cca gat agg caa aca gga aag ctt tcc gat tta ccg       48
Glu Met Ser Ala Pro Asp Arg Gln Thr Gly Lys Leu Ser Asp Leu Pro
1               5                   10                  15 cca ttt gct gag ctg cca cag ctg gca gaa ata cca aag ctc tcc gaa       96
Pro Phe Ala Glu Leu Pro Gln Leu Ala Glu Ile Pro Lys Leu Ser Glu
            20                  25                  30 ctt ccg aaa atc gcg gac atg ccg aaa ttt tcg gat atg ccc aag atg      144
Leu Pro Lys Ile Ala Asp Met Pro Lys Phe Ser Asp Met Pro Lys Met
```

```
gcc gag atg ccc aag tta tca gat ata ccc aag atg gct gag atg ccc       192
Ala Glu Met Pro Lys Leu Ser Asp Ile Pro Lys Met Ala Glu Met Pro
 50                  55                  60 aag tta tca gat ata ccc aag atg gct gag atg ccc aag tta tca gat       240
Lys Leu Ser Asp Ile Pro Lys Met Ala Glu Met Pro Lys Leu Ser Asp
 65                  70                  75                  80 ata ccc aag atg gct gag atg ccc aag ttt tca gat ata ccc aag atg       288
Ile Pro Lys Met Ala Glu Met Pro Lys Phe Ser Asp Ile Pro Lys Met
                 85                  90                  95 gct gag atg cca aag tta tca gat atg ccc aga atg gct gac att cca       336
Ala Glu Met Pro Lys Leu Ser Asp Met Pro Arg Met Ala Asp Ile Pro
            100                 105                 110 cag ttt cca gag atg cct agg atg gtt gac atg cct cag ttt cca gaa       384
Gln Phe Pro Glu Met Pro Arg Met Val Asp Met Pro Gln Phe Pro Glu
        115                 120                 125 atc ccc agg atg gct gat atg ccg caa ttt ccg cg                        419
Ile Pro Arg Met Ala Asp Met Pro Gln Phe Pro
    130                 135
```

<210> SEQ ID NO 112
<211> LENGTH: 139
<212> TYPE: PRT
<213> ORGANISM: Toxoplasma gondii

<400> SEQUENCE: 112

```
Glu Met Ser Ala Pro Asp Arg Gln Thr Gly Lys Leu Ser Asp Leu Pro
 1               5                  10                  15

Pro Phe Ala Glu Leu Pro Gln Leu Ala Glu Ile Pro Lys Leu Ser Glu
                20                  25                  30

Leu Pro Lys Ile Ala Asp Met Pro Lys Phe Ser Asp Met Pro Lys Met
            35                  40                  45

Ala Glu Met Pro Lys Leu Ser Asp Ile Pro Lys Met Ala Glu Met Pro
 50                  55                  60

Lys Leu Ser Asp Ile Pro Lys Met Ala Glu Met Pro Lys Leu Ser Asp
 65                  70                  75                  80

Ile Pro Lys Met Ala Glu Met Pro Lys Phe Ser Asp Ile Pro Lys Met
                 85                  90                  95

Ala Glu Met Pro Lys Leu Ser Asp Met Pro Arg Met Ala Asp Ile Pro
            100                 105                 110

Gln Phe Pro Glu Met Pro Arg Met Val Asp Met Pro Gln Phe Pro Glu
        115                 120                 125

Ile Pro Arg Met Ala Asp Met Pro Gln Phe Pro
    130                 135
```

<210> SEQ ID NO 113
<211> LENGTH: 303
<212> TYPE: DNA
<213> ORGANISM: Toxoplasma gondii
<220> FEATURE:
<221> NAME/KEY: CDS
<222> LOCATION: (1)..(303)
<223> OTHER INFORMATION:

<400> SEQUENCE: 113

```
gac gaa gct ctt cct ctc ttt gga gca aac ggt gga acc tca gtt cgg       48
Asp Glu Ala Leu Pro Leu Phe Gly Ala Asn Gly Gly Thr Ser Val Arg
 1               5                  10                  15 ctc tcc ctc gac cgc agc gtc ctg ctt gtt ctc gaa ccc gca gag ccc       96
Leu Ser Leu Asp Arg Ser Val Leu Leu Val Leu Glu Pro Ala Glu Pro
```

|     |     |     |     |     | 20  |     |     |     | 25  |     |     |     |     | 30  |     |     |
| --- | --- | --- | --- | --- | --- | --- | --- | --- | --- | --- | --- | --- | --- | --- | --- | --- |
| ctg | cta | tcc | tct | tgg | ccc | cac | ccg | ggg | aga | aga | gac | act | ttt | ctt | gaa | 144 |
| Leu | Leu | Ser | Ser | Trp | Pro | His | Pro | Gly | Arg | Arg | Asp | Thr | Phe | Leu | Glu |     |
|     |     | 35  |     |     |     |     | 40  |     |     |     |     | 45  |     |     |     |     |
| ggc | gat | ggc | gcg | ggc | atc | ccg | tct | cct | tca | tct | cgg | ccg | agt | cgc | gcg | 192 |
| Gly | Asp | Gly | Ala | Gly | Ile | Pro | Ser | Pro | Ser | Ser | Arg | Pro | Ser | Arg | Ala |     |
| 50  |     |     |     |     | 55  |     |     |     |     | 60  |     |     |     |     |     |     |
| gcc | gac | cat | tac | acg | aga | ctc | tcc | acg | att | cgg | tct | ctt | gcc | agg | gat | 240 |
| Ala | Asp | His | Tyr | Thr | Arg | Leu | Ser | Thr | Ile | Arg | Ser | Leu | Ala | Arg | Asp |     |
| 65  |     |     |     |     | 70  |     |     |     |     | 75  |     |     |     |     | 80  |     |
| gga | gag | gtc | gac | tcc | gag | ctg | gcg | ggg | gga | ccg | cag | gaa | aga | gaa | agt | 288 |
| Gly | Glu | Val | Asp | Ser | Glu | Leu | Ala | Gly | Gly | Pro | Gln | Glu | Arg | Glu | Ser |     |
|     |     |     |     | 85  |     |     |     |     | 90  |     |     |     |     | 95  |     |     |
| gtc | aga | gtg | gat | ccg |     |     |     |     |     |     |     |     |     |     |     | 303 |
| Val | Arg | Val | Asp | Pro |     |     |     |     |     |     |     |     |     |     |     |     |
|     |     |     |     | 100 |     |     |     |     |     |     |     |     |     |     |     |     |

<210> SEQ ID NO 114
<211> LENGTH: 101
<212> TYPE: PRT
<213> ORGANISM: Toxoplasma gondii

<400> SEQUENCE: 114

Asp Glu Ala Leu Pro Leu Phe Gly Ala Asn Gly Gly Thr Ser Val Arg
1               5                   10                  15

Leu Ser Leu Asp Arg Ser Val Leu Val Leu Glu Pro Ala Glu Pro
            20                  25                  30

Leu Leu Ser Ser Trp Pro His Pro Gly Arg Arg Asp Thr Phe Leu Glu
        35                  40                  45

Gly Asp Gly Ala Gly Ile Pro Ser Pro Ser Ser Arg Pro Ser Arg Ala
    50                  55                  60

Ala Asp His Tyr Thr Arg Leu Ser Thr Ile Arg Ser Leu Ala Arg Asp
65                  70                  75                  80

Gly Glu Val Asp Ser Glu Leu Ala Gly Gly Pro Gln Glu Arg Glu Ser
                85                  90                  95

Val Arg Val Asp Pro
            100

<210> SEQ ID NO 115
<211> LENGTH: 696
<212> TYPE: DNA
<213> ORGANISM: Toxoplasma gondii
<220> FEATURE:
<221> NAME/KEY: CDS
<222> LOCATION: (1)..(696)
<223> OTHER INFORMATION:

<400> SEQUENCE: 115

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cgc | ggt | aac | gaa | aaa | aca | tgc | tca | gat | gcc | aag | cat | cca | gtg | tac | atc | 48  |
| Arg | Gly | Asn | Glu | Lys | Thr | Cys | Ser | Asp | Ala | Lys | His | Pro | Val | Tyr | Ile |     |
| 1   |     |     |     | 5   |     |     |     |     | 10  |     |     |     |     | 15  |     |     |
| aaa | ctt | ggc | aaa | ggg | gaa | cgc | gag | gcc | gta | ttc | aag | tgt | ggc | gac | ggc | 96  |
| Lys | Leu | Gly | Lys | Gly | Glu | Arg | Glu | Ala | Val | Phe | Lys | Cys | Gly | Asp | Gly |     |
|     |     |     |     | 20  |     |     |     |     | 25  |     |     |     |     | 30  |     |     |
| ctc | act | act | ctt | gag | cca | tcg | cag | aac | aca | gat | aaa | cca | aaa | ttc | tgt | 144 |
| Leu | Thr | Thr | Leu | Glu | Pro | Ser | Gln | Asn | Thr | Asp | Lys | Pro | Lys | Phe | Cys |     |
|     |     |     | 35  |     |     |     |     | 40  |     |     |     |     | 45  |     |     |     |
| gaa | tcg | ata | gac | tgc | aac | gat | act | gca | gaa | ctt | gaa | aca | acg | ttc | cca | 192 |
| Glu | Ser | Ile | Asp | Cys | Asn | Asp | Thr | Ala | Glu | Leu | Glu | Thr | Thr | Phe | Pro |     |
|     | 50  |     |     |     |     | 55  |     |     |     |     | 60  |     |     |     |     |     |

```
ggg gcg tac tgg gac gag aga aac aaa aaa gcg aat ata tac aga ctg      240
Gly Ala Tyr Trp Asp Glu Arg Asn Lys Lys Ala Asn Ile Tyr Arg Leu
 65                  70                  75                  80 gtc att cct acc gtg agc aga aaa gac act cgg atg tat tat aaa tgt      288
Val Ile Pro Thr Val Ser Arg Lys Asp Thr Arg Met Tyr Tyr Lys Cys
                 85                  90                  95 aaa ggc act tcg gat tcc gcc gac cca tgc aca gta ctg ata aac gtg      336
Lys Gly Thr Ser Asp Ser Ala Asp Pro Cys Thr Val Leu Ile Asn Val
            100                 105                 110 aaa tct aca gag act gat gat gat gag gaa gag gac gtg cag gag tgc      384
Lys Ser Thr Glu Thr Asp Asp Asp Glu Glu Glu Asp Val Gln Glu Cys
        115                 120                 125 acg gtg ggc acc gag aag aaa gtc aca ctg tcc ccc acc gat acc gtg      432
Thr Val Gly Thr Glu Lys Lys Val Thr Leu Ser Pro Thr Asp Thr Val
    130                 135                 140 aaa ttc aag tgc aat ctc gga aca gtt gtg cag cca tca ttc tcc aca      480
Lys Phe Lys Cys Asn Leu Gly Thr Val Val Gln Pro Ser Phe Ser Thr
145                 150                 155                 160 gca act ccg aaa gtc ttt gac gac tcc gat ggc tcc tgc agt gca cag      528
Ala Thr Pro Lys Val Phe Asp Asp Ser Asp Gly Ser Cys Ser Ala Gln
                165                 170                 175 gct agc ctg acg tct ctg gta gat gcc tcg ctc acg gaa gac agt tca      576
Ala Ser Leu Thr Ser Leu Val Asp Ala Ser Leu Thr Glu Asp Ser Ser
            180                 185                 190 cat ggc aag tac aca atg tat acc atg aac ctg aac gca cgc cca gct      624
His Gly Lys Tyr Thr Met Tyr Thr Met Asn Leu Asn Ala Arg Pro Ala
        195                 200                 205 gag aca aag aat ctc tgt ctc caa tgt tcc tct gga aag cag aac tgc      672
Glu Thr Lys Asn Leu Cys Leu Gln Cys Ser Ser Gly Lys Gln Asn Cys
    210                 215                 220 aaa atg cgc atc cat gta ccc gcg                                      696
Lys Met Arg Ile His Val Pro Ala
225                 230

<210> SEQ ID NO 116
<211> LENGTH: 232
<212> TYPE: PRT
<213> ORGANISM: Toxoplasma gondii

<400> SEQUENCE: 116

Arg Gly Asn Glu Lys Thr Cys Ser Asp Ala Lys His Pro Val Tyr Ile
 1               5                  10                  15

Lys Leu Gly Lys Gly Glu Arg Glu Ala Val Phe Lys Cys Gly Asp Gly
                20                  25                  30

Leu Thr Thr Leu Glu Pro Ser Gln Asn Thr Asp Lys Pro Lys Phe Cys
            35                  40                  45

Glu Ser Ile Asp Cys Asn Asp Thr Ala Glu Leu Glu Thr Thr Phe Pro
        50                  55                  60

Gly Ala Tyr Trp Asp Glu Arg Asn Lys Lys Ala Asn Ile Tyr Arg Leu
 65                  70                  75                  80

Val Ile Pro Thr Val Ser Arg Lys Asp Thr Arg Met Tyr Tyr Lys Cys
                 85                  90                  95

Lys Gly Thr Ser Asp Ser Ala Asp Pro Cys Thr Val Leu Ile Asn Val
            100                 105                 110

Lys Ser Thr Glu Thr Asp Asp Asp Glu Glu Glu Asp Val Gln Glu Cys
        115                 120                 125

Thr Val Gly Thr Glu Lys Lys Val Thr Leu Ser Pro Thr Asp Thr Val
    130                 135                 140
```

```
Lys Phe Lys Cys Asn Leu Gly Thr Val Val Gln Pro Ser Phe Ser Thr
145                 150                 155                 160

Ala Thr Pro Lys Val Phe Asp Asp Ser Asp Gly Ser Cys Ser Ala Gln
            165                 170                 175

Ala Ser Leu Thr Ser Leu Val Asp Ala Ser Leu Thr Glu Asp Ser Ser
            180                 185                 190

His Gly Lys Tyr Thr Met Tyr Thr Met Asn Leu Asn Ala Arg Pro Ala
            195                 200                 205

Glu Thr Lys Asn Leu Cys Leu Gln Cys Ser Ser Gly Lys Gln Asn Cys
            210                 215                 220

Lys Met Arg Ile His Val Pro Ala
225                 230

<210> SEQ ID NO 117
<211> LENGTH: 173
<212> TYPE: DNA
<213> ORGANISM: Toxoplasma gondii
<220> FEATURE:
<221> NAME/KEY: CDS
<222> LOCATION: (1)..(171)
<223> OTHER INFORMATION:

<400> SEQUENCE: 117 act tgt gcg ggg gac ccc tcg gcc ttt ccg acg aag ctg ccg tcg aca      48
Thr Cys Ala Gly Asp Pro Ser Ala Phe Pro Thr Lys Leu Pro Ser Thr
1               5                   10                  15 cca ccc gct gct gtg ccg tct gac ggg ttg ctc gct ttg ccc tca gaa      96
Pro Pro Ala Ala Val Pro Ser Asp Gly Leu Leu Ala Leu Pro Ser Glu
            20                  25                  30 ctt gag gcg ccg gtg gag gac ggc gac cgc gag gct ttc gtt gga gtc     144
Leu Glu Ala Pro Val Glu Asp Gly Asp Arg Glu Ala Phe Val Gly Val
        35                  40                  45 gac ggc gcg gtc agc ggc tgg gac gag cg                              173
Asp Gly Ala Val Ser Gly Trp Asp Glu
    50                  55

<210> SEQ ID NO 118
<211> LENGTH: 57
<212> TYPE: PRT
<213> ORGANISM: Toxoplasma gondii

<400> SEQUENCE: 118

Thr Cys Ala Gly Asp Pro Ser Ala Phe Pro Thr Lys Leu Pro Ser Thr
1               5                   10                  15

Pro Pro Ala Ala Val Pro Ser Asp Gly Leu Leu Ala Leu Pro Ser Glu
            20                  25                  30

Leu Glu Ala Pro Val Glu Asp Gly Asp Arg Glu Ala Phe Val Gly Val
        35                  40                  45

Asp Gly Ala Val Ser Gly Trp Asp Glu
    50                  55

<210> SEQ ID NO 119
<211> LENGTH: 369
<212> TYPE: DNA
<213> ORGANISM: Toxoplasma gondii
<220> FEATURE:
<221> NAME/KEY: CDS
<222> LOCATION: (1)..(369)
<223> OTHER INFORMATION:

<400> SEQUENCE: 119 cgc tct gtg ttt cag gtc gcg agc gac gcg aga aac gcc cga cag gcg      48
```

| | | | | | | | | | | | | |
|---|---|---|---|---|---|---|---|---|---|---|---|---|
| Arg | Ser | Val | Phe | Gln | Val | Ala | Ser | Asp | Ala | Arg | Asn | Ala | Arg | Gln | Ala |
| 1 | | | | 5 | | | | | 10 | | | | | 15 | |

```
acc tcg ggc gtg ccg cgg cag agg gga aag aag gcc gtc acg gcg cga     96
Thr Ser Gly Val Pro Arg Gln Arg Gly Lys Lys Ala Val Thr Ala Arg
         20                  25                  30 gtc tct ttc ggc gct cta gag gag aga gac agt tcg agt tcg gac gtt    144
Val Ser Phe Gly Ala Leu Glu Glu Arg Asp Ser Ser Ser Ser Asp Val
     35                  40                  45 ccc gag gaa agg gat aaa gac gcc gaa aac ggc tct gcg cct cgc atc    192
Pro Glu Glu Arg Asp Lys Asp Ala Glu Asn Gly Ser Ala Pro Arg Ile
 50                  55                  60 ttc gcg tct tct tcc ctg acg cgg ctt tcg cct cct tct ctc tct ccg    240
Phe Ala Ser Ser Ser Leu Thr Arg Leu Ser Pro Pro Ser Leu Ser Pro
 65                  70                  75                  80 ctc tca agt tcg ggg cca tct tca ccg tct tct tcc gtt tcg cgg ttt    288
Leu Ser Ser Ser Gly Pro Ser Ser Pro Ser Ser Ser Val Ser Arg Phe
                 85                  90                  95 acc gac tcc ctg ccg cag tcg acg gct tcg tct cgt ctc tcc tct gct    336
Thr Asp Ser Leu Pro Gln Ser Thr Ala Ser Ser Arg Leu Ser Ser Ala
            100                 105                 110 tat tcg ctt gag tcg cgt cgg cct ctg gag ccg                        369
Tyr Ser Leu Glu Ser Arg Arg Pro Leu Glu Pro
        115                 120
```

<210> SEQ ID NO 120
<211> LENGTH: 123
<212> TYPE: PRT
<213> ORGANISM: Toxoplasma gondii

<400> SEQUENCE: 120

```
Arg Ser Val Phe Gln Val Ala Ser Asp Ala Arg Asn Ala Arg Gln Ala
 1               5                   10                  15

Thr Ser Gly Val Pro Arg Gln Arg Gly Lys Lys Ala Val Thr Ala Arg
             20                  25                  30

Val Ser Phe Gly Ala Leu Glu Glu Arg Asp Ser Ser Ser Ser Asp Val
         35                  40                  45

Pro Glu Glu Arg Asp Lys Asp Ala Glu Asn Gly Ser Ala Pro Arg Ile
     50                  55                  60

Phe Ala Ser Ser Ser Leu Thr Arg Leu Ser Pro Pro Ser Leu Ser Pro
 65                  70                  75                  80

Leu Ser Ser Ser Gly Pro Ser Ser Pro Ser Ser Ser Val Ser Arg Phe
                 85                  90                  95

Thr Asp Ser Leu Pro Gln Ser Thr Ala Ser Ser Arg Leu Ser Ser Ala
            100                 105                 110

Tyr Ser Leu Glu Ser Arg Arg Pro Leu Glu Pro
        115                 120
```

<210> SEQ ID NO 121
<211> LENGTH: 566
<212> TYPE: DNA
<213> ORGANISM: Toxoplasma gondii
<220> FEATURE:
<221> NAME/KEY: CDS
<222> LOCATION: (1)..(183)
<223> OTHER INFORMATION:

<400> SEQUENCE: 121

```
cgg cgg tgg atg acg ggt gct aat tac gag ggc cac cag gga caa tat     48
Arg Arg Trp Met Thr Gly Ala Asn Tyr Glu Gly His Gln Gly Gln Tyr
 1               5                   10                  15
```

-continued

```
ttg aac tac tgc acc att tct cac ttc ttg tgt tgc cct aat ggg atc        96
Leu Asn Tyr Cys Thr Ile Ser His Phe Leu Cys Cys Pro Asn Gly Ile
         20                  25                  30 tgt cgt ttt caa tgg gac aat cag ccc agt ctc gat agg gag gac tca       144
Cys Arg Phe Gln Trp Asp Asn Gln Pro Ser Leu Asp Arg Glu Asp Ser
 35                  40                  45 atc tgg tgc tct gaa tcg att tct cgt ttt cgc ctg agc taagataact        193
Ile Trp Cys Ser Glu Ser Ile Ser Arg Phe Arg Leu Ser
 50                  55                  60 gctgaagaca tttgtagacg ctttctacaa acccacgtgg caaaatctta cggaaggaca     253
aatgcctctt tcaacactct tctttcatcg ctgcttgtta cactcctgag aggccccaag     313
agccacggtg ccactttgct tccccagccg ctactgtgca aattctttat agaagagcac     373
aaatgttccc cgaagaagca gcagcaccct tgaggagcc tgaagagcga ccctacgaat      433
cacagcgttc agaaatagcc tactgtagta ttaaggagac taccaaagtg aaaatcgtga     493
tatgtctaca ggtggtatgc aagtgttggt tttccagata tacgctgcaa ctaaaacacc     553
aaaatgatag aat                                                        566
```

<210> SEQ ID NO 122
<211> LENGTH: 61
<212> TYPE: PRT
<213> ORGANISM: Toxoplasma gondii

<400> SEQUENCE: 122

```
Arg Arg Trp Met Thr Gly Ala Asn Tyr Glu Gly His Gln Gly Gln Tyr
 1               5                  10                  15

Leu Asn Tyr Cys Thr Ile Ser His Phe Leu Cys Cys Pro Asn Gly Ile
         20                  25                  30

Cys Arg Phe Gln Trp Asp Asn Gln Pro Ser Leu Asp Arg Glu Asp Ser
 35                  40                  45

Ile Trp Cys Ser Glu Ser Ile Ser Arg Phe Arg Leu Ser
 50                  55                  60
```

<210> SEQ ID NO 123
<211> LENGTH: 616
<212> TYPE: DNA
<213> ORGANISM: Toxoplasma gondii
<220> FEATURE:
<221> NAME/KEY: CDS
<222> LOCATION: (1)..(615)
<223> OTHER INFORMATION:

<400> SEQUENCE: 123

```
cac gag cgc cgt gtg gca gag caa aag gct cgt gaa gaa cgc gag aga        48
His Glu Arg Arg Val Ala Glu Gln Lys Ala Arg Glu Glu Arg Glu Arg
 1               5                  10                  15 cag gca gca tct cag cga aac gga tcg aca gaa ccc gct gtt gct ccc        96
Gln Ala Ala Ser Gln Arg Asn Gly Ser Thr Glu Pro Ala Val Ala Pro
         20                  25                  30 tcc tct tgt tcc tcc agc aac tca cag aac cct ccg caa gat tcc tcg       144
Ser Ser Cys Ser Ser Ser Asn Ser Gln Asn Pro Pro Gln Asp Ser Ser
 35                  40                  45 cac gtc tgc tgt ccc tcc tcc tct gcc ttc tcc cag ccg cgc tct tct       192
His Val Cys Cys Pro Ser Ser Ser Ala Phe Ser Gln Pro Arg Ser Ser
 50                  55                  60 ctg tcc tca tcc tca ccc tct tcg tct gcc gcg tta cca tcg ggg tct       240
Leu Ser Ser Ser Ser Pro Ser Ser Ala Ala Leu Pro Ser Gly Ser
 65                  70                  75                  80 tct ccc tcg gct gcg tct tcg tct cat gca ctt ggg gtg gtg gac tcg       288
Ser Pro Ser Ala Ala Ser Ser Ser His Ala Leu Gly Val Val Asp Ser
```

```
Ser Pro Ser Ala Ala Ser Ser His Ala Leu Gly Val Val Asp Ser
                85                  90                  95 gac cgg att tct gcg gag gag gcg gcg tcc ctc gag gag gcc cgg cgg      336
Asp Arg Ile Ser Ala Glu Glu Ala Ala Ser Leu Glu Glu Ala Arg Arg
                100                 105                 110 ctg cag aga cag ttc gag gcg gaa atg gtg ggc att cga ccg cca gac      384
Leu Gln Arg Gln Phe Glu Ala Glu Met Val Gly Ile Arg Pro Pro Asp
            115                 120                 125 gac acc tac gag gaa acg ctg att tct gag gac atc cat cct tcc cac      432
Asp Thr Tyr Glu Glu Thr Leu Ile Ser Glu Asp Ile His Pro Ser His
        130                 135                 140 cga gcc tgg tgg gaa aga cct agc gcc tcg ccg att cgt ctg tcg cgc      480
Arg Ala Trp Trp Glu Arg Pro Ser Ala Ser Pro Ile Arg Leu Ser Arg
145                 150                 155                 160 gcg gcg tcg atg aga agt gac ggt cgc aga ggt caa cag ccc ccg agt      528
Ala Ala Ser Met Arg Ser Asp Gly Arg Arg Gly Gln Gln Pro Pro Ser
                165                 170                 175 cga cag tct cct cag gac ggg gag gaa gac gac gcc gct ctc gcc aga      576
Arg Gln Ser Pro Gln Asp Gly Glu Glu Asp Asp Ala Ala Leu Ala Arg
            180                 185                 190 cga ctt cag gaa gaa gaa tac agc cga cat cga gag gtc g                616
Arg Leu Gln Glu Glu Glu Tyr Ser Arg His Arg Glu Val
        195                 200                 205

<210> SEQ ID NO 124
<211> LENGTH: 205
<212> TYPE: PRT
<213> ORGANISM: Toxoplasma gondii

<400> SEQUENCE: 124

His Glu Arg Arg Val Ala Glu Gln Lys Ala Arg Glu Glu Arg Glu Arg
1               5                   10                  15

Gln Ala Ala Ser Gln Arg Asn Gly Ser Thr Glu Pro Ala Val Ala Pro
            20                  25                  30

Ser Ser Cys Ser Ser Ser Asn Ser Gln Asn Pro Pro Gln Asp Ser Ser
        35                  40                  45

His Val Cys Cys Pro Ser Ser Ser Ala Phe Ser Gln Pro Arg Ser Ser
    50                  55                  60

Leu Ser Ser Ser Ser Pro Ser Ser Ala Ala Leu Pro Ser Gly Ser
65                  70                  75                  80

Ser Pro Ser Ala Ala Ser Ser Ser His Ala Leu Gly Val Val Asp Ser
                85                  90                  95

Asp Arg Ile Ser Ala Glu Glu Ala Ala Ser Leu Glu Glu Ala Arg Arg
                100                 105                 110

Leu Gln Arg Gln Phe Glu Ala Glu Met Val Gly Ile Arg Pro Pro Asp
            115                 120                 125

Asp Thr Tyr Glu Glu Thr Leu Ile Ser Glu Asp Ile His Pro Ser His
        130                 135                 140

Arg Ala Trp Trp Glu Arg Pro Ser Ala Ser Pro Ile Arg Leu Ser Arg
145                 150                 155                 160

Ala Ala Ser Met Arg Ser Asp Gly Arg Arg Gly Gln Gln Pro Pro Ser
                165                 170                 175

Arg Gln Ser Pro Gln Asp Gly Glu Glu Asp Asp Ala Ala Leu Ala Arg
            180                 185                 190

Arg Leu Gln Glu Glu Glu Tyr Ser Arg His Arg Glu Val
        195                 200                 205
```

<210> SEQ ID NO 125
<211> LENGTH: 762
<212> TYPE: DNA
<213> ORGANISM: Toxoplasma gondii
<220> FEATURE:
<221> NAME/KEY: CDS
<222> LOCATION: (1)..(762)
<223> OTHER INFORMATION:

<400> SEQUENCE: 125

```
cgg gat cag gct cct aag cca gtg ccc gag gca gcc gac gaa ttt gac      48
Arg Asp Gln Ala Pro Lys Pro Val Pro Glu Ala Ala Asp Glu Phe Asp
1               5                   10                  15 cag gct cct atg cca ctg ccc gaa gca ccc gaa gac ttt gac cag gct      96
Gln Ala Pro Met Pro Leu Pro Glu Ala Pro Glu Asp Phe Asp Gln Ala
            20                  25                  30 cct gag cca ctg cgc gag gca gcc gaa gaa ttt gac cag gct cct atg     144
Pro Glu Pro Leu Arg Glu Ala Ala Glu Glu Phe Asp Gln Ala Pro Met
        35                  40                  45 cca gtg ccc gag gca ccc gaa gac ttt gac cag att cct aag cca gtg     192
Pro Val Pro Glu Ala Pro Glu Asp Phe Asp Gln Ile Pro Lys Pro Val
    50                  55                  60 ccc gag gca ccc gaa gaa ttt gac cag gct cct atg cca gtg ccc gag     240
Pro Glu Ala Pro Glu Glu Phe Asp Gln Ala Pro Met Pro Val Pro Glu
65                  70                  75                  80 gca ccc gaa gac ttt gac cag att cct aag cca gtg ccc gag gca ccc     288
Ala Pro Glu Asp Phe Asp Gln Ile Pro Lys Pro Val Pro Glu Ala Pro
                85                  90                  95 gaa gaa ttt gac cag gct cct atg cca ctc ccc gaa gca ccc gaa gaa     336
Glu Glu Phe Asp Gln Ala Pro Met Pro Leu Pro Glu Ala Pro Glu Glu
            100                 105                 110 tcc gag cag gct cct gag cca ctg ccc gag gca ccc gaa gaa tcc gag     384
Ser Glu Gln Ala Pro Glu Pro Leu Pro Glu Ala Pro Glu Glu Ser Glu
        115                 120                 125 cag gct cct gag cca ctg ccc gag gca ccc gaa gaa tcc gag cag gct     432
Gln Ala Pro Glu Pro Leu Pro Glu Ala Pro Glu Glu Ser Glu Gln Ala
    130                 135                 140 cct gag cca ctg ccc gag gca ccc gaa gaa tcc gag cag gct cct gag     480
Pro Glu Pro Leu Pro Glu Ala Pro Glu Glu Ser Glu Gln Ala Pro Glu
145                 150                 155                 160 cca ctg ccc gag gca ccc gaa gaa tcc gag cag gct cct gag cca ctg     528
Pro Leu Pro Glu Ala Pro Glu Glu Ser Glu Gln Ala Pro Glu Pro Leu
                165                 170                 175 ccc gag gca ccc gaa gaa ttt gac cag gct cct atg cca ctg ccc gcg     576
Pro Glu Ala Pro Glu Glu Phe Asp Gln Ala Pro Met Pro Leu Pro Ala
            180                 185                 190 gcc ccc gaa gac ttt gac cag cct gct atg cca ctg ccc ccg gcc ccc     624
Ala Pro Glu Asp Phe Asp Gln Pro Ala Met Pro Leu Pro Pro Ala Pro
        195                 200                 205 gaa gac ttt gac cag gct ccc atg cca ctg ccg cag gca ccc gaa gaa     672
Glu Asp Phe Asp Gln Ala Pro Met Pro Leu Pro Gln Ala Pro Glu Glu
    210                 215                 220 ctc gag cag gct ccc gct tcc acc ccg agg agg cgg agc agg agg tgc     720
Leu Glu Gln Ala Pro Ala Ser Thr Pro Arg Arg Arg Ser Arg Arg Cys
225                 230                 235                 240 ctg aga gaa aaa ctg acg cag gaa gtg aac ctg aga agg atc             762
Leu Arg Glu Lys Leu Thr Gln Glu Val Asn Leu Arg Arg Ile
                245                 250
```

<210> SEQ ID NO 126
<211> LENGTH: 254
<212> TYPE: PRT

-continued

```
<213> ORGANISM: Toxoplasma gondii

<400> SEQUENCE: 126

Arg Asp Gln Ala Pro Lys Pro Val Pro Glu Ala Ala Asp Glu Phe Asp
 1               5                  10                  15

Gln Ala Pro Met Pro Leu Pro Glu Ala Pro Glu Asp Phe Asp Gln Ala
            20                  25                  30

Pro Glu Pro Leu Arg Glu Ala Ala Glu Glu Phe Asp Gln Ala Pro Met
        35                  40                  45

Pro Val Pro Glu Ala Pro Glu Asp Phe Asp Gln Ile Pro Lys Pro Val
    50                  55                  60

Pro Glu Ala Pro Glu Glu Phe Asp Gln Ala Pro Met Pro Val Pro Glu
65                  70                  75                  80

Ala Pro Glu Asp Phe Asp Gln Ile Pro Lys Pro Val Pro Glu Ala Pro
                85                  90                  95

Glu Glu Phe Asp Gln Ala Pro Met Pro Leu Pro Glu Ala Pro Glu Glu
            100                 105                 110

Ser Glu Gln Ala Pro Glu Pro Leu Pro Glu Ala Pro Glu Ser Glu
        115                 120                 125

Gln Ala Pro Glu Pro Leu Pro Glu Ala Pro Glu Glu Ser Gln Ala
    130                 135                 140

Pro Glu Pro Leu Pro Glu Ala Pro Glu Glu Ser Gln Ala Pro Glu
145                 150                 155                 160

Pro Leu Pro Glu Ala Pro Glu Glu Ser Glu Gln Ala Pro Glu Pro Leu
                165                 170                 175

Pro Glu Ala Pro Glu Glu Phe Asp Gln Ala Pro Met Pro Leu Pro Ala
            180                 185                 190

Ala Pro Glu Asp Phe Asp Gln Pro Ala Met Pro Leu Pro Pro Ala Pro
        195                 200                 205

Glu Asp Phe Asp Gln Ala Pro Met Pro Leu Pro Gln Ala Pro Glu Glu
    210                 215                 220

Leu Glu Gln Ala Pro Ala Ser Thr Pro Arg Arg Arg Ser Arg Arg Cys
225                 230                 235                 240

Leu Arg Glu Lys Leu Thr Gln Glu Val Asn Leu Arg Arg Ile
                245                 250

<210> SEQ ID NO 127
<211> LENGTH: 236
<212> TYPE: DNA
<213> ORGANISM: Toxoplasma gondii
<220> FEATURE:
<221> NAME/KEY: CDS
<222> LOCATION: (1)..(234)
<223> OTHER INFORMATION:

<400> SEQUENCE: 127 cgc gga gag ggg gag act gag aga ggg cag aat gag gag act cac gca    48
Arg Gly Glu Gly Glu Thr Glu Arg Gly Gln Asn Glu Glu Thr His Ala
 1               5                  10                  15 acg aac aag tcc tca ggc gtc gcc agt ttg gag gca cca gcg tcg ttc    96
Thr Asn Lys Ser Ser Gly Val Ala Ser Leu Glu Ala Pro Ala Ser Phe
            20                  25                  30 gcg cag gag ggc gac gga ggg cgg aga gaa gaa gca agc caa gca aaa   144
Ala Gln Glu Gly Asp Gly Gly Arg Arg Glu Glu Ala Ser Gln Ala Lys
        35                  40                  45 atg ggg acg tct ccc ccg tcg aat cag gtg atc aac gtt gta gac gaa   192
Met Gly Thr Ser Pro Pro Ser Asn Gln Val Ile Asn Val Val Asp Glu
    50                  55                  60
```

```
gac gag gag gac gac gag gaa gca gag gcg cta gag gct ccc gg         236
Asp Glu Glu Asp Asp Glu Glu Ala Glu Ala Leu Glu Ala Pro
 65                  70                  75
```

<210> SEQ ID NO 128
<211> LENGTH: 78
<212> TYPE: PRT
<213> ORGANISM: Toxoplasma gondii

<400> SEQUENCE: 128

```
Arg Gly Glu Gly Glu Thr Glu Arg Gly Gln Asn Glu Glu Thr His Ala
  1               5                  10                  15

Thr Asn Lys Ser Ser Gly Val Ala Ser Leu Glu Ala Pro Ala Ser Phe
                 20                  25                  30

Ala Gln Glu Gly Asp Gly Gly Arg Arg Glu Glu Ala Ser Gln Ala Lys
             35                  40                  45

Met Gly Thr Ser Pro Pro Ser Asn Gln Val Ile Asn Val Val Asp Glu
         50                  55                  60

Asp Glu Glu Asp Asp Glu Glu Ala Glu Ala Leu Glu Ala Pro
 65                  70                  75
```

<210> SEQ ID NO 129
<211> LENGTH: 569
<212> TYPE: DNA
<213> ORGANISM: Toxoplasma gondii
<220> FEATURE:
<221> NAME/KEY: CDS
<222> LOCATION: (1)..(567)
<223> OTHER INFORMATION:

<400> SEQUENCE: 129

```
cga tct cgt ttt ggt cct gag caa ttc gct att tcg gat gtc tca ggc      48
Arg Ser Arg Phe Gly Pro Glu Gln Phe Ala Ile Ser Asp Val Ser Gly
  1               5                  10                  15 aca ctt gtt aat gca agc tgg ctt ggt gcc tct gca ggg gag act atc      96
Thr Leu Val Asn Ala Ser Trp Leu Gly Ala Ser Ala Gly Glu Thr Ile
                 20                  25                  30 gct gat tca agg gct tta agg cgt gac cta tca ttc cca ctg tct agt     144
Ala Asp Ser Arg Ala Leu Arg Arg Asp Leu Ser Phe Pro Leu Ser Ser
             35                  40                  45 cgt caa ctg cga gaa cgt ggc ctt gct tct caa gat tcc tca ctt tca     192
Arg Gln Leu Arg Glu Arg Gly Leu Ala Ser Gln Asp Ser Ser Leu Ser
         50                  55                  60 agc act cca aaa ttg tcc ctg caa cac gac cac ttt gca aag act ctg     240
Ser Thr Pro Lys Leu Ser Leu Gln His Asp His Phe Ala Lys Thr Leu
 65                  70                  75                  80 gta aaa cga aga gcg ctg tct gca acg aac tcc aca gaa cgc agc ggc     288
Val Lys Arg Arg Ala Leu Ser Ala Thr Asn Ser Thr Glu Arg Ser Gly
                 85                  90                  95 aaa cca gtt cgt tgc ttt act gaa acc agc gtg agg tta ggt gca cct     336
Lys Pro Val Arg Cys Phe Thr Glu Thr Ser Val Arg Leu Gly Ala Pro
            100                 105                 110 act caa ccg gta atg gag gaa atg cct ttg gga gaa gga gag gta aat     384
Thr Gln Pro Val Met Glu Glu Met Pro Leu Gly Glu Gly Glu Val Asn
        115                 120                 125 ctg gtc tcc gaa cac gac gat tat gca gaa tcc acc agt cat ctg gat     432
Leu Val Ser Glu His Asp Asp Tyr Ala Glu Ser Thr Ser His Leu Asp
    130                 135                 140 acg gtg aat ggg aga gaa aga aga gag gaa agg cat tac gcg gag acg     480
Thr Val Asn Gly Arg Glu Arg Arg Glu Glu Arg His Tyr Ala Glu Thr
145                 150                 155                 160
```

```
gag gcg aca gac gaa ttc aaa tcc gca atg cac cac gtg acg tcg ccc      528
Glu Ala Thr Asp Glu Phe Lys Ser Ala Met His His Val Thr Ser Pro
            165                 170                 175 gga ggg gta ccc gca acg aaa aag gtg gtg tgg aag atc cg               569
Gly Gly Val Pro Ala Thr Lys Lys Val Val Trp Lys Ile
        180                 185
```

<210> SEQ ID NO 130
<211> LENGTH: 189
<212> TYPE: PRT
<213> ORGANISM: Toxoplasma gondii

<400> SEQUENCE: 130

```
Arg Ser Arg Phe Gly Pro Glu Gln Phe Ala Ile Ser Asp Val Ser Gly
  1               5                  10                  15

Thr Leu Val Asn Ala Ser Trp Leu Gly Ala Ser Ala Gly Glu Thr Ile
             20                  25                  30

Ala Asp Ser Arg Ala Leu Arg Arg Asp Leu Ser Phe Pro Leu Ser Ser
         35                  40                  45

Arg Gln Leu Arg Glu Arg Gly Leu Ala Ser Gln Asp Ser Ser Leu Ser
     50                  55                  60

Ser Thr Pro Lys Leu Ser Leu Gln His Asp His Phe Ala Lys Thr Leu
 65                  70                  75                  80

Val Lys Arg Arg Ala Leu Ser Ala Thr Asn Ser Thr Glu Arg Ser Gly
                 85                  90                  95

Lys Pro Val Arg Cys Phe Thr Glu Thr Ser Val Arg Leu Gly Ala Pro
            100                 105                 110

Thr Gln Pro Val Met Glu Glu Met Pro Leu Gly Glu Gly Glu Val Asn
        115                 120                 125

Leu Val Ser Glu His Asp Asp Tyr Ala Glu Ser Thr Ser His Leu Asp
    130                 135                 140

Thr Val Asn Gly Arg Glu Arg Arg Glu Glu Arg His Tyr Ala Glu Thr
145                 150                 155                 160

Glu Ala Thr Asp Glu Phe Lys Ser Ala Met His His Val Thr Ser Pro
                165                 170                 175

Gly Gly Val Pro Ala Thr Lys Lys Val Val Trp Lys Ile
            180                 185
```

<210> SEQ ID NO 131
<211> LENGTH: 232
<212> TYPE: DNA
<213> ORGANISM: Toxoplasma gondii

<400> SEQUENCE: 131

```
cggcgactca gatgggagtg agaaagatgc aaacaggtgc tgaaaaaaca ccacttaata     60
gaggagacaa accccggtgg agaaagcgaa acgagactgg aacggcaacg aaatagagaa    120
gacacagccc caaactcccg acagcgtgtt gctctgtcgg gcaggcaggc caagctggca    180
agccgctagc atgccacgtg ctgtactgct ggcccgaaac tacagtgcgc ac            232
```

<210> SEQ ID NO 132
<211> LENGTH: 276
<212> TYPE: DNA
<213> ORGANISM: Toxoplasma gondii
<220> FEATURE:
<221> NAME/KEY: CDS
<222> LOCATION: (1)..(276)
<223> OTHER INFORMATION:

```
<400> SEQUENCE: 132 ccc gga att ccg gct ccg ggt cgc aaa gcg atc cat ttg ata aaa gac      48
Pro Gly Ile Pro Ala Pro Gly Arg Lys Ala Ile His Leu Ile Lys Asp
1               5                   10                  15 tgc gtt ttc tgc ctt ggg gaa ctc ttc ttg aat ggc acg aga ggc cac      96
Cys Val Phe Cys Leu Gly Glu Leu Phe Leu Asn Gly Thr Arg Gly His
            20                  25                  30 aga cag aga gag agg gag gga aag cca aag aag caa aca ggc tcg gaa     144
Arg Gln Arg Glu Arg Glu Gly Lys Pro Lys Lys Gln Thr Gly Ser Glu
        35                  40                  45 gcg ccc aga ata cag gca gcc tct ccg aag tca ctc acc ttg tac gat     192
Ala Pro Arg Ile Gln Ala Ala Ser Pro Lys Ser Leu Thr Leu Tyr Asp
    50                  55                  60 ctt gtg cac agt gat gta ggg cgc atg cag aac gac gcc tcc aac atg     240
Leu Val His Ser Asp Val Gly Arg Met Gln Asn Asp Ala Ser Asn Met
65                  70                  75                  80 aat att ctc ctc ggc caa ggc cgc cgc caa gta gcg                     276
Asn Ile Leu Leu Gly Gln Gly Arg Arg Gln Val Ala
                85                  90

<210> SEQ ID NO 133
<211> LENGTH: 92
<212> TYPE: PRT
<213> ORGANISM: Toxoplasma gondii

<400> SEQUENCE: 133

Pro Gly Ile Pro Ala Pro Gly Arg Lys Ala Ile His Leu Ile Lys Asp
1               5                   10                  15

Cys Val Phe Cys Leu Gly Glu Leu Phe Leu Asn Gly Thr Arg Gly His
            20                  25                  30

Arg Gln Arg Glu Arg Glu Gly Lys Pro Lys Lys Gln Thr Gly Ser Glu
        35                  40                  45

Ala Pro Arg Ile Gln Ala Ala Ser Pro Lys Ser Leu Thr Leu Tyr Asp
    50                  55                  60

Leu Val His Ser Asp Val Gly Arg Met Gln Asn Asp Ala Ser Asn Met
65                  70                  75                  80

Asn Ile Leu Leu Gly Gln Gly Arg Arg Gln Val Ala
                85                  90

<210> SEQ ID NO 134
<211> LENGTH: 309
<212> TYPE: DNA
<213> ORGANISM: Toxoplasma gondii
<220> FEATURE:
<221> NAME/KEY: CDS
<222> LOCATION: (1)..(309)
<223> OTHER INFORMATION:

<400> SEQUENCE: 134 cgc gga cac act gga gag agg tgg tcg gac agg gag gga gaa tcc gag      48
Arg Gly His Thr Gly Glu Arg Trp Ser Asp Arg Glu Gly Glu Ser Glu
1               5                   10                  15 atg tgc agt gga gga caa atg gaa aag aga gag agc cga cgc gtt tct      96
Met Cys Ser Gly Gly Gln Met Glu Lys Arg Glu Ser Arg Arg Val Ser
            20                  25                  30 ttt gcg gat gaa gag atg cgg aat ccg aca gaa aac ctg aag gta gat     144
Phe Ala Asp Glu Glu Met Arg Asn Pro Thr Glu Asn Leu Lys Val Asp
        35                  40                  45 gcc aac tgt gtg ctc gaa ggt ctg tcc acc tca gtg tgt gcg agg cgg     192
Ala Asn Cys Val Leu Glu Gly Leu Ser Thr Ser Val Cys Ala Arg Arg
    50                  55                  60
```

-continued

```
ctg aag agg caa aag cga act gca ggt cag tct ggc ttc ctc gca ata      240
Leu Lys Arg Gln Lys Arg Thr Ala Gly Gln Ser Gly Phe Leu Ala Ile
 65                  70                  75                  80 cga aac gtc caa ggc acc gcg acc gcc cta aaa cac cct gat tcc aca      288
Arg Asn Val Gln Gly Thr Ala Thr Ala Leu Lys His Pro Asp Ser Thr
                 85                  90                  95 gga cga cgg tct tgg gat ccg                                          309
Gly Arg Arg Ser Trp Asp Pro
            100
```

<210> SEQ ID NO 135
<211> LENGTH: 103
<212> TYPE: PRT
<213> ORGANISM: Toxoplasma gondii

<400> SEQUENCE: 135

```
Arg Gly His Thr Gly Glu Arg Trp Ser Asp Arg Glu Gly Glu Ser Glu
  1               5                  10                  15

Met Cys Ser Gly Gly Gln Met Glu Lys Arg Glu Ser Arg Arg Val Ser
                 20                  25                  30

Phe Ala Asp Glu Glu Met Arg Asn Pro Thr Glu Asn Leu Lys Val Asp
             35                  40                  45

Ala Asn Cys Val Leu Glu Gly Leu Ser Thr Ser Val Cys Ala Arg Arg
         50                  55                  60

Leu Lys Arg Gln Lys Arg Thr Ala Gly Gln Ser Gly Phe Leu Ala Ile
 65                  70                  75                  80

Arg Asn Val Gln Gly Thr Ala Thr Ala Leu Lys His Pro Asp Ser Thr
                 85                  90                  95

Gly Arg Arg Ser Trp Asp Pro
            100
```

<210> SEQ ID NO 136
<211> LENGTH: 534
<212> TYPE: DNA
<213> ORGANISM: Toxoplasma gondii
<220> FEATURE:
<221> NAME/KEY: CDS
<222> LOCATION: (1)..(534)
<223> OTHER INFORMATION:

<400> SEQUENCE: 136

```
cgg atc gag gct gaa atc gct agg cag aag gag cgg gaa gcc aaa ctg       48
Arg Ile Glu Ala Glu Ile Ala Arg Gln Lys Glu Arg Glu Ala Lys Leu
  1               5                  10                  15 cgt cgc agg ctt gct gcg gtc gtg gcc tca atg ctg gta gca gcg agc       96
Arg Arg Arg Leu Ala Ala Val Val Ala Ser Met Leu Val Ala Ala Ser
                 20                  25                  30 ctc tac ggc ttg aac tcg ttc ctc cac ggt tct gac aag gag att tct      144
Leu Tyr Gly Leu Asn Ser Phe Leu His Gly Ser Asp Lys Glu Ile Ser
             35                  40                  45 tcg atg cca tcc tct atc gac aaa aaa cca gat tcc ccc ttt gcc gca      192
Ser Met Pro Ser Ser Ile Asp Lys Lys Pro Asp Ser Pro Phe Ala Ala
         50                  55                  60 cag ctg ggc acc tcg ctc gag tca gaa att ggt ata ccc gaa gaa aaa      240
Gln Leu Gly Thr Ser Leu Glu Ser Glu Ile Gly Ile Pro Glu Glu Lys
 65                  70                  75                  80 gca att cct gag gcg gcc gac ata agc agt ttt att gag aat ctt tcc      288
Ala Ile Pro Glu Ala Ala Asp Ile Ser Ser Phe Ile Glu Asn Leu Ser
                 85                  90                  95 gcg acg gtg gca ggc aat tct gtg caa gcc cag agc atc ggc ttt gtg      336
```

```
Ala Thr Val Ala Gly Asn Ser Val Gln Ala Gln Ser Ile Gly Phe Val
            100                 105                 110 ttg aca gtt gtt gta ctt ggt ctt gtc gcc ttc tca ctc aag gct gct         384
Leu Thr Val Val Val Leu Gly Leu Val Ala Phe Ser Leu Lys Ala Ala
        115                 120                 125 cga cgt tcc tcg cca aga gag gag cag gca ttc agc ctg ccg gca cac         432
Arg Arg Ser Ser Pro Arg Glu Glu Gln Ala Phe Ser Leu Pro Ala His
130                 135                 140 ccg cct cgc gag gaa aaa tca aaa tac ctg ctg aag ccg ccc cag cag         480
Pro Pro Arg Glu Glu Lys Ser Lys Tyr Leu Leu Lys Pro Pro Gln Gln
145                 150                 155                 160 ccc aag ccc agg cgg ctc aaa agg cag ctc cgc aag tac cga caa agg         528
Pro Lys Pro Arg Arg Leu Lys Arg Gln Leu Arg Lys Tyr Arg Gln Arg
                165                 170                 175 gtg ctg                                                                 534
Val Leu
```

<210> SEQ ID NO 137
<211> LENGTH: 178
<212> TYPE: PRT
<213> ORGANISM: Toxoplasma gondii

<400> SEQUENCE: 137

```
Arg Ile Glu Ala Glu Ile Ala Arg Gln Lys Gly Arg Glu Ala Lys Leu
1               5                   10                  15

Arg Arg Arg Leu Ala Ala Val Val Ala Ser Met Leu Val Ala Ala Ser
            20                  25                  30

Leu Tyr Gly Leu Asn Ser Phe Leu His Gly Ser Asp Lys Glu Ile Ser
        35                  40                  45

Ser Met Pro Ser Ser Ile Asp Lys Lys Pro Asp Ser Pro Phe Ala Ala
    50                  55                  60

Gln Leu Gly Thr Ser Leu Glu Ser Glu Ile Gly Ile Pro Glu Glu Lys
65                  70                  75                  80

Ala Ile Pro Glu Ala Ala Asp Ile Ser Ser Phe Ile Glu Asn Leu Ser
                85                  90                  95

Ala Thr Val Ala Gly Asn Ser Val Gln Ala Gln Ser Ile Gly Phe Val
            100                 105                 110

Leu Thr Val Val Val Leu Gly Leu Val Ala Phe Ser Leu Lys Ala Ala
        115                 120                 125

Arg Arg Ser Ser Pro Arg Glu Glu Gln Ala Phe Ser Leu Pro Ala His
    130                 135                 140

Pro Pro Arg Glu Glu Lys Ser Lys Tyr Leu Leu Lys Pro Pro Gln Gln
145                 150                 155                 160

Pro Lys Pro Arg Arg Leu Lys Arg Gln Leu Arg Lys Tyr Arg Gln Arg
                165                 170                 175

Val Leu
```

<210> SEQ ID NO 138
<211> LENGTH: 423
<212> TYPE: DNA
<213> ORGANISM: Toxoplasma gondii
<220> FEATURE:
<221> NAME/KEY: misc_feature
<222> LOCATION: (6)..(6)
<223> OTHER INFORMATION: n = unknown
<220> FEATURE:
<221> NAME/KEY: misc_feature
<222> LOCATION: (23)..(23)
<223> OTHER INFORMATION: n = unknown
<220> FEATURE:

<221> NAME/KEY: misc_feature
<222> LOCATION: (34)..(34)
<223> OTHER INFORMATION: n = unknown

<400> SEQUENCE: 138

| | |
|---|---|
| tggtgntgtt gaggccgcat cgngagggga gacntgctag agccaggggc agagccgcag | 60 |
| gtccggtgga ggatgttgtt gagcccccgt cgggagtgga agacctgccg cagccagagg | 120 |
| cagaggcgca agtaccgacc aagggtgttg accatgccgc gtcgggaggg gaggacatcg | 180 |
| tggagccaga ggcagagccg cagggactgg tggctggcgc tggtgaggcc gcatcgggag | 240 |
| gggaggacct gctagagcca ggggcagcgc cgcagggtcc ggtgaaggat gttgatgagg | 300 |
| cggcgtcggg agaggaagaa ctgctggagc cagaggcaaa gccgcagggt tcggtggagg | 360 |
| atgttgatga ggcagcgtcg ggaggggagg acctgctaga gccagaggca gaggcgcaag | 420 |
| tcc | 423 |

<210> SEQ ID NO 139
<211> LENGTH: 327
<212> TYPE: DNA
<213> ORGANISM: Toxoplasma gondii
<220> FEATURE:
<221> NAME/KEY: CDS
<222> LOCATION: (1)..(327)
<223> OTHER INFORMATION:

<400> SEQUENCE: 139

| | |
|---|---|
| cgc tct caa tca aca aag cca ccc gcg cct tca gac gta gag gac aca<br>Arg Ser Gln Ser Thr Lys Pro Pro Ala Pro Ser Asp Val Glu Asp Thr<br>1               5                   10                  15 | 48 |
| ggc tct tct gac aac ccg ggt gac aat gtg aca gag gac aca act gag<br>Gly Ser Ser Asp Asn Pro Gly Asp Asn Val Thr Glu Asp Thr Thr Glu<br>            20                  25                  30 | 96 |
| agt cca tca cag ggc acc gac ggt tca gca tcc gga ccc ggg tcg act<br>Ser Pro Ser Gln Gly Thr Asp Gly Ser Ala Ser Gly Pro Gly Ser Thr<br>        35                  40                  45 | 144 |
| cat ccg gaa aac gac gcg ggg gaa cat gag gat ggc gcg tca ctg ggg<br>His Pro Glu Asn Asp Ala Gly Glu His Glu Asp Gly Ala Ser Leu Gly<br>    50                  55                  60 | 192 |
| caa gac cag caa gag cgc atg gat aaa tct tcc cta ggc aaa gaa aca<br>Gln Asp Gln Gln Glu Arg Met Asp Lys Ser Ser Leu Gly Lys Glu Thr<br>65                  70                  75                  80 | 240 |
| ccc atg ctc gat cag gga aat tcg tca cca gca aca acg ggg tcc ggt<br>Pro Met Leu Asp Gln Gly Asn Ser Ser Pro Ala Thr Thr Gly Ser Gly<br>                85                  90                  95 | 288 |
| gcc cat gaa aaa aac gag agc gtg tca gga gtt cca gcg<br>Ala His Glu Lys Asn Glu Ser Val Ser Gly Val Pro Ala<br>            100                 105 | 327 |

<210> SEQ ID NO 140
<211> LENGTH: 109
<212> TYPE: PRT
<213> ORGANISM: Toxoplasma gondii

<400> SEQUENCE: 140

Arg Ser Gln Ser Thr Lys Pro Pro Ala Pro Ser Asp Val Glu Asp Thr
1               5                   10                  15

Gly Ser Ser Asp Asn Pro Gly Asp Asn Val Thr Glu Asp Thr Thr Glu
            20                  25                  30

Ser Pro Ser Gln Gly Thr Asp Gly Ser Ala Ser Gly Pro Gly Ser Thr
        35                  40                  45

```
His Pro Glu Asn Asp Ala Gly Glu His Glu Asp Gly Ala Ser Leu Gly
        50                  55                  60

Gln Asp Gln Gln Glu Arg Met Asp Lys Ser Ser Leu Gly Lys Glu Thr
 65                  70                  75                  80

Pro Met Leu Asp Gln Gly Asn Ser Ser Pro Ala Thr Thr Gly Ser Gly
                85                  90                  95

Ala His Glu Lys Asn Glu Ser Val Ser Gly Val Pro Ala
            100                 105
```

<210> SEQ ID NO 141
<211> LENGTH: 444
<212> TYPE: DNA
<213> ORGANISM: Toxoplasma gondii
<220> FEATURE:
<221> NAME/KEY: CDS
<222> LOCATION: (1)..(444)
<223> OTHER INFORMATION:

<400> SEQUENCE: 141

```
ccg gcg cga act ggc gac gcg cag cct gag ggc aga gag ggg cac agc      48
Pro Ala Arg Thr Gly Asp Ala Gln Pro Glu Gly Arg Glu Gly His Ser
 1               5                  10                  15 cca ctg gaa gac gaa ggg aga gat gcg ttt gga aga cgc gct gcg gaa      96
Pro Leu Glu Asp Glu Gly Arg Asp Ala Phe Gly Arg Arg Ala Ala Glu
                20                  25                  30 gac gag aga aac aga gga aat ccg aat gcg gct ggc gag act tcc caa     144
Asp Glu Arg Asn Arg Gly Asn Pro Asn Ala Ala Gly Glu Thr Ser Gln
            35                  40                  45 gac gag gca gag aac gcg caa gcg tcc ctg cgg ttc gct gcg aga gag     192
Asp Glu Ala Glu Asn Ala Gln Ala Ser Leu Arg Phe Ala Ala Arg Glu
        50                  55                  60 aaa cct ctc gaa gtc ctc aga ttc cga gaa gac act gca gac act ctg     240
Lys Pro Leu Glu Val Leu Arg Phe Arg Glu Asp Thr Ala Asp Thr Leu
 65                  70                  75                  80 acg tat gca gac tat cca aac agc gtg gag ttc aca ccc gca gac atg     288
Thr Tyr Ala Asp Tyr Pro Asn Ser Val Glu Phe Thr Pro Ala Asp Met
                85                  90                  95 ccg aat gcg aag gac cag acg cct ctg cat gca aag tac aat cac ttt     336
Pro Asn Ala Lys Asp Gln Thr Pro Leu His Ala Lys Tyr Asn His Phe
               100                 105                 110 tgc gcc tac tca tgc tgg ctg acc tcg cgc ttc aac cca gac aac cca     384
Cys Ala Tyr Ser Cys Trp Leu Thr Ser Arg Phe Asn Pro Asp Asn Pro
            115                 120                 125 aac agc cac tgt gga aaa gga aaa aac gag aaa cgc cga ttc gac gac     432
Asn Ser His Cys Gly Lys Gly Lys Asn Glu Lys Arg Arg Phe Asp Asp
        130                 135                 140 gac tac gat ccg                                                     444
Asp Tyr Asp Pro
145
```

<210> SEQ ID NO 142
<211> LENGTH: 148
<212> TYPE: PRT
<213> ORGANISM: Toxoplasma gondii

<400> SEQUENCE: 142

```
Pro Ala Arg Thr Gly Asp Ala Gln Pro Glu Gly Arg Glu Gly His Ser
 1               5                  10                  15

Pro Leu Glu Asp Glu Gly Arg Asp Ala Phe Gly Arg Arg Ala Ala Glu
                20                  25                  30

Asp Glu Arg Asn Arg Gly Asn Pro Asn Ala Ala Gly Glu Thr Ser Gln
```

```
            35                  40                  45
Asp Glu Ala Glu Asn Ala Gln Ala Ser Leu Arg Phe Ala Ala Arg Glu
         50                  55                  60
Lys Pro Leu Glu Val Leu Arg Phe Arg Glu Asp Thr Ala Asp Thr Leu
 65                  70                  75                  80
Thr Tyr Ala Asp Tyr Pro Asn Ser Val Glu Phe Thr Pro Ala Asp Met
                 85                  90                  95
Pro Asn Ala Lys Asp Gln Thr Pro Leu His Ala Lys Tyr Asn His Phe
            100                 105                 110
Cys Ala Tyr Ser Cys Trp Leu Thr Ser Arg Phe Asn Pro Asp Asn Pro
            115                 120                 125
Asn Ser His Cys Gly Lys Gly Lys Asn Glu Lys Arg Arg Phe Asp Asp
            130                 135                 140

Asp Tyr Asp Pro
145

<210> SEQ ID NO 143
<211> LENGTH: 928
<212> TYPE: DNA
<213> ORGANISM: Toxoplasma gondii
<220> FEATURE:
<221> NAME/KEY: CDS
<222> LOCATION: (1)..(57)
<223> OTHER INFORMATION:

<400> SEQUENCE: 143 cgg gat ccc gag cgg gac ctc ccg gtg tcc tcg act gct cat aca cca       48
Arg Asp Pro Glu Arg Asp Leu Pro Val Ser Ser Thr Ala His Thr Pro
 1               5                  10                  15 gag gag gat tgattccacg cagaacttaa cccgtgggac gcagcctcca              97
Glu Glu Asp cagagtctgt ggcggacgaa ggaaatgcag gaacagagag acctggaccg aaaaatggca    157
tggacgatgg gtgtccacgg gagaagacgg atactcgtgg aaagccgggg gaaagcgacg    217
gagggaaatg cgcgacaagc tggaaaagcg agctcacaac gacgaaacac gcactgtgca    277
tccgaacgac aatgaccctg tccttagtag acgagagggg gtaggcaacaa ttcctcagaa   337 gtccaccagc gaccggacag cgaccgcggc agcacgttga gggaggtctt actagcggcc    397
gagactcagg acaacaggag ccctctaccg ccatgcgaca cacgcagaac aacgctttag    457
attaaggtcg aaaaggaaa cctcaacgca gaacgagtca cttctttccc acaaaagtgc     517
tgtggaaaaa cagcgcatgc ggggctgggt gactcgaaaa tctgggaacg cgtctggcag    577
gcatcctgcc cgaaccccgat accagagaaa cggaacccgt actggctgga attcaacagt    637
acggacaaaa aacccaccgt gtaaagtgga caaaagccga caatggaaca actacttggg    697
agaaagcaaa tgctgcgttc accaggccag tgtcacgccg cgtcgtaaag aaggcggctc    757
agcgttgccg gtgtgcctgg cgttgtcgga cggcttccgt gtgtacccaa cagaaaagct    817
tttacactct tactatttc atttggccac gatttctttt ttgcctatct actgtaccta    877
gccacgtcgc cattctaagg aagttgtccc gttgcaacgc agaacgcgga g             928

<210> SEQ ID NO 144
<211> LENGTH: 19
<212> TYPE: PRT
<213> ORGANISM: Toxoplasma gondii

<400> SEQUENCE: 144

Arg Asp Pro Glu Arg Asp Leu Pro Val Ser Ser Thr Ala His Thr Pro
```

```
1               5                  10                 15
Glu Glu Asp
```

<210> SEQ ID NO 145
<211> LENGTH: 18
<212> TYPE: DNA
<213> ORGANISM: Artificial sequence
<220> FEATURE:
<223> OTHER INFORMATION: Synthetic Primer

<400> SEQUENCE: 145
cgcttcttgt gtcacctg                                                 18

<210> SEQ ID NO 146
<211> LENGTH: 23
<212> TYPE: DNA
<213> ORGANISM: Artificial sequence
<220> FEATURE:
<223> OTHER INFORMATION: Synthetic Primer

<400> SEQUENCE: 146
gcaccttgtt ctctctcttc gcc                                           23

<210> SEQ ID NO 147
<211> LENGTH: 18
<212> TYPE: DNA
<213> ORGANISM: Artificial sequence
<220> FEATURE:
<223> OTHER INFORMATION: Synthetic Primer

<400> SEQUENCE: 147
cgaggagacg gtgggagc                                                 18

<210> SEQ ID NO 148
<211> LENGTH: 21
<212> TYPE: DNA
<213> ORGANISM: Artificial sequence
<220> FEATURE:
<223> OTHER INFORMATION: Synthetic Primer

<400> SEQUENCE: 148
tgcccaagat gccgatctct g                                             21

<210> SEQ ID NO 149
<211> LENGTH: 20
<212> TYPE: DNA
<213> ORGANISM: Artificial sequence
<220> FEATURE:
<223> OTHER INFORMATION: Synthetic Primer

<400> SEQUENCE: 149
tctcccccat cgacgaaaac                                               20

<210> SEQ ID NO 150
<211> LENGTH: 22
<212> TYPE: DNA
<213> ORGANISM: Artificial sequence
<220> FEATURE:
<223> OTHER INFORMATION: Synthetic Primer

<400> SEQUENCE: 150
gctcatttcc tccgcaattt gg                                            22

<210> SEQ ID NO 151
<211> LENGTH: 23

```
<212> TYPE: DNA
<213> ORGANISM: Artificial sequence
<220> FEATURE:
<223> OTHER INFORMATION: Synthetic Primer

<400> SEQUENCE: 151
agctggcaga aataccaaag ctc                                           23

<210> SEQ ID NO 152
<211> LENGTH: 20
<212> TYPE: DNA
<213> ORGANISM: Artificial sequence
<220> FEATURE:
<223> OTHER INFORMATION: Synthetic Primer

<400> SEQUENCE: 152
tgtcggcaat actgggcatg                                               20

<210> SEQ ID NO 153
<211> LENGTH: 24
<212> TYPE: DNA
<213> ORGANISM: Artificial sequence
<220> FEATURE:
<223> OTHER INFORMATION: Synthetic Primer

<400> SEQUENCE: 153
actggagtgg aaagtctggt tttg                                          24

<210> SEQ ID NO 154
<211> LENGTH: 23
<212> TYPE: DNA
<213> ORGANISM: Artificial sequence
<220> FEATURE:
<223> OTHER INFORMATION: Synthetic Primer

<400> SEQUENCE: 154
gacgcagaga agaaagaaga gcc                                           23

<210> SEQ ID NO 155
<211> LENGTH: 22
<212> TYPE: DNA
<213> ORGANISM: Artificial sequence
<220> FEATURE:
<223> OTHER INFORMATION: Synthetic Primer

<400> SEQUENCE: 155
tccaaaactg tctcgtctcc cc                                            22

<210> SEQ ID NO 156
<211> LENGTH: 21
<212> TYPE: DNA
<213> ORGANISM: Artificial sequence
<220> FEATURE:
<223> OTHER INFORMATION: Synthetic Primer

<400> SEQUENCE: 156
tctggatacg ccgttccttt g                                             21

<210> SEQ ID NO 157
<211> LENGTH: 25
<212> TYPE: DNA
<213> ORGANISM: Artificial sequence
<220> FEATURE:
<223> OTHER INFORMATION: Synthetic Primer

<400> SEQUENCE: 157
```
gacatctacc tgtgagtgaa ccagg                                              25

<210> SEQ ID NO 158
<211> LENGTH: 22
<212> TYPE: DNA
<213> ORGANISM: Artificial sequence
<220> FEATURE:
<223> OTHER INFORMATION: Synthetic Primer

<400> SEQUENCE: 158
gtcaaaacct tgccagcatc tc                                                 22

<210> SEQ ID NO 159
<211> LENGTH: 24
<212> TYPE: DNA
<213> ORGANISM: Artificial sequence
<220> FEATURE:
<223> OTHER INFORMATION: Synthetic Primer

<400> SEQUENCE: 159
tccgactgaa tgactacctc tttc                                               24

<210> SEQ ID NO 160
<211> LENGTH: 22
<212> TYPE: DNA
<213> ORGANISM: Artificial sequence
<220> FEATURE:
<223> OTHER INFORMATION: Synthetic Primer

<400> SEQUENCE: 160
tccgaccaag tcctcagtga ac                                                 22

<210> SEQ ID NO 161
<211> LENGTH: 20
<212> TYPE: DNA
<213> ORGANISM: Artificial sequence
<220> FEATURE:
<223> OTHER INFORMATION: Synthetic Primer

<400> SEQUENCE: 161
tgggcatttc ctggaagagg                                                    20

<210> SEQ ID NO 162
<211> LENGTH: 21
<212> TYPE: DNA
<213> ORGANISM: Artificial sequence
<220> FEATURE:
<223> OTHER INFORMATION: Synthetic Primer

<400> SEQUENCE: 162
gaatccatct cgtgcaaacg g                                                  21

<210> SEQ ID NO 163
<211> LENGTH: 21
<212> TYPE: DNA
<213> ORGANISM: Artificial sequence
<220> FEATURE:
<223> OTHER INFORMATION: Synthetic Primer

<400> SEQUENCE: 163
caagacacag ggaaacgttg g                                                  21

<210> SEQ ID NO 164
<211> LENGTH: 22
<212> TYPE: DNA
<213> ORGANISM: Artificial sequence

```
<220> FEATURE:
<223> OTHER INFORMATION: Synthetic Primer

<400> SEQUENCE: 164
gaaagaatcg cacctcctct cc                                        22

<210> SEQ ID NO 165
<211> LENGTH: 23
<212> TYPE: DNA
<213> ORGANISM: Artificial sequence
<220> FEATURE:
<223> OTHER INFORMATION: Synthetic Primer

<400> SEQUENCE: 165
tttgagtcta accgccgtat gtc                                       23

<210> SEQ ID NO 166
<211> LENGTH: 23
<212> TYPE: DNA
<213> ORGANISM: Artificial sequence
<220> FEATURE:
<223> OTHER INFORMATION: Synthetic Primer

<400> SEQUENCE: 166
tcagacgatt ctcccattgt acg                                       23

<210> SEQ ID NO 167
<211> LENGTH: 22
<212> TYPE: DNA
<213> ORGANISM: Artificial sequence
<220> FEATURE:
<223> OTHER INFORMATION: Synthetic Primer

<400> SEQUENCE: 167
tcgacttggg tccgattgtt ag                                        22

<210> SEQ ID NO 168
<211> LENGTH: 24
<212> TYPE: DNA
<213> ORGANISM: Artificial sequence
<220> FEATURE:
<223> OTHER INFORMATION: Synthetic Primer

<400> SEQUENCE: 168
gatcttttgc gtgactttgt ctgc                                      24

<210> SEQ ID NO 169
<211> LENGTH: 24
<212> TYPE: DNA
<213> ORGANISM: Artificial sequence
<220> FEATURE:
<223> OTHER INFORMATION: Synthetic Primer

<400> SEQUENCE: 169
gaagatgctt gtcttgttcg gttc                                      24

<210> SEQ ID NO 170
<211> LENGTH: 23
<212> TYPE: DNA
<213> ORGANISM: Artificial sequence
<220> FEATURE:
<223> OTHER INFORMATION: Synthetic Primer

<400> SEQUENCE: 170
gaggggtttc cttctttatt gcc                                       23
```

<210> SEQ ID NO 171
<211> LENGTH: 20
<212> TYPE: DNA
<213> ORGANISM: Artificial sequence
<220> FEATURE:
<223> OTHER INFORMATION: Synthetic Primer

<400> SEQUENCE: 171
tgttggacat cccgagcatc                                        20

<210> SEQ ID NO 172
<211> LENGTH: 20
<212> TYPE: DNA
<213> ORGANISM: Artificial sequence
<220> FEATURE:
<223> OTHER INFORMATION: Synthetic Primer

<400> SEQUENCE: 172
ggtccttgtt tttcaggcgg                                        20

<210> SEQ ID NO 173
<211> LENGTH: 22
<212> TYPE: DNA
<213> ORGANISM: Artificial sequence
<220> FEATURE:
<223> OTHER INFORMATION: Synthetic Primer

<400> SEQUENCE: 173
tcgtgcagac agtgaagcaa tg                                     22

<210> SEQ ID NO 174
<211> LENGTH: 21
<212> TYPE: DNA
<213> ORGANISM: Artificial sequence
<220> FEATURE:
<223> OTHER INFORMATION: Synthetic Primer

<400> SEQUENCE: 174
ttttgtcagc acagagtggc g                                      21

<210> SEQ ID NO 175
<211> LENGTH: 23
<212> TYPE: DNA
<213> ORGANISM: Artificial sequence
<220> FEATURE:
<223> OTHER INFORMATION: Synthetic Primer

<400> SEQUENCE: 175
cgcaagtgag ttttggcttt acc                                    23

<210> SEQ ID NO 176
<211> LENGTH: 22
<212> TYPE: DNA
<213> ORGANISM: Artificial sequence
<220> FEATURE:
<223> OTHER INFORMATION: Synthetic Primer

<400> SEQUENCE: 176
cctggaagag atatgcagac ac                                     22

<210> SEQ ID NO 177
<211> LENGTH: 22
<212> TYPE: DNA
<213> ORGANISM: Artificial sequence
<220> FEATURE:
<223> OTHER INFORMATION: Synthetic Primer

```
<400> SEQUENCE: 177
tcaccgttcg ctcttctttc tc                                              22

<210> SEQ ID NO 178
<211> LENGTH: 20
<212> TYPE: DNA
<213> ORGANISM: Artificial sequence
<220> FEATURE:
<223> OTHER INFORMATION: Synthetic Primer

<400> SEQUENCE: 178
cgactgaagc atggattgcc                                                 20

<210> SEQ ID NO 179
<211> LENGTH: 24
<212> TYPE: DNA
<213> ORGANISM: Artificial sequence
<220> FEATURE:
<223> OTHER INFORMATION: Synthetic Primer

<400> SEQUENCE: 179
acatattcct gaggaggagt tccc                                            24

<210> SEQ ID NO 180
<211> LENGTH: 22
<212> TYPE: DNA
<213> ORGANISM: Artificial sequence
<220> FEATURE:
<223> OTHER INFORMATION: Synthetic Primer

<400> SEQUENCE: 180
aacacacctc cgacgacacc ac                                              22

<210> SEQ ID NO 181
<211> LENGTH: 22
<212> TYPE: DNA
<213> ORGANISM: Artificial sequence
<220> FEATURE:
<223> OTHER INFORMATION: Synthetic Primer

<400> SEQUENCE: 181
ctcggcttct ccacatacaa gg                                              22

<210> SEQ ID NO 182
<211> LENGTH: 23
<212> TYPE: DNA
<213> ORGANISM: Artificial sequence
<220> FEATURE:
<223> OTHER INFORMATION: Synthetic Primer

<400> SEQUENCE: 182
ggatctaggc atttgggttt cac                                             23

<210> SEQ ID NO 183
<211> LENGTH: 21
<212> TYPE: DNA
<213> ORGANISM: Artificial sequence
<220> FEATURE:
<223> OTHER INFORMATION: Synthetic Primer

<400> SEQUENCE: 183
atcgaagaag ctgaagcgga g                                               21

<210> SEQ ID NO 184
```

-continued

```
<211> LENGTH: 22
<212> TYPE: DNA
<213> ORGANISM: Artificial sequence
<220> FEATURE:
<223> OTHER INFORMATION: Synthetic Primer

<400> SEQUENCE: 184
gtgcttgtct ctgacgaaac cc                                                  22

<210> SEQ ID NO 185
<211> LENGTH: 22
<212> TYPE: DNA
<213> ORGANISM: Artificial sequence
<220> FEATURE:
<223> OTHER INFORMATION: Synthetic Primer

<400> SEQUENCE: 185
tatcattgta tcccgtcgtc cc                                                  22

<210> SEQ ID NO 186
<211> LENGTH: 21
<212> TYPE: DNA
<213> ORGANISM: Artificial sequence
<220> FEATURE:
<223> OTHER INFORMATION: Synthetic Primer

<400> SEQUENCE: 186
tgatgcctgg atttgcacaa c                                                   21

<210> SEQ ID NO 187
<211> LENGTH: 22
<212> TYPE: DNA
<213> ORGANISM: Artificial sequence
<220> FEATURE:
<223> OTHER INFORMATION: Synthetic Primer

<400> SEQUENCE: 187
cggatcgctc tgagtctctt tg                                                  22

<210> SEQ ID NO 188
<211> LENGTH: 23
<212> TYPE: DNA
<213> ORGANISM: Artificial sequence
<220> FEATURE:
<223> OTHER INFORMATION: Synthetic Primer

<400> SEQUENCE: 188
atcctgtgtc ttctcttcga ccc                                                 23

<210> SEQ ID NO 189
<211> LENGTH: 20
<212> TYPE: DNA
<213> ORGANISM: Artificial sequence
<220> FEATURE:
<223> OTHER INFORMATION: Synthetic Primer

<400> SEQUENCE: 189
gatcgctctg agtctctttg                                                     20

<210> SEQ ID NO 190
<211> LENGTH: 24
<212> TYPE: DNA
<213> ORGANISM: Artificial sequence
<220> FEATURE:
<223> OTHER INFORMATION: Synthetic Primer

<400> SEQUENCE: 190
```

```
acgtgaggga gaagaagaga gtgc                                      24

<210> SEQ ID NO 191
<211> LENGTH: 22
<212> TYPE: DNA
<213> ORGANISM: Artificial sequence
<220> FEATURE:
<223> OTHER INFORMATION: Synthetic Primer

<400> SEQUENCE: 191
ttcatcgtcg cctctgatgt cc                                        22

<210> SEQ ID NO 192
<211> LENGTH: 23
<212> TYPE: DNA
<213> ORGANISM: Artificial sequence
<220> FEATURE:
<223> OTHER INFORMATION: Synthetic Primer

<400> SEQUENCE: 192
tgtagacagc gtttagggag tgc                                       23

<210> SEQ ID NO 193
<211> LENGTH: 22
<212> TYPE: DNA
<213> ORGANISM: Artificial sequence
<220> FEATURE:
<223> OTHER INFORMATION: Synthetic Primer

<400> SEQUENCE: 193
gtccttggaa gtgcagaagc ag                                        22

<210> SEQ ID NO 194
<211> LENGTH: 21
<212> TYPE: DNA
<213> ORGANISM: Artificial sequence
<220> FEATURE:
<223> OTHER INFORMATION: Synthetic Primer

<400> SEQUENCE: 194
aagcgaggaa aaggaggtgt c                                         21

<210> SEQ ID NO 195
<211> LENGTH: 23
<212> TYPE: DNA
<213> ORGANISM: Artificial sequence
<220> FEATURE:
<223> OTHER INFORMATION: Synthetic Primer

<400> SEQUENCE: 195
cgggaaggtt ggtgatgtct gtg                                       23

<210> SEQ ID NO 196
<211> LENGTH: 18
<212> TYPE: DNA
<213> ORGANISM: Artificial sequence
<220> FEATURE:
<223> OTHER INFORMATION: Synthetic Primer

<400> SEQUENCE: 196
cccgaagact ttgacctg                                             18

<210> SEQ ID NO 197
<211> LENGTH: 18
<212> TYPE: DNA
```

```
<213> ORGANISM: Artificial sequence
<220> FEATURE:
<223> OTHER INFORMATION: Synthetic Primer

<400> SEQUENCE: 197
agtggcatag gaggctgg                                                    18

<210> SEQ ID NO 198
<211> LENGTH: 23
<212> TYPE: DNA
<213> ORGANISM: Artificial sequence
<220> FEATURE:
<223> OTHER INFORMATION: Synthetic Primer

<400> SEQUENCE: 198
gcaccttcaa tgccacaggt atc                                              23

<210> SEQ ID NO 199
<211> LENGTH: 22
<212> TYPE: DNA
<213> ORGANISM: Artificial sequence
<220> FEATURE:
<223> OTHER INFORMATION: Synthetic Primer

<400> SEQUENCE: 199
tcgtgtgctt ctcgcttctc tg                                               22

<210> SEQ ID NO 200
<211> LENGTH: 25
<212> TYPE: DNA
<213> ORGANISM: Artificial sequence
<220> FEATURE:
<223> OTHER INFORMATION: Synthetic Primer

<400> SEQUENCE: 200
cactgtcgat cagaagaagg cttac                                            25

<210> SEQ ID NO 201
<211> LENGTH: 20
<212> TYPE: DNA
<213> ORGANISM: Artificial sequence
<220> FEATURE:
<223> OTHER INFORMATION: Synthetic Primer

<400> SEQUENCE: 201
gctccgtggg cacatttttg                                                  20

<210> SEQ ID NO 202
<211> LENGTH: 25
<212> TYPE: DNA
<213> ORGANISM: Artificial sequence
<220> FEATURE:
<223> OTHER INFORMATION: Synthetic Primer

<400> SEQUENCE: 202
cagtttacga ggtacaaggc aacag                                            25

<210> SEQ ID NO 203
<211> LENGTH: 22
<212> TYPE: DNA
<213> ORGANISM: Artificial sequence
<220> FEATURE:
<223> OTHER INFORMATION: Synthetic Primer

<400> SEQUENCE: 203
gattgcgtgg gcagtgtaga ag                                               22
```

```
<210> SEQ ID NO 204
<211> LENGTH: 23
<212> TYPE: DNA
<213> ORGANISM: Artificial sequence
<220> FEATURE:
<223> OTHER INFORMATION: Synthetic Primer

<400> SEQUENCE: 204
tgtttgtttc cccagtcaac gac                                              23

<210> SEQ ID NO 205
<211> LENGTH: 24
<212> TYPE: DNA
<213> ORGANISM: Artificial sequence
<220> FEATURE:
<223> OTHER INFORMATION: Synthetic Primer

<400> SEQUENCE: 205
cggaagaggt tgttggactc cttc                                             24

<210> SEQ ID NO 206
<211> LENGTH: 25
<212> TYPE: DNA
<213> ORGANISM: Artificial sequence
<220> FEATURE:
<223> OTHER INFORMATION: Synthetic Primer

<400> SEQUENCE: 206
caaccgagag agaagagagg aacag                                            25

<210> SEQ ID NO 207
<211> LENGTH: 22
<212> TYPE: DNA
<213> ORGANISM: Artificial sequence
<220> FEATURE:
<223> OTHER INFORMATION: Synthetic Primer

<400> SEQUENCE: 207
tggggagaac agcagacatc ag                                               22

<210> SEQ ID NO 208
<211> LENGTH: 22
<212> TYPE: DNA
<213> ORGANISM: Artificial sequence
<220> FEATURE:
<223> OTHER INFORMATION: Synthetic Primer

<400> SEQUENCE: 208
ggatgaacac tggtgcatca tg                                               22

<210> SEQ ID NO 209
<211> LENGTH: 15
<212> TYPE: DNA
<213> ORGANISM: Artificial sequence
<220> FEATURE:
<223> OTHER INFORMATION: Synthetic Primer

<400> SEQUENCE: 209
cgacttggtc cgctc                                                       15

<210> SEQ ID NO 210
<211> LENGTH: 18
<212> TYPE: DNA
<213> ORGANISM: Artificial sequence
<220> FEATURE:
```

```
<223> OTHER INFORMATION: Synthetic Primer

<400> SEQUENCE: 210
cggcggcaac aaatgggc                                              18

<210> SEQ ID NO 211
<211> LENGTH: 22
<212> TYPE: DNA
<213> ORGANISM: Artificial sequence
<220> FEATURE:
<223> OTHER INFORMATION: Synthetic Primer

<400> SEQUENCE: 211
gtccgagata tgaggatgcg ac                                         22

<210> SEQ ID NO 212
<211> LENGTH: 21
<212> TYPE: DNA
<213> ORGANISM: Artificial sequence
<220> FEATURE:
<223> OTHER INFORMATION: Synthetic Primer

<400> SEQUENCE: 212
tcagagcacc attgttgcga c                                          21

<210> SEQ ID NO 213
<211> LENGTH: 22
<212> TYPE: DNA
<213> ORGANISM: Artificial sequence
<220> FEATURE:
<223> OTHER INFORMATION: Synthetic Primer

<400> SEQUENCE: 213
tttgacgctc aagtggaggc tg                                         22

<210> SEQ ID NO 214
<211> LENGTH: 19
<212> TYPE: DNA
<213> ORGANISM: Artificial sequence
<220> FEATURE:
<223> OTHER INFORMATION: Synthetic Primer

<400> SEQUENCE: 214
gcctgcaacg ctcgatggc                                             19

<210> SEQ ID NO 215
<211> LENGTH: 23
<212> TYPE: DNA
<213> ORGANISM: Artificial sequence
<220> FEATURE:
<223> OTHER INFORMATION: Synthetic Primer

<400> SEQUENCE: 215
cttcttgact accttcacgt ctg                                        23

<210> SEQ ID NO 216
<211> LENGTH: 18
<212> TYPE: DNA
<213> ORGANISM: Artificial sequence
<220> FEATURE:
<223> OTHER INFORMATION: Synthetic Primer

<400> SEQUENCE: 216
aaggacaagc ctggtttg                                              18
```

```
<210> SEQ ID NO 217
<211> LENGTH: 18
<212> TYPE: DNA
<213> ORGANISM: Artificial sequence
<220> FEATURE:
<223> OTHER INFORMATION: Synthetic Primer

<400> SEQUENCE: 217
tttgcccttc gcacaatc                                                 18

<210> SEQ ID NO 218
<211> LENGTH: 22
<212> TYPE: DNA
<213> ORGANISM: Artificial sequence
<220> FEATURE:
<223> OTHER INFORMATION: Synthetic Primer

<400> SEQUENCE: 218
ccagttttgc cagaggaaga cc                                            22

<210> SEQ ID NO 219
<211> LENGTH: 22
<212> TYPE: DNA
<213> ORGANISM: Artificial sequence
<220> FEATURE:
<223> OTHER INFORMATION: Synthetic Primer

<400> SEQUENCE: 219
atccgtcaat gcaggtttca tc                                            22

<210> SEQ ID NO 220
<211> LENGTH: 23
<212> TYPE: DNA
<213> ORGANISM: Artificial sequence
<220> FEATURE:
<223> OTHER INFORMATION: Synthetic Primer

<400> SEQUENCE: 220
agacaccaga gacagcagca gtc                                           23

<210> SEQ ID NO 221
<211> LENGTH: 23
<212> TYPE: DNA
<213> ORGANISM: Artificial sequence
<220> FEATURE:
<223> OTHER INFORMATION: Synthetic Primer

<400> SEQUENCE: 221
acttcgcccg acaatcgctt tcc                                           23

<210> SEQ ID NO 222
<211> LENGTH: 18
<212> TYPE: DNA
<213> ORGANISM: Artificial sequence
<220> FEATURE:
<223> OTHER INFORMATION: Synthetic Primer

<400> SEQUENCE: 222
cgatcctccc gagggacc                                                 18

<210> SEQ ID NO 223
<211> LENGTH: 22
<212> TYPE: DNA
<213> ORGANISM: Artificial sequence
<220> FEATURE:
<223> OTHER INFORMATION: Synthetic Primer
```

-continued

```
<400> SEQUENCE: 223
gcctttacgc attcaagtcg tg                                                   22

<210> SEQ ID NO 224
<211> LENGTH: 20
<212> TYPE: DNA
<213> ORGANISM: Artificial sequence
<220> FEATURE:
<223> OTHER INFORMATION: Synthetic Primer

<400> SEQUENCE: 224
ttcagcgggt ctttcctcac                                                      20

<210> SEQ ID NO 225
<211> LENGTH: 22
<212> TYPE: DNA
<213> ORGANISM: Artificial sequence
<220> FEATURE:
<223> OTHER INFORMATION: Synthetic Primer

<400> SEQUENCE: 225
caacgagaaa gatggagctt cg                                                   22

<210> SEQ ID NO 226
<211> LENGTH: 21
<212> TYPE: DNA
<213> ORGANISM: Artificial sequence
<220> FEATURE:
<223> OTHER INFORMATION: Synthetic Primer

<400> SEQUENCE: 226
aacttcttgc acttggtccc g                                                    21

<210> SEQ ID NO 227
<211> LENGTH: 23
<212> TYPE: DNA
<213> ORGANISM: Artificial sequence
<220> FEATURE:
<223> OTHER INFORMATION: Synthetic Primer

<400> SEQUENCE: 227
aagcgaggaa aaggaggtgt ctc                                                  23

<210> SEQ ID NO 228
<211> LENGTH: 21
<212> TYPE: DNA
<213> ORGANISM: Artificial sequence
<220> FEATURE:
<223> OTHER INFORMATION: Synthetic Primer

<400> SEQUENCE: 228
ggaaggttgg tgatgtctgt g                                                    21

<210> SEQ ID NO 229
<211> LENGTH: 23
<212> TYPE: DNA
<213> ORGANISM: Artificial sequence
<220> FEATURE:
<223> OTHER INFORMATION: Synthetic Primer

<400> SEQUENCE: 229
tcccccagga attgttgaaa cag                                                  23

<210> SEQ ID NO 230
<211> LENGTH: 25
```

```
<212> TYPE: DNA
<213> ORGANISM: Artificial sequence
<220> FEATURE:
<223> OTHER INFORMATION: Synthetic Primer

<400> SEQUENCE: 230
actaccgaca acgtctcagt ccttc                                              25

<210> SEQ ID NO 231
<211> LENGTH: 22
<212> TYPE: DNA
<213> ORGANISM: Artificial sequence
<220> FEATURE:
<223> OTHER INFORMATION: Synthetic Primer

<400> SEQUENCE: 231
cgtgcgtctg tgaggaaaag tg                                                 22

<210> SEQ ID NO 232
<211> LENGTH: 22
<212> TYPE: DNA
<213> ORGANISM: Artificial sequence
<220> FEATURE:
<223> OTHER INFORMATION: Synthetic Primer

<400> SEQUENCE: 232
ttgttgctcg tgttgcaggt gc                                                 22

<210> SEQ ID NO 233
<211> LENGTH: 20
<212> TYPE: DNA
<213> ORGANISM: Artificial sequence
<220> FEATURE:
<223> OTHER INFORMATION: Synthetic Primer

<400> SEQUENCE: 233
ttgttctcga acccgcagag                                                    20

<210> SEQ ID NO 234
<211> LENGTH: 20
<212> TYPE: DNA
<213> ORGANISM: Artificial sequence
<220> FEATURE:
<223> OTHER INFORMATION: Synthetic Primer

<400> SEQUENCE: 234
tggcaagaga ccgaatcgtg                                                    20

<210> SEQ ID NO 235
<211> LENGTH: 20
<212> TYPE: DNA
<213> ORGANISM: Artificial sequence
<220> FEATURE:
<223> OTHER INFORMATION: Synthetic Primer

<400> SEQUENCE: 235
aaacttggca aagggaacg                                                     20

<210> SEQ ID NO 236
<211> LENGTH: 21
<212> TYPE: DNA
<213> ORGANISM: Artificial sequence
<220> FEATURE:
<223> OTHER INFORMATION: Synthetic Primer

<400> SEQUENCE: 236
```

```
tgctgtggag aatgatggct g                                              21

<210> SEQ ID NO 237
<211> LENGTH: 17
<212> TYPE: DNA
<213> ORGANISM: Artificial sequence
<220> FEATURE:
<223> OTHER INFORMATION: Synthetic Primer

<400> SEQUENCE: 237
tttccgacga agctgcc                                                   17

<210> SEQ ID NO 238
<211> LENGTH: 19
<212> TYPE: DNA
<213> ORGANISM: Artificial sequence
<220> FEATURE:
<223> OTHER INFORMATION: Synthetic Primer

<400> SEQUENCE: 238
gactccaacg aaagcctcg                                                 19

<210> SEQ ID NO 239
<211> LENGTH: 20
<212> TYPE: DNA
<213> ORGANISM: Artificial sequence
<220> FEATURE:
<223> OTHER INFORMATION: Synthetic Primer

<400> SEQUENCE: 239
ggaaagggat aaagacgccg                                                20

<210> SEQ ID NO 240
<211> LENGTH: 24
<212> TYPE: DNA
<213> ORGANISM: Artificial sequence
<220> FEATURE:
<223> OTHER INFORMATION: Synthetic Primer

<400> SEQUENCE: 240
aagcagagga gagacgagac gaag                                           24

<210> SEQ ID NO 241
<211> LENGTH: 24
<212> TYPE: DNA
<213> ORGANISM: Artificial sequence
<220> FEATURE:
<223> OTHER INFORMATION: Synthetic Primer

<400> SEQUENCE: 241
ctgcaccatt tctcacttct tgtg                                           24

<210> SEQ ID NO 242
<211> LENGTH: 24
<212> TYPE: DNA
<213> ORGANISM: Artificial sequence
<220> FEATURE:
<223> OTHER INFORMATION: Synthetic Primer

<400> SEQUENCE: 242
gcaaaagcgg actcgattct attg                                           24

<210> SEQ ID NO 243
<211> LENGTH: 20
<212> TYPE: DNA
<213> ORGANISM: Artificial sequence
```

<220> FEATURE:
<223> OTHER INFORMATION: Synthetic Primer

<400> SEQUENCE: 243
tgtggcagag caaaaggctc         20

<210> SEQ ID NO 244
<211> LENGTH: 22
<212> TYPE: DNA
<213> ORGANISM: Artificial sequence
<220> FEATURE:
<223> OTHER INFORMATION: Synthetic Primer

<400> SEQUENCE: 244
ctgtggatgc tcctttgcga ct         22

<210> SEQ ID NO 245
<211> LENGTH: 20
<212> TYPE: DNA
<213> ORGANISM: Artificial sequence
<220> FEATURE:
<223> OTHER INFORMATION: Synthetic Primer

<400> SEQUENCE: 245
cgaggcaccc gaagaatttg         20

<210> SEQ ID NO 246
<211> LENGTH: 22
<212> TYPE: DNA
<213> ORGANISM: Artificial sequence
<220> FEATURE:
<223> OTHER INFORMATION: Synthetic Primer

<400> SEQUENCE: 246
cttctcaggt tcacttcctg cg         22

<210> SEQ ID NO 247
<211> LENGTH: 21
<212> TYPE: DNA
<213> ORGANISM: Artificial sequence
<220> FEATURE:
<223> OTHER INFORMATION: Synthetic Primer

<400> SEQUENCE: 247
tcacgcaacg aacaagtcct c         21

<210> SEQ ID NO 248
<211> LENGTH: 20
<212> TYPE: DNA
<213> ORGANISM: Artificial sequence
<220> FEATURE:
<223> OTHER INFORMATION: Synthetic Primer

<400> SEQUENCE: 248
cccatttttg cttggcttgc         20

<210> SEQ ID NO 249
<211> LENGTH: 20
<212> TYPE: DNA
<213> ORGANISM: Artificial sequence
<220> FEATURE:
<223> OTHER INFORMATION: Synthetic Primer

<400> SEQUENCE: 249
agcggcaaac cagttcgttg         20

```
<210> SEQ ID NO 250
<211> LENGTH: 20
<212> TYPE: DNA
<213> ORGANISM: Artificial sequence
<220> FEATURE:
<223> OTHER INFORMATION: Synthetic Primer

<400> SEQUENCE: 250
caccaccttt ttcgttgcgg                                               20

<210> SEQ ID NO 251
<211> LENGTH: 16
<212> TYPE: DNA
<213> ORGANISM: Artificial sequence
<220> FEATURE:
<223> OTHER INFORMATION: Synthetic Primer

<400> SEQUENCE: 251
cggcgactca gatggg                                                   16

<210> SEQ ID NO 252
<211> LENGTH: 23
<212> TYPE: DNA
<213> ORGANISM: Artificial sequence
<220> FEATURE:
<223> OTHER INFORMATION: Synthetic Primer

<400> SEQUENCE: 252
ggggctgtgt cttctctatt tcg                                           23

<210> SEQ ID NO 253
<211> LENGTH: 20
<212> TYPE: DNA
<213> ORGANISM: Artificial sequence
<220> FEATURE:
<223> OTHER INFORMATION: Synthetic Primer

<400> SEQUENCE: 253
aagcaaacag gctcggaagc                                               20

<210> SEQ ID NO 254
<211> LENGTH: 20
<212> TYPE: DNA
<213> ORGANISM: Artificial sequence
<220> FEATURE:
<223> OTHER INFORMATION: Synthetic Primer

<400> SEQUENCE: 254
tcatgttgga ggcgtcgttc                                               20

<210> SEQ ID NO 255
<211> LENGTH: 21
<212> TYPE: DNA
<213> ORGANISM: Artificial sequence
<220> FEATURE:
<223> OTHER INFORMATION: Synthetic Primer

<400> SEQUENCE: 255
tgtgcagtgg aggacaaatg g                                             21

<210> SEQ ID NO 256
<211> LENGTH: 21
<212> TYPE: DNA
<213> ORGANISM: Artificial sequence
<220> FEATURE:
<223> OTHER INFORMATION: Synthetic Primer
```

<400> SEQUENCE: 256
gaatcagggt gttttagggc g                                      21

<210> SEQ ID NO 257
<211> LENGTH: 19
<212> TYPE: DNA
<213> ORGANISM: Artificial sequence
<220> FEATURE:
<223> OTHER INFORMATION: Synthetic Primer

<400> SEQUENCE: 257
attctgtgca agcccagag                                         19

<210> SEQ ID NO 258
<211> LENGTH: 20
<212> TYPE: DNA
<213> ORGANISM: Artificial sequence
<220> FEATURE:
<223> OTHER INFORMATION: Synthetic Primer

<400> SEQUENCE: 258
cgaccaaggg tgttgaccat                                        20

<210> SEQ ID NO 259
<211> LENGTH: 22
<212> TYPE: DNA
<213> ORGANISM: Artificial sequence
<220> FEATURE:
<223> OTHER INFORMATION: Synthetic Primer

<400> SEQUENCE: 259
ctaggcaaag aaacacccat gc                                     22

<210> SEQ ID NO 260
<211> LENGTH: 18
<212> TYPE: DNA
<213> ORGANISM: Artificial sequence
<220> FEATURE:
<223> OTHER INFORMATION: Synthetic Primer

<400> SEQUENCE: 260
cgctggaact cctgacac                                          18

<210> SEQ ID NO 261
<211> LENGTH: 21
<212> TYPE: DNA
<213> ORGANISM: Artificial sequence
<220> FEATURE:
<223> OTHER INFORMATION: Synthetic Primer

<400> SEQUENCE: 261
acgaagggag agatgcgttt g                                      21

<210> SEQ ID NO 262
<211> LENGTH: 20
<212> TYPE: DNA
<213> ORGANISM: Artificial sequence
<220> FEATURE:
<223> OTHER INFORMATION: Synthetic Primer

<400> SEQUENCE: 262
tggctgtttg ggttgtctgg                                        20

<210> SEQ ID NO 263

```
<211> LENGTH: 20
<212> TYPE: DNA
<213> ORGANISM: Artificial sequence
<220> FEATURE:
<223> OTHER INFORMATION: Synthetic Primer

<400> SEQUENCE: 263
tcaccgcaga acttaacccg                                              20

<210> SEQ ID NO 264
<211> LENGTH: 20
<212> TYPE: DNA
<213> ORGANISM: Artificial sequence
<220> FEATURE:
<223> OTHER INFORMATION: Synthetic Primer

<400> SEQUENCE: 264
ctcgcttttc cagcttgtcg                                              20

<210> SEQ ID NO 265
<211> LENGTH: 311
<212> TYPE: DNA
<213> ORGANISM: Toxoplasma gondii
<220> FEATURE:
<221> NAME/KEY: CDS
<222> LOCATION: (1)..(288)
<223> OTHER INFORMATION:

<400> SEQUENCE: 265
```

| cgg | gat | cca | gct | gca | cct | aac | agc | aca | cag | gct | gtg | gca | gcc | gct | cgt | 48 |
|---|---|---|---|---|---|---|---|---|---|---|---|---|---|---|---|---|
| Arg | Asp | Pro | Ala | Ala | Pro | Asn | Ser | Thr | Gln | Ala | Val | Ala | Ala | Ala | Arg | |
| 1 | | | | 5 | | | | | 10 | | | | | 15 | | |

| acc | gtg | gta | gtg | atg | aaa | acc | gac | gca | gaa | gtg | tcc | ggt | gac | aac | ctc | 96 |
|---|---|---|---|---|---|---|---|---|---|---|---|---|---|---|---|---|
| Thr | Val | Val | Val | Met | Lys | Thr | Asp | Ala | Glu | Val | Ser | Gly | Asp | Asn | Leu | |
| | | | 20 | | | | | 25 | | | | | 30 | | | |

| agt | cag | ccg | ggt | agg | cgt | ccg | ccg | tcg | cca | aag | ccg | caa | acg | acg | aag | 144 |
|---|---|---|---|---|---|---|---|---|---|---|---|---|---|---|---|---|
| Ser | Gln | Pro | Gly | Arg | Arg | Pro | Pro | Ser | Pro | Lys | Pro | Gln | Thr | Thr | Lys | |
| | 35 | | | | | 40 | | | | | 45 | | | | | |

| ttt | ccg | cgg | aga | gag | tca | cca | gac | cgc | agg | ggg | acg | agg | cgg | aga | act | 192 |
|---|---|---|---|---|---|---|---|---|---|---|---|---|---|---|---|---|
| Phe | Pro | Arg | Arg | Glu | Ser | Pro | Asp | Arg | Arg | Gly | Thr | Arg | Arg | Arg | Thr | |
| 50 | | | | | 55 | | | | | 60 | | | | | | |

| gaa | agc | cga | ggc | gct | gtt | agc | agg | gta | tgg | cca | ggg | gaa | aac | cag | cga | 240 |
|---|---|---|---|---|---|---|---|---|---|---|---|---|---|---|---|---|
| Glu | Ser | Arg | Gly | Ala | Val | Ser | Arg | Val | Trp | Pro | Gly | Glu | Asn | Gln | Arg | |
| 65 | | | | 70 | | | | | 75 | | | | | 80 | | |

| aga | cgg | tct | gcc | gtc | gac | gat | tcg | ata | ccg | gct | aac | ccc | atc | gct | ttg | 288 |
|---|---|---|---|---|---|---|---|---|---|---|---|---|---|---|---|---|
| Arg | Arg | Ser | Ala | Val | Asp | Asp | Ser | Ile | Pro | Ala | Asn | Pro | Ile | Ala | Leu | |
| | | | 85 | | | | | 90 | | | | | 95 | | | |

```
aacgcgtggc gccctgcgat ccg                                         311

<210> SEQ ID NO 266
<211> LENGTH: 96
<212> TYPE: PRT
<213> ORGANISM: Toxoplasma gondii

<400> SEQUENCE: 266

Arg Asp Pro Ala Ala Pro Asn Ser Thr Gln Ala Val Ala Ala Ala Arg
1               5                   10                  15

Thr Val Val Val Met Lys Thr Asp Ala Glu Val Ser Gly Asp Asn Leu
            20                  25                  30

Ser Gln Pro Gly Arg Arg Pro Pro Ser Pro Lys Pro Gln Thr Thr Lys
        35                  40                  45

Phe Pro Arg Arg Glu Ser Pro Asp Arg Arg Gly Thr Arg Arg Arg Thr
    50                  55                  60
```

```
Glu Ser Arg Gly Ala Val Ser Arg Val Trp Pro Gly Glu Asn Gln Arg
 65                  70                  75                  80

Arg Arg Ser Ala Val Asp Asp Ser Ile Pro Ala Asn Pro Ile Ala Leu
                 85                  90                  95
```

<210> SEQ ID NO 267
<211> LENGTH: 303
<212> TYPE: DNA
<213> ORGANISM: Toxoplasma gondii
<220> FEATURE:
<221> NAME/KEY: CDS
<222> LOCATION: (1)..(303)
<223> OTHER INFORMATION:

<400> SEQUENCE: 267

```
gac gaa gct ctt cct ctc ttt gga gca aac gat gga acc tca gtt cgg      48
Asp Glu Ala Leu Pro Leu Phe Gly Ala Asn Asp Gly Thr Ser Val Arg
1               5                   10                  15 ctc tcc ctc gac cgc agc gtc ctg ctt gtt ctc gaa ccc gca gag ccc      96
Leu Ser Leu Asp Arg Ser Val Leu Leu Val Leu Glu Pro Ala Glu Pro
            20                  25                  30 ctg cta tcc tct tgg ccc cac ccg ggg aga aga gac act ttt ctt gaa     144
Leu Leu Ser Ser Trp Pro His Pro Gly Arg Arg Asp Thr Phe Leu Glu
        35                  40                  45 ggc gat ggc gcg ggc atc ccg tct cct tca tct cgg ccg agt cgc gcg     192
Gly Asp Gly Ala Gly Ile Pro Ser Pro Ser Ser Arg Pro Ser Arg Ala
 50                  55                  60 gcc gac cat tac acg aga ctc tcc acg att cgg tct ctt gcc agg gat     240
Ala Asp His Tyr Thr Arg Leu Ser Thr Ile Arg Ser Leu Ala Arg Asp
65                  70                  75                  80 gga gag gtc gac tcc gag ctg gcg ggg gga ccg cag gaa aga gaa agt     288
Gly Glu Val Asp Ser Glu Leu Ala Gly Gly Pro Gln Glu Arg Glu Ser
                85                  90                  95 gtc aga gtg gat ccg                                                  303
Val Arg Val Asp Pro
            100
```

<210> SEQ ID NO 268
<211> LENGTH: 101
<212> TYPE: PRT
<213> ORGANISM: Toxoplasma gondii

<400> SEQUENCE: 268

```
Asp Glu Ala Leu Pro Leu Phe Gly Ala Asn Asp Gly Thr Ser Val Arg
1               5                   10                  15

Leu Ser Leu Asp Arg Ser Val Leu Leu Val Leu Glu Pro Ala Glu Pro
            20                  25                  30

Leu Leu Ser Ser Trp Pro His Pro Gly Arg Arg Asp Thr Phe Leu Glu
        35                  40                  45

Gly Asp Gly Ala Gly Ile Pro Ser Pro Ser Ser Arg Pro Ser Arg Ala
 50                  55                  60

Ala Asp His Tyr Thr Arg Leu Ser Thr Ile Arg Ser Leu Ala Arg Asp
65                  70                  75                  80

Gly Glu Val Asp Ser Glu Leu Ala Gly Gly Pro Gln Glu Arg Glu Ser
                85                  90                  95

Val Arg Val Asp Pro
            100
```

<210> SEQ ID NO 269
<211> LENGTH: 236

```
<212> TYPE: DNA
<213> ORGANISM: Toxoplasma gondii
<220> FEATURE:
<221> NAME/KEY: CDS
<222> LOCATION: (1)..(234)
<223> OTHER INFORMATION:

<400> SEQUENCE: 269 cgc gga gag ggg gag act gag aga ggg cag aat gag gag act cac gca      48
Arg Gly Glu Gly Glu Thr Glu Arg Gly Gln Asn Glu Glu Thr His Ala
1               5                   10                  15 acg aac aag tcc tca ggc gtc gcc agt ttg gag gca cca gcg tcg ttc      96
Thr Asn Lys Ser Ser Gly Val Ala Ser Leu Glu Ala Pro Ala Ser Phe
            20                  25                  30 gcg cag gag ggc gac gga ggg cgg aga gaa gaa gca agc caa gca aaa     144
Ala Gln Glu Gly Asp Gly Gly Arg Arg Glu Glu Ala Ser Gln Ala Lys
        35                  40                  45 atg ggg acg tct tcc ccg tcg aat cag gtg atc aac gtt gta gac gaa     192
Met Gly Thr Ser Ser Pro Ser Asn Gln Val Ile Asn Val Val Asp Glu
    50                  55                  60 gac gag gag gac gac gag gaa gca gag gcg caa gag gca ccc gg          236
Asp Glu Glu Asp Asp Glu Glu Ala Glu Ala Gln Glu Ala Pro
65                  70                  75

<210> SEQ ID NO 270
<211> LENGTH: 78
<212> TYPE: PRT
<213> ORGANISM: Toxoplasma gondii

<400> SEQUENCE: 270

Arg Gly Glu Gly Glu Thr Glu Arg Gly Gln Asn Glu Glu Thr His Ala
1               5                   10                  15

Thr Asn Lys Ser Ser Gly Val Ala Ser Leu Glu Ala Pro Ala Ser Phe
            20                  25                  30

Ala Gln Glu Gly Asp Gly Gly Arg Arg Glu Glu Ala Ser Gln Ala Lys
        35                  40                  45

Met Gly Thr Ser Ser Pro Ser Asn Gln Val Ile Asn Val Val Asp Glu
    50                  55                  60

Asp Glu Glu Asp Asp Glu Glu Ala Glu Ala Gln Glu Ala Pro
65                  70                  75

<210> SEQ ID NO 271
<211> LENGTH: 423
<212> TYPE: DNA
<213> ORGANISM: Toxoplasma gondii
<220> FEATURE:
<221> NAME/KEY: CDS
<222> LOCATION: (1)..(423)
<223> OTHER INFORMATION:

<400> SEQUENCE: 271 cgc gga att ccg gat cag cgt agc agt cgc agc cac act gga gtg gaa      48
Arg Gly Ile Pro Asp Gln Arg Ser Ser Arg Ser His Thr Gly Val Glu
1               5                   10                  15 agt ctg gtt ttg ccc tcc aga ggg gag gaa gag gcg aga gag gag acg      96
Ser Leu Val Leu Pro Ser Arg Gly Glu Glu Glu Ala Arg Glu Glu Thr
            20                  25                  30 tct gca acg cgc cag atg ccg acg ctt ctc tct tcg ccg agg cct cca     144
Ser Ala Thr Arg Gln Met Pro Thr Leu Leu Ser Ser Pro Arg Pro Pro
        35                  40                  45 ctc gcg ctg ggg ttg gga gac gag tct ccc tgc gga gag tgg gtg tcg     192
Leu Ala Leu Gly Leu Gly Asp Glu Ser Pro Cys Gly Glu Trp Val Ser
    50                  55                  60
```

```
ccg aat gac atg gtt tct gcg ttg tcc ctc tgg gaa gca ggc gag gct      240
Pro Asn Asp Met Val Ser Ala Leu Ser Leu Trp Glu Ala Gly Glu Ala
 65              70                  75                  80 tgg cag ttc aag aca gcg aaa att ctt gac tct ttc gaa ggg gag acc      288
Trp Gln Phe Lys Thr Ala Lys Ile Leu Asp Ser Phe Glu Gly Glu Thr
                 85                  90                  95 cca gaa ggg gag gga tgc ggc gca cag gaa aag gac agc cgc atg caa      336
Pro Glu Gly Glu Gly Cys Gly Ala Gln Glu Lys Asp Ser Arg Met Gln
                100                 105                 110 gct ggt gcg act ccc ggt gaa cgt gga ggg gcg gtc gac gaa ggt gtg      384
Ala Gly Ala Thr Pro Gly Glu Arg Gly Gly Ala Val Asp Glu Gly Val
                115                 120                 125 gag ctt ggc tct tct ttc ttc tct gcg tct gaa gat ccg                  423
Glu Leu Gly Ser Ser Phe Phe Ser Ala Ser Glu Asp Pro
    130                 135                 140

<210> SEQ ID NO 272
<211> LENGTH: 141
<212> TYPE: PRT
<213> ORGANISM: Toxoplasma gondii

<400> SEQUENCE: 272

Arg Gly Ile Pro Asp Gln Arg Ser Ser Arg Ser His Thr Gly Val Glu
  1               5                  10                  15

Ser Leu Val Leu Pro Ser Arg Gly Glu Glu Ala Arg Glu Thr
                 20                  25                  30

Ser Ala Thr Arg Gln Met Pro Thr Leu Leu Ser Ser Pro Arg Pro Pro
                 35                  40                  45

Leu Ala Leu Gly Leu Gly Asp Glu Ser Pro Cys Gly Glu Trp Val Ser
     50                  55                  60

Pro Asn Asp Met Val Ser Ala Leu Ser Leu Trp Glu Ala Gly Glu Ala
 65              70                  75                  80

Trp Gln Phe Lys Thr Ala Lys Ile Leu Asp Ser Phe Glu Gly Glu Thr
                 85                  90                  95

Pro Glu Gly Glu Gly Cys Gly Ala Gln Glu Lys Asp Ser Arg Met Gln
                100                 105                 110

Ala Gly Ala Thr Pro Gly Glu Arg Gly Gly Ala Val Asp Glu Gly Val
                115                 120                 125

Glu Leu Gly Ser Ser Phe Phe Ser Ala Ser Glu Asp Pro
    130                 135                 140

<210> SEQ ID NO 273
<211> LENGTH: 514
<212> TYPE: DNA
<213> ORGANISM: Toxoplasma gondii
<220> FEATURE:
<221> NAME/KEY: CDS
<222> LOCATION: (1)..(513)
<223> OTHER INFORMATION:

<400> SEQUENCE: 273 cgg gat cag gct tct atg cca ctg ccc ccg gcc ccc gaa gac ttt gac       48
Arg Asp Gln Ala Ser Met Pro Leu Pro Pro Ala Pro Glu Asp Phe Asp
  1               5                  10                  15 ctg cct cct atg cca ctg ccc gaa gca ccc gaa gac ttt gac cag gct       96
Leu Pro Pro Met Pro Leu Pro Glu Ala Pro Glu Asp Phe Asp Gln Ala
                 20                  25                  30 cct atg cca ctg ccc gag gca ccc gaa gac ttt gac cag gct cct atg      144
Pro Met Pro Leu Pro Glu Ala Pro Glu Asp Phe Asp Gln Ala Pro Met
                 35                  40                  45
```

```
cca ctg ccc gag gca ccc gaa gac ttt gac cag cct cct atg cca ctg      192
Pro Leu Pro Glu Ala Pro Glu Asp Phe Asp Gln Pro Pro Met Pro Leu
    50                  55                  60 ccc gag gca ccc gaa gac ttt gac cag gct cct atg cca ctg ccc gaa      240
Pro Glu Ala Pro Glu Asp Phe Asp Gln Ala Pro Met Pro Leu Pro Glu
65                  70                  75                  80 gca ccc gaa gtc ttt gac cag gct cct atg cca ctg ccc gag gca ccc      288
Ala Pro Glu Val Phe Asp Gln Ala Pro Met Pro Leu Pro Glu Ala Pro
                85                  90                  95 gaa gtc ttt gac cag gct cct atg cca ctg ccc gaa gca ccc gaa gac      336
Glu Val Phe Asp Gln Ala Pro Met Pro Leu Pro Glu Ala Pro Glu Asp
            100                 105                 110 ttt gac cag gct cct atg cca ctg ccc gaa gca ccc gaa gtc ttt gac      384
Phe Asp Gln Ala Pro Met Pro Leu Pro Glu Ala Pro Glu Val Phe Asp
        115                 120                 125 cag gct cct atg cca ctg ccc gag gca ccc gaa gac ttt gac cag gct      432
Gln Ala Pro Met Pro Leu Pro Glu Ala Pro Glu Asp Phe Asp Gln Ala
    130                 135                 140 cct atg cca gtg ccc gag gca ccc gaa gac ttt gac cag gct cct gag      480
Pro Met Pro Val Pro Glu Ala Pro Glu Asp Phe Asp Gln Ala Pro Glu
145                 150                 155                 160 cca ctg ccc gag gca gcc gaa gaa ttt gat ccc g                        514
Pro Leu Pro Glu Ala Ala Glu Glu Phe Asp Pro
                165                 170

<210> SEQ ID NO 274
<211> LENGTH: 171
<212> TYPE: PRT
<213> ORGANISM: Toxoplasma gondii

<400> SEQUENCE: 274

Arg Asp Gln Ala Ser Met Pro Leu Pro Ala Pro Glu Asp Phe Asp
1               5                   10                  15

Leu Pro Pro Met Pro Leu Pro Glu Ala Pro Glu Asp Phe Asp Gln Ala
                20                  25                  30

Pro Met Pro Leu Pro Glu Ala Pro Glu Asp Phe Asp Gln Ala Pro Met
            35                  40                  45

Pro Leu Pro Glu Ala Pro Glu Asp Phe Asp Gln Pro Pro Met Pro Leu
    50                  55                  60

Pro Glu Ala Pro Glu Asp Phe Asp Gln Ala Pro Met Pro Leu Pro Glu
65                  70                  75                  80

Ala Pro Glu Val Phe Asp Gln Ala Pro Met Pro Leu Pro Glu Ala Pro
                85                  90                  95

Glu Val Phe Asp Gln Ala Pro Met Pro Leu Pro Glu Ala Pro Glu Asp
            100                 105                 110

Phe Asp Gln Ala Pro Met Pro Leu Pro Glu Ala Pro Glu Val Phe Asp
        115                 120                 125

Gln Ala Pro Met Pro Leu Pro Glu Ala Pro Glu Asp Phe Asp Gln Ala
    130                 135                 140

Pro Met Pro Val Pro Glu Ala Pro Glu Asp Phe Asp Gln Ala Pro Glu
145                 150                 155                 160

Pro Leu Pro Glu Ala Ala Glu Glu Phe Asp Pro
                165                 170

<210> SEQ ID NO 275
<211> LENGTH: 16
<212> TYPE: DNA
<213> ORGANISM: Artificial sequence
```

```
<220> FEATURE:
<223> OTHER INFORMATION: Synthetic Primer

<400> SEQUENCE: 275
tgcttctcaa aagccg                                                    16

<210> SEQ ID NO 276
<211> LENGTH: 21
<212> TYPE: DNA
<213> ORGANISM: Artificial sequence
<220> FEATURE:
<223> OTHER INFORMATION: Synthetic Primer

<400> SEQUENCE: 276
cgattgcctg caagaagtgt g                                              21

<210> SEQ ID NO 277
<211> LENGTH: 20
<212> TYPE: DNA
<213> ORGANISM: Artificial sequence
<220> FEATURE:
<223> OTHER INFORMATION: Synthetic Primer

<400> SEQUENCE: 277
acagttttct ccatttcagg                                                20

<210> SEQ ID NO 278
<211> LENGTH: 19
<212> TYPE: DNA
<213> ORGANISM: Artificial sequence
<220> FEATURE:
<223> OTHER INFORMATION: Synthetic Primer

<400> SEQUENCE: 278
atatactttg cgtgggcgg                                                 19

<210> SEQ ID NO 279
<211> LENGTH: 17
<212> TYPE: DNA
<213> ORGANISM: Artificial sequence
<220> FEATURE:
<223> OTHER INFORMATION: Synthetic Primer

<400> SEQUENCE: 279
tcctgggttt gatgctg                                                   17

<210> SEQ ID NO 280
<211> LENGTH: 20
<212> TYPE: DNA
<213> ORGANISM: Artificial sequence
<220> FEATURE:
<223> OTHER INFORMATION: Synthetic Primer

<400> SEQUENCE: 280
ctgttctgaa aacggtgcgg                                                20

<210> SEQ ID NO 281
<211> LENGTH: 18
<212> TYPE: DNA
<213> ORGANISM: Artificial sequence
<220> FEATURE:
<223> OTHER INFORMATION: Synthetic Primer

<400> SEQUENCE: 281
gaaaacggtg ccctaaag                                                  18
```

<210> SEQ ID NO 282
<211> LENGTH: 1225
<212> TYPE: DNA
<213> ORGANISM: Toxoplasma gondii
<220> FEATURE:
<221> NAME/KEY: CDS
<222> LOCATION: (1)..(87)
<223> OTHER INFORMATION:

<400> SEQUENCE: 282

```
ggt cga gtg tcg cag aaa aag acg ctt gtc tgt gcc cgg cgt aga caa        48
Gly Arg Val Ser Gln Lys Lys Thr Leu Val Cys Ala Arg Arg Arg Gln
1               5                   10                  15 tct ctt cgg cct ctc gga cga acc gag ttt tca cgg tga acctttgtg         97
Ser Leu Arg Pro Leu Gly Arg Thr Glu Phe Ser Arg
            20                  25 cttactttc gtctcagact gtgttgttgt tccctgcttc tcaaaagccg cccttccctc      157
acttcttgtt cgccgattgc cttcaagaag tgtggagttc ccttcctttt ttccgggttc     217
tccggaagcc tcctgtagca aaatgcgctg aaattttgga cacttctcga cggtgtctcg     277
ctttaggacg gacctcatgg tctttagggc accgttttct ttcactttt ctaggaacat     337
cacagttttc tccatttcag ggaacgaaca atctgcaagc gtccacttgt cctgtggctg    397
ctgggctcgg atgccgcctc tgtttagcaa ttgtagcagg caccggatgg caagctaggt    457
ccacttcact gcagtttcaa cttccaaacc aaggcatctc aatttgtatc gtgttctctg    517
tcaacaagct gttgaacctg tcgacggagt gtcgtcccgg ctcctatccc gcgttcgcaa    577
gccgcaccgt tttcagaaca gtgttccccg tggtgttgaa agcgggctgc gaagcgcgag    637
cgtttcgttt tgtggttttt tctgggaaac gatgggatc tcttcgtgtg gcagacgct     697
tgcctcctgt ttcaaggcgg tgaagtccgg aaccgttgac ttcaagggc aggagcgagt    757
atactcgtgg ttgatatact ttgcgtgggc gggtggcctc agcgggtttt tcgtcggagg    817
gattctggaa gacttcacgg tcacagtgta cacgatcttg atgtgcatgg ccattgcggc    877
gattctctgt tttccgtcgt ggccatgttt ccacagacac cctgtcgagt ggacgccgca    937
cgaccccgcc aggctggctg ctctcttcac gcagcatcaa acccaggaag aaactcctca    997
gaaaggtgcg gggaaaaaac gagggaagaa gagcgctgaa gtgcaacgga aaaactgagt   1057
gtgtgtgcgt atgtagacaa gtgagtcttc ccagagttcg tccggattgt tgcgtggatc   1117
gtgtcaactg gacttctcgt tcgtcaaaga cctggtcgtc tgacccatct gctctccata   1177
aaaaagcttg ttaacgctcc taaaaaaaaa aaaaaaaaa aaaaaaaa                  1225
```

<210> SEQ ID NO 283
<211> LENGTH: 28
<212> TYPE: PRT
<213> ORGANISM: Toxoplasma gondii

<400> SEQUENCE: 283

```
Gly Arg Val Ser Gln Lys Lys Thr Leu Val Cys Ala Arg Arg Arg Gln
1               5                   10                  15

Ser Leu Arg Pro Leu Gly Arg Thr Glu Phe Ser Arg
            20                  25
```

<210> SEQ ID NO 284
<211> LENGTH: 1225
<212> TYPE: DNA
<213> ORGANISM: Toxoplasma gondii

<400> SEQUENCE: 284

-continued

```
tttttttttt tttttttttt tttttttagg agcgttaaca agcttttta tggagagcag      60 atgggtcaga cgaccaggtc tttgacgaac gagaagtcca gttgacacga tccacgcaac    120
aatccggacg aactctggga agactcactt gtctacatac gcacacacac tcagtttttc    180
cgttgcactt cagcgctctt cttccctcgt tttttcccg cacctttctg aggagtttct     240
tcctgggttt gatgctgcgt gaagagagca gccagcctgg cggggtcgtg cggcgtccac    300
tcgacagggt gtctgtggaa acatggccac gacggaaaac agagaatcgc cgcaatggcc    360
atgcacatca agatcgtgta cactgtgacc gtgaagtctt ccagaatccc tccgacgaaa    420
aacccgctga ggccacccgc ccacgcaaag tatatcaacc acgagtatac tcgctcctgc    480
cccttgaagt caacggttcc ggacttcacc gccttgaaac aggaggcaag cgtctcgcca    540
cacgaagaga tccccatcgt ttcccagaaa aaaccacaaa acgaaacgct cgcgcttcgc    600
agcccgcttt caacaccacg gggaacactg ttctgaaaac ggtgcggctt gcgaacgcgg    660
gataggagcc gggacgacac tccgtcgaca ggttcaacag cttgttgaca gagaacacga    720
tacaaattga gatgccttgg tttggaagtt gaaactgcag tgaagtggac ctagcttgcc    780
atccggtgcc tgctacaatt gctaaacaga ggcggcatcc gagcccagca gccacaggac    840
aagtggacgc ttgcagattg ttcgttccct gaaatggaga aaactgtgat gttcctagaa    900
aaagtgaaag aaaacggtgc cctaaagacc atgaggtccg tcctaaagcg agacaccgtc    960
gagaagtgtc caaatttca gcgcatttg ctacaggagg cttccggaga acccggaaaa     1020
aaggaaggga actccacact tcttgaaggc aatcggcgaa caagaagtga gggaagggcg   1080
gcttttgaga agcagggaac aacaacacag tctgagacga aaagtaagca caaaaggttc   1140
accgtgaaaa ctcggttcgt ccgagaggcc gaagagattg tctacgccgg gcacagacaa   1200
gcgtcttttt ctgcgacact cgacc                                        1225
```

<210> SEQ ID NO 285
<211> LENGTH: 20
<212> TYPE: DNA
<213> ORGANISM: Artificial sequence
<220> FEATURE:
<223> OTHER INFORMATION: Synthetic Primer

<400> SEQUENCE: 285

```
gggcgagaac atcaccattg                                                20
```

<210> SEQ ID NO 286
<211> LENGTH: 19
<212> TYPE: DNA
<213> ORGANISM: Artificial sequence
<220> FEATURE:
<223> OTHER INFORMATION: Synthetic Primer

<400> SEQUENCE: 286

```
acacgaagga cctgtatgg                                                 19
```

<210> SEQ ID NO 287
<211> LENGTH: 19
<212> TYPE: DNA
<213> ORGANISM: Artificial sequence
<220> FEATURE:
<223> OTHER INFORMATION: Synthetic Primer

<400> SEQUENCE: 287

```
gtgcttcgat ttgaatgcg                                                 19
```

<210> SEQ ID NO 288
<211> LENGTH: 17
<212> TYPE: DNA
<213> ORGANISM: Artificial sequence
<220> FEATURE:
<223> OTHER INFORMATION: Synthetic Primer

<400> SEQUENCE: 288
tcaaatcgaa gcacatg                                            17

<210> SEQ ID NO 289
<211> LENGTH: 19
<212> TYPE: DNA
<213> ORGANISM: Artificial sequence
<220> FEATURE:
<223> OTHER INFORMATION: Synthetic Primer

<400> SEQUENCE: 289
tttcccagac cttgctgtc                                          19

<210> SEQ ID NO 290
<211> LENGTH: 20
<212> TYPE: DNA
<213> ORGANISM: Artificial sequence
<220> FEATURE:
<223> OTHER INFORMATION: Synthetic Primer

<400> SEQUENCE: 290
tcattcaggt ccatcgtcgg                                         20

<210> SEQ ID NO 291
<211> LENGTH: 20
<212> TYPE: DNA
<213> ORGANISM: Artificial sequence
<220> FEATURE:
<223> OTHER INFORMATION: Synthetic Primer

<400> SEQUENCE: 291
cgaggcacaa gtctgcaatg                                         20

<210> SEQ ID NO 292
<211> LENGTH: 1573
<212> TYPE: DNA
<213> ORGANISM: Toxoplasma gondii
<220> FEATURE:
<221> NAME/KEY: CDS
<222> LOCATION: (1)..(222)
<223> OTHER INFORMATION:

<400> SEQUENCE: 292

```
gca gcc tct ctc ttc acc ctc cgt aaa aat gaa act cct gac gcc caa        48
Ala Ala Ser Leu Phe Thr Leu Arg Lys Asn Glu Thr Pro Asp Ala Gln
1               5                  10                  15 gga cga tgt gcg cgg ccg gaa ggt gca gtt ggt ggc ggc ttt cct gga        96
Gly Arg Cys Ala Arg Pro Glu Gly Ala Val Gly Gly Gly Phe Pro Gly
            20                  25                  30 cct gcc gct gca gac tgt gcc ttt cac cgt ggg gaa gga cga caa gga       144
Pro Ala Ala Ala Asp Cys Ala Phe His Arg Gly Glu Gly Arg Gln Gly
        35                  40                  45 tcc ggc gtt ctt ggc caa gtc gcc tct ggg gcg tct gcc cct gtt gga       192
Ser Gly Val Leu Gly Gln Val Ala Ser Gly Ala Ser Ala Pro Val Gly
    50                  55                  60 gtc cga ggt cgg cgg cgt gtg tct gtt tga aagcaacgcg atttgccgct         242
Val Arg Gly Arg Arg Arg Val Ser Val
65                  70
```

-continued

```
tcctcgcgcg acttcgcgcc gacaagtgcc tgtacggcga gacgcttgcg gagcagggac      302
aagtggacat gtggttggac ttctcgaccc tcgaagtcga gattccgatg tgttgcttgg      362
tgcagggggg aaaggttgcg gagcgcgcgc agagcgacct ggcgcaggca ctgaacgcgg      422
tcgacgccca cctgaagacg cgcaccttca tggtgggcga gaacatcacc attgcagact      482
tgtgcctcgt cgcggtgctg agctacggct tccggtccgg caaggtggac gccgcagcgc      542
tgctcgagaa gcgtccgtac ttgaagcgct tctacgagac cgtggtgaat cagaagagct      602
tcaagaagat cttcggcgag gcgaaggcag cgccacaggc cgccgccaag aaggagactc      662
ccaaagccgc ggcgaagcct gcacagagcg ccggcgatga cgaagaaccg gcgaagaagc      722
ctgcagtcaa gtgcgagttg gacttgctcc cagagccgac gatggacctg aatgagtgga      782
agcgcgtgta ctccaacacg aaggacctgt atggcacagc gatgaaatgg ttctgggaac      842
acctcgacgg ggcagggtat tccttgtggt acatgaaata tcagaaactc gagggcgagt      902
gcaccgtcgc gttcgtcacc tcgaaccagc tcggcggctt cctgcagcgg atcgacccgg      962
ccttccgcaa atactccttc ggcgtcgtcg acgtgatggg cgagaacggc tgcttcgaca     1022
tcgagggtgt ctggctgttc cgcggccaag acgtacccag cttgatgaag gaccacccgt     1082
cgtacgagta ccacacttgg cagaaactcg acgtcgccag cgcaaaagac aagcaactcg     1142
tcgcagactt ttggtgcgcg tgcgacgaca tccaaggtcg ccccatcgcc gacagcaagg     1202
tctggaaata aaaggaaata acgcacttcg cgaaacgaag gggcggcaac agaggtgtgt     1262
gtctttggtg ctgtgaaaaa aagcgacgcg taaaaaacgg cgagaaatgt tcgtggcgtg     1322
gcgtgcggtg agagggtac agtggcgaag ggtcacaaac ccatgtgctt cgatttgaat     1382
gcgcttccat ctgtacacct ggctcttccg tgcgtccttt cagtctctcc taaaaatctc     1442
gtttcacgcg ggtgcagttg cggtacttca ggagcttcgc aggcgccgct cgcgcgcgct     1502
ccccgctcta ggaactctca cacgacccca tttatgtcaa ctcgaaaaaa aaaaaaaaaa     1562
aaaaaaaaa a                                                          1573
```

<210> SEQ ID NO 293
<211> LENGTH: 73
<212> TYPE: PRT
<213> ORGANISM: Toxoplasma gondii

<400> SEQUENCE: 293

```
Ala Ala Ser Leu Phe Thr Leu Arg Lys Asn Glu Thr Pro Asp Ala Gln
  1               5                  10                  15

Gly Arg Cys Ala Arg Pro Glu Gly Ala Val Gly Gly Phe Pro Gly
             20                  25                  30

Pro Ala Ala Ala Asp Cys Ala Phe His Arg Gly Glu Gly Arg Gln Gly
         35                  40                  45

Ser Gly Val Leu Gly Gln Val Ala Ser Gly Ala Ser Ala Pro Val Gly
     50                  55                  60

Val Arg Gly Arg Arg Val Ser Val
 65                  70
```

<210> SEQ ID NO 294
<211> LENGTH: 1573
<212> TYPE: DNA
<213> ORGANISM: Toxoplasma gondii

<400> SEQUENCE: 294

```
tttttttttt tttttttttt ttttttttcga gttgacataa atgggtcgt gtgagagttc       60
```

```
ctagagcggg gagcgcgcgc gagcggcgcc tgcgaagctc ctgaagtacc gcaactgcac      120
ccgcgtgaaa cgagattttt aggagagact gaaaggacgc acggaagagc caggtgtaca      180
gatggaagcg cattcaaatc gaagcacatg ggtttgtgac ccttcgccac tgtacccctc      240
tcaccgcacg ccacgccacg aacatttctc gccgtttttt acgcgtcgct ttttttcaca      300
gcaccaaaga cacacacctc tgttgccgcc ccttcgtttc gcgaagtgcg ttatttcctt      360
ttatttccag accttgctgt cggcgatggg gcgaccttgg atgtcgtcgc acgcgcacca      420
aaagtctgcg acgagttgct tgtcttttgc gctggcgacg tcgagtttct gccaagtgtg      480
gtactcgtac gacgggtggt ccttcatcaa gctgggtacg tcttggccgc ggaacagcca      540
gacaccctcg atgtcgaagc agccgttctc gcccatcacg tcgacgacgc cgaaggagta      600
tttgcggaag gccgggtcga tccgctgcag gaagccgccg agctggttcg aggtgacgaa      660
cgcgacggtg cactcgccct cgagtttctg atatttcatg taccacaagg aatacccgc      720 cgcgtcgagg tgttcccaga accatttcat cgctgtgcca tacaggtcct tcgtgttgga      780
gtacacgcgc ttccactcat tcaggtccat cgtcggctct gggagcaagt ccaactcgca      840
cttgactgca ggcttcttcg ccggttcttc gtcatcgccg gcgctctgtg caggcttcgc      900
cgcggctttg ggagtctcct tcttggcggc ggcctgtggc gctgccttcg cctcgccgaa      960
gatcttcttg aagctcttct gattcaccac ggtctcgtag aagcgcttca agtacggacg     1020
cttctcgagc agcgctgcgg cgtccacctt gccggaccgg aagccgtagc tcagcaccgc     1080
gacgaggcac aagtctgcaa tggtgatgtt ctcgcccacc atgaaggtgc gcgtcttcag     1140
gtgggcgtcg accgcgttca gtgcctgcgc caggtcgctc tgcgcgcgct ccgcaacctt     1200 tccccctgc accaagcaac acatcggaat ctcgacttcg agggtcgaga agtccaacca     1260
catgtccact tgtccctgct ccgcaagcgt tcgccgtac aggcacttgt cggcgcgaag     1320
tcgcgcgagg aagcggcaaa tcgcgttgct ttcaaacaga cacacgccgc cgacctcgga     1380
ctccaacagg ggcagacgcc ccagaggcga cttggccaag aacgccggat ccttgtcgtc     1440
cttccccacg gtgaaaggca cagtctgcag cggcaggtcc aggaaagccg ccaccaactg     1500
caccttccgg ccgcgcacat cgtccttggg cgtcaggagt ttcattttta cggagggtga     1560
agagagaggc tgc                                                          1573

<210> SEQ ID NO 295
<211> LENGTH: 20
<212> TYPE: DNA
<213> ORGANISM: Artificial sequence
<220> FEATURE:
<223> OTHER INFORMATION: Synthetic Primer

<400> SEQUENCE: 295
ttatttcccc gcctcgtctc                                                     20

<210> SEQ ID NO 296
<211> LENGTH: 20
<212> TYPE: DNA
<213> ORGANISM: Artificial sequence
<220> FEATURE:
<223> OTHER INFORMATION: Synthetic Primer

<400> SEQUENCE: 296
cctactgtga ctcccatcac                                                     20

<210> SEQ ID NO 297
```

```
<211> LENGTH: 19
<212> TYPE: DNA
<213> ORGANISM: Artificial sequence
<220> FEATURE:
<223> OTHER INFORMATION: Synthetic Primer

<400> SEQUENCE: 297
atcaccacta agcgtaggg                                              19

<210> SEQ ID NO 298
<211> LENGTH: 19
<212> TYPE: DNA
<213> ORGANISM: Artificial sequence
<220> FEATURE:
<223> OTHER INFORMATION: Synthetic Primer

<400> SEQUENCE: 298
tcgaaagaac gaagctgcc                                              19

<210> SEQ ID NO 299
<211> LENGTH: 20
<212> TYPE: DNA
<213> ORGANISM: Artificial sequence
<220> FEATURE:
<223> OTHER INFORMATION: Synthetic Primer

<400> SEQUENCE: 299
cgaagggtgt catcctctac                                             20

<210> SEQ ID NO 300
<211> LENGTH: 21
<212> TYPE: DNA
<213> ORGANISM: Artificial sequence
<220> FEATURE:
<223> OTHER INFORMATION: Synthetic Primer

<400> SEQUENCE: 300
tatcgccaac agagtgaacc g                                           21

<210> SEQ ID NO 301
<211> LENGTH: 22
<212> TYPE: DNA
<213> ORGANISM: Artificial sequence
<220> FEATURE:
<223> OTHER INFORMATION: Synthetic Primer

<400> SEQUENCE: 301
gtggacccaa gcatttgtgt gg                                          22

<210> SEQ ID NO 302
<211> LENGTH: 21
<212> TYPE: DNA
<213> ORGANISM: Artificial sequence
<220> FEATURE:
<223> OTHER INFORMATION: Synthetic Primer

<400> SEQUENCE: 302
gcgtttcgac agttctatca c                                           21

<210> SEQ ID NO 303
<211> LENGTH: 20
<212> TYPE: DNA
<213> ORGANISM: Artificial sequence
<220> FEATURE:
<223> OTHER INFORMATION: Synthetic Primer

<400> SEQUENCE: 303
```

```
acggaagaag acggagatgg                                                    20

<210> SEQ ID NO 304
<211> LENGTH: 20
<212> TYPE: DNA
<213> ORGANISM: Artificial sequence
<220> FEATURE:
<223> OTHER INFORMATION: Synthetic Primer

<400> SEQUENCE: 304
gagattccct acgcttagtg                                                    20

<210> SEQ ID NO 305
<211> LENGTH: 19
<212> TYPE: DNA
<213> ORGANISM: Artificial sequence
<220> FEATURE:
<223> OTHER INFORMATION: Synthetic Primer

<400> SEQUENCE: 305
gttcgtcttt cgccataac                                                     19

<210> SEQ ID NO 306
<211> LENGTH: 2417
<212> TYPE: DNA
<213> ORGANISM: Toxoplasma gondii
<220> FEATURE:
<221> NAME/KEY: CDS
<222> LOCATION: (1)..(27)
<223> OTHER INFORMATION:

<400> SEQUENCE: 306 gtt tcc tcc gtt ctt ctt cgt ttt aaa ctgcaggaag tttctcctcg               47
Val Ser Ser Val Leu Leu Arg Phe Lys
1               5 ccttcgaccg cgtccgggga ctgaggtctg ctgtccacgc aggacttcct cttctccttt       107
ttcgcgccgc cagacgaggt cttcccgact tttcgtctgc acgcttctcc gcatctccgc       167
atctccccat ctccgtcttc ttccgttttt gactgtctgc gctctttctc cgacctcgct       227
cgaacgccgc gattctcgcc ttttatttcc ccgcctcgtc tccggccgtt ccacgcacct       287
tcctcggccg ttgcctcgcg ttcctcgggt gtacagacac ctgagcgctc tgcgttgtcg       347
cagcatttct ctgagccgca acatggggaa tgcgcagcct cgcggcggag gcttcccagg       407
aggctctgaa gaagacaaga agaaggagag aaagagactt gaagctgcgc ctccaacgca       467
cattggaaaa agaaagaaga aggaaaaagg ccccgtcggt cacagcagac ttcctactgt       527
gactcccatc accaagtgtc gcctgcgtct gctccgactc gagcgcataa aagactacct       587
tcttctggag gaagagtata ttctcaacca ggagcagcgg aagccggcgg aggagaagaa       647
cgaagaagat gtgaatcgcg tggacgagct ccgtggatca ccactaagcg tagggaatct       707
cgaggaaatc atcgatgaac agcatgcaat cgtttcttcc tccatcggtc ccgagtacta       767
cgtcaacatc ctctctttcg tcgacaaaga cctgctcgag cctggatgca gtgtccttct       827
tcacaacaaa acgagcagca ttgtcggaat tttgaacgac gaggtggacc ctctcatctc       887
ggtcatgaaa gtgagaaagg caccgcttga gactatgca gacatcggcg gactggagaa       947
gcagattcag gaggtgaagg aggccgtgga atttcctctc acgcatccgg agttcttcga      1007
cgacatcggt atcagccctc gaagggtgt catcctctac ggaccccccg ggacaggaaa      1067
gactctgctc gcgaaggccg tggcgaacga gacgtcggct acgttccttc gcgtcgtcgg      1127
```

```
aagtgaactc attcaaaaat atttgggaga cggcccgaag ctggtccggg aaatgtttaa    1187
actcgctcac gagcacgcgc cgagcatcgt cttcatcgtc ttcatcgaga gtctagaccc    1247
tgcgctcatt cggcctggac gcattgatcg gaaaattcaa ctccccaatc cggacgcgaa    1307
aaccaagcga aaaatcttcc agatccacac agcgaaaatg accatggccg acgacgtcga    1367
cctcgaggaa tttgttatgg cgaaagacga actgtcgggt gcagatatca aggcgacatg    1427
cacggaggcg gggttgctgg ccttgcgaga gcgacgcatg aaaatcaccc aggaagatct    1487
gcggaaggcg aaggagaagg cgctgtatca gaagaaaggg aacattccag agagtctgta    1547
tctgtgaaga ggcgggagaa aacaatggtg tctccccaga gcgtcgagac agctcgaaga    1607
acgaagctgc ctcttcagca ccctccagat ctgagccagg agcccaactc gatttgtggc    1667
ctcccaagaa ggactgacat ctcgaggcga agaagagact ggaaaatgtc acagcaggct    1727
tcagagacat cttctgctga gaagaaaggc tgtgcgagcg ctttcgactc gtcagttttg    1787
aggcgccgcc ggtagcgcac accctgtggc ttcggtttct ctgtgataga actgtcgaaa    1847
cgctgcgaaa atagaaatga cgaggtcgca ctgcaagaag acaagagaga ttcaaaagaa    1907
aaggttgttt gcccgaaaac ttagcgtctg cgtgtctgat tttttcgagt tgagttgcca    1967
gtgtggacac gcatgatcgc ggagtggggg cactcaaagc gaaaccgttt atcgccaaca    2027
gagtgaaccg ttcagacctt ttttcttggc gcatgcaaga aaaaagatgt gaactgcgta    2087
gtcgcactcg gcgattcccg cgggtgaggg agtgggagta gcgaattcag tcgaaagcga    2147
agaggctttc cagagcgcag acgcgacaga tttgccgaag gaaaaaagtc acgaacgtgt    2207
ctgtttgaga gaagaaccag ggccggcaca ggttctccgt gtattttta ggaaggatcg    2267 tgttgacagc gacaagaaag ccacacaaat gcttgggtcc acgggagcgc tgtcccccag    2327
acacacgcag aaatacgagt gaaacttact ctgcttcctg cgacaacttt cgcaattacg    2387
agtggaacgc ttcaaaaaaa aaaaaaaaa                                      2417
```

<210> SEQ ID NO 307
<211> LENGTH: 9
<212> TYPE: PRT
<213> ORGANISM: Toxoplasma gondii

<400> SEQUENCE: 307

Val Ser Ser Val Leu Leu Arg Phe Lys
1               5

<210> SEQ ID NO 308
<211> LENGTH: 2417
<212> TYPE: DNA
<213> ORGANISM: Toxoplasma gondii

<400> SEQUENCE: 308

```
tttttttttt tttttttgaa gcgttccact cgtaattgcg aaagttgtcg caggaagcag      60
agtaagtttc actcgtattt ctgcgtgtgt ctgggggaca gcgctcccgt ggacccaagc     120
atttgtgtgg ctttcttgtc gctgtcaaca cgatccttcc taaaaatac acggagaacc     180 tgtgccggcc ctggttcttc tctcaaacag acacgttcgt gacttttttc cttcggcaaa     240
tctgtcgcgt ctgcgctctg gaaagcctct tcgctttcga ctgaattcgc tactcccact     300
ccctcacccg cgggaatcgc cgagtgcgac tacgcagttc acatctttt tcttgcatgc     360 gccaagaaaa aaggtctgaa cggttcactc tgttggcgat aaacggtttc gctttgagtg     420
cccccactcc gcgatcatgc gtgtccacac tggcaactca actcgaaaaa atcagacacg     480
```

```
cagacgctaa gttttcgggc aaacaacctt ttcttttgaa tctctcttgt cttcttgcag    540
tgcgacctcg tcatttctat tttcgcagcg tttcgacagt tctatcacag agaaaccgaa    600
gccacagggt gtgcgctacc ggcggcgcct caaaactgac gagtcgaaag cgctcgcaca    660
gcctttcttc tcagcagaag atgtctctga agcctgctgt gacattttcc agtctcttct    720
tcgcctcgag atgtcagtcc ttcttgggag gccacaaatc gagttgggct cctggctcag    780
atctggaggg tgctgaagag gcagcttcgt tcttcgagct gtctcgacgc tctggggaga    840
caccattgtt ttctcccgcc tcttcacaga tacagactct ctggaatgtt ccctttcttc    900
tgatacagcg ccttctcctt cgccttccgc agatcttcct gggtgatttt catgcgtcgc    960
tctcgcaagg ccagcaaccc cgcctccgtg catgtcgcct tgatatctgc acccgacagt   1020
tcgtctttcg ccataacaaa ttcctcgagg tcgacgtcgt cggccatggt cattttcgct   1080
gtgtggatct ggaagatttt tcgcttggtt ttcgcgtccg gattggggag ttgaattttc   1140
cgatcaatgc gtccaggccg aatgagcgca gggtctagac tctcgatgaa gacgatgaag   1200
acgatgctcg gcgcgtgctc gtgagcgagt ttaaacattt cccggaccag cttcgggccg   1260
tctcccaaat attttgaat gagttcactt ccgacgacg aaggaacgt agccgacgtc   1320 tcgttcgcca cggccttcgc gagcagagtc tttcctgtcc cgggggtcc gtagaggatg   1380 acacccttcg gagggctgat accgatgtcg tcgaagaact ccggatgcgt gagaggaaat   1440 tccacgcct cctcacctc ctgaatctgc ttctccagtc cgccgatgtc tgcatacgtc   1500
tcaagcggtg ccttctccac tttcatgacc gagatgagag ggtccacctc gtcgttcaaa   1560
attccgacaa tgctgctcgt tttgttgtga agaaggacac tgcatccagg ctcgagcagg   1620
tctttgtcga cgaaagagag gatgttgacg tagtactcgg gaccgatgga ggaagaaacg   1680
attgcatgct gttcatcgat gatttcctcg agattccta cgcttagtgg tgatccacgg   1740
agctcgtcca cgcgattcac atcttcttcg ttcttctcct ccgccggctt ccgctgctcc   1800
tggttgagaa tatactcttc ctccagaaga aggtagtctt ttatgcgctc gagtcggagc   1860
agacgcaggc gacacttggt gatgggagtc acagtaggaa gtctgctgtg accgacgggg   1920 cctttcctt tcttctttct ttttccaatg tgcgttggag gcgcagcttc aagtctcttt   1980
ctctccttct tcttgtcttc ttcagagcct cctgggaagc ctccgccgcg aggctgcgca   2040 ttcccccatgt tgcggctcag agaaatgctg cgacaacgca gagcgctcag gtgtctgtac   2100
acccgaggaa cgcgaggcaa cggccgagga aggtgcgtgg aacggccgga gacgaggcgg   2160
ggaaataaaa ggcgagaatc gcggcgttcg agcgaggtcg gagaaagagc gcagacagtc   2220
aaaaacggaa gaagacggag atggggagat gcggagatgc ggagaagcgt gcagacgaaa   2280
agtcgggaag acctcgtctg gcggcgcgaa aaaggagaag aggaagtcct gcgtggacag   2340
cagacctcag tccccggacg cggtcgaagg cgaggagaaa cttcctgcag tttaaaacga   2400
agaagaacgg aggaaac                                                  2417
```

<210> SEQ ID NO 309
<211> LENGTH: 20
<212> TYPE: DNA
<213> ORGANISM: Artificial sequence
<220> FEATURE:
<223> OTHER INFORMATION: Synthetic Primer

<400> SEQUENCE: 309

```
cggactgcgt tatcgttacc                                                  20
```

-continued

```
<210> SEQ ID NO 310
<211> LENGTH: 18
<212> TYPE: DNA
<213> ORGANISM: Artificial sequence
<220> FEATURE:
<223> OTHER INFORMATION: Synthetic Primer

<400> SEQUENCE: 310
ctgttgcctt cggatatg                                                    18

<210> SEQ ID NO 311
<211> LENGTH: 1785
<212> TYPE: DNA
<213> ORGANISM: Toxoplasma gondii
<220> FEATURE:
<221> NAME/KEY: CDS
<222> LOCATION: (1)..(75)
<223> OTHER INFORMATION:

<400> SEQUENCE: 311 gaa ccg gtg cac ttt tgc acg tgt acg caa gac agc ttc gca gac aac      48
Glu Pro Val His Phe Cys Thr Cys Thr Gln Asp Ser Phe Ala Asp Asn
1               5                   10                  15 atc tgg cag cct ccc gct cat ttt tag tcagcaaaaa tggcacccgc            95
Ile Trp Gln Pro Pro Ala His Phe
            20 acttgtgcag aggagaaaga aggtggccat gattggctct ggcatgattg gtggcactat     155 gggctacctg tgcgctctcc gtgagctcgt tgacgtcgtt ctctacgatg ttgtcaaagg     215 tatgcccgag ggtaaggctc ttgacctgag ccatgtgacc tccgtggtcg acaccaacgt     275 ttccgtccgt gctgagtact cttacgaggc gcgctcacc ggtgcggact gcgttatcgt      335 taccgccggt ctgaccaagg tgccgggcaa gcccgactcc gagtggagcc gaaacgatct     395 gctcccgttc aactcgaaga tcattcgcga gatcggtcag aacatcaaga agtactgccc     455 caagaccttc atcatcgtgg tcaccaaccc gctggactgc atggtcaagg tcatgtgcga     515 ggcctctggc gtcccgacca acatgatctg cggtatggcc tgcatgctcg actctggtcg     575 cttccgccga tacgtcgccg acgcgctgtc tgtctctccc cgcgacgtcc aggccaccgt     635 catcggcaca cacggcgact gcatggtccc gcttgtccgg tacattaccg tgaacgacta     695 cccgatccag aagttcatca aggacggcgt agtcacggag aagcagctcg aggagatcgc     755 tgagcacacc aaagtgtctg gcggcgagat cgtccgcttc ctcggccagg gttccgctta     815 ctacgccccc gccgcatccg ctgtcgccat ggcaacatcc ttcttgaacg acgaaaagcg     875 cgtcatcccg tgcagtgtgt actgcaacgg agagtacggc ttgaaggaca tgttcattgg     935 tctcccggcc gtcattggag gcgccggcat cgagcgcgtc atcgagctcg agctgaacga     995 ggaggagaag aagcagttcc agaagtccgt cgacgacgtc atggcgctca acaaggcggt    1055 tgctgctctt caggcgtaag cgttggcaaa acaggagcgg aatgccactt tactgcgcgg    1115 ggcccatgat ttatacacgc gtttgcaacg gaagcgaaaa gacggttccg gttcgcacca    1175 cgcgctcgtc ccgaaaaagg gaagtcgcgg cgctgtcggt caacgctgtg cgggttgcag    1235 gtgcgtgctt aagcatcaca aagtggcaga gccattttgt ccaggaagt agcgtctcaa     1295 acaggtgaac gcgtgcaagc atgagaggca tccgtcgctg cgttcgctca catatccgaa    1355 ggcaacagat tttggtcggc aaaagcctct gcacaaccgt ggcaagatga tggaaacagt    1415 tcgtgttttgg acagcaaccg cgttcgctct cactcaaaac cctgtagtcg agagggggtgt   1475 cgcatgactt ggcttttgtg ggagtgccca atcgtctgt gttcgaggtg aagatcacat     1535
```

-continued

| | |
|---|---|
| gtccgctgca gtactgaaaa acacttggtg cgcagaggcg agcgataggt gcgctgactt | 1595 |
| ttttttttgtt tgttcaagga aggcatcttt ttttttttta ccggttgtcc actgtcatgt | 1655 |
| cgaaaacgta gtccgtgtga agtggttggt ccctgttgt cctttgtcta gccgcgcgtg | 1715 |
| tctcatggag cattttcaa cgttgcttca aacgaatgct ggtttcaaac aaaaaaaaaa | 1775 |
| aaaaaaaaaa | 1785 |

<210> SEQ ID NO 312
<211> LENGTH: 24
<212> TYPE: PRT
<213> ORGANISM: Toxoplasma gondii

<400> SEQUENCE: 312

Glu Pro Val His Phe Cys Thr Cys Thr Gln Asp Ser Phe Ala Asp Asn
1               5                   10                  15

Ile Trp Gln Pro Pro Ala His Phe
            20

<210> SEQ ID NO 313
<211> LENGTH: 1785
<212> TYPE: DNA
<213> ORGANISM: Toxoplasma gondii

<400> SEQUENCE: 313

| | |
|---|---|
| gaaccggtgc acttttgcac gtgtacgcaa gacagcttcg cagacaacat ctggcagcct | 60 |
| cccgctcatt tttagtcagc aaaaatggca cccgcacttg tgcagaggag aaagaaggtg | 120 |
| gccatgattg gctctggcat gattggtggc actatgggct acctgtgcgc tctccgtgag | 180 |
| ctcgctgacg tcgttctcta cgatgttgtc aaaggtatgc ccgagggtaa ggctcttgac | 240 |
| ctgagccatg tgacctccgt ggtcgacacc aacgtttccg tccgtgctga gtactcttac | 300 |
| gaggccgcgc tcaccggtgc ggactgcgtt atcgttaccg ccgtctgac caaggtgccg | 360 |
| ggcaagcccg actccgagtg gagccgaaac gatctgctcc cgttcaactc gaagatcatt | 420 |
| cgcgagatcg gtcagaacat caagaagtac tgccccaaga ccttcatcat cgtggtcacc | 480 |
| aacccgctgg actgcatggt caaggtcatg tgcgaggcct ctggcgtccc gaccaacatg | 540 |
| atctgcggta tggcctgcat gctcgactct ggtcgcttcc gccgatacgt cgccgacgcg | 600 |
| ctgtctgtct ctccccgcga cgtccaggcc accgtcatcg gcacacacgg cgactgcatg | 660 |
| gtcccgcttg tccggtacat taccgtgaac gactacccga tccagaagtt catcaaggac | 720 |
| ggcgtagtca cggagaagca gctcgaggag atcgctgagc acaccaaagt gtctggcggc | 780 |
| gagatcgtcc gcttcctcgg ccagggttcc gcttactacg cccccgccgc atccgctgtc | 840 |
| gccatggcaa catccttctt gaacgacgaa aagcgcgtca tcccgtgcag tgtgtactgc | 900 |
| aacggagagt acggcttgaa ggacatgttc attggtctcc cggccgtcat ggaggcgcc | 960 |
| ggcatcgagc gcgtcatcga gctcgagctg aacgaggagg agaagaagca gttccagaag | 1020 |
| tccgtcgacg acgtcatggc gctcaacaag gcggttgctg ctcttcaggc gtaagcgttg | 1080 |
| gcaaaacagg agcggaatgc cactttactg cgcggggccc atgatttata cacgcgtttg | 1140 |
| caacggaagc gaaagacgg ttccggttcg caccacgcgc tcgtcccgaa aagggaagt | 1200 |
| cgcggcgctg tcggtcaacg ctgtgcgggt tgcaggtgcg tgcttaagca tcacaaagtg | 1260 |
| gcagagccat tttgtccagg gaagtagcgt ctcaaacagg tgaacgcgtg caagcatgag | 1320 |
| aggcatccgt cgctgcgttc gctcacatat ccgaaggcaa cagattttgg tcggcaaaag | 1380 |
| cctctgcaca accgtggcaa gatgatggaa acagttcgtg tttggacagc aaccgcgttc | 1440 |

```
gctctcactc aaaaccctgt agtcgagagg ggtgtcgcat gacttggctt ttgtgggagt    1500
gcccaaatcg tctgtgttcg aggtgaagat cacatgtccg ctgcagtact gaaaaacact    1560
tggtgcgcag aggcgagcga taggtgcgct gactttttt ttgtttgttc aaggaaggca     1620
tctttttttt ttttaccggt tgtccactgt catgtcgaaa acgtagtccg tgtgaagtgg    1680 ttggtccct gttgtccttt gtctagccgc gcgtgtctca tggagcattt ttcaacgttg     1740
cttcaaacga atgctggttt caaacaaaaa aaaaaaaaaa aaaaa                    1785
```

<210> SEQ ID NO 314
<211> LENGTH: 18
<212> TYPE: DNA
<213> ORGANISM: Artificial sequence
<220> FEATURE:
<223> OTHER INFORMATION: Synthetic Primer

<400> SEQUENCE: 314
tctccgactg tggagtgc                                                  18

<210> SEQ ID NO 315
<211> LENGTH: 18
<212> TYPE: DNA
<213> ORGANISM: Artificial sequence
<220> FEATURE:
<223> OTHER INFORMATION: Synthetic Primer

<400> SEQUENCE: 315
gatggcatgg atttgacc                                                  18

<210> SEQ ID NO 316
<211> LENGTH: 17
<212> TYPE: DNA
<213> ORGANISM: Artificial sequence
<220> FEATURE:
<223> OTHER INFORMATION: Synthetic Primer

<400> SEQUENCE: 316
tgaggagacc gaaaagg                                                   17

<210> SEQ ID NO 317
<211> LENGTH: 19
<212> TYPE: DNA
<213> ORGANISM: Artificial sequence
<220> FEATURE:
<223> OTHER INFORMATION: Synthetic Primer

<400> SEQUENCE: 317
tcagtgctct gacgaatcc                                                 19

<210> SEQ ID NO 318
<211> LENGTH: 20
<212> TYPE: DNA
<213> ORGANISM: Artificial sequence
<220> FEATURE:
<223> OTHER INFORMATION: Synthetic Primer

<400> SEQUENCE: 318
gccttcagga gagaagctac                                                20

<210> SEQ ID NO 319
<211> LENGTH: 20
<212> TYPE: DNA
<213> ORGANISM: Artificial sequence
<220> FEATURE:

<223> OTHER INFORMATION: Synthetic Primer

<400> SEQUENCE: 319
gatcgaagat gacgcatggg                                              20

<210> SEQ ID NO 320
<211> LENGTH: 20
<212> TYPE: DNA
<213> ORGANISM: Artificial sequence
<220> FEATURE:
<223> OTHER INFORMATION: Synthetic Primer

<400> SEQUENCE: 320
gaaactctgg ggaaaacggc                                              20

<210> SEQ ID NO 321
<211> LENGTH: 20
<212> TYPE: DNA
<213> ORGANISM: Artificial sequence
<220> FEATURE:
<223> OTHER INFORMATION: Synthetic Primer

<400> SEQUENCE: 321
cttcttcgct ctcaaacatc                                              20

<210> SEQ ID NO 322
<211> LENGTH: 17
<212> TYPE: DNA
<213> ORGANISM: Artificial sequence
<220> FEATURE:
<223> OTHER INFORMATION: Synthetic Primer

<400> SEQUENCE: 322
atcacggttt gtcgcac                                                 17

<210> SEQ ID NO 323
<211> LENGTH: 19
<212> TYPE: DNA
<213> ORGANISM: Artificial sequence
<220> FEATURE:
<223> OTHER INFORMATION: Synthetic Primer

<400> SEQUENCE: 323
cggacttcct tatgatcgg                                               19

<210> SEQ ID NO 324
<211> LENGTH: 20
<212> TYPE: DNA
<213> ORGANISM: Artificial sequence
<220> FEATURE:
<223> OTHER INFORMATION: Synthetic Primer

<400> SEQUENCE: 324
agtcggagaa ggcaccatag                                              20

<210> SEQ ID NO 325
<211> LENGTH: 17
<212> TYPE: DNA
<213> ORGANISM: Artificial sequence
<220> FEATURE:
<223> OTHER INFORMATION: Synthetic Primer

<400> SEQUENCE: 325
ttcctcctcc ttttcgg                                                 17

```
<210> SEQ ID NO 326
<211> LENGTH: 2167
<212> TYPE: DNA
<213> ORGANISM: Toxoplasma gondii
<220> FEATURE:
<221> NAME/KEY: CDS
<222> LOCATION: (1)..(1716)
<223> OTHER INFORMATION:

<400> SEQUENCE: 326 gtg agc acc cgc cgg aga gaa gac acc gag agc gag gcg tgc gtc aac      48
Val Ser Thr Arg Arg Arg Glu Asp Thr Glu Ser Glu Ala Cys Val Asn
1               5                  10                  15 caa gtc gaa acc atg gag tgc cca act cag gct ggg caa gca tgc ggc      96
Gln Val Glu Thr Met Glu Cys Pro Thr Gln Ala Gly Gln Ala Cys Gly
            20                  25                  30 aac tat ggt gcc ttc tcc gac tgt gga gtg cct ctt cgc ggc ttc gcc     144
Asn Tyr Gly Ala Phe Ser Asp Cys Gly Val Pro Leu Arg Gly Phe Ala
        35                  40                  45 atg gcc ttc ccc gag aac tgc cca gag ctc gtg gcc ttc gcc gcc tgc     192
Met Ala Phe Pro Glu Asn Cys Pro Glu Leu Val Ala Phe Ala Ala Cys
    50                  55                  60 gat gct ccc gcg cct ccc caa gag gac cgc tgc cat tct ttc tcg gcc     240
Asp Ala Pro Ala Pro Pro Gln Glu Asp Arg Cys His Ser Phe Ser Ala
65                  70                  75                  80 tgg tcc aag tgc aca cac ata ccc ggc act act ctg tac gag cag acg     288
Trp Ser Lys Cys Thr His Ile Pro Gly Thr Thr Leu Tyr Glu Gln Thr
                85                  90                  95 cgc tcc tgc gat ggc atg gat ttg acc gag tcc cgc ttc tgc act ccc     336
Arg Ser Cys Asp Gly Met Asp Leu Thr Glu Ser Arg Phe Cys Thr Pro
            100                 105                 110 gac gag gag gtc ggc tcg gac gtt tcc act gac gtc gct tcc gaa tgc     384
Asp Glu Glu Val Gly Ser Asp Val Ser Thr Asp Val Ala Ser Glu Cys
        115                 120                 125 ggt tcc ctc ggc gag ttc ggc gag tgt gtg aac ggc ctt cag gag aga     432
Gly Ser Leu Gly Glu Phe Gly Glu Cys Val Asn Gly Leu Gln Glu Arg
    130                 135                 140 agc tac tcg gac tgc ccc gat cat aag gaa gtc cgt cag tgc tct gac     480
Ser Tyr Ser Asp Cys Pro Asp His Lys Glu Val Arg Gln Cys Ser Asp
145                 150                 155                 160 gaa tcc tgc tct gcc ttc ggc gag tgg tca ccc tgc ggg gaa ccc cag     528
Glu Ser Cys Ser Ala Phe Gly Glu Trp Ser Pro Cys Gly Glu Pro Gln
                165                 170                 175 caa ggc ctg cgt atc cgc aag aga cgt gca tgc gac aac gtg cac tgc     576
Gln Gly Leu Arg Ile Arg Lys Arg Arg Ala Cys Asp Asn Val His Cys
            180                 185                 190 gcc tgt gtc gag gcc gag gtc tgc ggc gat gtc acc cca gag att gag     624
Ala Cys Val Glu Ala Glu Val Cys Gly Asp Val Thr Pro Glu Ile Glu
        195                 200                 205 gag gaa gaa ggc gaa cat ttc ccc cct gaa gaa ggc gag gtc ttg cct     672
Glu Glu Glu Gly Glu His Phe Pro Pro Glu Glu Gly Glu Val Leu Pro
    210                 215                 220 cca tat gaa gag ggt cct ggt gag ggt gag ctt gtt cct ccc gag gag     720
Pro Tyr Glu Glu Gly Pro Gly Glu Gly Glu Leu Val Pro Pro Glu Glu
225                 230                 235                 240 gag atc cct gaa gga gaa cat gtt cct gag gag gaa atc cct gaa gga     768
Glu Ile Pro Glu Gly Glu His Val Pro Glu Glu Glu Ile Pro Glu Gly
                245                 250                 255 gaa cat att cct gaa gag ctc cca gaa ggc gag cat gtt cct gag gag     816
Glu His Ile Pro Glu Glu Leu Pro Glu Gly Glu His Val Pro Glu Glu
            260                 265                 270
```

-continued

| | |
|---|---|
| gaa atc cct gaa gga gaa cat gtt cct gaa gag gaa atc cct gaa gga<br>Glu Ile Pro Glu Gly Glu His Val Pro Glu Glu Ile Pro Glu Gly<br>      275                      280                    285 | 864 |
| gag cat gtt cct gaa gag ttc cca gaa ggc gag cat gtt cct gag gag<br>Glu His Val Pro Glu Glu Phe Pro Glu Gly Glu His Val Pro Glu Glu<br>     290                      295                      300 | 912 |
| gaa atc cct gaa gga gaa cat gtt cct gaa gag gaa atc cct gaa gga<br>Glu Ile Pro Glu Gly Glu His Val Pro Glu Glu Ile Pro Glu Gly<br>305                      310                      315                    320 | 960 |
| gag cat gtt cct gaa gag ttc cct gaa gga gag cat att cct gag gag<br>Glu His Val Pro Glu Glu Phe Pro Glu Gly Glu His Ile Pro Glu Glu<br>                  325                      330                    335 | 1008 |
| ctc cct gaa ggc gag cat atc cct gaa gag ttc cct gaa gga gag cat<br>Leu Pro Glu Gly Glu His Ile Pro Glu Glu Phe Pro Glu Gly Glu His<br>            340                      345                    350 | 1056 |
| att cct gag gag ctc cct gaa ggc gag cat gtt cct gag gag gag atc<br>Ile Pro Glu Glu Leu Pro Glu Gly Glu His Val Pro Glu Glu Glu Ile<br>                  355                      360                    365 | 1104 |
| cct gaa gga gag cat att cct gaa gag ttc cca gaa ggc gag cat gtt<br>Pro Glu Gly Glu His Ile Pro Glu Glu Phe Pro Glu Gly Glu His Val<br>     370                      375                      380 | 1152 |
| cct gag gag gaa atc cct gaa gga gaa cat att cct gag gag gag ttc<br>Pro Glu Glu Glu Ile Pro Glu Gly Glu His Ile Pro Glu Glu Glu Phe<br>385                      390                      395                    400 | 1200 |
| cct gaa gga gag cat gtt cct gag gag gag atc cct gaa ggc gag cat<br>Pro Glu Gly Glu His Val Pro Glu Glu Glu Ile Pro Glu Gly Glu His<br>                  405                      410                    415 | 1248 |
| gtt cct gag gag gag ctc cct gga gga gaa ctt att cct gag gag gag<br>Val Pro Glu Glu Glu Leu Pro Gly Gly Glu Leu Ile Pro Glu Glu Glu<br>            420                      425                    430 | 1296 |
| atc cct gaa gga gag cat gtt cct gaa gag ctc cct gaa ggc gag cat<br>Ile Pro Glu Gly Glu His Val Pro Glu Glu Leu Pro Glu Gly Glu His<br>                  435                      440                    445 | 1344 |
| gtt cct gag gag gag atc cct gaa gga gag cat gtt cct gaa gag gaa<br>Val Pro Glu Glu Glu Ile Pro Glu Gly Glu His Val Pro Glu Glu Glu<br>     450                      455                      460 | 1392 |
| atc cct gaa ggc gag cat gtt cct gag gag gag acc cct gaa gga gaa<br>Ile Pro Glu Gly Glu His Val Pro Glu Glu Glu Thr Pro Glu Gly Glu<br>465                      470                      475                    480 | 1440 |
| cat gct cca gag gaa gag act cct gca cct gag gag acc gaa aag gag<br>His Ala Pro Glu Glu Glu Thr Pro Ala Pro Glu Glu Thr Glu Lys Glu<br>                  485                      490                    495 | 1488 |
| gag gaa gaa ggc gtg cca gtc gca gcg att gcc ggt ggt gtc gtc gga<br>Glu Glu Glu Gly Val Pro Val Ala Ala Ile Ala Gly Gly Val Val Gly<br>            500                      505                    510 | 1536 |
| ggt gtg ttg ctc att gct ggt ggt gca ggt gct gcc gtg tac gca aac<br>Gly Val Leu Leu Ile Ala Gly Gly Ala Gly Ala Ala Val Tyr Ala Asn<br>                  515                      520                    525 | 1584 |
| caa ggt ggc gtt gaa gca gct gaa gac gaa gtg atg ttt gag agc gaa<br>Gln Gly Gly Val Glu Ala Ala Glu Asp Glu Val Met Phe Glu Ser Glu<br>     530                      535                      540 | 1632 |
| gaa gac gga acc cag gct ggc gag aac cgc gag agc gag acg gtc att<br>Glu Asp Gly Thr Gln Ala Gly Glu Asn Arg Glu Ser Glu Thr Val Ile<br>545                      550                      555                    560 | 1680 |
| gag atc gaa gat gac gca tgg gca gac atg gac taa agtagactag<br>Glu Ile Glu Asp Asp Ala Trp Ala Asp Met Asp<br>                  565                      570 | 1726 |
| tagtctgtgt gggcacatgc aggcgtgcga caaaaccgtg atcgcgaggt attctgtgtt | 1786 |
| acgggcggag cgtctgcggc tgtccttcga aggggaggcg gcgtgacact ctgagctagg | 1846 |

```
taccagacga acgcagccat tgtgtccgt ccgctctttc ttgatcacgt gccattttat    1906
tttacgtttt ccactggtgt atctttccca gcagcttata tataggctgc cgcagcttcg    1966
tgtgtcacaa gccgctgtag acagtaagcc tactgcggcc tccttgtgga aagccgtttt    2026
ccccagagtt tcctgttttc cttccctccg cgtgccatct tgtttttcgc ccgcgcggat    2086
gtgttaatgc gataaataac taatgaagca aggttatgaa cagcttcgtg agctatattc    2146
ccagccaaaa aaaaaaaaaa a                                               2167
```

<210> SEQ ID NO 327
<211> LENGTH: 571
<212> TYPE: PRT
<213> ORGANISM: Toxoplasma gondii

<400> SEQUENCE: 327

```
Val Ser Thr Arg Arg Glu Asp Thr Glu Ser Glu Ala Cys Val Asn
  1               5                  10                  15

Gln Val Glu Thr Met Glu Cys Pro Thr Gln Ala Gly Gln Ala Cys Gly
             20                  25                  30

Asn Tyr Gly Ala Phe Ser Asp Cys Gly Val Pro Leu Arg Gly Phe Ala
         35                  40                  45

Met Ala Phe Pro Glu Asn Cys Pro Glu Leu Val Ala Phe Ala Ala Cys
     50                  55                  60

Asp Ala Pro Ala Pro Gln Glu Asp Arg Cys His Ser Phe Ser Ala
 65                  70                  75                  80

Trp Ser Lys Cys Thr His Ile Pro Gly Thr Thr Leu Tyr Glu Gln Thr
                 85                  90                  95

Arg Ser Cys Asp Gly Met Asp Leu Thr Glu Ser Arg Phe Cys Thr Pro
            100                 105                 110

Asp Glu Glu Val Gly Ser Asp Val Ser Thr Asp Val Ala Ser Glu Cys
        115                 120                 125

Gly Ser Leu Gly Glu Phe Gly Glu Cys Val Asn Gly Leu Gln Glu Arg
    130                 135                 140

Ser Tyr Ser Asp Cys Pro Asp His Lys Glu Val Arg Gln Cys Ser Asp
145                 150                 155                 160

Glu Ser Cys Ser Ala Phe Gly Glu Trp Ser Pro Cys Gly Glu Pro Gln
                165                 170                 175

Gln Gly Leu Arg Ile Arg Lys Arg Arg Ala Cys Asp Asn Val His Cys
            180                 185                 190

Ala Cys Val Glu Ala Glu Val Cys Gly Asp Val Thr Pro Glu Ile Glu
        195                 200                 205

Glu Glu Glu Gly Glu His Phe Pro Pro Glu Gly Glu Val Leu Pro
    210                 215                 220

Pro Tyr Glu Glu Gly Pro Gly Glu Gly Glu Leu Val Pro Pro Glu Glu
225                 230                 235                 240

Glu Ile Pro Glu Gly Glu His Val Pro Glu Glu Ile Pro Glu Gly
                245                 250                 255

Glu His Ile Pro Glu Glu Leu Pro Gly Glu His Val Pro Glu Glu
            260                 265                 270

Glu Ile Pro Glu Gly Glu His Val Pro Glu Glu Ile Pro Glu Gly
        275                 280                 285

Glu His Val Pro Glu Glu Phe Pro Glu Gly Glu His Val Pro Glu Glu
    290                 295                 300

Glu Ile Pro Glu Gly Glu His Val Pro Glu Glu Ile Pro Glu Gly
```

-continued

| | | | | | | | | | | | | | | |
|---|---|---|---|---|---|---|---|---|---|---|---|---|---|---|
| | | 305 | | | | 310 | | | | 315 | | | | 320 |
| Glu | His | Val | Pro | Glu | Glu | Phe | Pro | Glu | Gly | Glu | His | Ile | Pro | Glu Glu |
| | | | | 325 | | | | | 330 | | | | | 335 |
| Leu | Pro | Glu | Gly | Glu | His | Ile | Pro | Glu | Glu | Phe | Pro | Glu | Gly | Glu His |
| | | | 340 | | | | | 345 | | | | | 350 | |
| Ile | Pro | Glu | Glu | Leu | Pro | Glu | Gly | Glu | His | Val | Pro | Glu | Glu | Glu Ile |
| | | | 355 | | | | | 360 | | | | | 365 | |
| Pro | Glu | Gly | Glu | His | Ile | Pro | Glu | Glu | Phe | Pro | Glu | Gly | Glu | His Val |
| | | 370 | | | | | 375 | | | | | 380 | | |
| Pro | Glu | Glu | Glu | Ile | Pro | Glu | Gly | Glu | His | Ile | Pro | Glu | Glu | Glu Phe |
| 385 | | | | | 390 | | | | | 395 | | | | 400 |
| Pro | Glu | Gly | Glu | His | Val | Pro | Glu | Glu | Ile | Pro | Glu | Gly | Glu | His |
| | | | | 405 | | | | | 410 | | | | | 415 |
| Val | Pro | Glu | Glu | Leu | Pro | Gly | Gly | Glu | Leu | Ile | Pro | Glu | Glu | Glu |
| | | | 420 | | | | | 425 | | | | | 430 | |
| Ile | Pro | Glu | Gly | Glu | His | Val | Pro | Glu | Glu | Leu | Pro | Glu | Gly | Glu His |
| | | | 435 | | | | | 440 | | | | | 445 | |
| Val | Pro | Glu | Glu | Glu | Ile | Pro | Glu | Gly | Glu | His | Val | Pro | Glu | Glu Glu |
| | | 450 | | | | | 455 | | | | | 460 | | |
| Ile | Pro | Glu | Gly | Glu | His | Val | Pro | Glu | Glu | Thr | Pro | Glu | Gly | Glu |
| 465 | | | | | 470 | | | | | 475 | | | | 480 |
| His | Ala | Pro | Glu | Glu | Glu | Thr | Pro | Ala | Pro | Glu | Glu | Thr | Glu | Lys Glu |
| | | | | 485 | | | | | 490 | | | | | 495 |
| Glu | Glu | Glu | Gly | Val | Pro | Val | Ala | Ala | Ile | Ala | Gly | Val | Val | Gly |
| | | | 500 | | | | | 505 | | | | | 510 | |
| Gly | Val | Leu | Leu | Ile | Ala | Gly | Gly | Ala | Gly | Ala | Ala | Val | Tyr | Ala Asn |
| | | | 515 | | | | | 520 | | | | | 525 | |
| Gln | Gly | Gly | Val | Glu | Ala | Ala | Glu | Asp | Glu | Val | Met | Phe | Glu | Ser Glu |
| | | | 530 | | | | | 535 | | | | | 540 | |
| Glu | Asp | Gly | Thr | Gln | Ala | Gly | Glu | Asn | Arg | Glu | Ser | Glu | Thr | Val Ile |
| 545 | | | | | 550 | | | | | 555 | | | | 560 |
| Glu | Ile | Glu | Asp | Asp | Ala | Trp | Ala | Asp | Met | Asp | | | | |
| | | | | 565 | | | | | 570 | | | | | |

<210> SEQ ID NO 328
<211> LENGTH: 2167
<212> TYPE: DNA
<213> ORGANISM: Toxoplasma gondii

<400> SEQUENCE: 328

| | |
|---|---|
| tttttttttt ttttggctg ggaatatagc tcacgaagct gttcataacc ttgcttcatt | 60 |
| agttatttat cgcattaaca catccgcgcg ggcgaaaaac aagatggcac gcggagggaa | 120 |
| ggaaaacagg aaactctggg gaaacggct tccacaagg aggccgcagt aggcttactg | 180 |
| tctacagcgg cttgtgacac acgaagctgc ggcagcctat atataagctg ctggaaaaga | 240 |
| tacaccagtg gaaaacgtaa aataaaatgg cacgtgatca agaaagagcg gacggacaca | 300 |
| aatggctgcg ttcgtctggt acctagctca gagtgtcacg ccgcctcccc ttcgaaggac | 360 |
| agccgcagac gctccgcccg taacacagaa tacctcgcga tcacggtttt gtcgcacgcc | 420 |
| tgcatgtgcc cacacagact actagtctac tttagtccat gtctgcccat gcgtcatctt | 480 |
| cgatctcaat gaccgtctcg ctctcgcggt tctcgccagc ctgggttccg tcttcttcgc | 540 |
| tctcaaacat cacttcgtct tcagctgctt caacgccacc ttggtttgcg tacacggcag | 600 |
| cacctgcacc accagcaatg agcaacacac ctccgacgac accaccggca atcgctgcga | 660 |

```
ctggcacgcc ttcttcctcc tccttttcgg tctcctcagg tgcaggagtc tcttcctctg    720
gagcatgttc tccttcaggg gtctcctcct caggaacatg ctcgccttca gggatttcct    780
cttcaggaac atgctctcct tcagggatct cctcctcagg aacatgctcg ccttcaggga    840
gctcttcagg aacatgctct ccttcaggga tctcctcctc aggaataagt tctcctccag    900
ggagctcctc ctcaggaaca tgctcgcctt cagggatctc ctcctcagga acatgctctc    960
cttcagggaa ctcctcctca ggaatatgtt ctccttcagg gatttcctcc tcaggaacat   1020
gctcgccttc tgggaactct tcaggaatat gctctccttc agggatctcc tcctcaggaa   1080
catgctcgcc ttcagggagc tcctcaggaa tatgctctcc ttcagggaac tcttcaggga   1140
tatgctcgcc ttcagggagc tcctcaggaa tatgctctcc ttcagggaac tcttcaggaa   1200
catgctctcc ttcagggatt tcctcttcag gaacatgttc tccttcaggg atttcctcct   1260
caggaacatg ctcgccttct gggaactctt caggaacatg ctctccttca gggatttcct   1320
cttcaggaac atgttctcct tcagggattt cctcctcagg aacatgctcg ccttctggga   1380
gctcttcagg aatatgttct ccttcaggga tttcctcctc aggaacatgt tctccttcag   1440
ggatctcctc ctcgggagga acaagctcac cctcaccagg accctcttca tatggaggca   1500
agacctcgcc ttcttcaggg gggaaatgtt cgccttcttc ctcctcaatc tctgggtga    1560 catcgccgca gacctcggcc tcgacacagg cgcagtgcac gttgtcgcat gcacgtctct   1620
tgcggatacg caggccttgc tggggttccc cgcagggtga ccactcgccg aaggcagagc   1680
aggattcgtc agagcactga cggacttcct tatgatcggg gcagtccgag tagcttctct   1740
cctgaaggcc gttcacacac tcgccgaact cgccgaggga accgcattcg gaagcgacgt   1800
cagtggaaac gtccgagccg acctcctcgt cgggagtgca gaagcgggac tcggtcaaat   1860
ccatgccatc gcaggagcgc gtctgctcgt acagagtagt gccgggtatg tgtgtgcact   1920
tggaccaggc cgagaaagaa tggcagcggt cctcttgggg aggcgcggga gcatcgcagg   1980
cggcgaaggc cacgagctct gggcagttct cggggaaggc catggcgaag ccgcgaagag   2040
gcactccaca gtcggagaag gcaccatagt tgccgcatgc ttgcccagcc tgagttgggc   2100
actccatggt ttcgacttgg ttgacgcacg cctcgctctc ggtgtcttct ctccggcggg   2160
tgctcac                                                             2167
```

<210> SEQ ID NO 329
<211> LENGTH: 2393
<212> TYPE: DNA
<213> ORGANISM: Toxoplasma gondii
<220> FEATURE:
<221> NAME/KEY: CDS
<222> LOCATION: (1)..(594)
<223> OTHER INFORMATION:

<400> SEQUENCE: 329

```
gca gga att ctt gca acc act gga gtg cat tca ctc gct gcg atc ccg     48
Ala Gly Ile Leu Ala Thr Thr Gly Val His Ser Leu Ala Ala Ile Pro
 1               5                  10                  15 aga ctc acc tca gca gcc gct act gtg tgg acc tcc cag aca agg ttg     96
Arg Leu Thr Ser Ala Ala Ala Thr Val Trp Thr Ser Gln Thr Arg Leu
             20                  25                  30 agt cga tca cct gcg aag tcg gct ccc tgc ccc agc ccc cga ctg tcg    144
Ser Arg Ser Pro Ala Lys Ser Ala Pro Cys Pro Ser Pro Arg Leu Ser
         35                  40                  45 ccc ccg gcg agg gtg gtg agg aag acg gca acg cat gtg gac cgt ggg    192
Pro Pro Ala Arg Val Val Arg Lys Thr Ala Thr His Val Asp Arg Gly
     50                  55                  60
```

```
            50                 55                     60
tcc gtg gag ccc gtg tcc cgg cga agg aaa caa cat gag cac ccg ccg    240
Ser Val Glu Pro Val Ser Arg Arg Arg Lys Gln His Glu His Pro Pro
65                  70                  75                  80 gag aga aga cac cga gag cga ggc gtg cgt caa cca agt cga aac cat    288
Glu Arg Arg His Arg Glu Arg Gly Val Arg Gln Pro Ser Arg Asn His
                85                  90                  95 gga gtg ccc aac tca ggc tgg gca agc atg cgg caa cta tgg tgc ctt    336
Gly Val Pro Asn Ser Gly Trp Ala Ser Met Arg Gln Leu Trp Cys Leu
            100                 105                 110 ctc cga ctg tgg aat gcc tct tcg cgg ctt cgc cat ggc ctt ccc cga    384
Leu Arg Leu Trp Asn Ala Ser Ser Arg Leu Arg His Gly Leu Pro Arg
        115                 120                 125 gaa ctg ccc aga gct cgt ggc ctt cgc cgc ctg cga tgc tcc cgc gcc    432
Glu Leu Pro Arg Ala Arg Gly Leu Arg Arg Leu Arg Cys Ser Arg Ala
    130                 135                 140 tcc cca aga gga ccg ctg cca ttc ttt ctc ggc ctg gtc caa gtg cac    480
Ser Pro Arg Gly Pro Leu Pro Phe Phe Leu Gly Leu Val Gln Val His
145                 150                 155                 160 aca cat acc cgg cac tac tct gta cga gca gac gcg ctc ctg cga tgg    528
Thr His Thr Arg His Tyr Ser Val Arg Ala Asp Ala Leu Leu Arg Trp
                165                 170                 175 cat gga ttt gac cga gtc ccg ctt ctg cac tcc cga cga gga ggt cgg    576
His Gly Phe Asp Arg Val Pro Leu Leu His Ser Arg Arg Gly Gly Arg
            180                 185                 190 ctc gga cgt ttc cac tga cgtcgcttcc gaatgcggtt ccctcggcga           624
Leu Gly Arg Phe His
        195 gttcggcgag tgtgtgaacg gccttcagga gagaagctac tcggactgcc ccgatcataa  684 ggaagtccgt cagtgctctg acgaatcctg ctctgccttc ggcgagtggt caccctgcgg  744 ggaaccccag caaggcctgc gtatccgcaa gagacgtgca tgcgacaacg tgcactgcgc  804 ctgtgtcgag gccgaggtct gcggcgatgt cacccagag attgaggagg aagaaggcga   864 acatttcccc cctgaagaag gcgaggtctt gcctccatat gaagagggtc ctggtgaggg  924 tgagcttgtt cctcccgagg aggagatccc tgaaggagaa catgttcctg aggaggaaat  984 ccctgaagga gaacatattc ctgaagagct cccagaaggc gagcatgttc ctgaggagga  1044 aatccctgaa ggagaacatg ttcctgaaga ggaaatccct gaaggagagc atgttcctga  1104 agagttccca gaaggcgaac atgttcctga ggaggaaatc cctgaaggag aacatgttcc  1164 tgaagaggaa atccctgaag gagaacatgt tcctgaagag ttccctgaag gagaacatat  1224 tcctgaggag ctccctgaag gagagcatat tcatgaagag ttccctgaag gagagcatat  1284 tcatgaggag ctccctgaag gcgagcatgt tcctgaagag gagatccctg aaggagaaca  1344 tattcctgag gagttccctg aaggcgagca tgttcctgag gaggaaatcc ctgaaggaga  1404 acatattcct gaggaggagt tccctgaagg agagcatgtt cctgaggagg agatccctga  1464 aggcgagcat gttcctgagg aggagctccc tggaggagaa cttattcctg aggaggagat  1524 ccctgaagga gagcatgttc ctgaagagct ccctgaaggc gagcatgttc ctgaggagga  1584 gatccctgaa ggagagcatg ttcctgaaga ggaaatccct gaaggcgagc atgttcctga  1644 ggaggagacc cctgaaggag aacatgctcc agaggaagag actcctgcac tgaggagac   1704 cgaaaaggag gaggaagaag gcgtgccagt cgcagcgatt gccggtggtg tcgtcggagg  1764 tgtgttgctc attgctggtg gtgcaggtgc tgccgtgtac gcaaaccaag gtggcgttga  1824 agcagctgaa gacgaagtga tgtttgagag cgaagaagac ggaacccagg ctggcgagaa  1884
```

```
ccgcgagagc gagacggtca ttgagatcga agatgacgca tgggcagaca tggactaaag    1944
tagactagta gtctgtgtgg gcacatgcag gcgtgcgaca aaaccgtgat cgcgaggtat    2004
tctgtgttac gggcggagcg tctgcggctg tccttcgaag gggaggcggc gtgacactct    2064
gagctaggta ccagacgaac gcagccattt gtgtccgtcc gctctttctt gatcacgtgc    2124
cattttattt tacgttttcc actggtgtat cttttccagc agcttatata taggctgccg    2184
cagcttcgtg tgtcacaagc cgctgtagac agtaagccta ctgcggcctc cttgtggaaa    2244
gccgttttcc ccagagtttc ctgttttcct tccctccgcg tgccatcttg tttttcgccc    2304
gcgcggatgt gttaatgcga taaataacta atgaagcaag gttatgaaca gcttcgtgag    2364
ctatattccc agccaaaaaa aaaaaaaaa                                      2393
```

<210> SEQ ID NO 330
<211> LENGTH: 197
<212> TYPE: PRT
<213> ORGANISM: Toxoplasma gondii

<400> SEQUENCE: 330

```
Ala Gly Ile Leu Ala Thr Thr Gly Val His Ser Leu Ala Ala Ile Pro
  1               5                  10                  15

Arg Leu Thr Ser Ala Ala Ala Thr Val Trp Thr Ser Gln Thr Arg Leu
             20                  25                  30

Ser Arg Ser Pro Ala Lys Ser Ala Pro Cys Pro Ser Pro Arg Leu Ser
         35                  40                  45

Pro Pro Ala Arg Val Val Arg Lys Thr Ala Thr His Val Asp Arg Gly
     50                  55                  60

Ser Val Glu Pro Val Ser Arg Arg Lys Gln His Glu His Pro Pro
 65                  70                  75                  80

Glu Arg Arg His Arg Glu Arg Gly Val Arg Gln Pro Ser Arg Asn His
                 85                  90                  95

Gly Val Pro Asn Ser Gly Trp Ala Ser Met Arg Gln Leu Trp Cys Leu
            100                 105                 110

Leu Arg Leu Trp Asn Ala Ser Ser Arg Leu Arg His Gly Leu Pro Arg
        115                 120                 125

Glu Leu Pro Arg Ala Arg Gly Leu Arg Arg Leu Arg Cys Ser Arg Ala
    130                 135                 140

Ser Pro Arg Gly Pro Leu Pro Phe Phe Leu Gly Leu Val Gln Val His
145                 150                 155                 160

Thr His Thr Arg His Tyr Ser Val Arg Ala Asp Ala Leu Leu Arg Trp
                165                 170                 175

His Gly Phe Asp Arg Val Pro Leu Leu His Ser Arg Arg Gly Gly Arg
            180                 185                 190

Leu Gly Arg Phe His
        195
```

<210> SEQ ID NO 331
<211> LENGTH: 2392
<212> TYPE: DNA
<213> ORGANISM: Toxoplasma gondii

<400> SEQUENCE: 331

```
tttttttttt tttttggctg ggaatatagc tcacgaagct gttcataacc ttgcttcatt      60
agttatttat cgcattaaca catccgcgcg ggcgaaaaac aagatggcac gcggagggaa     120
ggaaaacagg aaactctggg gaaacggct ttccacaagg aggccgcagt aggcttactg     180
```

```
tctacagcgg cttgtgacac acgaagctgc ggcagcctat atataagctg ctggaaaaga      240
tacaccagtg gaaaacgtaa aataaaatgg cacgtgatca agaaagagcg gacggacaca      300
aatggctgcg ttcgtctggt acctagctca gagtgtcacg ccgcctcccc ttcgaaggac      360
agccgcagac gctccgcccg taacacagaa tacctcgcga tcacggtttt gtcgcacgcc      420
tgcatgtgcc cacacagact actagtctac tttagtccat gtctgcccat gcgtcatctt      480
cgatctcaat gaccgtctcg ctctcgcggt tctcgccagc ctgggttccg tcttcttcgc      540
tctcaaacat cacttcgtct tcagctgctt caacgccacc ttggtttgcg tacacggcag      600
cacctgcacc accagcaatg agcaacacac ctccgacgac accaccggca atcgctgcga      660
ctggcacgcc ttcttcctcc tccttttcgg tctcctcagg tgcaggagtc tcttcctctg      720
gagcatgttc tccttcaggg gtctcctcct caggaacatg ctcgccttca gggatttcct      780
cttcaggaac atgctctcct tcagggatct cctcctcagg aacatgctcg ccttcaggga      840
gctcttcagg aacatgctct ccttcaggga tctcctcctc aggaataagt tctcctccag      900
ggagctcctc ctcaggaaca tgctcgcctt cagggatctc ctcctcagga acatgctctc      960
cttcagggaa ctcctcctca ggaatatgtt ctccttcagg gatttcctcc tcaggaacat     1020
gctcgccttc agggaactcc tcaggaatat gttctccttc agggatctcc tcttcaggaa     1080
catgctcgcc ttcagggagc tcctcatgaa tatgctctcc ttcagggaac tcttcatgaa     1140
tatgctctcc ttcagggagc tcctcaggaa tatgttctcc ttcagggaac tcttcaggaa     1200
catgttctcc ttcagggatt tcctcttcag gaacatgttc tccttcaggg atttcctcct     1260
caggaacatg ttcgccttct gggaactctt caggaacatg ctctccttca gggatttcct     1320
cttcaggaac atgttctcct tcagggattt cctcctcagg aacatgctcg ccttctggga     1380
gctcttcagg aatatgttct ccttcaggga tttcctcctc aggaacatgt tctccttcag     1440
ggatctcctc ctcgggagga acaagctcac cctcaccagg accctcttca tatggaggca     1500
agacctcgcc ttcttcaggg gggaaatgtt cgccttcttc ctcctcaatc tctgggtga     1560 catcgccgca gacctcggcc tcgacacagg cgcagtgcac gttgtcgcat gcacgtctct     1620
tgcggatacg caggccttgc tggggttccc cgcagggtga ccactcgccg aaggcagagc     1680
aggattcgtc agagcactga cggacttcct tatgatcggg gcagtccgag tagcttctct     1740
cctgaaggcc gttcacacac tcgccgaact cgccgaggga accgcattcg gaagcgacgt     1800
cagtggaaac gtccgagccg acctcctcgt cgggagtgca gaagcgggac tcggtcaaat     1860
ccatgccatc gcaggagcgc gtctgctcgt acagagtagt gccgggtatg tgtgtgcact     1920
tggaccaggc cgagaaagaa tggcagcggt cctcttgggg aggcgcggga gcatcgcagg     1980
cggcgaaggc cacgagctct gggcagttct cggggaaggc catggcgaag ccgcgaagag     2040
gcattccaca gtcggagaag gcaccatagt tgccgcatgc ttgcccagcc tgagttgggc     2100
actccatggt ttcgacttgg ttgacgcacg cctcgctctc ggtgtcttct ctccggcggg     2160
tgctcatgtt gtttccttcg ccgggacacg ggctccacgg acccacggtc cacatgcgtt     2220
gccgtcttcc tcaccaccct cgccgggggc gacagtcggg ggctggggca gggagccgac     2280
ttcgcaggtg atcgactcaa ccttgtctgg gaggtccaca cagtagcggc tgctgaggtg     2340
agtctcggga tcgcagcgag tgaatgcact ccagtggttg caagaattcc tg             2392
```

<210> SEQ ID NO 332
<211> LENGTH: 21
<212> TYPE: DNA

```
<213> ORGANISM: Artificial sequence
<220> FEATURE:
<223> OTHER INFORMATION: Synthetic Primer

<400> SEQUENCE: 332
ggaactgcat ccgttcatga g                                              21

<210> SEQ ID NO 333
<211> LENGTH: 19
<212> TYPE: DNA
<213> ORGANISM: Artificial sequence
<220> FEATURE:
<223> OTHER INFORMATION: Synthetic Primer

<400> SEQUENCE: 333
tcttaaagcg ttcgtggtc                                                 19

<210> SEQ ID NO 334
<211> LENGTH: 23
<212> TYPE: DNA
<213> ORGANISM: Artificial sequence
<220> FEATURE:
<223> OTHER INFORMATION: Synthetic Primer

<400> SEQUENCE: 334
ggcgaccaat ctgcgaatac acc                                            23

<210> SEQ ID NO 335
<211> LENGTH: 24
<212> TYPE: DNA
<213> ORGANISM: Artificial sequence
<220> FEATURE:
<223> OTHER INFORMATION: Synthetic Primer

<400> SEQUENCE: 335
gcatccttgg agacagagct tgag                                           24

<210> SEQ ID NO 336
<211> LENGTH: 24
<212> TYPE: DNA
<213> ORGANISM: Artificial sequence
<220> FEATURE:
<223> OTHER INFORMATION: Synthetic Primer

<400> SEQUENCE: 336
gggttctctt ctcgctcatc tttc                                           24

<210> SEQ ID NO 337
<211> LENGTH: 19
<212> TYPE: DNA
<213> ORGANISM: Artificial sequence
<220> FEATURE:
<223> OTHER INFORMATION: Synthetic Primer

<400> SEQUENCE: 337
agtcagaagc agtcaaggc                                                 19

<210> SEQ ID NO 338
<211> LENGTH: 647
<212> TYPE: DNA
<213> ORGANISM: Toxoplasma gondii

<400> SEQUENCE: 338
gatcctttag ccacttagac cgattcccca gacttgctcg gagatagtgt cagtgtcact    60
actacacagc tcaaagaagc cacatcccgt gaaaaatttt atcgtctaca agcgtgggcc   120
```

```
ggttctttgt tcactgttca cgtcacgtgt ggacatgccg ttgtgtcgtg gcagcaaata    180
cgaagaagcc aaagacatcc gaaaccgccc gttcagagtc ggggagactg cctgggtttt    240
cccacgagct gcatgttcca gctagatgca agcacctgca gtggggatgt atctccgaaa    300
aggcgagcaa ttttgtccaa aaaggggtgag ctaatcgtga aatgtccact gacatgcagc    360
gtccgcttct gtctcagtac cgatcttcac ttcgcgtgct acccgcgttc gtttcgtttc    420
cccccattcc agatatccct gccgctgtgg cgcctggaag cgctcctcga ctgcattgag    480
cattccgccg tcacaagact tttttttccc ttttgccaac gtcgagaacc tctcacgggc    540
gagcaaagtc tagtgtttgg tttcagtacg gcggtcgctg gctctgtgta tgactgacct    600
gaagaagcaa agacttcttg caacgtagaa acgcaaaggc gcttctt                  647
```

<210> SEQ ID NO 339
<211> LENGTH: 647
<212> TYPE: DNA
<213> ORGANISM: Toxoplasma gondii

<400> SEQUENCE: 339

```
aagaagcgcc tttgcgtttc tacgttgcaa gaagtctttg cttcttcagg tcagtcatac     60
acagagccag cgaccgccgt actgaaacca aacactagac tttgctcgcc cgtgagaggt    120
tctcgacgtt ggcaaaaggg aaaaaaaagt cttgtgacgg cggaatgctc aatgcagtcg    180
aggagcgctt ccaggcgcca cagcggcagg atatctgga atgggggggaa acgaaacgaa    240 cgcgggtagc acgcgaagtg aagatcggta ctgagacaga agcggacgct gcatgtcagt    300
ggacatttca cgattagctc accctttttg gacaaaattg ctcgcctttt cggagataca    360
tccccactgc aggtgcttgc atctagctgg aacatgcagc tcgtgggaaa acccaggcag    420 tctcccgac tctgaacggg cggtttcgga tgtctttggc ttcttcgtat ttgctgccac    480
gacacaacgg catgtccaca cgtgacgtga acagtgaaca aagaaccggc ccacgcttgt    540
agacgataaa attttcacg ggatgtggct tctttgagct gtgtagtagt gacactgaca    600
ctatctccga gcaagtctgg ggaatcggtc taagtggcta aaggatc                   647
```

<210> SEQ ID NO 340
<211> LENGTH: 867
<212> TYPE: DNA
<213> ORGANISM: Toxoplasma gondii
<220> FEATURE:
<221> NAME/KEY: CDS
<222> LOCATION: (1)..(867)
<223> OTHER INFORMATION:

<400> SEQUENCE: 340

```
atg gca gga agg cag gcg gcg ttg ttt ttg gtg gtg ctg tct gtg gcg        48
Met Ala Gly Arg Gln Ala Ala Leu Phe Leu Val Val Leu Ser Val Ala
1               5                  10                  15 gcg ggc cct gtc tcc cag ctt gct cgg gcg agc gac gac agc gtc gac        96
Ala Gly Pro Val Ser Gln Leu Ala Arg Ala Ser Asp Asp Ser Val Asp
            20                  25                  30 agc gtc gaa acc gcg cgt cag cac atg gag ctg gct atc gag gct gac       144
Ser Val Glu Thr Ala Arg Gln His Met Glu Leu Ala Ile Glu Ala Asp
        35                  40                  45 gaa gag atg cac gag gcc tac gac cct ttg ttg gaa ttc gtt gag acg       192
Glu Glu Met His Glu Ala Tyr Asp Pro Leu Leu Glu Phe Val Glu Thr
    50                  55                  60 ttt cgg gaa atc aaa aaa gct gtt gag gaa gat gcg gct ctg agt aca       240
Phe Arg Glu Ile Lys Lys Ala Val Glu Glu Asp Ala Ala Leu Ser Thr
65                  70                  75                  80
```

```
                65                  70                  75                  80
gat gcg atc gac cgc gtg tcc cag ttc gat ctg gtt tcc ctc cta gat         288
Asp Ala Ile Asp Arg Val Ser Gln Phe Asp Leu Val Ser Leu Leu Asp
                85                  90                  95 gtc atc cga gag gct gca caa gca aag ttc gat ctc ctc gga cgc ctc         336
Val Ile Arg Glu Ala Ala Gln Ala Lys Phe Asp Leu Leu Gly Arg Leu
            100                 105                 110 att aca gac atc gcc agc gga atc ggc gag ggt gcc atg gct ctg atg         384
Ile Thr Asp Ile Ala Ser Gly Ile Gly Glu Gly Ala Met Ala Leu Met
            115                 120                 125 gga gag gag gct gcg ttc att agg cca agg agg tca aag aga ggg aaa         432
Gly Glu Glu Ala Ala Phe Ile Arg Pro Arg Arg Ser Lys Arg Gly Lys
        130                 135                 140 aag act aca act aca acc agt tca tcc aca agt acg agt aca acg acc         480
Lys Thr Thr Thr Thr Ser Ser Ser Thr Ser Thr Ser Thr Thr Thr
145                 150                 155                 160 acg aca tca act acc act act acc act acc act acg act act act             528
Thr Thr Ser Thr Thr Thr Thr Thr Thr Thr Thr Thr Thr Thr Thr
                165                 170                 175 aca act acg aca cca aca aca act aca aca acc aca aca act aca cca         576
Thr Thr Thr Thr Pro Thr Thr Thr Thr Thr Thr Thr Thr Thr Thr Pro
            180                 185                 190 aca aca acg aca aca acc aca aca act aca cca aca aca acg aca aca         624
Thr Thr Thr Thr Thr Thr Thr Thr Thr Thr Pro Thr Thr Thr Thr Thr
        195                 200                 205 acc aca aca act aca cca aca aca acg aca aca acc aca acg cca act         672
Thr Thr Thr Thr Thr Pro Thr Thr Thr Thr Thr Thr Thr Thr Pro Thr
    210                 215                 220 aca acg aca tct acg aca acc act acg act acc aca act act act aca         720
Thr Thr Thr Ser Thr Thr Thr Thr Thr Thr Thr Thr Thr Thr Thr Thr
225                 230                 235                 240 cca act aca aca acg aca acc acg gaa cca aca act aca aca aca acc         768
Pro Thr Thr Thr Thr Thr Thr Thr Glu Pro Thr Thr Thr Thr Thr Thr
                245                 250                 255 acg gaa cca acc aca act aca agc aca acg acg act acg aca act aca         816
Thr Glu Pro Thr Thr Thr Thr Ser Thr Thr Thr Thr Thr Thr Thr Thr
            260                 265                 270 acg act acg aca cca tct acg acg aca tcc acc acc act acc ctc gat         864
Thr Thr Thr Thr Pro Ser Thr Thr Thr Ser Thr Thr Thr Leu Asp
        275                 280                 285 tag                                                                     867

<210> SEQ ID NO 341
<211> LENGTH: 288
<212> TYPE: PRT
<213> ORGANISM: Toxoplasma gondii

<400> SEQUENCE: 341

Met Ala Gly Arg Gln Ala Ala Leu Phe Leu Val Val Leu Ser Val Ala
1               5                   10                  15

Ala Gly Pro Val Ser Gln Leu Ala Arg Ala Ser Asp Asp Ser Val Asp
            20                  25                  30

Ser Val Glu Thr Ala Arg Gln His Met Glu Leu Ala Ile Glu Ala Asp
        35                  40                  45

Glu Glu Met His Glu Ala Tyr Asp Pro Leu Leu Glu Phe Val Glu Thr
    50                  55                  60

Phe Arg Glu Ile Lys Lys Ala Val Glu Glu Asp Ala Ala Leu Ser Thr
65                  70                  75                  80
```

```
Asp Ala Ile Asp Arg Val Ser Gln Phe Asp Leu Val Ser Leu Leu Asp
                85                  90                  95

Val Ile Arg Glu Ala Ala Gln Ala Lys Phe Asp Leu Leu Gly Arg Leu
            100                 105                 110

Ile Thr Asp Ile Ala Ser Gly Ile Gly Glu Gly Ala Met Ala Leu Met
            115                 120                 125

Gly Glu Glu Ala Ala Phe Ile Arg Pro Arg Arg Ser Lys Arg Gly Lys
    130                 135                 140

Lys Thr Thr Thr Thr Thr Ser Ser Ser Thr Ser Thr Ser Thr Thr Thr
145                 150                 155                 160

Thr Thr Ser Thr Thr Thr Thr Thr Thr Thr Thr Thr Thr Thr Thr Thr
                165                 170                 175

Thr Thr Thr Thr Pro Thr Thr Thr Thr Thr Thr Thr Thr Thr Thr Pro
                180                 185                 190

Thr Thr Thr Thr Thr Thr Thr Thr Thr Pro Thr Thr Thr Thr Thr Thr
                195                 200                 205

Thr Thr Thr Thr Thr Pro Thr Thr Thr Thr Thr Thr Thr Thr Pro Thr
                210                 215                 220

Thr Thr Thr Ser Thr Thr Thr Thr Thr Thr Thr Thr Thr Thr Thr Thr
225                 230                 235                 240

Pro Thr Thr Thr Thr Thr Thr Thr Glu Pro Thr Thr Thr Thr Thr Thr
                245                 250                 255

Thr Glu Pro Thr Thr Thr Thr Thr Ser Thr Thr Thr Thr Thr Thr Thr
                260                 265                 270

Thr Thr Thr Thr Pro Ser Thr Thr Thr Ser Thr Thr Thr Thr Leu Asp
                275                 280                 285
```

<210> SEQ ID NO 342
<211> LENGTH: 867
<212> TYPE: DNA
<213> ORGANISM: Toxoplasma gondii

<400> SEQUENCE: 342

```
atggcaggaa ggcaggcggc gttgtttttg gtggtgctgt ctgtggcggc gggccctgtc      60
tcccagcttg ctcgggcgag cgacgacagc gtcgacagcg tcgaaaccgc gcgtcagcac     120
atggagctgg ctatcgaggc tgacgaagag atgcacgagg cctacgaccc tttgttggaa     180
ttcgttgaga cgtttcggga aatcaaaaaa gctgttgagg aagatgcggc tctgagtaca     240
gatgcgatcg accgcgtgtc ccagttcgat ctggtttccc tcctagatgt catccgagag     300
gctgcacaag caaagttcga tctcctcgga cgcctcatta cagacatcgc cagcggaatc     360
ggcgagggtg ccatggctct gatggagag gaggctgcgt tcattaggcc aaggaggtca     420
aagagaggga aaaagactac aactacaacc agttcatcca caagtacgag tacaacgacc     480
acgacatcaa ctaccactac taccactacc accactacga ctactactac aactacgaca     540
ccaacaacaa ctacaacaac cacaacaact acaccaacaa caacgacaac aaccacaaca     600
actacaccaa caacaacgac aacaaccaca caactacac caacaacaac gacaacaacc     660
acaacgccaa ctacaacgac atctacgaca accactacga ctaccacaac tactactaca     720
ccaactacaa caacgacaac cacggaacca caactacaa caacaaccac ggaaccaacc      780
acaactacaa gcacaacgac gactacgaca actacaacga ctacgacacc atctacgacg     840
acatccacca ccactaccct cgattag                                         867
```

<210> SEQ ID NO 343

```
<211> LENGTH: 1397
<212> TYPE: DNA
<213> ORGANISM: Toxoplasma gondii
<220> FEATURE:
<221> NAME/KEY: CDS
<222> LOCATION: (238)..(1104)
<223> OTHER INFORMATION:

<400> SEQUENCE: 343
```

| | | |
|---|---|---|
| ccccattcca gatatccctg ccgctgtggc gcctggaagc gctcctcgac tgcattgagc | 60 | |
| attccgccgt cacaagactt tttttccct tttgccaacg tcgagaacct ctcacggacg | 120 | |
| agcaaagtct agtgtttggt ttcagtacgg cggtcgctgg ctctgtgtat gactgacctg | 180 | |
| aagaagcaaa gacttcttgc aacgtagaaa cgcaaaggcg cttctttttt gtgcaat | 237 | |

| | | |
|---|---|---|
| atg gca gga agg cag gcg gcg ttg ttt ttg gtg gtg ctg tct gtg gcg<br>Met Ala Gly Arg Gln Ala Ala Leu Phe Leu Val Val Leu Ser Val Ala<br>1              5                    10              15 | 285 |
| gcg ggc cct gtc tcc cag ctt gct cgg gcg agc gac gac agc gtc gac<br>Ala Gly Pro Val Ser Gln Leu Ala Arg Ala Ser Asp Asp Ser Val Asp<br>            20                    25                    30 | 333 |
| agc gtc gaa acc gcg cgt cag cac atg gag ctg gct atc gag gct gac<br>Ser Val Glu Thr Ala Arg Gln His Met Glu Leu Ala Ile Glu Ala Asp<br>                  35                    40                    45 | 381 |
| gaa gag atg cac gag gcc tac gac cct ttg ttg gaa ttc gtt gag acg<br>Glu Glu Met His Glu Ala Tyr Asp Pro Leu Leu Glu Phe Val Glu Thr<br>50                      55                    60 | 429 |
| ttt cgg gaa atc aaa aaa gct gtt gag gaa gat gcg gct ctg agt aca<br>Phe Arg Glu Ile Lys Lys Ala Val Glu Glu Asp Ala Ala Leu Ser Thr<br>65                      70                    75                    80 | 477 |
| gat gcg atc gac cgc gtg tcc cag ttc gat ctg gtt tcc ctc cta gat<br>Asp Ala Ile Asp Arg Val Ser Gln Phe Asp Leu Val Ser Leu Leu Asp<br>                  85                    90                    95 | 525 |
| gtc atc cga gag gct gca caa gca aag ttc gat ctc ctc gga cgc ctc<br>Val Ile Arg Glu Ala Ala Gln Ala Lys Phe Asp Leu Leu Gly Arg Leu<br>                    100                    105                    110 | 573 |
| att aca gac atc gcc agc gga atc ggc gag ggt gcc atg gct ctg atg<br>Ile Thr Asp Ile Ala Ser Gly Ile Gly Glu Gly Ala Met Ala Leu Met<br>                115                    120                    125 | 621 |
| gga gag gag gct gcg ttc att agg cca agg agg tca aag aga ggg aaa<br>Gly Glu Glu Ala Ala Phe Ile Arg Pro Arg Arg Ser Lys Arg Gly Lys<br>130                    135                    140 | 669 |
| aag act aca act aca acc agt tca tcc aca agt acg agt aca acg acc<br>Lys Thr Thr Thr Thr Thr Ser Ser Ser Thr Ser Thr Ser Thr Thr Thr<br>145                    150                    155                    160 | 717 |
| acg aca tca act acc act act acc act acc acc act acg act act act<br>Thr Thr Ser Thr Thr Thr Thr Thr Thr Thr Thr Thr Thr Thr Thr Thr<br>                    165                    170                    175 | 765 |
| aca act acg aca cca aca aca act aca aca acc aca aca act aca cca<br>Thr Thr Thr Thr Pro Thr Thr Thr Thr Thr Thr Thr Thr Thr Thr Pro<br>                180                    185                    190 | 813 |
| aca aca acg aca aca acc aca aca act aca cca aca aca acg aca aca<br>Thr Thr Thr Thr Thr Thr Thr Thr Thr Thr Pro Thr Thr Thr Thr Thr<br>                195                    200                    205 | 861 |
| acc aca aca act aca cca aca aca acg aca aca acc aca acg cca act<br>Thr Thr Thr Thr Thr Pro Thr Thr Thr Thr Thr Thr Thr Thr Pro Thr<br>                210                    215                    220 | 909 |
| aca acg aca tct acg aca acc act acg acc aca act act act aca<br>Thr Thr Thr Ser Thr Thr Thr Thr Thr Thr Thr Thr Thr Thr Thr Thr<br>225                    230                    235                    240 | 957 |
| cca act aca aca acg aca acc acg gaa cca aca act aca aca aca acc | 1005 |

```
Pro Thr Thr Thr Thr Thr Thr Thr Glu Pro Thr Thr Thr Thr Thr
                    245                 250                 255 acg gaa cca acc aca act aca agc aca acg acg act acg aca act aca       1053
Thr Glu Pro Thr Thr Thr Thr Ser Thr Thr Thr Thr Thr Thr Thr
                260                 265                 270 acg act acg aca cca tct acg acg aca tcc acc acc act acc ctc gat       1101
Thr Thr Thr Thr Pro Ser Thr Thr Thr Ser Thr Thr Thr Leu Asp
            275                 280                 285 tag accaaagtgt ttttgccgca cagattgtac atgcatcaaa aaacgcgata             1154
tttctttctc gtttgcgctg gcgtcatctg cgtctgccat ttgaatctgt cagcgctgcc     1214
agctccatag ggcgtgctcc ctgattacgt atttgcacga agggatgtct tggcttctac     1274
attggcgaac cgttttttggc actccaaaat ttttattaac acaaagcctt gcactggcct   1334
cattgtctat tcatagaacg ataatgtgtt gacctcgaaa aaaaaaaaaa aaaaaaaaa      1394 aaa                                                                   1397

<210> SEQ ID NO 344
<211> LENGTH: 288
<212> TYPE: PRT
<213> ORGANISM: Toxoplasma gondii

<400> SEQUENCE: 344

Met Ala Gly Arg Gln Ala Ala Leu Phe Leu Val Val Leu Ser Val Ala
1               5                   10                  15

Ala Gly Pro Val Ser Gln Leu Ala Arg Ala Ser Asp Asp Ser Val Asp
            20                  25                  30

Ser Val Glu Thr Ala Arg Gln His Met Glu Leu Ala Ile Glu Ala Asp
        35                  40                  45

Glu Glu Met His Glu Ala Tyr Asp Pro Leu Leu Glu Phe Val Glu Thr
    50                  55                  60

Phe Arg Glu Ile Lys Lys Ala Val Glu Glu Asp Ala Ala Leu Ser Thr
65                  70                  75                  80

Asp Ala Ile Asp Arg Val Ser Gln Phe Asp Leu Val Ser Leu Leu Asp
                85                  90                  95

Val Ile Arg Glu Ala Ala Gln Ala Lys Phe Asp Leu Leu Gly Arg Leu
            100                 105                 110

Ile Thr Asp Ile Ala Ser Gly Ile Gly Glu Gly Ala Met Ala Leu Met
        115                 120                 125

Gly Glu Glu Ala Ala Phe Ile Arg Pro Arg Arg Ser Lys Arg Gly Lys
    130                 135                 140

Lys Thr Thr Thr Thr Ser Ser Ser Thr Ser Thr Ser Thr Thr Thr
145                 150                 155                 160

Thr Thr Ser Thr Thr Thr Thr Thr Thr Thr Thr Thr Thr Thr Thr
                165                 170                 175

Thr Thr Thr Thr Pro Thr Thr Thr Thr Thr Thr Thr Thr Thr Pro
            180                 185                 190

Thr Thr Thr Thr Thr Thr Thr Thr Thr Pro Thr Thr Thr Thr Thr
        195                 200                 205

Thr Thr Thr Thr Pro Thr Thr Thr Thr Thr Thr Thr Pro Thr
    210                 215                 220

Thr Thr Thr Ser Thr Thr Thr Thr Thr Thr Thr Thr Thr Thr Thr
225                 230                 235                 240

Pro Thr Thr Thr Thr Thr Thr Thr Glu Pro Thr Thr Thr Thr Thr
                245                 250                 255
```

```
Thr Glu Pro Thr Thr Thr Thr Ser Thr Thr Thr Thr Thr Thr Thr
            260                 265                 270

Thr Thr Thr Thr Pro Ser Thr Thr Thr Ser Thr Thr Thr Leu Asp
        275                 280                 285

<210> SEQ ID NO 345
<211> LENGTH: 1397
<212> TYPE: DNA
<213> ORGANISM: Toxoplasma gondii

<400> SEQUENCE: 345
tttttttttt tttttttttt tttttcgag gtcaacacat tatcgttcta tgaatagaca      60
atgaggccag tgcaaggctt tgtgttaata aaaattttgg agtgccaaaa acggttcgcc    120
aatgtagaag ccaagacatc ccttcgtgca aatacgtaat cagggagcac gccctatgga    180
gctggcagcg ctgacagatt caaatggcag acgcagatga cgccagcgca acgagaaag    240
aaatatcgcg ttttttgatg catgtacaat ctgtgcggca aaaacacttt ggtctaatcg    300
agggtagtgg tggtggatgt cgtcgtagat ggtgtcgtag tcgttgtagt tgtcgtagtc    360
gtcgttgtgc ttgtagttgt ggttggttcc gtggttgttg ttgtagttgt tggttccgtg    420
gttgtcgttg ttgtagttgg tgtagtagta gttgtggtag tcgtagtggt tgtcgtagat    480
gtcgttgtag ttggcgttgt ggttgttgtc gttgttgttg gtgtagttgt tgtggttgtt    540
gtcgttgttg ttggtgtagt tgttgtggtt gttgtcgttg ttgttggtgt agttgttgtg    600
gttgttgtag ttgttgttgg tgtcgtagtt gtagtagtag tcgtagtggt ggtagtggta    660
gtagtggtag ttgatgtcgt ggtcgttgta ctcgtacttg tggatgaact ggttgtagtt    720
gtagtctttt tccctctctt tgacctcctt ggcctaatga acgcagcctc ctctcccatc    780
agagccatgg caccctcgcc gattccgctg gcgatgtctg taatgaggcg tccgaggaga    840
tcgaactttg cttgtgcagc ctctcggatg acatctagga gggaaaccag atcgaactgg    900
gacacgcggt cgatcgcatc tgtactcaga gccgcatctt cctcaacagc ttttttgatt    960
tcccgaaacg tctcaacgaa ttccaacaaa gggtcgtagg cctcgtgcat ctcttcgtca   1020
gcctcgatag ccagctccat gtgctgacgc gcggtttcga cgctgtcgac gctgtcgtcg   1080
ctcgcccgag caagctggga gacagggccc gccgccacag acagcaccac caaaaacaac   1140
gccgcctgcc ttcctgccat attgcacaaa aaagaagcgc ctttgcgttt ctacgttgca   1200
agaagtcttt gcttcttcag gtcagtcata cacagagcca gcgaccgccg tactgaaacc   1260
aaacactaga ctttgctcgt ccgtgagagg ttctcgacgt tggcaaaagg gaaaaaaaag   1320
tcttgtgacg gcggaatgct caatgcagtc gaggagcgct tccaggcgcc acagcggcag   1380
ggatatctgg aatgggg                                                  1397

<210> SEQ ID NO 346
<211> LENGTH: 18
<212> TYPE: DNA
<213> ORGANISM: Artificial sequence
<220> FEATURE:
<223> OTHER INFORMATION: Synthetic Primer

<400> SEQUENCE: 346
caggaaacag ctatgacc                                                   18

<210> SEQ ID NO 347
<211> LENGTH: 20
<212> TYPE: DNA
<213> ORGANISM: Artificial sequence
```

<220> FEATURE:
<223> OTHER INFORMATION: Synthetic Primer

<400> SEQUENCE: 347
attaaccctc actaaaggga                                              20

<210> SEQ ID NO 348
<211> LENGTH: 20
<212> TYPE: DNA
<213> ORGANISM: Artificial sequence
<220> FEATURE:
<223> OTHER INFORMATION: Synthetic Primer

<400> SEQUENCE: 348
taatacgact cactataggg                                              20

<210> SEQ ID NO 349
<211> LENGTH: 23
<212> TYPE: DNA
<213> ORGANISM: Artificial sequence
<220> FEATURE:
<223> OTHER INFORMATION: Synthetic Primer

<400> SEQUENCE: 349
gccagtgtga tggatatctg cag                                          23

<210> SEQ ID NO 350
<211> LENGTH: 18
<212> TYPE: DNA
<213> ORGANISM: Artificial sequence
<220> FEATURE:
<223> OTHER INFORMATION: Synthetic Primer

<400> SEQUENCE: 350
cgagctcgga tccactag                                                18

<210> SEQ ID NO 351
<211> LENGTH: 23
<212> TYPE: DNA
<213> ORGANISM: Artificial sequence
<220> FEATURE:
<223> OTHER INFORMATION: Synthetic Primer

<400> SEQUENCE: 351
ggttctctcc agaggttcat tac                                          23

<210> SEQ ID NO 352
<211> LENGTH: 22
<212> TYPE: DNA
<213> ORGANISM: Artificial sequence
<220> FEATURE:
<223> OTHER INFORMATION: Synthetic Primer

<400> SEQUENCE: 352
ggatgcaatg aagagagggc tc                                           22

<210> SEQ ID NO 353
<211> LENGTH: 24
<212> TYPE: DNA
<213> ORGANISM: Artificial sequence
<220> FEATURE:
<223> OTHER INFORMATION: Synthetic Primer

<400> SEQUENCE: 353
aactagaagg cacagtcgag gctg                                         24

-continued

<210> SEQ ID NO 354
<211> LENGTH: 24
<212> TYPE: DNA
<213> ORGANISM: Artificial sequence
<220> FEATURE:
<223> OTHER INFORMATION: Synthetic Primer

<400> SEQUENCE: 354
gggaacaaaa gctggagctc cacc                                              24

<210> SEQ ID NO 355
<211> LENGTH: 23
<212> TYPE: DNA
<213> ORGANISM: Artificial sequence
<220> FEATURE:
<223> OTHER INFORMATION: Synthetic Primer

<400> SEQUENCE: 355
cggacgttgc atgtcagtgg aca                                               23

<210> SEQ ID NO 356
<211> LENGTH: 24
<212> TYPE: DNA
<213> ORGANISM: Artificial sequence
<220> FEATURE:
<223> OTHER INFORMATION: Synthetic Primer

<400> SEQUENCE: 356
cacgaagctg catgttccag ctag                                              24

<210> SEQ ID NO 357
<211> LENGTH: 24
<212> TYPE: DNA
<213> ORGANISM: Artificial sequence
<220> FEATURE:
<223> OTHER INFORMATION: Synthetic Primer

<400> SEQUENCE: 357
acactttggt ctaatcgagg gtag                                              24

<210> SEQ ID NO 358
<211> LENGTH: 23
<212> TYPE: DNA
<213> ORGANISM: Artificial sequence
<220> FEATURE:
<223> OTHER INFORMATION: Synthetic Primer

<400> SEQUENCE: 358
acaacgacca cgacatcaac tac                                               23

<210> SEQ ID NO 359
<211> LENGTH: 24
<212> TYPE: DNA
<213> ORGANISM: Artificial sequence
<220> FEATURE:
<223> OTHER INFORMATION: Synthetic Primer

<400> SEQUENCE: 359
gttgtcgtag atgtcgttgt agtt                                              24

<210> SEQ ID NO 360
<211> LENGTH: 24
<212> TYPE: DNA
<213> ORGANISM: Artificial sequence
<220> FEATURE:
<223> OTHER INFORMATION: Synthetic Primer

```
<400> SEQUENCE: 360
agaagcgcct ttgcgtttct acgt                                          24

<210> SEQ ID NO 361
<211> LENGTH: 24
<212> TYPE: DNA
<213> ORGANISM: Artificial sequence
<220> FEATURE:
<223> OTHER INFORMATION: Synthetic Primer

<400> SEQUENCE: 361
gaggagatcg aactttgctt gtgc                                          24

<210> SEQ ID NO 362
<211> LENGTH: 46
<212> TYPE: DNA
<213> ORGANISM: Artificial sequence
<220> FEATURE:
<223> OTHER INFORMATION: Synthetic Primer

<400> SEQUENCE: 362
aaggataggc ggccgcaggt accatggcag gaaggcaggc ggcgtt                  46

<210> SEQ ID NO 363
<211> LENGTH: 40
<212> TYPE: DNA
<213> ORGANISM: Artificial sequence
<220> FEATURE:
<223> OTHER INFORMATION: Synthetic Primer

<400> SEQUENCE: 363
accgctcgag aagcttgaag ccaagacatc ccttcgtgca                         40

<210> SEQ ID NO 364
<211> LENGTH: 34
<212> TYPE: DNA
<213> ORGANISM: Artificial sequence
<220> FEATURE:
<223> OTHER INFORMATION: Synthetic Primer

<400> SEQUENCE: 364
ggccacgcgt cgactacttt tttttttttt tttt                               34

<210> SEQ ID NO 365
<211> LENGTH: 20
<212> TYPE: DNA
<213> ORGANISM: Artificial sequence
<220> FEATURE:
<223> OTHER INFORMATION: ggtggcgacg actcctggag

<400> SEQUENCE: 365
ggtggcgacg actcctggag                                               20

<210> SEQ ID NO 366
<211> LENGTH: 22
<212> TYPE: DNA
<213> ORGANISM: Artificial sequence
<220> FEATURE:
<223> OTHER INFORMATION: ccagaccaac tggtaatggt ag

<400> SEQUENCE: 366
ccagaccaac tggtaatggt ag                                            22
```

METHODS FOR THE DETECTION OF ENCYSTED PARASITES

This application is a continuation-in-part of application Ser. No. 08/994,825, filed Dec. 19, 1997, now abandoned.

FIELD OF THE INVENTION

The present invention relates to *Toxoplasma gondii* nucleic acid molecules, proteins encoded by such nucleic acid molecules, antibodies raised against such proteins and methods to identify such nucleic acid molecules, proteins or antibodies. The present invention also includes compositions comprising such nucleic acid molecules, proteins and antibodies, as well as their use for inhibiting oocyst shedding by cats infected with *T. gondii* and for protecting animals from diseases caused by *T. gondii*.

BACKGROUND OF THE INVENTION

Various attempts to develop a vaccine to both the asexual systemic stage and the sexual entero-epithelial stage of the Toxoplasma life cycle have been reported over the last thirty years (Hermentin, K. and Aspock, H. (1988), *Zbl. Bakt. Hyg. A*, 269:423–436). These attempts can be grouped into the following categories: 1) immunization with whole killed organism, 2) immunization with selected antigens, either purified native or recombinant protein, 3) immunization with attenuated strains, and 4) immunization with irradiated organisms. Little success has been achieved with immunizations using whole killed organism (Frenkel, J. K. and Smith, D. D. (1982), *Journal of Parasitology*, 68:744–748). Partial success has been observed with the pure native protein P30 (Bulow, R., and Boothroyd, J. C. (1991), *J. Immunol.* 147:3496) and with selected fractions of parasite lysates (Lunden, A. Lovgren, K. Uggla, A., and Araujo, F. G.; (1993) *Infection and Immunity*, 61:2639–2643). However, attempts with purified recombinant antigens have not been successful (Lunden, A., Parmley, S. F., Bengtsson, K. L. and Araujo, F. G. (1997) *Parasitology Research*, 83:6–9). Studies with irradiated organisms have reported 0–90% protection and are complicated by the uncertainty of truly inactivated irradiated preparations. Effective vaccines have been produced using attenuated strains. Two such mutant strains, ts-4 (Waldeland, H., Pfefferkom, E. R., and Frenkel, J. K. (1983), *Journal of Parasitology*, 69:171–175) and S48 (Hartley, W. J. and Marshall, S. C. (1957), *New Zealand Veterinary Journal*, 5:119–124), successfully protect animals against the asexual systemic disease. These strains are delivered in the tachyzoite form and do not protect cats from oocyst shedding. Another strain, T-263 (Frenkel, J. K.; Pfefferkom, E. R.; Smith, D. D.; and Fishback, J. L. (1991), *American Journal of Veterinary Research*, 52:759–763) is an oocyst minus strain, but was shown to progress through most of the entero-epithelial stages in the cat intestine. Exposure to this strain induces immunity in the cat to oocyst shedding upon subsequent challenge. There remains a need for an effective vaccine for prevention of the diseases caused by infection with *Toxoplasma gondii*.

SUMMARY OF THE INVENTION

The present invention relates to novel compositions and methods to inhibit *Toxoplasma gondii* (*T. gondii*) oocyst shedding by cats, thereby preventing the spread of *T. gondii* infection. According to the present invention there are provided isolated immunogenic *T. gondii* proteins and mimetopes thereof, *T. gondii* nucleic acid molecules, including those that encode such proteins; recombinant molecules including such nucleic acid molecules; recombinant viruses including such nucleic acid molecules; recombinant cells including such nucleic acid molecules; and antibodies that selectively bind to such immunogenic *T. gondii* proteins.

The present invention also includes methods to obtain and/or identify proteins, nucleic acid molecules, recombinant molecules, recombinant viruses, recombinant cells, and antibodies of the present invention. Also included are compositions comprising such proteins, nucleic acid molecules, recombinant molecules, recombinant viruses, recombinant cells, and antibodies, as well as use of such compositions to inhibit *T. gondii* oocyst shedding by cats infected with *T. gondii*, or for preventing *T. gondii* infection in an animal.

The present invention further includes the use of the nucleic acid molecules or proteins of the present invention as diagnostic reagents for the detection of *T. gondii* infection. In a preferred embodiment, the present invention includes a novel detection method and kit for detecting *T. gondii* oocysts in the feces of *T. gondii* infected cats.

One embodiment of the present invention is an isolated nucleic acid molecule encoding an immunogenic *T. gondii* protein that can be identified by a method that includes the steps of: a) immunoscreening a *T. gondii* genomic expression library or cDNA expression library with an antiserum, including an antiserum derived from intestinal secretions; and b) identifying a nucleic acid molecule in the library that expresses a protein that selectively binds to an antibody in the antiserum. Antisera to be used for screening include antiserum raised against *T. gondii* oocysts, antiserum raised against *T. gondii* bradyzoites, antiserum raised against *T. gondii* infected cat gut, and antiserum isolated from a cat immune to *T. gondii* infection. Another embodiment is an isolated immunogenic *T. gondii* protein that can be identified by a method that includes the steps of: a) immunoscreening a *T. gondii* genomic expression library or cDNA expression library with such an antiserum; and b) identifying a protein expressed by the library that selectively binds to antibodies in the antiserum. Also included are methods to identify and isolate such nucleic acid molecules and proteins.

The present application also includes an isolated nucleic acid molecule that hybridizes under stringent hybridization conditions with a gene that includes a nucleic acid sequence cited in Table 1. Also included in the present invention is an isolated nucleic acid molecule that hybridizes under stringent hybridization conditions with a gene that includes a nucleic acid molecule cited in Table 1. Preferred nucleic acid molecules encode immunogenic *T. gondii* proteins. More preferred nucleic acid molecules are those cited in Table 1.

The present invention also relates to recombinant molecules, recombinant viruses and recombinant cells that include an isolated nucleic acid molecule of the present invention. Also included are methods to produce such nucleic acid molecules, recombinant molecules, recombinant viruses and recombinant cells.

Another embodiment of the present invention is an isolated immunogenic protein encoded by a nucleic acid molecule that hybridizes under stringent hybridization conditions with a gene (i.e., with either the coding strand or the non-coding strand) comprising a nucleic acid sequence cited in Table 1 and/or a nucleic acid molecule cited in Table 1. Note that the nucleic acid molecule hybridizes with the non-coding strand of the gene, that is, with the complement of the coding strand of the gene. A preferred protein is an immunogenic *T. gondii* protein. More preferred proteins are those encoded by nucleic acid molecules cited in Table 1. Also preferred are the proteins cited in Table 1.

The present invention also relates to: mimetopes of immunogenic *T. gondii* proteins and isolated antibodies that selectively bind to immunogenic *T. gondii* proteins or mimetopes thereof. Also included are methods, including recombinant methods, to produce proteins, mimetopes and antibodies of the present invention.

Yet another embodiment of the present invention is a composition to inhibit *T. gondii* oocyst shedding in a cat due to infection with *T. gondii*. Such a composition includes one or more of the following protective compounds: an isolated immunogenic *T. gondii* protein encoded by a nucleic acid molecule that hybridizes under stringent hybridization conditions with a gene comprising a nucleic acid sequence cited in Table 1, and specifically with the non-coding-strand of that gene; an isolated antibody that selectively binds to said immunogenic *T. gondii* protein; and an isolated nucleic acid molecule that hybridizes under stringent hybridization conditions with a gene comprising a nucleic acid sequence cited in Table 1. Such a composition can also include an excipient, adjuvant or carrier. Preferred compositions comprising a nucleic acid molecule of the present invention include genetic vaccines, recombinant virus vaccines and recombinant cell vaccines. Also included in the present invention is a method to protect an animal, including a human, from disease caused by *T. gondii*, comprising the step of administering to the animal a composition of the present invention. Preferred animals to treat are cats in order to prevent oocyst shedding caused by *T. gondii* infection.

DETAILED DESCRIPTION OF THE INVENTION

The present invention provides for isolated immunogenic *T. gondii* proteins, isolated *T. gondii* nucleic acid molecules including those encoding such *T. gondii* proteins, recombinant molecules comprising such nucleic acid molecules, recombinant viruses comprising such nucleic acid molecules, cells transformed with such nucleic acid molecules (i.e., recombinant cells), and antibodies that selectively bind to immunogenic *T. gondii* proteins. As used herein, the terms isolated immunogenic *T. gondii* protein and isolated nucleic acid molecule refer to an immunogenic *T. gondii* protein and a *T. gondii* nucleic acid molecule, respectively, derived from *T. gondii* which can be obtained from its natural source or can be produced using, for example, recombinant nucleic acid technology or chemical synthesis. Also included in the present invention is the use of these proteins, nucleic acid molecules, and antibodies as compositions to protect animals from diseases caused by *T. gondii* and to inhibit *T. gondii* oocyst shedding in cats. As used herein, a cat refers to any member of the cat family (i.e., Felidae), including domestic cats, wild cats and zoo cats. Examples of cats include, but are not limited to, domestic cats, lions, tigers, leopards, panthers, cougars, bobcats, lynx, jaguars, cheetahs, and servals. A preferred cat to protect is a domestic cat. Further included in the present invention is the use of these proteins, nucleic acid molecules and antibodies for the detection of *T. gondii* infection in an animal or as targets for the development of chemotherapeutic agents against parasitic infection.

Immunogenic *T. gondii* protein and nucleic acid molecules of the present invention have utility because they represent novel targets for anti-parasite vaccines or chemotherapeutic agents. Compositions of the present invention can also be used as reagents for the diagnosis of *T. gondii* infection in cats and other animals, including humans. The products and processes of the present invention are advantageous because they enable the inhibition of *T. gondii* oocyst shedding in cats, the definitive hosts for *T. gondii* (i.e., the animals in which *T. gondii* reproduction takes place). It is to be noted that the proteins and nucleic acid molecules of the present invention have uses beyond eliciting an immune response despite denoting proteins of the present invention as immunogenic proteins.

As described in more detail in the Examples, it was very difficult to isolate a nucleic acid molecule encoding an immunogenic *T. gondii* protein selectively bound by antisera directed against *T. gondii* intestinal stages. Such stages are preferred because they represent the sexual cycle of *T. gondii*, the preferred target for development of a composition to inhibit oocyst shedding. Unfortunately, however, the *T. gondii* sexual cycle cannot currently be reproduced in culture, and, there is not a simple method by which to produce a cDNA (i.e., complementary DNA) library containing only *T. gondii* nucleic acid molecules of various stages of the sexual cycle. For example, the infected cat gut is the source of many of the sexual stages of *T. gondii*, and, as such, material to be used in identifying *T. gondii* immunogenic proteins are contaminated with cat material. The present invention describes the development of new techniques to isolate and identify nucleic acid molecules encoding immunogenic *T. gondii* proteins. These techniques include (a) the isolation and enrichment of antisera against a variety of *T. gondii* life stages, several of which are only present in infected cats, at least predominantly in infected cat guts, and (b) the use of such antisera to screen cDNA and genomic expression libraries to identify nucleic acid molecules that express *T. gondii* proteins that selectively bind to such antisera.

One embodiment of the present invention is an isolated protein that includes an immunogenic *T. gondii* protein. The terms "one or more" and "at least one" can be used interchangeably herein. It is also to be noted that the terms "comprising", "including", and "having" can be used interchangeably. According to the present invention, an isolated, or biologically pure, protein is a protein that has been removed from its natural milieu. The terms "isolated" and "biologically pure" do not necessarily reflect the extent to which the protein has been purified. An isolated protein of the present invention can be obtained from its natural source, can be produced using recombinant DNA technology, or can be produced by chemical synthesis."

An isolated protein of the present invention, including a homolog, can be identified in a straight-forward manner by the protein's ability to elicit an immune response against a naturally occurring *T. gondii* protein. Examples of *T. gondii* immunogenic proteins include proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a *T. gondii* immunogenic protein, and/or of binding to an antibody directed against a *T. gondii* immunogenic protein. That is, when the homolog is administered to an animal as an immunogen, using techniques known to those skilled in the art, the animal will produce an immune response against at least one epitope of a *T. gondii* immunogenic protein. The ability of a protein to effect an immune response can be measured using techniques known to those skilled in the art. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids, at least about 50 amino acids, at least about 100 amino acids, at least about 150 amino acids, at least about 200 amino acids, at least about 250 amino acids, or at least about 300 amino acids.

Immunogenic *T. gondii* protein homologs can be the result of natural allelic variation or natural mutation. Immunogenic *T. gondii* protein homologs of the present invention can also be produced using techniques known in the art including, but not limited to, direct modifications to the protein or modifications to the gene encoding the protein using, for example, classic or recombinant DNA techniques to effect random or targeted mutagenesis.

As used herein, a nucleic acid molecule encoding an immunogenic *T. gondii* protein includes nucleic acid sequences related to a natural *T. gondii* gene. As used herein, a *T. gondii* gene includes all regions of the genome related to the gene, such as regulatory regions that control production of the immunogenic *T. gondii* protein encoded by the gene (for example, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a full-length protein, i.e., a complete protein as would be initially translated in its natural milieu, prior to any post-translational modifications.

In one embodiment, a *T. gondii* gene of the present invention includes at least one of the nucleic acid molecules cited in Table 1 (i.e., the cited nucleic acid molecules). The coding strands of the cited nucleic acid molecules are represented, respectively, by the nucleic acid sequences (i.e., the cited nucleic acid sequences) shown in Table 1. Also presented in Table 1 are the deduced amino acid sequences encoded by each of the cited nucleic acid molecules (i.e., the cited amino acid sequences) and the protein name designations (i.e., the cited proteins).

TABLE 1

| SEQ ID NO | TYPE | Nucleic Acid Molecules | Amino Acid Molecules | Original Designation |
|---|---|---|---|---|
| 1 | DNA | $nTG1_{357}$ | | Tg-41 |
| 2 | Protein | | $nTG1_{119}$ | PTG-41 |
| 3 | DNA | $nTG2_{339}$ | | Tg-45 |
| 4 | Protein | | $PTG2_{108}$ | PTG-45 |
| 5 | DNA | $nTG4_{526}$ | | Tg-50 |
| 6 | Protein | | $PTG4_{175}$ | PTG-50 |
| 7 | cDNA | $nTG4_{1478}$ | | Tg-50c |
| 8 | Protein | | $PTG4_{381}$ | PTG-50c |
| 9 | DNA | $nTG5_{657}$ | | Q2-4 |
| 10 | Protein | | $PTG5_{219}$ | PQ2-4 |
| 11 | cDNA | $nTG5_{1029}$ | | Q2-4c |
| 12 | Protein | | $PTG5_{273}$ | PQ2-4c |
| 13 | DNA | $nTG6_{425}$ | | Q2-9 |
| 14 | Protein | | $PTG6_{142}$ | PQ2-9 |
| 15 | DNA | $nTG7_{417}$ | | Q2-10 |
| 16 | Protein | | $PTG7_{139}$ | PQ2-10 |
| 17 | DNA | $nTG8_{507}$ | | Q2-11 |
| 18 | Protein | | $PTG8_{51}$ | PQ2-11 |
| 19 | DNA | $nTG9_{718}$ | | 4499-9 |
| 20 | Protein | | $PTG9_{99}$ | P4499-9 |
| 21 | DNA | $nTG10_{441}$ | | 4604-2 |
| 22 | Protein | | $PTG10_{147}$ | P4604-2 |
| 23 | DNA | $nTG11_{428}$ | | 4604-3 |
| 24 | Protein | | $PTG11_{134}$ | P4604-3 |
| 25 | DNA | $nTG13_{282}$ | | 4604-5 |
| 26 | DNA | $nTG15_{304}$ | | 4604-10 |
| 27 | Protein | | $PTG15_{101}$ | P4604-10 |
| 28 | DNA | $nTG16_{284}$ | | 4604-17 |
| 29 | Protein | | $PTG16_{95}$ | P4604-17 |
| 30 | DNA | $nTG17_{690}$ | | 4604-54 |
| 31 | Protein | | $PTG17_{230}$ | P4604-54 |
| 32 | DNA | $nTG18_{313}$ | | 4604-62 |
| 33 | Protein | | $PTG18_{54}$ | P4604-62 |
| 34 | DNA | $nTG19_{389}$ | | 4604-63 |
| 35 | Protein | | $PTG19_{65}$ | P4604-63 |
| 36 | DNA | $nTG21_{548}$ | | 4604-69 |
| 37 | Protein | | $PTG21_{183}$ | P4604-69 |
| 38 | DNA | $nTG22_{310}$ | | BZ1-2 |
| 39 | Protein | | $PTG22_{95}$ | PBZ1-2 |
| 40 | DNA | $nTG23_{220}$ | | BZ1-3 |
| 41 | Protein | | $PTG23_{73}$ | PBZ1-3 |
| 42 | DNA | $nTG24_{642}$ | | BZ1-6 |
| 43 | Protein | | $PTG24_{34}$ | PBZ1-6 |
| 44 | DNA | $nTG25_{381}$ | | BZ2-3 |
| 45 | Protein | | $PTG25_{27}$ | PBZ2-3 |
| 46 | DNA | $nTG26_{432}$ | | BZ2-5 |
| 47 | Protein | | $PTG26_{85}$ | PBZ2-5 |
| 48 | DNA | $nTG27_{282}$ | | BZ3-2 |
| 49 | Protein | | $PTG27_{35}$ | PBZ3-2 |
| 50 | DNA | $nTG28_{466}$ | | BZ4-3 |
| 51 | Protein | | $PTG28_{71}$ | PBZ4-3 |
| 52 | DNA | $nTG30_{539}$ | | BZ4-6 |
| 53 | Protein | | $PTG30_{20}$ | PBZ4-6 |
| 54 | DNA | $nTG31_{1233}$ | | AMX/I-5 |
| 55 | DNA | $nTG32_{411}$ | | AMX/I-6 |
| 56 | Protein | | $PTG32_{60}$ | PAMX/I-6 |
| 57 | DNA | $nTG33_{441}$ | | AMX/I-7 |
| 58 | Protein | | $PTG33_{118}$ | PAMX/I-7 |
| 59 | DNA | $nTG34_{491}$ | | AMX/I-9 |
| 60 | Protein | | $PTG34_{34}$ | PAMX/I-9 |
| 61 | DNA | $nTG35_{387}$ | | AMX/I-10 |
| 62 | Protein | | $PTG35_{129}$ | PAMX/I-10 |
| 63 | DNA | $nTG36_{417}$ | | AMI-23 |
| 64 | Protein | | $PTG36_{139}$ | PAMI-23 |
| 65 | DNA | $nTG37_{416}$ | | AMI-24 |
| 66 | Protein | | $PTG37_{138}$ | PAMI-24 |
| 67 | DNA | $nTG38_{500}$ | | AMI-28 |
| 68 | DNA | $nTG40_{321}$ | | AMI-47 |
| 69 | Protein | | $PTG40_{73}$ | PAMI-47 |
| 70 | DNA | $nTG41_{513+C86}$ | | OC-1 |
| 71 | Protein | | $PTG41_{171}$ | POC-1 |
| 72 | DNA | $nTG42_{528}$ | | OC-2 |
| 73 | Protein | | $PTG42_{176}$ | POC-2 |
| 74 | DNA | $nTG43_{375}$ | | OC-13 |
| 75 | Protein | | $PTG43_{125}$ | POC-13 |
| 76 | DNA | $nTG44_{543}$ | | OC-14 |
| 77 | Protein | | $PTG44_{89}$ | POC-14 |
| 78 | DNA | $nTG45_{573}$ | | OC-22 |
| 79 | Protein | | $PTG45_{191}$ | POC-22 |
| 80 | DNA | $nTG46_{1835}$ | | OC-23 |
| 81 | Protein | | $PTG46_{612}$ | POC-23 |
| 82 | DNA | $nTG48_{604}$ | | 4CQA7f |
| 83 | Protein | | $PTG48_{112}$ | P4CQA7f |
| 84 | DNA | $nTG48_{549}$ | | 4CQA7r |
| 85 | DNA | $nTG49_{270}$ | | 4CQA11 |
| 86 | Protein | | $PTG49_{90}$ | P4CQA11 |

TABLE 1-continued

| SEQ ID NO | TYPE | Nucleic Acid Molecules | Amino Acid Molecules | Original Designation |
|---|---|---|---|---|
| 87 | DNA | nTG50$_{306}$ | | 4CQA19 |
| 88 | Protein | | PTG50$_{102}$ | P4CQA19 |
| 89 | DNA | nTG51$_{804}$ | | 4CQA21 |
| 90 | Protein | | PTG51$_{268}$ | P4CQA21 |
| 91 | DNA | nTG52$_{867}$ | | 4CQA22 |
| 92 | Protein | | PTG52$_{289}$ | P4CQA22 |
| 93 | DNA | nTG53$_{1434}$ | | 4CQA24 |
| 94 | Protein | | PTG53$_{164}$ | P4CQA24 |
| 95 | DNA | nTG54$_{680}$ | | 4CQA25 |
| 96 | Protein | | PTG54$_{227}$ | P4CQA25 |
| 97 | DNA | nTG55$_{296}$ | | 4CQA26 |
| 98 | Protein | | PTG55$_{99}$ | P4CQA26 |
| 99 | DNA | nTG56$_{723}$ | | 4CQA27 |
| 100 | Protein | | PTG56$_{53}$ | P4CQA27 |
| 101 | DNA | nTG57$_{270}$ | | 4CQA29 |
| 102 | Protein | | PTG57$_{90}$ | P4CQA29 |
| 103 | DNA | nTG58$_{503}$ | | R8050-2 |
| 104 | Protein | | PTG58$_{62}$ | PR8050-2 |
| 105 | DNA | nTG60$_{322}$ | | R8050-5 |
| 106 | Protein | | PTG60$_{73}$ | PR8050-5 |
| 107 | DNA | nTG61$_{390}$ | | R8050-6 |
| 108 | Protein | | PTG61$_{67}$ | PR8050-6 |
| 109 | DNA | nTG62$_{699}$ | | M2A1 |
| 110 | Protein | | PTG62$_{233}$ | PM2A1 |
| 111 | DNA | nTG63$_{419}$ | | M2A2 |
| 112 | Protein | | PTG63$_{140}$ | PM2A2 |
| 113 | DNA | nTG64$_{303}$ | | M2A3 |
| 114 | Protein | | PTG64$_{101}$ | PM2A3 |
| 115 | DNA | nTG65$_{696}$ | | M2A4 |
| 116 | Protein | | PTG65$_{232}$ | PM2A4 |
| 117 | DNA | nTG66$_{173}$ | | M2A5 |
| 118 | Protein | | PTG66$_{58}$ | PM2A5 |
| 119 | DNA | nTG67$_{369}$ | | M2A6 |
| 120 | Protein | | PTG67$_{123}$ | PM2A6 |
| 121 | DNA | nTG68$_{566}$ | | M2A7 |
| 122 | Protein | | PTG68$_{61}$ | PM2A7 |
| 123 | DNA | nTG69$_{616}$ | | M2A11 |
| 124 | Protein | | PTG69$_{205}$ | PM2A11 |
| 125 | DNA | nTG70$_{762}$ | | M2A16 |
| 126 | Protein | | PTG70$_{254}$ | PM2A16 |
| 127 | DNA | nTG71$_{236}$ | | M2A18 |
| 128 | Protein | | PTG71$_{79}$ | PM2A18 |
| 129 | DNA | nTG72$_{569}$ | | M2A19 |
| 130 | Protein | | PTG72$_{190}$ | PM2A19 |
| 131 | DNA | nTG73$_{232}$ | | M2A20 |
| 132 | DNA | nTG74$_{276}$ | | M2A21 |
| 133 | Protein | | PTG74$_{92}$ | PM2A21 |
| 134 | DNA | nTG75$_{309}$ | | M2A22 |
| 135 | Protein | | PTG75$_{103}$ | PM2A22 |
| 136 | DNA | nTG76$_{534}$ | | M2A23 |
| 137 | Protein | | PTG76$_{178}$ | PM2A23 |
| 138 | DNA | nTG76$_{423}$ | | M2A23 |
| 139 | DNA | nTG77$_{327}$ | | M2A24 |
| 140 | Protein | | PTG77$_{109}$ | PM2A24 |
| 141 | DNA | nTG78$_{444}$ | | M2A25 |
| 142 | Protein | | PTG78$_{148}$ | PM2A25 |
| 143 | DNA | nTG79$_{928}$ | | M2A29 |
| 144 | Protein | | PTG79$_{19}$ | PM2A29 |
| 265 | DNA | nTG22$_{310a}$ | | BZ1-2-a |
| 266 | Protein | | PTG22$_{95a}$ | PBZ1-2-a |
| 267 | DNA | nTG64$_{303a}$ | | M2A3-a |
| 268 | Protein | | PTG64$_{101a}$ | PM2A3-a |
| 269 | DNA | nTG71$_{236a}$ | | M2A18-a |
| 270 | Protein | | PTG71$_{79a}$ | PM2A18-a |
| 271 | DNA | nTG6$_{425a}$ | | Q2-9-1-a |
| 272 | Protein | | PTG6$_{142a}$ | PQ2-9-a |
| 273 | DNA | nTG41$_{513a}$ | | OC-1-a |
| 274 | Protein | | PTG41$_{171a}$ | POC-1-a |
| 282 | cDNA | nTG$_{1225}$ | | MGIS42 |
| 283 | Protein | | PTG$_{28}$ | PMGIS42 |
| 284 | DNA | nTG$_{1225}$ | | rc |
| 292 | cDNA | nTG$_{1573}$ | | MGIS44 |
| 293 | Protein | | PTG$_{73}$ | PMGIS44 |
| 294 | DNA | nTG$_{1573}$ | | rc |
| 306 | cDNA | nTG$_{2417}$ | | MGIS48 |
| 307 | Protein | | PTG$_{9}$ | PMGIS48 |
| 308 | DNA | nTG$_{2417}$ | | rc |
| 311 | cDNA | nTG$_{1785}$ | | MGIS65 |
| 312 | Protein | | PTG$_{24}$ | PMGIS65 |
| 313 | DNA | nTG$_{1785}$ | | rc |
| 338 | DNA | nTG$_{647}$ | | 511-44 genomic |
| 339 | DNA | nTG$_{647}$ | | rc |
| 340 | cDNA | nTG$_{867}$ | | 511-44 coding region |
| 341 | Protein | | PTG$_{288}$ | P511-44 |
| 342 | DNA | nTG$_{867}$ | | rc |
| 343 | cDNA | nTG$_{1397}$ | | 511-44cDNA |
| 345 | DNA | nTG$_{1397}$ | | rc |

It should be noted that because nucleic acid sequencing technology is not entirely error-free, the nucleic acid sequences disclosed in the present invention (as well as other nucleic acid and protein sequences presented herein) represent the apparent nucleic acid sequences of the nucleic acid molecules encoding *T. gondii* proteins of the present invention. The nucleic acid molecules cited in Table 1 also include the complementary (i.e., apparently non-coding) strands. As used herein the terms "complementary strand" and "complement" refer to the nucleic acid sequence of the DNA strand that is fully complementary to the DNA strand having the listed sequence, which can easily be determined by those skilled in the art. Likewise, a nucleic acid sequence complement of any nucleic acid sequence of the present invention refers to the nucleic acid sequence of the nucleic acid strand that is fully complementary to (i.e., can form a complete double helix with) the strand for which the sequence is cited. Production of the cited nucleic acid molecules is disclosed in the Examples as are methods to obtain nucleic acid sequences of the coding strands of such molecules and the amino acid sequences deduced therefrom.

In another embodiment, a *T. gondii* gene or nucleic acid molecule can be a naturally occurring allelic variant that includes a similar but not identical sequence to the cited nucleic acid molecules. A naturally occurring allelic variant of a *T. gondii* gene including any of the above-listed nucleic acid sequences is a gene that occurs at essentially the same locus (or loci) in the genome as the gene including at least one of the above-listed sequences, but which, due to natural variations caused by, for example, mutation or recombination, has a similar but not identical sequence. Because natural selection typically selects against alterations that affect function, allelic variants usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to be found within a given *T. gondii* organism or population, because, for example, the genome goes through a diploid stage, and sexual reproduction results in the reassortment of alleles.

In one embodiment of the present invention, an isolated immunogenic *T. gondii* protein is encoded by a nucleic acid molecule that hybridizes under stringent hybridization conditions to a gene encoding an immunogenic *T. gondii* protein. The minimal size of a *T. gondii* protein of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the *T. gondii* nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding an immunogenic *T. gondii* protein is typically at least about 12 to about 15 nucleotides in length if the nucleic acid molecule is GC-rich and at least about 15 to about 17 bases in length if it is AT-rich. The minimal size of a nucleic acid molecule used to encode an immunogenic *T. gondii* protein homolog of the present invention is from about 12 to about 18 nucleotides in length. Thus, the minimal size of an immunogenic *T. gondii* protein homolog of the present invention is from about 4 to about 6 amino acids in length. There is no limit, other than a practical limit, on the maximal size of a nucleic acid molecule encoding an immunogenic *T. gondii* protein of the present invention because a nucleic acid molecule of the present invention can include a portion of a gene, an entire gene, or multiple genes. A preferred nucleic acid molecule of the present invention is a nucleic acid molecule that is at least 12 nucleotides in length. Also preferred are nucleic acid molecules that are at least 18 nucleotides, or at least 20 nucleotides, or at least 25 nucleotides, or at least 30 nucleotides, or at least 40 nucleotides, or at least 50 nucleotides, or at least 70 nucleotides, or at least 100 nucleotides, or at least 150 nucleotides, or at least 200 nucleotides, or at least 250 nucleotides, or at least 300 nucleotides, or at least 350 nucleotides, or at least 400 nucleotides, or at least 500 nucleotides, or at least 750 nucleotides, or at least 1000 nucleotides, or at least 1500 nucleotides, or at least 1750 nucleotides, or at least 2000 nucleotides, or at least 2250 nucleotides, or at least 2417 nucleotides in length, The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual,* Cold Spring Harbor Labs Press, and Meinkoth, et al., 1984, *Anal. Biochem.* 138, 267–284, each of which is incorporated by reference herein in its entirety. As explained in detail in the cited references, the determination of hybridization conditions involves the manipulation of a set of variables including the ionic strength (M, in moles/liter), the hybridization temperature (°C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m=81.5°\ C.+16.6 \log M+0.41(\%\ G+C)-500/n-0.61(\%\ formamide).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d=4(G+C)+2(A+T).$$

A temperature of 5° C. below $T_d$ is used to detect hybridization between perfectly matched molecules.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a *T. gondii* nucleic acid molecule of about 150 bp in length, the following conditions could preferably be used. As an example, the average G+C content of *Dirofilaria immitis* DNA is about 35%. The unknown nucleic acid molecules would be attached to a support membrane, and the 150 bp probe would be labeled, e.g. with a radioactive tag. The hybridization reaction could be carried out in a solution comprising 2×SSC and 0% formamide, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1×SSC and 0% formamide, the $T_m$ of perfect hybrids would be about 79° C.:

$$81.5° C.+16.6 \log (0.15M)+(0.41\times35)-(500/150)-(0.61\times0)=79° C.$$

Thus, to achieve hybridization with nucleic acid molecules having about 30% base-pair mismatch, hybridization washes would be carried out at a temperature of about 49° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 49° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the GCG™ program, Bestfit function with default parameter settings, or a gap weight of 12, a length weight of 4, an average match of 2.912, and an average mismatch of −2.003.

A preferred immunogenic *T. gondii* protein of the present invention is a compound that, when administered to an animal in an effective manner, is capable of protecting that animal from disease caused by *T. gondii* or, in the case of cats, is capable of preventing *T. gondii* oocyst shedding in cats infected with *T. gondii*. In accordance with the present invention, the ability of an immunogenic *T. gondii* protein of the present invention to protect an animal from *T. gondii* disease refers to the ability of that protein to, for example, treat, ameliorate and/or prevent disease caused by *T. gondii*. In one embodiment, an immunogenic *T. gondii* protein of the present invention can elicit an immune response (including a humoral and/or cellular immune response) against *T. gondii*.

The present invention also includes mimetopes of immunogenic *T. gondii* proteins of the present invention. As used herein, a mimetope of an immunogenic *T. gondii* protein of the present invention refers to any compound that is able to mimic the activity of such an immunogenic *T. gondii* protein, often because the mimetope has a structure that mimics the particular *T. gondii* protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of an immunogenic *T. gondii* protein of the present invention is a fusion protein that includes an immunogenic *T. gondii* protein-containing domain attached to one or more fusion segments. Suitable fusion segments for use with the present invention include, but are not limited to, segments that can: enhance a protein's stability; act as an immunopotentiator to enhance an immune response against an immunogenic *T. gondii* protein; and/or assist in purification of an immunogenic *T. gondii* protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the immunogenic *T. gondii* protein-containing domain of the protein and can be susceptible to cleavage in order to enable straightforward recovery of an immunogenic *T. gondii* protein. Fusion proteins are preferably produced by culturing a recombinant cell transformed with a nucleic acid molecule that encodes a protein including the fusion segment attached to either the carboxyl and/or amino terminal end of an immunogenic *T. gondii* protein-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

In another embodiment, an immunogenic *T. gondii* protein of the present invention also includes at least one additional protein segment that is capable of protecting an animal from one or more diseases. Such a multivalent protective protein can be produced, for example, by culturing a cell transformed with a nucleic acid molecule comprising two or more nucleic acid domains joined together in such a manner that the resulting nucleic acid molecule is expressed as a multivalent protective compound containing at least two protective compounds capable of protecting an animal from diseases caused, for example, by at least one infectious agent.

Examples of multivalent protective compounds include, but are not limited to, an immunogenic *T. gondii* protein of the present invention attached to one or more compounds protective against one or more other infectious agents, particularly an agent that infects cats. In another embodiment, one or more protective compounds can be included in a multivalent vaccine comprising an immunogenic *T. gondii* protein of the present invention and one or more other protective molecules as separate compounds.

A preferred isolated immunogenic *T. gondii* protein of the present invention includes a protein that is encoded by a nucleic acid molecule that hybridizes under stringent hybridization conditions with a gene (i.e., with the non-coding strand which is a complement of the coding strand) comprising at least one of the nucleic acid molecules cited in Table 1. As such, also preferred is a protein that is encoded by a nucleic acid molecule that hybridizes under stringent hybridization conditions with the non-coding strand of a gene comprising at least one of the nucleic acid sequences cited in Table 1. More preferred is a protein encoded by a nucleic acid molecule that hybridizes under stringent hybridization conditions with at least one of the cited nucleic acid molecules particularly since those nucleic acid molecules have been shown to encode proteins that selectively bind to antiserum that either was raised against *T. gondii* oocysts, bradyzoites, or infected cat gut, or was isolated from a cat immune to *T. gondii* infection. As such, also preferred is a protein encoded by a nucleic acid molecule that hybridizes under stringent hybridization conditions with the complement of at least one of the cited nucleic acid sequences.

Even more preferred are isolated proteins having an amino acid sequence encoded by a nucleic acid molecules that are at least about 75%, preferably at least about 80%, more preferably at least about 85%, even more preferably at least about 90%, even more preferably at least about 95%, and even more preferably at least about 98% identical to one of the nucleic acid molecules and/or nucleic acid sequences cited in Table 1. Also preferred are proteins that comprise one or more epitopes of any of the proteins having such amino acid sequences.

A particularly preferred isolated protein of the present invention is a protein having an amino acid sequence encoded by at least one of the cited nucleic acid molecules and/or cited nucleic acid sequences, a protein encoded by an allelic variant of at least one of the cited nucleic acid molecules and/or nucleic acid sequences, or a protein comprising an epitope of any of the proteins having such amino acid sequences.

In one embodiment, preferred immunogenic *T. gondii* proteins of the present invention include proteins that are at least about 75%, preferably at least about 80%, more preferably at least about 85%, even more preferably at least about 90%, and even more preferably at least about 95% identical to at least one of the proteins cited in Table 1. As such, also preferred are proteins that are at least about 75%, preferably at least about 80%, more preferably at least about 85%, even more preferably at least about 90%, and even more preferably at least about 95% identical to at least one of the amino acid sequences cited in Table 1. Also preferred are proteins that comprise one or more epitopes of any of such proteins. More preferred are immunogenic *T. gondii* proteins comprising the cited proteins and/or having the cited amino acid sequences, proteins encoded by allelic variants of nucleic acid molecules encoding proteins including the cited proteins and/or having the cited amino acid sequences, and proteins having one or more epitopes of such proteins.

Another embodiment of the present invention is an isolated nucleic acid molecule comprising a *T. gondii* nucleic acid molecule that encodes an immunogenic *T. gondii* protein. The identifying characteristics of such nucleic acid molecules are heretofore described. A nucleic acid molecule of the present invention can include an isolated natural *T. gondii* nucleic acid molecule or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. The minimal size of an *T. gondii* nucleic acid molecule of the present invention is from about 12 to about 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. Accordingly, the term "isolated", as used herein to describe a nucleic acid molecule, does not reflect the extent to which the nucleic acid molecule has been purified. An isolated *T. gondii* nucleic acid molecule of the present invention can be isolated from its natural source or produced using recombinant nucleic acid technology (e.g., polymerase chain reaction (PCR) amplification or cloning) or chemical synthesis. Isolated *T. gondii* nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an immunogenic *T. gondii* protein of the present invention.

A homolog of a nucleic acid molecule encoding an immunogenic *T. gondii* protein can be produced using a number of methods known to those skilled in the art, see, for example, Sambrook et al., 1989, *Molecular Cloning. A Laboratory Manual,* Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with a nucleic acid molecule encoding an immunogenic *T. gondii* protein or by screening the function of a protein encoded by the nucleic acid molecule (e.g., ability to elicit an immune response against at least one epitope of an immunogenic *T. gondii* protein).

An isolated nucleic acid molecule of the present invention can include a nucleic acid sequence that encodes at least one immunogenic *T. gondii* protein of the present invention, examples of which are disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, capable of encoding an *T. gondii* protein.

A preferred nucleic acid molecule of the present invention, when administered to a cat, is capable of preventing *T. gondii* oocyst shedding. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an immunogenic *T. gondii* protein of the present invention), the nucleic acid molecule being delivered to the animal, for example, by direct injection (i.e, as a genetic vaccine) or in a vehicle such as a recombinant virus vaccine or a recombinant cell vaccine. Another preferred nucleic acid molecule of the present invention, when administered to an animal, is capable of preventing disease in that animal caused by *T. gondii*.

One embodiment of the present invention is an isolated nucleic acid molecule that hybridizes under stringent hybridization conditions with a nucleic acid molecule comprising at least one of the nucleic acid molecules cited in Table 1. As such, also preferred is a nucleic acid molecule that hybridizes under stringent hybridization conditions with at least one of the nucleic acid sequences cited in Table 1 or with a complement of such a sequence. More preferred is a nucleic acid molecule that hybridizes under stringent hybridization conditions with at least one of the cited nucleic acid molecules. As such, also preferred is a nucleic acid molecule that hybridizes under stringent hybridization conditions with at least one of the cited nucleic acid sequences or with a complement thereof.

Even more preferred are isolated nucleic acid molecules that are at least about 75%, preferably at least about 80%, more preferably at least about 85%, even more preferably at least about 90%, even more preferably at least about 95%, and even more preferably at least about 98% identical to one of the nucleic acid molecules and/or nucleic acid sequences cited in Table 1. Also preferred are nucleic acid molecules that form stable hybrids with nucleic acid molecules having those percent identities.

A particularly preferred isolated nucleic acid molecule of the present invention is a nucleic acid molecule that comprises at least one of the cited nucleic acid molecules and/or cited nucleic acid sequences, a nucleic acid molecule that is an allelic variant of at least one of the cited nucleic acid molecules and/or nucleic acid sequences, or a nucleic acid molecule that is a portion thereof (i.e., a nucleic acid molecule that forms a stable hybrid with at least one of the cited nucleic acid molecules or allelic variants thereof).

In one embodiment, a nucleic acid molecule encoding an immunogenic *T. gondii* protein of the present invention encodes a protein that is at least about 75%, preferably at least about 80%, more preferably at least about 85%, even more preferably at least about 90%, and even more preferably at least about 95% identical to the proteins cited in Table 1. Even more preferred is a nucleic acid molecule encoding a protein cited in Table 1 or an allelic variant of such a nucleic acid molecule. Also preferred are nucleic acid molecules encoding proteins comprising one or more epitopes of proteins having the cited percent identities or epitopes of proteins cited in Table 1 or encoded by nucleic acid molecules that are allelic variants of nucleic acid molecules cited in Table 1.

In another embodiment, a nucleic acid molecule encoding an immunogenic *T. gondii* protein of the present invention encodes a protein having an amino acid sequence that is at least about 75%, preferably at least about 80%, more preferably at least about 85%, even more preferably at least about 90%, and even more preferably at least about 95% identical to at least one of the amino acid sequences cited in Table 1. Even more preferred is a nucleic acid molecule encoding a protein having an amino acid sequence cited in Table 1 or an allelic variant of such a nucleic acid molecule. Also preferred are nucleic acid molecules encoding proteins comprising one or more epitopes of proteins having the cited percent identities or epitopes of proteins having amino acid sequences cited in Table 1 or encoded by nucleic acid molecules that are allelic variants of nucleic acid molecules cited in Table 1.

Note that nucleic acid molecules of the present invention can include nucleotide sequences in addition to those disclosed above, such as, but not limited to, nucleotide sequences comprising a full-length gene, a full-length coding region, a nucleic acid molecule encoding a fusion protein, or a nucleic acid molecule encoding a multivalent protective compound. Also included in the present invention are nucleic acid molecules that have been modified to accommodate codon usage properties of the cells in which such nucleic acid molecules are to be expressed. Preferred nucleic acid molecules of the present invention include fragments of the nucleic acid molecules disclosed in Table 1.

Knowing the nucleic acid sequences of certain nucleic acid molecules encoding immunogenic *T. gondii* proteins of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other nucleic acid molecules encoding an immunogenic *T. gondii* proteins. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include *T. gondii* cDNA libraries as well as genomic DNA libraries. Similarly, preferred DNA sources from which to amplify nucleic acid molecules include *T. gondii* EDNA and genomic DNA. Techniques to clone and amplify nucleic acid molecules are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising nucleic acid molecules encoding immunogenic *T. gondii* proteins. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of about 100 nucleotides. The present invention includes oligonucleotides that can be used as, for example, probes to identify nucleic acid molecules encoding immunogenic *T. gondii* proteins, primers to produce nucleic acid molecules encoding immunogenic *T. gon-*

*dii* proteins, or reagents to inhibit immunogenic *T. gondii* protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of nucleic acid molecule encoding immunogenic *T. gondii* proteins of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be operative in either prokaryotic or eukaryotic cells, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, *T. gondii* and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other endoparasite, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with *T. gondii*.

Suitable and preferred nucleic acid molecules to include in recombinant vectors of the present invention are as disclosed herein. Preferred nucleic acid molecules to include in recombinant vectors, and particularly in recombinant molecules, include those cited in Table 1. Particularly preferred recombinant molecules of the present invention include those recombinant molecules, the production of which are described in the Examples section.

Recombinant molecules of the present invention may also (a) contain secretory signals (i.e., signal segment nucleic acid sequences) to enable an expressed *T. gondii* protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include nucleic acid molecules encoding immunogenic *T. gondii* proteins disclosed herein. Particularly preferred nucleic acid molecules with which to transform a cell include those listed in Table 1.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing *T. gondii* proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), insect, other animal and plant cells. Preferred host cells include bacterial, mycobacterial, yeast, protozoan, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_{\chi}$3987 and SR-11 $_{\chi}$4072; *Spodoptera frugiperda*; *Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein. Particularly preferred recombinant cells include those recombinant cells, the production of which are disclosed in the Examples section.

Recombinant cells of the present invention can also be co-transformed with one or more recombinant molecules including a nucleic acid molecule encoding at least one immunogenic *T. gondii* protein of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated *T. gondii* proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an immunogenic *T. gondii* protein of the present invention. Effective media typically comprise an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Suitable culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a composition to inhibit *T. gondii* oocyst shedding in a cat due to infection with *T. gondii,* or for preventing *T. gondii* infection in an animal, or as a diagnostic reagent. A composition for inhibiting *T. gondii* oocyst shedding in a cat due to infection with *T. gondii* animals, or for preventing *T.*

*gondii* infection in an animal for example, should exhibit no substantial toxicity and preferably should be capable of stimulating the production of antibodies in a treated animal.

The present invention also includes isolated (i.e., removed from their natural milieu) antibodies that selectively bind to an immunogenic *T. gondii* protein of the present invention or a mimetope thereof (e.g., anti-*T. gondii* antibodies). As used herein, the term "selectively binds to" an immunogenic *T. gondii* protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual,* Cold Spring Harbor Labs Press; Harlow et al., ibid., is incorporated by reference herein in its entirety. An anti-*T. gondii* antibody of the present invention preferably selectively binds to an immunogenic *T. gondii* protein in such a way as to inhibit the function of that protein.

Isolated antibodies of the present invention can include antibodies in any bodily fluid that has been collected (e.g., recovered) from an animal. Suitable bodily fluids include, but are not limited to, blood, serum, plasma, urine, tears, aqueous humor, central nervous system fluid (CNF), saliva, lymph, nasal secretions, milk and feces. Thus, serum containing antibodies (i.e., antiserum) or mucosal secretions, such as intestinal secretions, are examples of isolated antibodies. Other embodiments of antibodies include antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce *T. gondii* proteins of the present invention. Antibodies raised against defined proteins or mimetopes can be advantageous because such antibodies are not substantially contaminated with antibodies against other substances that might otherwise cause interference in a diagnostic assay or side effects if used in a composition for inhibiting *T. gondii* oocyst shedding in a cat due to infection with *T. gondii,* or for preventing *T. gondii* infection in an animal.

Antibodies of the present invention have a variety of potential uses that are within the scope of the present invention. For example, such antibodies can be used (a) as compounds to passively immunize a cat in order to inhibit the cat from shedding *T. gondii* oocysts, (b) as reagents in assays to detect infection by *T. gondii* and/or (c) as tools to screen expression libraries and/or to recover desired proteins of the present invention from a mixture of proteins and other contaminants.

One embodiment of the present invention includes a method for identifying a nucleic acid molecule encoding an immunogenic *T. gondii* protein. According to this method, antiserum (comprising either monoclonal or polyclonal antibodies) raised against a *T. gondii* developmental stage or stages, or against oocysts, is used to immunoscreen a *T. gondii* genomic expression library or a *T. gondii* cDNA expression library, and a nucleic acid molecule expressing an immunogenic *T. gondii* protein is identified by its ability to selectively bind to at least one antibody within the antiserum. As used herein, the term immunoscreen refers to a method in which antibodies are mixed with a sample to determine whether the sample contains a substance to which the antibodies can selectively bind. A substance is identified by its ability to selectively bind to such antibodies. Although general methods to accomplishing immunoscreening of expression libraries are known to those skilled in the art, the exact method to use such a technique to identify *T. gondii* immunogenic proteins was not previously known. The present invention includes the identification of antisera that are useful in the identification and isolation of nucleic acid molecules encoding *T. gondii* immunogenic proteins. Such antisera include antiserum raised against *T. gondii* oocysts, antiserum raised against *T. gondii* bradyzoites, antiserum raised against *T. gondii* infected cat gut, and antiserum isolated from a cat immune to *T. gondii* infection. In one embodiment, antiserum as described above is enriched for antibodies specific to *T. gondii* gametogenic stages. In a preferred embodiment, polyclonal antiserum is produced by exposing an animal to a *T. gondii* antigen or antigens, then isolating the antiserum from the animal so exposed. Methods to produce and use the various antisera are described in the Examples section.

In another embodiment, immunoscreening as described above can be used to identify an immunogenic *T. gondii* protein. According to this method, antiserum as described above is used to immunoscreen a *T. gondii* genomic expression library or cDNA expression library, and an immunogenic *T. gondii* protein is identified. *T. gondii* immunogenic proteins can also be identified by immunoscreening preparations containing *T. gondii* antigens (e.g., *T. gondii* oocysts, bradyzoites, infected cat guts) using antiserum as described above.

Nucleic acid molecules and proteins identified using such techniques can be isolated (i.e., recovered) and purified to a desired state of purity using techniques known to those skilled in the art.

One embodiment of the present invention is a composition that, when administered to a cat in an effective manner, is capable of preventing that cat from shedding *T. gondii* oocysts. Compositions of the present invention, useful for inhibiting *T. gondii* oocyst shedding in a cat due to infection with *T. gondii* (i.e., infection with *T. gondii* causes oocyst shedding in cats), include at least one of the following protective compounds: an isolated immunogenic *T. gondii* protein or a mimetope thereof, an isolated nucleic acid molecule that hybridizes under stringent hybridization conditions with a nucleic acid molecule comprising one of the nucleic acid molecules and/or nucleic acid sequences cited in Table 1, an isolated antibody that selectively binds to an immunogenic *T. gondii* protein, an inhibitor of *T. gondii* function identified by its ability to bind to an immunogenic *T. gondii* protein and thereby impede development and/or the production of oocysts, or a mixture thereof (i.e., combination of at least two of the compounds). As used herein, a protective compound refers to a compound that, when administered to a cat in an effective manner, is able to inhibit the cat from shedding *T. gondii* oocysts upon infection with *T. gondii*. The term protective compound also refers to a compound that, when administered to a cat or other animal, including a human, in an effective manner, is able to prevent or ameliorate disease caused by infection with *T. gondii*. Examples of proteins, nucleic acid molecules, antibodies and inhibitors of the present invention are disclosed herein.

The present invention also includes a composition comprising at least one *T. gondii* protein-based compound of the present invention in combination with at least one additional compound protective against one or more infectious agents. Examples of such compounds and infectious agents are disclosed herein.

Compositions of the present invention that are useful for preventing *T. gondii* infection can be administered to any animal susceptible to such therapy, preferably to mammals.

In order to inhibit a cat from shedding *T. gondii* oocysts, a composition of the present invention is administered to the cat in a manner effective to inhibit that cat from shedding *T. gondii* oocysts. In a preferred embodiment, compositions of the present invention are administered to cats prior to infection in order to prevent oocyst shedding (i.e., as a preventative vaccine). In another embodiment, compositions of the present invention can be administered to animals after infection in order to treat disease caused by *T. gondii* (e.g., as a therapeutic vaccine).

Compositions of the present invention, useful for inhibiting *T. gondii* oocyst shedding in a cat due to infection with *T. gondii,* or for preventing *T. gondii* infection in an animal, can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, -or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a composition useful for inhibiting oocyst shedding in a cat infected with *T. gondii,* or for preventing *T. gondii* infection in an animal, can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a composition useful for inhibiting oocyst shedding in a cat infected with *T. gondii,* or for preventing *T. gondii* infection in an animal, can include a carrier. Carriers include compounds that increase the half-life of a composition of the present invention in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain dose levels of the composition effective to either inhibit oocyst shedding by cats, or to protect an animal from disease caused by *T. gondii*. The composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Compositions of the present invention can be administered to cats prior to infection in order to inhibit oocyst shedding, and/or can be administered to cats or other animals, including humans, before infection in order to prevent disease caused by *T. gondii* infection, or after infection in order to treat disease caused by *T. gondii*. For example, nucleic acid molecules, proteins, mimetopes thereof, antibodies thereof, and inhibitors thereof can be used to treat or prevent disease caused by *T. gondii* infection. Acceptable protocols to administer compositions of the present invention include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody composition of the present invention is from about 1 microgram ($\mu$g) to about 10 milligrams (mg) of the composition per kilogram body weight of the animal. Booster doses can be administered from about 2 weeks to several years after the original administration. Booster administrations preferably are administered when the immune response of the animal becomes insufficient to protect the animal from disease. A preferred administration schedule is one in which from about 10 μg to about 1 mg of the composition per kg body weight of the animal is administered from about one to about two times over a time period of from about 2 weeks to about 12 months. Modes of administration can include, but are not limited to, injection, oral administration, inhalation, nasal administration, intraocular administration, anal administration, topical administration, particle bombardment, and intradermal scarification. Preferred injection methods include intradermal, intramuscular, subcutaneous, intravenous methods, with intradermal injection and intramuscular injection being more preferred. A particularly preferred method is mucosal administration.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a nucleic acid not packaged in a viral coat or cell as a genetic vaccine (e.g., as "naked" DNA or RNA molecules with or without a non-viral/non-cellular carrier (e.g., liposome, hydrogel, etc.) or (b) administering a nucleic acid molecule packaged as a recombinant virus vaccine or as a recombinant cell vaccine (i.e., the nucleic acid molecule is delivered by a viral or cellular vehicle).

A genetic vaccine of the present invention includes a recombinant molecule of the present invention. As such, a genetic vaccine comprises at least one isolated nucleic acid molecule encoding an immunogenic *T. gondii* protein operatively linked to a eukaryotic or prokaryotic transcription control region. A genetic vaccine can be either RNA or DNA, can have components from prokaryotic as well as eukaryotic sources, and can have the ability, by methods described herein, to enter either eukaryotic or prokaryotic cells and direct expression of isolated nucleic acid molecules of the present invention in those cells. In a preferred embodiment, a genetic vaccine of the present invention includes a recombinant virus genome (i.e., a nucleic acid molecule of the present invention ligated to at least one viral genome in which transcription of the nucleic acid molecule is directed either by a transcription control region on the genome or a separate transcription control region) or a recombinant plasmid that includes a nucleic acid molecule of the present invention ligated into a vector that is not a viral genome such that the nucleic acid molecule is operatively linked to a transcription control region.

A genetic vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector) and a nucleic acid molecule of the present invention. Preferred viral vectors include those based on alphaviruses, poxviruses, adenoviruses, adeno-associated viruses, herpesviruses, picornaviruses, and retroviruses, with those based on alphaviruses (e.g., Sindbis virus or Semliki forest virus), picornaviruses (e.g., poliovirus or mengovirus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intraocular, intranasal and oral routes of administration being preferred. A preferred single dose of a genetic vaccine ranges from about 1 nanogram (ng) to about 600 μg, depending on the route of administration and/or method of delivery, as can be determined by those skilled in the art. Suitable delivery methods include, for example, by injection, by gene gun, as drops, as inhaled aerosols, ingested in microparticles or microcapsules, and/or topical delivery. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging—or replication—deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (e.g., Sindbis virus), picornaviruses (e.g., poliovirus, mengovirus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of preventing a cat from shedding oocysts as disclosed herein. For example, a recombinant virus vaccine comprising a nucleic acid molecule encoding an immunogenic *T. gondii* protein of the present invention is administered according to a protocol that results in the subject cat producing a sufficient immune response to inhibit shedding *T. gondii* oocysts. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intraocular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a composition of the present invention to inhibit oocyst shedding caused by *T. gondii* can be tested in a variety of ways including, but not limited to, detection of protective antibodies (using, for example, proteins or mimetopes of the present invention), detection of cellular immunity within the treated animal, or challenge of the treated animal with *T. gondii* to determine whether the treated animal is resistant to oocyst shedding. Challenge studies can include direct administration of *T. gondii* tachyzoites or tissue cysts or sporulated oocysts (the infective stages) to the treated animal. In one embodiment, compositions of the present invention can be tested in animal models such as mice. Such techniques are known to those skilled in the art.

One preferred embodiment of the present invention is the use of immunogenic *T. gondii* proteins, nucleic acid molecules encoding immunogenic *T. gondii* proteins, antibodies and inhibitors of the present invention, to inhibit a cat from shedding oocysts. It is particularly preferred to prevent intestinal stages of the parasite from developing into oocysts. Preferred compositions are those that are able to inhibit at least one step in the portion of the parasite's development cycle that occurs in the intestines prior to the development of oocysts. In cats infected with tissue cysts, for example, the prepatent period for oocyst shedding is three to five days. When cats are infected with sporulated oocysts, for example, the prepatent period can range from 19 to 45 days. Particularly preferred compositions useful for inhibiting oocyst shedding in a cat infected with *T. gondii* include *T. gondii*-based compositions of the present invention. Such compositions include nucleic acid molecules encoding immunogenic *T. gondii* proteins, immunogenic *T. gondii* proteins and mimetopes thereof and anti-*T. gondii* antibodies. Compositions of the present invention are administered to cats in a manner effective to inhibit the cats from shedding *T. gondii* oocysts. Additional protection may be obtained by administering additional protective compounds, including other *T. gondii* proteins, nucleic acid molecules and antibodies, as disclosed herein.

It is also within the scope of the present invention to use isolated proteins, mimetopes, nucleic acid molecules and antibodies of the present invention as diagnostic reagents to detect infection by *T. gondii*. These diagnostic reagents can further be supplemented with additional compounds that can specifically detect any or all phases of the parasite's life cycle. General methods to use diagnostic reagents in the diagnosis of disease are known to those skilled in the art. A method or a kit for the detection of *T. gondii* infection could be combined with reagents for the detection of additional infectious agents, for example viruses (e.g. Coronaviruses), bacteria (e.g. Campylobacter, Clostridium, Salmonella), protozoa (e.g. Cryptosporidium, Giardia, Isospora, Hammondia, Sarcocystis, Besnoitia, Microsporidium), and/or multi-cellular organisms (e.g. Teania, Anclostoma, Toxocara, Physaloptera, Paragonimus, Strongyloides, Trichuris).

Another embodiment of the present invention is a method to detect microscopic parasite cysts or oocysts in feces using PCR amplification techniques. By microscopic, it is meant cysts or oocysts that are too small to be conveniently detected by simple visual observation of the feces. Preferred organisms to be detected include oocysts from infectious protozoan parasites including members of the apicomplexa and others including, for example, Toxoplasma, Cryptosporidium, Isospora, Giardia, Eimeria, Hammondia, Sarcocystis, Besnoitia, Microsporidium. Additional infectious agents to detect include, for example, viruses (e.g. Coronaviruses), bacteria (e.g. Campylobacter, Clostridium, Salmonella), and/or multi-cellular organisms (e.g. Teania, Anclostoma, Toxocara, Physaloptera, Paragonimus, Strongyloides, Trichuris). Particularly preferred oocysts to be detected include Toxoplasma and Cryptosporidium oocysts. Preferred cysts to be detected include any cysts capable of binding to a solid support and remaining bound to the support through a washing step. Preferred cysts include Giardia cysts. According to this embodiment of the invention, a solid support that is capable of binding cysts or oocysts is contacted with a sample of feces, which may or may not have been partially solubilized first in an aqueous solution, and the sample of feces is allowed to dry on the support. The solid support can be of any material to which the cysts or oocyts will bind and remain bound during washing in an aqueous solution. The support can comprise one or more compounds that aid in PCR amplification of the sample, for example by allowing the inhibitors to be released in the wash step, or by binding inhibitors of PCR that are not released in the elution step, or by otherwise inactivating inhibitors of PCR amplification. Preferred supports comprise a paper substrate to which the oocysts or cysts can bind. Preferred supports include IsoCodeJ™ Stix, or their equivalent, S&S® #903™, or their equivalent, or Nobuto Blood Filter Strips, or their equivalent. The support, or the portion of the support contacted with the sample of feces, is preferably small enough to fit into a container convenient for the wash step; eg., a size that will fit into a 1.5. ml conical centrifuge tube. The portion of the support that is contacted with the sample of feces can be removed from the rest of the support in order to achieve a convenient size. The portion of the support that includes the dried sample of feces is then washed with an aqueous solution. In a preferred embodiment the aqueous solution is water, preferably distilled water. The solution can comprise one or more compounds that aid in PCR amplification of the sample, for example by inactivating or removing inhibitors of PCR amplification. DNA associated with the sample is eluted by adding an aqueous solution to the support and then heating the solution to a temperature sufficient to elute DNA from the sample, into the solution. In a preferred embodiment, the aqueous solution into which the sample is eluted is water, preferably distilled water. This solution can comprise one or more compounds that aid in PCR amplification of the sample, for example by inactivating inhibitors of PCR amplification, or by improving reaction conditions for the PCR reaction. The heating step comprises heating to a temperature sufficient to elute DNA from the sample. A preferred temperature is approximately 95° C. Oocyst or cyst-specific DNA in the elution solution is then PCR amplified using primers specific to the oocysts or cysts being detected. The amplification products indicative of oocysts or cysts are then detected using any means available for the detection of PCR amplification products. These can include, for example, separation and observation of the PCR products on a gel, or detection and/or quantification by PCR ELISA. In a preferred embodiment of the present invention, nucleic acid molecules of the present invention are used for the detection of *T. gondii* oocysts in cat feces by PCR amplification using nucleic acid molecules of the present invention as primers. According to the present invention, detection of oocysts can be accomplished by direct analysis of feces. Methods to conduct such an assay are described further in the Examples section.

The following examples are provided for the purposes of illustration and are not intended to limit the scope of the present invention.

EXAMPLES

It is to be noted that the examples include a number of molecular biology, microbiology, immunology and biochemistry techniques considered to be familiar to those skilled in the art. Disclosure of such techniques can be found, for example, in Sambrook et al., ibid. and Ausubel, et al., 1993, *Current Protocols in Molecular Biology*, Greene/Wiley Interscience, New York, N.Y., and related references. Ausubel, et al, ibid. is incorporated by reference herein in its entirety. DNA sequence analysis and protein translations were carried out using the DNAsis program (available from Hitachi Software, San Bruno, Calif.) or MacVector program (available from International Biotechnologies, Inc., Hew Haven, Conn.). It should also be noted that since nucleic acid sequencing technology, and in particular the sequencing of PCR products, is not entirely error-free, that the nucleic acid sequences presented herein represent apparent nucleic acid sequences of the nucleic acid molecules encoding immunogenic *T. gondii* proteins of the present invention.

Example 1

This example discloses the construction of a *T. gondii* genomic expression library.

Pure mRNA from *T. gondii* parasite present in the infected cat gut cannot presently be obtained. Therefore, a true cDNA library for the gametogenic stages cannot be produced. In order to get around the unavailability of pure mRNA from gut stages of *T. gondii*, a genomic expression library in λ gt11 was constructed using Toxoplasma genomic DNA obtained from tachyzoites produced in tissue culture. This library represented genes expressed at all stages of the Toxoplasma life cycle, including the gametogenic genes.

Construction of the library was modeled on procedures used previously for standard lambda cloning (see, for example, Sambrook, et al., ibid.). In brief, a series of high frequency cutting restriction enzymes were used to generate near random fragments of DNA representing the tachyzoite genome. DNA fragments of approximately 500 to 2000 bp were size selected and then inserted in frame with the expressed fusion protein in λ gt11. Construction of this library is described in greater detail below.

Standard Production of Tachyzoites from liquid nitrogen stocks: Liquid nitrogen stocks of Toxoplasma tachyzoites (TZ) (1 ml samples at $2-4\times10^6$ TZ/ml) were thawed in a 37° C. waterbath. The samples were thawed completely without attaining 37° C. Room temperature TMM (DMEM+3% FBS+0.1 ml 50 mg/ml gentamicin per 100 ml media) was added to the thawed sample according to the following timetable: 0.3 ml added at 0 minutes; 0.6 ml added at 5 minutes; 1.5 ml added at 10 minutes. The samples were maintained at room temperature for 5 minutes longer, then centrifuged for 10 minutes at 2,000 RPM at room temperature. The supernatant was discarded and the pellet resuspended in 12 ml of TMM.

Human foreskin fibroblasts (HSF)cells (ATCC CRL 1637) were infected with the thawed tachyzoites as follows: Passage 15-25 HSF cells were split 1:3 and grown to confluence in a T75 flask with DMEM+10% FBS (fetal bovine serum, available from Summit Biotechnology, Fort Collins, Colo.)+0.1 ml gentamicin per 100 ml media in an incubator at 37° C. with 5% $CO_2$. HSF cells were infected by replacing the media with the thawed tachyzoites in TMM. Infections were allowed to progress until 30–50% of the cell monolayer was destroyed. The medium in the infected T75 flask was replaced with fresh TMM the day before harvesting tachyzoites for expansion of the culture.

Passage 19–25 HSF cells cultured in roller bottles (850 $cm^2$), were split 1:3 and grown to confluence in a roller bottle incubator apparatus under conditions as described above. The medium from a single roller bottle was decanted and replaced with 100 ml of TMM. The cells in this roller bottle were then infected by adding medium from an infected T75 flask (described above). Infection was allowed to progress until 30–50% of the cell monolayer was destroyed. Fresh TMM was replaced in the infected roller bottle the day before using the supernatant to infect new HSF cells. Four new roller bottles with confluent HSF cells were each infected with $2.5\times10^7$ tachyzoites harvested from a previously infected roller bottle. This cycle of infection of four roller bottles, for the purpose of tachyzoite production, was continued on a weekly basis.

Tachyzoite Purification: Extracellular tachyzoites were collected from tissue culture and concentrated. To collect and concentrate tachyzoites, media from roller bottles containing extracellular tachyzoites were poured into 50 ml conical tubes and centrifuged at 2,000 RPM for 10 minutes. The resulting pellets were pooled and the volume was brought up to 50 ml using TMM. The tachyzoites were diluted and counted using a haemacytometer, and then purified by either the CF-11 column method or the nucleopore method as follows:

CF-11 Method of Purifying Tachyzoites: 1.5 g of CF-11 (available from Whatman, Inc., Clifton, N.J.) was mixed throughly in 50 ml of DMEM (no FBS), then added to an econo-column chromatography column (available from Biorad, Hercules, Calif.) and allowed to settle, forming a flat bed. The stopcock was then opened and the excess DMEM was drained until ¼ inch of media remained above the bed. The column was washed by gently adding 50 ml of DMEM and then bringing the media level down to 1 inch above the CF-11 bed. The 50 ml of tachyzoites in TMM (prepared as described above) was then added to the column. The stopcock was opened and the tachyzoites were eluted at a rate of 1 drop/second and collected into 50 ml conical tubes on ice. The media was eluted to ¼ inch above the gel bed. Two additional 5 ml elutions were performed, followed by a 40 ml elution. The 100 ml total eluate was then centrifuged at 2,000 RPM for 10 minutes. The pellets were again pooled by resuspension in 50 ml of DMEM. The tachyzoites were counted and the final number of organisms determined. The tachyzoites were centrifuged at 2,000 rpm for 10 minutes, and the pellet resuspended in 1 ml of Hanks Balanced Salt Solution (HBSS). The tachyzoites were washed 3 times with 1 ml of HBSS by centrifugation at 5000 rpm for 5 minutes in an Eppendorf centrifuge. The pellets were stored at −70° C. until needed.

Nucleopore Method of Purifying Tachyzoites: 47 mm nucleopore units (available from Corning Costar Corp., Cambridge, Mass.) with a polycarbonate 3 um capillary pore membrane were assembled according to manufacturer's specifications. The nucleopore units were then placed on top of an open 50 ml conical tube. Five ml of DMEM was gently forced through the unit using a 30 cc syringe that connects to the top of the nucleopore unit. Twenty-five ml of the extracellular tachyzoite preparation collected from tissue culture in DMEM were passed through the unit by gently pushing on the 30 cc syringe. The maximum number of tachyzoites per nucleopore filter did not exceed $5\times10^8$. Filtration was followed by 2, 5 ml washes of DMEM. The nucleopore-purified tachyzoites were then centrifuged at 2,000 RPM for 10 minutes, and the pelleted tachyzoites resuspended in 50 ml of DMEM. The number of tachyzoites was determined by counting in a hemacytometer. Following centrifugation at 2,000 rpm for 10 minutes, the pellet was resuspended in 1 ml HBSS. The tachyzoites were washed 3 times with 1 ml of HBSS by centrifugation at 5,000 rpm for 5 minutes in an Eppendorf centrifuge. The pellets were stored at −70° C. until needed.

Isolation of tachyzoite DNA: DNA from all sources (for example, DNA from Toxoplasma or mammalian tissue) was isolated using standard techniques that can be can be found, for example, in Sambrook et al, ibid. In particular, $2\times10^9$ tachyzoites were resuspended in 10 ml of 10 mM Tris, pH 8, 0.1 M EDTA, 0.5% SDS and 20 µg/ml pancreatic RNase (available from Sigma Chemical Co., St. Louis, Mo.). After incubating for 1 hour at 37° C., 1 ml of 5M NaCl and 100 µl of 10 mg/ml proteinase K (available from Boehringer Mannheim Corp., Indianapolis, Ind.) was added and the solution incubated for 3 hours at 50° C. The solution was then extracted with phenol and the DNA precipitated with EtOH.

Preparation of Restricted and Size Selected DNA: Six, four-base recognition site restriction enzymes, Alu I, Mbo I, Msp I, Rsa I, Sau3A I, and Taq$^\alpha$I, (available from New England Biolabs, Beverly, Mass.) and one six-nucleotide recognition site restriction enzyme, Dra I, were used to cut *T. gondii* genomic DNA to completion. Ten µg of tachyzoite DNA was digested to completion according to the manufacturer's recommended protocols for each enzyme. All seven digests of DNA were combined and electrophoresed on an 0.8% preparative agarose gel. The region of the gel representing double stranded DNA between 500 and 2000 bp was excised and the DNA recovered using a Gene Clean Kit (available from BIO 101 Inc., Vista, Calif.). The eluted DNA was quantitated using an ethidium bromide sensitivity assay on agarose, using calf thymus DNA as a standard. The DNA was then ethanol precipitated.

Addition of Linkers: Four µg of the digested and size selected DNA was then prepared for the addition of linkers by filling in the restriction site overhangs as follows: First, the DNA was resuspended into Klenow buffer, 0.2 mM dNTPs, and Klenow fragment (available from Boehringer Mannheim Biochemicals, Indianapolis, Ind.), and the reaction mix was incubated for 30 minutes at room temperature. The reaction was stopped by incubating the reaction mix at 65° C. for 10 minutes. The DNA was then methylated using standard conditions including 0.1 mM s-adenosylmethionine and 120 units of EcoR I methylase (available from Promega Corp., Madison, Wis.). Following reprecipitation with ethanol, the DNA pellet was dissolved in water and standard T4 DNA ligase buffer (see, for example, Sambrook, et al., ibid.). Three separate EcoR I linkers, constructed to allow three different reading frames (available from Stratagene, La Jolla, Calif.) were added along with T4 DNA ligase (available from Promega, Corp.) and incubated for 16 hours at 15° C. The solution was then diluted directly into EcoR I restriction buffer and EcoR I enzyme (available from Promega Corp.) and incubated at 37° C. for 2 hours. The DNA fragments were separated from the free linkers using a Sephacryl S-400 spin column. The recovered DNA was ethanol precipitated.

Ligation and Packaging of the Restricted DNA: The entire fraction of DNA obtained from the above reaction mixture was ligated into 1 µg of EcoR I-cut and phosphatase treated λ gt11 arms (available from Stratagene) with T4 DNA ligase at 15° C. for 16 hours. The phage was then packaged, titered and amplified using the Gigapack® II Packaging system (available from Stratagene) according to the manufacturer's directions. The resulting library is referred to herein as the Toxoplasma or *T. gondii* genomic expression library or as the λ gt11:Toxoplasma genomic expression library.

Example 2

This Example discloses a method of isolation of *T. gondii* nucleic acid molecules encoding immunogenic *T. gondii* proteins recognized by antisera specific for a Toxoplasma intestinal stage: oocysts. This Example further discloses recombinant nucleic acid molecules, proteins and cells of the present invention.

The final stage of *T. gondii* gametogony is the unsporulated oocyst. Antisera was raised directly against Toxoplasma oocysts. In addition to the antisera reacting with their respective immunogens, the ability of this antisera to react with *T. gondii* gametogenic stages in intestinal tissue sections from infected animals was assessed. When used in immunofluorescence assays conducted on infected cat gut samples, the anti-oocyst antisera reacted with various parasite structures in the ICG tissue sections, indicating some cross-reactivity with gametogenic stages. This antisera was made as follows.

Production of antibody to a Toxoplasma intestinal stage:oocysts: Oocysts from a wild type strain designated Maggie, a recent isolate from a cat with Toxoplasmosis (Veterinary Teaching Hospital, Colorado State University, 1993), were obtained from the feces of cats fed mouse brains from mice previously infected with the Maggie strain. The oocysts were purified by the standard method of repeated sugar flotation (described in Dubey, J. P. and Beattie, C. P., (1988) *Toxoplasmosis ofAnimals and Man,* CRC Press, Boca Raton, Fla.). The oocysts ($3\times10^7$) were vortexed vigorously in 2 ml of PBS, and then frozen and thawed four times using liquid nitrogen and a 37° C. water bath. Each thaw was followed with vigorous vortexing. The suspension was then sonicated for 20 seconds. The protein concentration of the sonicate was determined as described above, and the suspension stored at −70° until used.

The thawed oocyst suspension was mixed with Freunds Complete Adjuvant for the first injection and Freund's Incomplete Adjuvant for three subsequent boosts. The protein concentrations of each injection in the series were 9 ug, 50 ug, 90 ug, and 90 ug respectively, delivered at four week intervals. The single cat #1959 (designated Queen 4) used for production of antibody to unsporulated oocysts had been orally infected with 100 mouse brain-derived C strain tissue cysts one month before the initial protein injection. Serum obtained from this cat (designated herein as Q4-1959) was analyzed for the presence of antibody specific to *T. gondii* oocysts by Western blot and immunohistochemistry on a monthly schedule during the injection period.

Immunoscreening the λ gt11:Toxoplasma genomic expression library and isolation of Toxoplasma-specific nucleic acid molecules reactive with antisera to oocysts: Antisera Q4-1959 was used to isolate nucleic acid molecules herein designated OC-1, OC-2, OC-13, OC-14, OC-22, OC-23 as follows: *E. coli* Y1090 was infected with approximately $5\times10^6$ plaque forming units (PFU) of the λ gt11:Toxoplasma genomic expression library, and then evenly spread on 20 LB-amp agarose culture plates. The phage were allowed to grow for about four hours at 37° C. The plates were then overlayed with nitrocellulose filters impregnated with 10 mM isopropyl-B-D-thiogalactoside (IPTG) to induce the expression of the recombinant Toxoplasma protein. The induction proceeded for between 4 hours to overnight and then the filters were marked to establish orientation. The filters were removed and, following several washes in TBST (Tris-buffered saline (TBS)+ Tween 20:20 mM Tris, pH 7.5, 150 mM NaCl, 0.5% Tween-20), and an incubation in blocking solution (TBS+

5% powdered milk), incubated with a 1:40 dilution of antisera Q4-1959 for about 3 hours at room temperature or overnight at 4° C. After 3 to 5 washes with TBST the filters were incubated with a 1:1000 dilution of alkaline phospatase (AP) -conjugated goat anti-cat IgG (available from Kirkegaard & Perry Laboratories Inc., Gaithersburg, Md.) at room temperature for two hours. The filters were washed two times with TBST and once with TBS. The color indicator was developed in AP buffer (100 mM Tris pH 9, 100 mM NaCl, 5 mM MgCl) containing 0.7% NBT (nitroblue tetrazolium) and 0.3% BCIP (5-bromo-4-chloro-3-indolyl phosphate).

Plaques in the area corresponding to the positive signals were picked into SM buffer (50 mM Tris, pH 7.5, 100 mM NaCl, 8 mM MgSO$_4$, and 0.01% gelatin) and the phage replated at a lower density. The same screening procedure was repeated three or four times until a pure plaque was isolated. Of the approximately 5×10$^6$ plaques screened in this manner, 6 nucleic acid molecules capable of expressing proteins recognized by antisera Q4-1959 were plaque purified.

Characterization of Immunogenic T. gondii proteins encoded by nucleic acid molecules selected from the T. gondii genomic expression library:

The nucleic acid molecules identified as positive for expression of immunogenic T. gondii proteins by immunoscreening with antisera Q4-1959 were screened for expression of proteins reactive with intestinal secretions from immune cats. The production of immune intestinal secretions is described in detail in Example 6, below. Prior to being used for screening, pooled intestinal secretions were preabsorbed with *E. coli* lysates as follows. Individual cultures of *E. coli* Y1090 cells and XL-1 blue cells (available from Stratagene) were grown overnight in LB Amp medium at 37° C. The cells were harvested by centrifugation, then resuspended in PBS, pH 7.4. The cell suspensions were then frozen and thawed 3 times, using a dry ice-acetone bath and a 37° C. water bath, then sonicated on ice for 10 minutes. The protein concentrations of the resulting cell lysates were adjusted to approximately 20 mg/ml, then diluted 1:10 in PBS. Fresh nitrocellulose filters (82 mm) were coated with bacterial proteins by immersing them in the diluted *E. coli* lysates at room temperature for 1 hour. The filters were further incubated in a solution of 4% (w/v) powdered milk in PBS, pH 7.4 for 30 minutes. The filters were then washed with PBS three times for 10 minutes each at room temperature. Pooled immune cat intestinal secretions were diluted 1:20 with 4% (w/v) powdered milk in PBS, pH 7.4. The diluted secretions mixture was incubated with the *E. coli* lysate-treated filters at room temperature for 1 hour, at a ratio of 20 ml per six filters. The resulting absorbed immune intestinal secretions were used without further dilution to screen nucleic acid molecules identified as positive by immunoscreening as described below. Essentially the same protocol was followed when characterizing the proteins expressed by nucleic acid molecules isolated by immunoscreening with other antisera(as described below).

Plaque pure phage identified as positive by immunoscreening were diluted in SM buffer to approximately 50 PFU/3 μl. 3 μl of each clone was dropped onto an LB/Amp agar plate which was previously overlayed with top agar containing a 1:20 dilution of a fresh culture of *E. coli* Y1090 at mid-log growth. The plates were then incubated at 37° C. for 5 hours. IPTG-treated nitrocellulose filters were placed on the top agar and incubated for 5 hours. The filters were marked, washed in TBS buffer, pH 8.0 at room temperature for 15 minutes and then blocked with 4% (w/v) powdered milk in TBS for 30 minutes, at room temperature. The filters were incubated with absorbed intestinal secretions at 4° C. overnight. All further manipulations were at room temperature. The filters were washed in TBS buffer for 10 minutes, 3 times. The filters were incubated for 2 hours with a 1:300 dilution of horse radish peroxidase (HRP) -conjugated goat anti-cat IgA polyclonal antibody (available from Bethyl Laboratories Inc.) in TBS buffer. The filters were washed in TBS for 10 minutes, 3 times, then incubated with 4-chloro-1-naphthol substrate. Clones were judged to be either positive or negative by the intensity of the color reaction relative to wild type phage controls. The results of this assay are summarized in Table 2. Of the six nucleic acid molecules expressing proteins recognized by antisera Q4-1959, only OC-1 expressed a protein that was positive for reactivity to immune cat intestinal secretions.

TABLE 2

Nucleic Acid Molecules Selected with Cat Sera Specific to Unsporulated Oocysts

| | ORIGINAL | DETECTION | | | | EXPRESSION | | pDVAC | | REACTIVITY | |
|---|---|---|---|---|---|---|---|---|---|---|---|
| SEQ ID NO | DESIGNATION | ICG | UCG | TZ | BZ | pTrCHIS | λCRO | IN VITRO | IN VIVO | SERUM | IS |
| 70 | OC-1 | + | + | + | + | − | ND | ND | ND | ND | + |
| 72 | OC-2 | + | − | 2+ | + | + | ND | ND | ND | ND | − |
| 74 | 0C-13 | 2+ | − | + | + | + | ND | + | + | ND | − |
| 76 | 0C-14 | + | − | + | + | − | ND | ND | ND | ND | − |
| 78 | 0C-22 | 2+ | − | + | 2+ | + | ND | + | + | ND | − |
| 80 | 0C-23 | 2+ | − | 2+ | + | + | ND | ND | ND | ND | − |

Table 2 Legend

"SEQ ID NO" is the nucleic acid sequence designation for the nucleic acid molecule; "Original designation" is the original name for each nucleic acid molecule; "Detection" represent2s the results of RT-PCR assays to assess cDNA from infected cat gut cells (ICG), uninfected cat gut cells (UCG), tachyzoites (TZ), and bradyzoites (BZ); "Expression" refers to results of subcloning the nucleic acid molecule into one or both of two *E. coli* expression plasmids, pTrCHIS and λ CRO; "pDVAC" refers to subcloning into and expression from the eukaryotic expression vector pDVACI, as tested in vitro (BHK cells) and in vivo (mice); "Reactivity", indicates specific recognition by cat immune sera (serum) and/or cat immune intestinal secretion (IS) of the expressed product. In all cases, (+) indicates a positive response, (−) a negative response, and (ND) indicates not done. In the column labeled "Detection", the numbers associated with the positive responses indicate the relative signal strength for each primer assayed with each of the four cDNA samples, i.e., ICG, UCG, TZ, and BZ cDNA, and are not a comparison between primers.

Some of the nucleic acid molecules identified as positive by immunoscreening were also assessed for expression of proteins reactive with Mozart II (immune) sera. Reactivity was assessed by spotting the purified phage directly on a lawn of host *E. coli* and inducing the expression of protein encoded by the cloned DNA insert using IPTG-soaked filters, similar to the phage screening protocol. The filters were then probed with the Mozart II sera, in essentially the same manner as was used to select the plaque purified phage identified as positive by immunoscreening. The results of these assays are summarized in Table 2.

The Toxoplasma inserts in λ gt11, herein referred to as λ gt11:Toxoplasma nucleic acid molecules were sequenced either by direct sequencing, or by first subcloning the λ gt11:Toxoplasma nucleic acid molecules into a cloning vector, then sequencing. Direct sequencing of each insert was performed as follows: the Toxoplasma-specific insert in λ gt11 was PCR amplified under standard conditions well known in the art using a λ gt11 forward primer (5' GGTG-GCGACGACTCCTGGAG 3') designated SEQ ID NO:365, and a λ gt11 reverse primer (5' CCAGACCAACTGG-TAATGGTAG 3') designated SEQ ID NO:366, and the major PCR reaction product was separated from the rest of the PCR reaction products on a 1% agarose gel. The band representing the major PCR product was excised, and the gel slice was processed using the QIAquick kit (available from Qiagen Inc., Santa Clarita, Calif.) according to manufacturer's instructions in order to release the DNA. The isolated DNA fragment was sequenced under standard conditions using an ABI PRISM 377 automated DNA sequencer (available from Applied Biosystems, Foster City, Calif.). Each of the amplification primers were used separately as sequencing primers to obtain sequence from both directions.

Subcloning, then sequencing, was performed as follows: the Toxoplasma-specific insert was PCR amplified and gel purified as described above. The purified DNA was then cloned into a TA cloning vector (available from Invitrogen Corp., San Diego, Calif.) according to the manufacturer's instructions, and sequenced under standard conditions.

Sequence analysis of nucleic acid molecules selected for expression of proteins recognized by antisera Q4-1959:

The nucleic acid molecules selected for expression of proteins recognized by antisera Q4-1959 were sequenced as described above. BLASTn and BLASTp homology searches were performed on these sequences using the NCBI Gen-Bank™ non-redundant (nr) nucleotide (n) and amino acid (p) databases, and the dbEST (est) database as described above. The results of these searches are summarized in Table 3. Nucleic acid molecule OC-1 was sequenced again and some changes found between the first and second sequence. The resequenced nucleic acid molecule is referred to herein as OC-1-a.

TABLE 3

| SEQ ID | Size bp | Size aa | # P(N)<1e-10 n vs nr | n vs est | p vs nr | Score | Gene | Name | Size | Clone/Match | Identities | % |
|---|---|---|---|---|---|---|---|---|---|---|---|---|
| 19 | 718 | 99 | — | — | — | | | | | | | |
| 21 | 441 | 147 | — | — | — | | | | | | | |
| 23 | 428 | 142 | — | — | — | | | | | | | |
| 26 | 304 | 101 | — | — | — | | | | | | | |
| 28 | 284 | 95 | — | — | — | | | | | | | |
| 30 | 690 | 230 | — | — | — | | | | | | | |
| 32 | 313 | 54 | — | — | — | | | | | | | |
| 34 | 389 | 65 | — | — | — | | | | | | | |
| 36 | 548 | 183 | — | — | — | | | | | | | |
| 82 | 604 | 112 | — | 2 | — | 1.20E-112 | AA531653 | TgESTzz29d08.r1 invivo Bradyzoite cDNA | 553 | 302-2/8-308 | 291-301 | 96 |
| | | | | | | | | | | 446-345/8-109 | 84-102 | 82 |
| | | | | | | | | | | 590-489/8-109 | 82-102 | 80 |
| | | | | | | | | | | 349-135/129/342 | 122-214 | 57 |
| | | | | | | | | | | 493-418/129-204 | 51-76 | 67 |
| | | | | | | | | | | 137-16/5-126 | 69-122 | 56 |
| 84 | 549 | | | 2 | — | 3.10E-33 | AA520213 | TgESTzz43d05.s1 TgME49 invivo Bradyzoite | 574 | 363-127/192-428 | 162-237 | 68 |
| | | | | | | | | | | 500-364/340-476 | 117-137 | 85 |
| | | | | | | | | | | 356-220/340-476 | 113-137 | 82 |
| | | | | | | | | | | 601-515/383-469 | 77/87 | 88 |
| | | | | | | | | | | 178-106/350-422 | 51-73 | 69 |
| | | | | | | | | | | 241-205/456-492 | 26-37 | 70 |
| | | | | | | | | | | 373-349/468-492 | 20-25 | 80 |
| | | | | | | 4.30E-35 | 520213 | TgESTzz43d05.s1 TgME49 invivo Bradyzoite | 574 | 113-249/340-476 | 121-137 | 88 |
| | | | | | | | | | | 257-403/340-486 | 123-147 | 83 |
| | | | | | | | | | | 2-105/373-476 | 93-104 | 89 |
| | | | | | | | | | | 409-530/348-469 | 84-122 | 68 |
| | | | | | | 1.50E-30 | AA531653 | TgESTzz29d08.r1 TgME49 invivo Bradyzoite | 553 | 96-120/468-492 | 20/25 | 80 |
| | | | | | | | | | | 23-124/8-109 | 87-102 | 85 |
| | | | | | | | | | | 167-268/8-109 | 86/102 | 84 |
| | | | | | | | | | | 311-4128-109 | 77-102 | 75 |
| | | | | | | | | | | 120-195/129-204 | 54-76 | 71 |
| 85 | 270 | 90 | — | — | — | | | | | | | |
| 87 | 306 | 102 | — | — | — | | | | | | | |
| 89 | 804 | 268 | — | 2 | — | 6.80E-150 | N82167 | TgESTzy44c02.r1 TgRH tachyzoite cDNA | 613 | 247-498/2-253 | 245-252 | 97 |
| | | | | | | | | | | 498-557/255-336 | 79-82 | 96 |
| | | | | | | | | | | 575-620/334-379 | 44-46 | 95 |
| | | | | | | 8.00E-40 | AA012353 | TgESTzz17b0.r1 TgME49 tachyzoite cDNA | 380 | 671-780/1-100 | 99-100 | 99 |
| | | | | | | | | | | 769-804/98-133 | 35-36 | 97 |
| 91 | 867 | 289 | — | 1 | — | 1.00E-113 | N81503 | TgESTzy57e07.r1 TgRH tachyzoite cDNA | 343 | 329-541/97-309 | 211-213 | 99 |
| | | | | | | | | | | 3-151/161-309 | 147-149 | 98 |
| 93 | 1424 | 164 | — | 2 | — | 2.40E-142 | AA531653 | TgESTzz29d08.r1 invivo bradyzoite | 553 | 882-1086/8-212 | 198-205 | 96 |
| | | | | | | | | | | 1078-1262/206-390 | 176-185 | 95 |
| | | | | | | | | | | 452-553/8-109 | 93-102 | 91 |
| | | | | | | | | | | 24-125/8-109 | 87-102 | 85 |

TABLE 3-continued

| SEQ ID | Size bp | Size aa | # P (N) < 1e-10 n vs nr | # P (N) < 1e-10 n vs est | p vs nr | Score | TOP HITS Gene | Homologies Name | Size | Clone/Match | Identities | % |
|---|---|---|---|---|---|---|---|---|---|---|---|---|
| 95 | 680 | 227 | — | 2 | — | 1.20E-33 | AA520213 | TgESTzz43d.s1 TgME49 invivo bradyzoite | 574 | 114–250/340–476 | 119–137 | 86 |
|  |  |  |  |  |  |  |  |  |  | 684–820/340–476 | 117–0137 | 85 |
|  |  |  |  |  |  |  |  |  |  | 849–1084/220–455 | 161–236 | 68 |
|  |  |  |  |  |  | 3.80E-149 | AA520213 | TgESTzz43d05.s1 TgME49 invivo Bradyzoite | 574 | 3–352/127–476 | 343–350 | 98 |
|  |  |  |  |  |  |  |  |  |  | 237–493/220–476 | 202–257 | 78 |
|  |  |  |  |  |  | 1.50E-37 | AA531653 | TgESTzz29d08.r1 TgME49 invivo bradyzoite | 553 | 267–501/5–239 | 168–235 | 71 |
|  |  |  |  |  |  |  |  |  |  | 411–512/8–109 | 86–102 | 84 |
| 97 | 296 | 99 | — | — | — |  |  |  |  |  |  |  |
| 99 | 723 | 53 | — | — | — |  |  |  |  |  |  |  |
| 101 | 270 | 90 | — | 1 | — | 4.50E-57 | AA531653 | TgESTzz29d08.r1 TgME49 invivo bradyzoite | 553 | 3–157/236–390 | 149–155 | 96 |
|  |  |  |  |  |  |  |  |  |  | 80–187/283–390 | 77–108 | 71 |
| 63 | 417 | 139 | — | — | — |  |  |  |  |  |  |  |
| 65 | 416 | 136 | — | — | — |  |  |  |  |  |  |  |
| 67 | 500 |  | — | — | — |  |  |  |  |  |  |  |
| 68 | 321 | 73 | — | — | — |  |  |  |  |  |  |  |
| 54 | 1233 |  | — | 1 | — | 4.50E-176 | AA520348 | TgESTzz69d04.r1 TgME49 invivo bradyzoites | 607 | 2–216/147–361 | 162–215 | 75 |
|  |  |  |  |  |  |  |  |  |  | 161–407/144–390 | 239–247 | 96 |
|  |  |  |  |  |  |  |  |  |  | 408–577/390–559 | 156–170 | 91 |
| 55 | 411 | 60 | — | — | — |  |  |  |  |  |  |  |
| 57 | 441 | 118 | — | — | — |  |  |  |  |  |  |  |
| 59 | 491 | 34 | — | — | — |  |  |  |  |  |  |  |
| 61 | 387 | 129 | — | — | — |  |  |  |  |  |  |  |
| 38 | 310 | 95 | — | — | — |  |  |  |  |  |  |  |
| 40 | 220 | 73 | — | — | — |  |  |  |  |  |  |  |
| 42 | 642 | 34 | — | 11 | — | 6.20E-190 | AA519977 | TgESTzz36d07.r1 TgME49 invivo bradyzoite | 653 | 385–150/199–434 | 221–236 | 93 |
|  |  |  |  |  |  |  |  |  |  | 642–479/32–195 | 155–164 | 94 |
|  |  |  |  |  |  |  |  |  |  | 148–1/435–582 | 124–148 | 83 |
|  |  |  |  |  |  | 9.50E-162 | AA520558 |  |  |  |  |  |
|  |  |  |  |  |  | 8.90E-122 | AA531849 |  |  |  |  |  |
|  |  |  |  |  |  | 1.30E-117 | AA520976 |  |  |  |  |  |
|  |  |  |  |  |  | 4.90E-106 | AA274332 |  |  |  |  |  |
|  |  |  |  |  |  | 5.20E-102 | W99585 |  |  |  |  |  |
|  |  |  |  |  |  | 8.10E-94 | AA520425 |  |  |  |  |  |
|  |  |  |  |  |  | 8.40E-90 | AA274257 |  |  |  |  |  |
|  |  |  |  |  |  | 1.70E-87 | AA532000 |  |  |  |  |  |
|  |  |  |  |  |  | 5.00E-81 | AA520339 |  |  |  |  |  |
|  |  |  |  |  |  | 2.10E-55 | AA012063 |  |  |  |  |  |
| 44 | 381 | 27 | — | 9 | — | 4.70E-123 | AA532000 | TgESTzz46d07.r1 TgME49 invivo bradyzoites | 577 | 328–3/11–336 | 316–326 | 96 |
|  |  |  |  |  |  | 5.50E-116 | AA520339 |  |  |  |  |  |
|  |  |  |  |  |  | 1.60E-112 | AA531849 |  |  |  |  |  |
|  |  |  |  |  |  | 1.70E-100 | AA520425 |  |  |  |  |  |
|  |  |  |  |  |  | 3.20E-95 | AA519977 |  |  |  |  |  |
|  |  |  |  |  |  | 1.60E-83 | AA520558 |  |  |  |  |  |
|  |  |  |  |  |  | 6.80E-59 | AA012063 |  |  |  |  |  |
|  |  |  |  |  |  | 4.00E-13 | AA274257 |  |  |  |  |  |
|  |  |  |  |  |  | 7.40E-10 | W99585 |  |  |  |  |  |

TABLE 3-continued

| | Size | | # P (N) < 1e-10 | | | TOP HITS | | Homologies HOMOLOGIES | | | | |
|---|---|---|---|---|---|---|---|---|---|---|---|---|
| SEQ ID | bp | aa | n vs nr | n vs est | p vs nr | Score | Gene | Name | Size | Clone/Match | Identities | % |
| 46 | 432 | 85 | — | 9 | — | 4.30E-124 | AA520558 | TgESTzz62b09.r1 TgME49 invivo bradyzoite | 441 | 207–430/91–314 | 224–224 | 100 |
| | | | | | | 8.10E-120 | AA532000 | | | 119–210/2–93 | 91–92 | 98 |
| | | | | | | 8.90E-113 | AA520339 | | | | | |
| | | | | | | 2.20E-110 | AA531849 | | | | | |
| | | | | | | 2.40E-97 | AA520425 | | | | | |
| | | | | | | 9.90E-94 | AA519977 | | | | | |
| | | | | | | 8.20E-53 | AA012063 | | | | | |
| | | | | | | 8.20E-14 | AA274257 | | | | | |
| | | | | | | 150E-10 | W99585 | | | | | |
| 48 | 282 | 35 | — | — | — | 1.70E-125 | AA520558 | TgESTzz62b09.r1 TgME49 invivo bradyzoite | 441 | 119–418/2–316 | 314–315 | 99 |
| 50 | 466 | 71 | — | 9 | — | 1.30E-116 | AA532000 | | | | | |
| | | | | | | 7.70E-110 | AA520339 | | | | | |
| | | | | | | 4.70E-106 | AA531849 | | | | | |
| | | | | | | 2.60E-97 | AA520425 | | | | | |
| | | | | | | 2.90E-95 | AA519977 | | | | | |
| | | | | | | 1.60E-55 | AA012063 | | | | | |
| | | | | | | 6.40E-14 | AA274257 | | | | | |
| | | | | | | 1.20E-10 | W99585 | | | | | |
| 52 | 539 | 20 | — | 8 | — | 9.50E-130 | AA532000 | TgESTzz46d07.r1 TgME49 invivo bradyzoites | 577 | 191–400/85–294 | 208–210 | 99 |
| | | | | | | 9.00E-124 | AA531849 | | | 108–190/1–83 | 80–83 | 96 |
| | | | | | | 2.50E-109 | AA520339 | | | 397–443/290–336 | 46–47 | 97 |
| | | | | | | 2.90E-98 | AA520425 | | | | | |
| | | | | | | 7.70E-86 | AA519977 | | | | | |
| | | | | | | 8.30E-83 | AA520558 | | | | | |
| | | | | | | 4.40E-55 | AA012063 | | | | | |
| | | | | | | 6.30E-11 | W99585 | | | | | |
| 109 | 699 | 233 | — | — | 100 | 2.70E-40 | P46531 | Notch protein homolog Homo sapiens | 2444 | 36–72/658–694 | 19–37 | 51 |
| | | | | | | | | | | 42–71/243–272 | 18–30 | 60 |
| | | | | | | | | | | 188–227/893–932 | 15–40 | 37 |
| | | | | | | 3.60E-40 | A40043 | | | | | |
| | | | | | | 1.60E-35 | A36666 | | | | | |
| 111 | 419 | 140 | 1 | — | 6 | 1.30E-28 | P27951 | IGA FC/beta antigen Streptococcus agalactiae | 1164 | 22–139/827–944 | 40–118 | 33 |
| | | | | | | | | | | 6–128/823–945 | 41–123 | 33 |
| 113 | 303 | 101 | — | — | — | 3.40E-28 | FCSOAG | | | | | |
| 115 | 696 | 232 | — | — | — | 6.20E-22 | A60234 | | | | | |
| 117 | 173 | 58 | — | — | — | | | | | | | |
| 119 | 369 | 123 | — | — | — | | | | | | | |

TABLE 3-continued

| SEQ ID | Size bp | Size aa | # P (N) < 1e-10 n vs nr | # P (N) < 1e-10 n vs est | # P (N) < 1e-10 p vs nr | TOP HITS Score | TOP HITS Gene | Homologies HOMOLOGIES Name | Size | Clone/Match | Identities | % |
|---|---|---|---|---|---|---|---|---|---|---|---|---|
| 121 | 566 | 61 | 1 | — | — | 2.80E-13 | X60241 | T. gondii mitochondria-like REP2 | 1105 | 459–542/937–1020 | 69–84 | 82 |
|  |  |  |  |  |  | 2.90E-13 | N61888 | TgESTzy31c05.r1 TgRH tachyzoite |  | 542–460/167–249 | 68–83 | 81 |
| 123 | 616 | 205 | — | — | 2 | 5.30E-12 | d1017785 | hypothetical protein: PE . . . Synechocystis. | 253 |  |  |  |
| 125 | 762 | 254 |  |  |  | 7.10E-12 | S14959 |  | 1749 | 5–96/1137–1228 | 32–92 | 34 |
| 127 | 236 | 79 | — | — | — |  |  |  |  |  |  |  |
| 129 | 569 | 190 | — | — | — |  |  |  |  |  |  |  |
| 131 | 232 |  | — | — | — |  |  |  |  |  |  |  |
| 132 | 276 | 92 | — | — | — |  |  |  |  |  |  |  |
| 134 | 309 | 103 | — | — | — |  |  |  |  |  |  |  |
| 136 | 534 | 178 | — | — | — |  |  |  |  |  |  |  |
| 139 | 327 | 109 | — | — | — |  |  |  |  |  |  |  |
| 141 | 444 | 148 | — | — | — |  |  |  |  |  |  |  |
| 143 | 928 | 19 | — | — | — |  |  |  |  |  |  |  |
| 70 | 513 | 171 | — | — | 6 | 3.60E-15 | S14959 | proline-rich protein Triticum aestivum | 378 | 10–149/192–331 | 46–140 | 32 |
|  |  |  |  |  |  | 3.60E-13 | d1017785 |  |  |  |  |  |
|  |  |  |  |  |  | 1.40E-13 | 160171 |  |  |  |  |  |
|  |  |  |  |  |  | 4.10E-13 | 1372954 |  |  |  |  |  |
|  |  |  |  |  |  | 4.20E-11 | S20500 |  |  |  |  |  |
|  |  |  |  |  |  | 2.90E-10 | Q15428 |  |  |  |  |  |
| 72 | 528 | 176 | — | — | — |  |  |  |  |  |  |  |
| 74 | 375 | 125 | — | 2 | — | 2.00E-72 | N82029 | TgESTzy39d03.r1 | 251 | 525–384/56–197 | 139–142 | 97 |
|  |  |  |  |  |  |  |  |  |  | 386–331/196–251 | 53–56 | 94 |
|  |  |  |  |  |  |  |  |  |  | 542–524/38–56 | 18–19 | 94 |
| 76 | 543 | 89 | — | — | — | 1.40E-49 | W00112 | TgESTzy77b07.r1 | 401 | 542–399/136–279 | 142–144 | 98 |
| 78 | 573 | 191 | — | — | — |  |  |  |  |  |  |  |
| 80 | 1835 | 612 | — | — | — |  |  |  |  |  |  |  |
| 9 | 657 | 219 | — | — | 8 | 5.40E-31 | P27951 | IGA FC/beta antigen Streptococcus agalactiae | 1164 | 22–107/827–975 | 45–149 | 30 |
|  |  |  |  |  |  | 1.40E-30 | FCSOAG |  |  | 67–188/824–945 | 41–122 | 33 |
|  |  |  |  |  |  | 2.60E-22 | A60234 |  |  |  |  |  |
|  |  |  |  |  |  | 4.90E-14 | 1620100 |  |  |  |  |  |
|  |  |  |  |  |  | 1.40E-12 | Q01456 |  |  |  |  |  |
|  |  |  |  |  |  | 2.50E-10 | JC4749 |  |  |  |  |  |
|  |  |  |  |  |  | 6.90E-10 | d1014692 |  |  |  |  |  |
|  |  |  |  |  |  | 8.30E-10 | 703450 |  |  |  |  |  |
| 11 | 1029 | 273 | 1 | — | 5 | 1.70E-27 | P27951 | IGA FC/beta antigen Streptococcus agalactiae | 1164 | 22–170/827–975 | 45–149 | 30 |
|  |  |  |  |  |  | 6.70E-27 | FCSOAG |  |  | 67–188/824–945 | 41–122 | 33 |
|  |  |  |  |  |  | 1.10E-20 | A60234 |  |  |  |  |  |
|  |  |  |  |  |  | 7.80E-14 | 1620100 |  |  |  |  |  |
|  |  |  |  |  |  | 3.50E-12 | Q01456 |  |  |  |  |  |
| 13 | 425 | 142 | — | — | — |  |  |  |  |  |  |  |
| 16 | 417 | 139 | — | — | — |  |  |  |  |  |  |  |

TABLE 3-continued

| SEQ ID | Size | | # P (N) < 1e-10 | | | | TOP HITS | | Homologies HOMOLOGIES | | | | |
| --- | --- | --- | --- | --- | --- | --- | --- | --- | --- | --- | --- | --- | --- |
| | bp | aa | n vs nr | n vs est | p vs nr | Score | Gene | Name | Size | Clone/Match | Identities | % |
| 17 | 507 | 51 | — | 1 | — | 1.70E-51 | N61591 | TgESTzy18d02.r1 TgRH tachyzoite | 149 | 331–446/4–149 | 144–146 | 98 |
| 103 | 503 | 62 | — | 1 | — | 1.70E-51 | N61591 | TgESTzy18d02.r1 TgRH tachyzoite | 149 | 331–446/4–149 | 144–146 | 98 |
| 105 | 322 | 73 | — | — | — | | | | | | | |
| 107 | 390 | 67 | — | — | — | | | | | | | |
| 1 | 357 | 119 | — | — | — | | | | | | | |
| 3 | 339 | 108 | — | — | — | | | | | | | |
| 5 | 526 | 175 | — | 2 | — | 4.40E-65 | W96667 | TgESTzy98f02.r1 TgME49 tachyzoite | 454 | 369–502/55–188 | 123–134 | 91 |
| | | | | | | | | | | 314–385/1–72 | 72–72 | 100 |
| | | | | | | 3.10E-43 | AA037916 | TgESTzy55c09.r1 TgRH tachyzoite | 385 | 372–502/2–132 | 128–131 | 97 |
| 7 | 1478 | 381 | — | 5 | — | 4.60E-128 | W96667 | TgESTzy98f02.r1 TgME49 tachyzoite | 454 | 864–1126/55–317 | 251–263 | 95 |
| | | | | | | | | | | 809–868/1–60 | 72–72 | 100 |
| | | | | | | 4.70E-119 | AA037916 | | | | | |
| | | | | | | 4.50E-43 | N82635 | | | | | |
| | | | | | | 1.20E-36 | N96576 | | | | | |
| | | | | | | 2.20E-36 | N82193 | | | | | |

Table 3 Legend
Results of BLASTn and BLASTp search of the NCBI GenBank™ non-redundant (nr) nucleotide (n) and amino acid (p) databases, and the dbEST (est) database. The algorithm used was as described in S.F. Altschul, W. Gish, W. Miller, E.W. Myers, and D.J. Lipman, J. Mol. Biol. 215, 403–10 (1990) and the NCBI. From left to right: are the sequence identification number (SEQ ID No), the size of the nucleic acid molecule (Size) in either base pairs (bp) or amino acids (aa), the number of hits below the sum probability score of $1^{e-10}$ (# P(N) < 1e-10), and a section of the hits with the highest homology (HOMOLOGIES). The homologies section is sub–divided to include the sum probability (Score) of the homology, the gene accession number (Gene), the name or identifier of the gene (Name), the size of the gene either in nucleotides, if it is a match in the BLASTn or amino acids if it is in the BLASTp (Size), the range of either nucleotides or amino acids in which a match was identified in the clone versus the match in the database (Clone/Match), the number of identities compared with the range matched (Identities), and the percentage homology of the match (%). A dash (—) indicates the search was done and there were no matches.

RT-PCR analysis of nucleic acid sequences encoding Immunogenic *T. gondii* proteins:

The sequence data obtained as described above were used to design unique primers specific to each nucleic acid molecule of the present invention. These primer sequences are listed in Table 4.

TABLE 4

Nucleic Acid Molecules Primer Sequences

| SEQ ID NO. | ORIGINAL DESIGNATION | NAME | PRIMER SEQUENCE | BASE PAIR NUMBERS |
|---|---|---|---|---|
| 144 | | | | |
| 145 | Tg-41 (5') | nTG1 | CGCTTCTTGTGTCACCTG | 1–18 |
| 146 | Tg-41 (3') | nTG1 | GCACCTTGTTCTCTCTCTTCGCC | 317–295 |
| 147 | Tg-45-2T (5') | nTG2 | CGAGGAGACGGTGGGAGC | 1–18 |
| 148 | Tg-45-2T (3') | nTG2 | TGCCCAAGATGCCGATCTCTG | 289–269 |
| 149 | Tg-50 (5') | nTG4 | TCTCCCCCATCGACGAAAAC | 95–114 |
| 150 | Tg-50 (3') | nTG4 | GCTCATTTCCTCCGCAATTTGG | 456–435 |
| 151 | Q2-4 (5') | nTG5 | AGCTGGCAGAAATACCAAAGCTC | 67–90 |
| 152 | Q2-4 (3') | nTG5 | TGTCGGCAATACTGGGCATG | 529–510 |
| 153 | Q2-9 (5') | nTG6 | ACTGGAGTGGAAAGTCTGGTTTTG | 37–60 |
| 154 | Q2-9 (3') | nTG6 | GACGCAGAGAAGAAAGAAGAGCC | 415–393 |
| 155 | Q2-10 (5') | nTG7 | TCCAAAACTGTCTCGTCTCCCC | 165–186 |
| 156 | Q2-10 (3') | nTG7 | TCTGGATACGCCGTTCCTTTG | 305–284 |
| 157 | Q2-11 (5') | nTG8 | GACATCTACCTGTGAGTGAACCAGG | 50–74 |
| 158 | Q2-11 (3') | nTG8 | GTCAAAACCTTGCCAGCATCTC | 475–454 |
| 159 | 4499-9 (5') | nTG9 | TCCGACTGAATGACTACCTCTTTC | 45–28 |
| 160 | 4499-9 (3') | nTG9 | TCCGACCAAGTCCTCAGTGAAC | 537–516 |
| 161 | 4604-2 (5') | nTG10 | TGGGCATTTCCTGGAAGAGG | 36–55 |
| 162 | 4604-2 (3') | nTG10 | GAATCCATCTCGTGCAAACGG | 378–358 |
| 163 | 4604-3 (5') | nTG11 | CAAGACACAGGGAAACGTTGG | 102–122 |
| 164 | 4604-3 (3') | nTG11 | GAAAGAATCGCACCTCCTCTCC | 424–403 |
| 165 | 4604-5 (5') | nTG13 | TTTGAGTCTAACCGCCGTATGTC | 20–42 |
| 166 | 4604-5 (3') | nTG13 | TCAGACGATTCTCCCATTGTACG | 216–194 |
| 167 | 4604-10 (5') | nTG15 | TCGACTTGGGTCCGATTGTTAG | 43–64 |
| 168 | 4604-10 (3') | nTG15 | GATCTTTTGCGTGACTTTGTCTGC | 289–266 |
| 169 | 4604-17 (5') | nTG16 | GAAGATGCTTGTCTTGTTCGGTTC | 19–42 |
| 170 | 4604-17 (3') | nTG16 | GAGGGGTTTCCTTCTTTATTGCC | 178–156 |
| 171 | 4604-54 (5') | nTG17 | TGTTGGACATCCCGAGCATC | 23–42 |
| 172 | 4604-54 (3') | nTG17 | GGTCCTTGTTTTTCAGGCGG | 472–453 |
| 173 | 4604-62 (5') | nTG18 | TCGTGCAGACAGTGAAGCAATG | 35–56 |
| 174 | 4604-62 (3') | nTG18 | TTTTGTCAGCACAGAGTGGCG | 201–281 |
| 175 | 4604-63 (5') | nTG19 | CGCAAGTGAGTTTTGGCTTTACC | 15–37 |
| 176 | 4604-63 (3') | nTG19 | CCTGGAAGAGATATGCAGACAC | 389–368 |
| 177 | 4604-69 (5') | nTG21 | TCACCGTTCGCTCTTCTTTCT | 12–33 |
| 178 | 4604-69 (3') | nTG21 | CGACTGAAGCATGGATTGCC | 367–348 |
| 179 | AMX/I-5 (5') | nTG31 | ACATATTCCTGAGGAGGAGTTCCC | 82–105 |
| 180 | AMX/I-5 (3') | nTG31 | AACACACCTCCGACGACACCAC | 447–426 |
| 181 | AMX/I-6 (5') | nTG32 | CTCGGCTTCTCCACATACAAGG | 8–29 |
| 182 | AMX/I-6 (3') | nTG32 | GGATCTAGGCATTTGGGTTTCAC | 411–389 |
| 183 | AMX/I-7 (5') | nTG33 | ATCGAAGAAGCTGAAGCGGAG | 4–24 |
| 184 | AMX/I-7 (3') | nTG33 | GTGCTTGTCTCTGACGAAACCC | 193–172 |
| 185 | AMX/I-9 (5') | nTG34 | TATCATTGTATCCCGTCGTCCC | 47–68 |
| 186 | AMX/I-9 (3') | nTG34 | TGATGCCTGGATTTGCACAAC | 363–343 |
| 187 | AMX/I-10 (5') | nTG35 | CGGATCGCTCTGAGTCTCTTTG | 1–22 |
| 188 | AMX/I-10 (3') | nTG35 | ATCCTGTGTCTTCTCTTCGACCC | 384–362 |
| 189 | AMI-23 (5') | nTG36 | GATCGCTCTGAGTCTCTTTG | 88–110 |
| 190 | AMI-24 (5') | nTG37 | ACGTGAGGGAGAAGAAGAGAGTGC | 21–44 |
| 191 | AMI-24 (3') | nTG37 | TTCATCGTCGCCTCTGATGCC | 347–326 |
| 192 | AMI-28 (5') | nTG38 | TGTAGACAGCGTTTAGGGAGTGC | 21–43 |
| 193 | AMI-28 (3') | nTG38 | GTCCTTGGAAGTGCAGAAGCAG | 440–419 |
| 194 | AMI-47 (5') | nTG40 | AAGCGAGGAAAAGGAGGTGTC | 95–115 |
| 195 | AMI-47 (3') | nTG40 | CGGGAAGGTTGGTGATGTCTGTG | 252–230 |
| 196 | OC-1 (5') | nTG41 | CCCGAAGACTTTGACCTG | 34–51 |
| 197 | OC-1 (3') | nTG41 | AGTGGCATAGGAGGCTGG | 191–174 |
| 198 | OC-2 (5') | nTG42 | GCACCTTCAATGCCACAGGTATC | 90–112 |
| 199 | OC-2 (3') | nTG42 | TCGTGTGCTTCTCGCTTCTCTG | 484–463 |
| 200 | OC-13 (5') | nTG43 | CACTGTCGATCAGAAGAAGGCTTAC | 84–108 |
| 201 | OC-13 (3') | nTG43 | GCTCCGTGGGCACATTTTTG | 367–348 |
| 202 | OC-14 (5') | nTG44 | CAGTTTACGAGGTACAAGGCAACAG | 9–33 |
| 203 | OC-14 (3') | nTG44 | GATTGCGTGGGCAGTGTAGAAG | 237–216 |
| 204 | OC-22 (5') | nTG45 | TGTTTGTTTCCCCAGTCAACGAC | 89–111 |
| 205 | OC-22 (3') | nTG45 | CGGAAGAGGTTGTTGGACTCCTTC | 570–547 |
| 206 | OC-23 (5') | nTG46 | CAACCGAGAGAGAAGAGAGGAACAG | 62–86 |
| 207 | OC-23 (3') | nTG46 | TGGGGAGAACAGCAGACATCAG | 602–581 |
| 208 | 4CQA11 (5') | nTG49 | GGATGAACACTGGTGCATCATG | 6–27 |

TABLE 4-continued

Nucleic Acid Molecules Primer Sequences

| SEQ ID NO. | ORIGINAL DESIGNATION | NAME | PRIMER SEQUENCE | BASE PAIR NUMBERS |
|---|---|---|---|---|
| 209 | 4CQA11 (3') | nTG49 | CGACTTGGTCCGCTC | 270–256 |
| 210 | 4CQA19 (5') | nTG50 | CGGCGGCAACAAATGGGC | 1–18 |
| 211 | 4CQA19 (3') | nTG50 | GTCCGAGATATGAGGATGCGAC | 129–108 |
| 212 | 4CQA21 (5') | nTG51 | TCAGAGCACCATTGTTGCGAC | 39–59 |
| 213 | 4CQA21 (3') | nTG51 | TTTGACGCTCAAGTGGAGGCTG | 556–535 |
| 214 | 4CQA22 (5') | nTG52 | GCCTGCAACGCTCGATGGC | 615–633 |
| 215 | 4CQA22 (3') | nTG52 | CTTCTTGACTACCTTCACGTCTG | 810–788 |
| 216 | 4CQA24 (5') | nTG53 | AAGGACAAGCCTGGTTTG | 283–300 |
| 217 | 4CQA24 (3') | nTG53 | TTTGCCCTTCGCACAATC | 1130–1113 |
| 218 | 4CQA25 (5') | nTG54 | CCAGTTTTGCCAGAGGAAGACC | 82–103 |
| 219 | 4CQA25 (3') | nTG54 | ATCCGTCAATGCAGGTTTCATC | 459–438 |
| 220 | 4CQA26 (5') | nTG55 | AGACACCAGAGACAGCAGCAGTC | 45–67 |
| 221 | 4CQA26 (3') | nTG55 | ACTTCGCCCGACAATCGCTTTCC | 266–244 |
| 222 | 4CQA27 (5') | nTG56 | CGATCCTCCCGAGGGACC | 1–18 |
| 223 | 4CQA27 (3') | nTG56 | GCCTTTACGCATTCAAGTCGTG | 174–153 |
| 224 | 4CQA29 (3') | nTG57 | TTCAGCGGGTCTTTCCTCAC | 129–110 |
| 225 | R8050-2 (5') | nTG58 | CAACGAGAAAGATGGAGCTTCG | 34–55 |
| 226 | R8050-2 (3') | nTG58 | AACTTCTTGCACTTGGTCCCG | 404–384 |
| 227 | R8050-5 (5') | nTG60 | AAGCGAGGAAAAGGAGGTGTCTC | 95–118 |
| 228 | R8050-5 (3') | nTG60 | GGAAGGTTGGTGATGTCTGTG | 250–230 |
| 229 | R8050-6 (5') | nTG61 | TCCCCCAGGAATTGTTGAAACAG | 8–30 |
| 230 | R8050-6 (3') | nTG61 | ACTACCGACAACGTCTCAGTCCTTC | 254–230 |
| 231 | M2A1 (5') | nTG62 | CGTGCGTCTGTGAGGAAAAGTG | 2–23 |
| 232 | M2A1 (3') | nTG62 | TTGTTGCTCGTGTTGCAGGTGC | 341–320 |
| 233 | M2A3 (5') | nTG64 | TTGTTCTCGAACCCGCAGAG | 74–93 |
| 234 | M2A3 (3') | nTG64 | TGGCAAGAGACCGAATCGTG | 235–216 |
| 235 | M2A4 (5') | nTG65 | AAACTTGGCAAAGGGGAACG | 49–68 |
| 236 | M2A4 (3') | nTG65 | TGCTGTGGAGAATGATGGCTG | 483–463 |
| 237 | M2A5 (5') | nTG66 | TTTCCGACGAAGCTGCC | 25–41 |
| 238 | M2A5 (3') | nTG66 | GACTCCAACGAAAGCCTCG | 144–126 |
| 239 | M2A6 (5') | nTG67 | GGAAAGGGATAAAGACGCCG | 150–169 |
| 240 | M2A6 (3') | nTG67 | AAGCAGAGGAGAGACGAGACGAAG | 337–314 |
| 241 | M2A7 (5') | nTG68 | CTGCACCATTCTCACTTCTTGTG | 57–80 |
| 242 | M2A7 (3') | nTG68 | GCAAAAGCGGACTCGATTCTATTG | 192–169 |
| 243 | M2A11 (5') | nTG69 | TGTGGCAGAGCAAAAGGCTC | 12–31 |
| 244 | M2A11 (3') | nTG69 | CTGTGGATGCTCCTTTGCGACT | 406–385 |
| 245 | M2A16 (5') | nTG70 | CGAGGCACCCGAAGAATTTG | 195–214 |
| 246 | M2A16 (3') | nTG70 | CTTCTCAGGTTCACTTCCTGCG | 759–738 |
| 247 | M2A18 (5') | nTG71 | TCACGCAACGAACAAGTCCTC | 42–62 |
| 248 | M2A18 (3') | nTG71 | CCCATTTTTGCTTGGCTTGC | 149–130 |
| 249 | M2A19 (5') | nTG72 | AGCGGCAAACCAGTTCGTTG | 283–302 |
| 250 | M2A19 (3') | nTG72 | CACCACCTTTTTCGTTGCGG | 558–539 |
| 251 | M2A20 (5') | nTG73 | CGGCGACTCAGATGGG | 1–16 |
| 252 | M2A20 (3') | nTG73 | GGGGCTGTGTCTTCTCTATTTCG | 131–109 |
| 253 | M2A21 (5') | nTG74 | AAGCAAACAGGCTCGGAAGC | 127–146 |
| 254 | M2A21 (3') | nTG74 | TCATGTTGGAGGCGTCGTTC | 241–222 |
| 255 | M2A22 (5') | nTG75 | TGTGCAGTGGAGGACAAATGG | 50–70 |
| 256 | M2A22 (3') | nTG75 | GAATCAGGGTGTTTTAGGGCG | 284–264 |
| 257 | M2A23 (5') | nTG76 | ATTCTGTGCAAGCCCAGAG | 305–323 |
| 258 | M2A23 (3') | nTG76 | CGACCAAGGGTGTTGACCAT | 136–155 |
| 259 | M2A24 (5') | nTG77 | CTAGGCAAAGAAACACCCATGC | 226–247 |
| 260 | M2A24 (3') | nTG77 | CGCTGGAACTCCTGACAC | 327–310 |
| 261 | M2A25 (5') | nTG78 | ACGAAGGGAGAGATGCGTTTG | 59–79 |
| 262 | M2A25 (3') | nTG78 | TGGCTGTTTGGGTTGTCTGG | 392–373 |
| 263 | M2A29 (5') | nTG79 | TCACCGCAGAACTTAACCCG | 62–81 |
| 264 | M2A29 (3') | nTG79 | CTCGCTTTTCCAGCTTGTCG | 249–230 |

Table 4 Legend
Primer Sequences to Nucleic Acid Molecules. The original name (Original Designation) and the present name (Name) for each nucleic acid molecule are listed in the second and third columns. Separate 5' and 3' primer sequences are listed for the nucleic acid molecules under Primer Sequence. Identification of each primer sequence as 5' or 3' is shown in the column labeled Original Designation. The location of each primer sequences in its respective nucleic acid molecule is shown in the column, Base Pair Numbers. The sequence identification number for each primer is listed in the first column (Seq ID NO).

The unique primers listed in Table 4 were used in reverse transcriptase-polymerase chain reaction (RT-PCR) assays to assess the expression of the particular nucleic acid sequence in ICG, bradyzoites and tachyzoites. DNA templates were generated from total or poly A+RNA using an RT-PCT kit (available from Stratagene) according to the manufacturer's instructions. The resulting DNA templates were then amplified by standard PCR reaction. The RT-PCR reactions were performed using RNA isolated from infected cat gut (ICG), bradyzoites (BZ), tachyzoites (TZ), and the appropriate controls (e.g., uninfected cat gut (UCG) RNA). In addition to UCG controls, clone-specific primers were used in PCR reactions using DNA from the following sources: *T. gondii*, mouse cells, cat intestinal cells, and human cells. These results are summarized in Table 2.

Subcloning *T. gondii* nucleic acid molecules encoding Immunogenic *T. gondii* proteins into the expression vector pTrcHisB:

*T. gondii* nucleic acid molecules encoding immunogenic *T. gondii* proteins isolated as described above were subcloned into the expression vector pTrcHisB (available from Invitrogen Corp., San Diego, Calif.). The vector pTrcHisB is designed for expression of fusion proteins in *E. coli* and purification of proteins encoded by nucleic acid molecules of interest. Expression of fusion proteins from this vector was assessed following induction and subsequent Western blot analysis of the *E. coli* lysates using both a monoclonal antibody to the T7 phage amino acid tag sequence and the original sera used to select the nucleic acid molecule. The fusion proteins all contain a poly histidine amino acid sequence which was used to purify the fusion proteins using metal chelate chromatography.

Recombinant molecules containing nucleic acid sequences encoding immunogenic *T. gondii* proteins were produced by PCR amplifying plaque purified λ gt11:Toxoplasma nucleic acid molecules using a λ gt11 forward primer (5' GGTGGCGACGACTCCTGGAG 3') desginated SEQ ID NO:365, and a λ gt11 reverse primer (5' CCAGACCAACTGGTAATGGTAG 3'), designated SEQ ID NO:366. Amplifying the Toxoplasma inserts in this way produced DNA fragments with EcoR I sites at the junctions between the Toxoplasma insert and the lambda vector. These PCR fragments were then digested with the restriction endonuclease EcoR I, gel purified and subcloned into the EcoR I-cleaved expression vector, pTrcHisB. The resultant recombinant molecules were transformed into DH5a competent cells to form recombinant cells, and assayed for the expression of an immunogenic *T. gondii* protein. The results of these assays are summarized in Table 2.

The recombinant cells were cultured in enriched bacterial growth medium containing 0.1 mg/ml ampicillin and 0.1% glucose at about 37° C. When the cells reached an $OD_{600}$ of about 0.4–0.5, expression of recombinant proteins was induced by the addition of 0.5 mM isopropyl-B-D-thiogalactoside (IPTG), and the cells were cultured for about 4 hours at about 37° C. Immunoblot analysis of the recombinant cell lysates using a T7 tag monoclonal antibody (available from Novagen Inc., Madison, Wis.) directed against the fusion portion of the recombinant Toxoplasma fusion protein was used to confirm the expression of the fusion proteins and to identify their size. In addition, the original selecting antisera were used to determine whether the recombinant expression molecule expressed a protein that could be recognized by the sera originally used to isolate the Toxoplasma-specific portion of the recombinant molecule. The results of these immunoblot assays are summarized in Table 2. Of the six nucleic acid molecules selected by immunoscreening with antiserum raised against oocysts (Q4-1959 serum), six were positive by this immunoblot assay.

Example 3

This Example discloses a method of isolation of *T. gondii* nucleic acid molecules encoding immunogenic *T. gondii* proteins recognized by antisera raised against the initiating stage of *T. gondii* gametogony: the bradyzoite. This Example further discloses recombinant nucleic acid molecules, proteins and cells of the present invention.

Antibody To Bradyzoites: Purified C strain bradyzoites ($3 \times 10^7$) from mouse brain tissue cysts were used to generate stage-specific antibody to *T. gondii* as follows:

*T. gondii* C-strain tissue cysts containing bradyzoites were passaged in mice by harvesting tissue cysts from chronically infected mice that had been infected, either intraperitoneally with tachyzoites produced in vitro, or by oral gavage with tissues cysts. Between four and eight weeks post-infection, tissue cysts were harvested and used to inoculate naive mice. Harvest was accomplished by dissecting out the brains of infected mice euthanized by inhalation of $CO_2$. The brains were added to a tube of 30% Dextran in HBSS (Hanks Balanced Salt Solution, available from Life Technologies Inc. (Gibco/BRL), Gaithersburg, Md.), and placed on ice until further purified. Each tube contained a maximum of 8 brains per 20 ml of 30% Dextran solution. Tissue cysts were purified by homogenizing the brains for 20–30 seconds with a Tissuemizer (available from Tekmar-Dohrmann, Cincinnati, Ohio). The homogenized brains were centrifuged for 10 minutes at 3,300 g at 4° C. The supernatant was poured off and the pellet was resuspended in 2.0 ml of HBSS. The pellets from multiple tubes were combined and the tissue cysts were counted using a hemacytometer. To produce a new lot of chronically infected mice, tissue cysts purified as described above were diluted in HBSS to a concentration of 100 tissue cysts/ml. Mice were inoculated by oral gavage with 100 $\mu$l (10 tissue cysts). After six weeks there were approximately 600 tissue cysts per mouse.

Bradyzoites were purified from tissue cysts by pepsin digestion and passage through a CF-11 cellulose column. Pepsin digestion was initiated by adding approximately 1.0 ml of pepsin digestion fluid (0.5% pepsin, 0.17 M NaCl, and 1.16 M HCl) fluid per 1.0 ml of cyst suspension. The sample was incubated for 10 min in a 37° C. waterbath with occasional swirling. After incubation, approximately 0.9 ml of 0.5% sodium carbonate per 1.0 ml of sample was added slowly and with constant gentle mixing. The solution was then centrifuged for 10 minutes at 2,000 rpm. The supernatant was removed and the pellet resuspended in 5.0 ml of Dulbecco's Modified Eagle's Medium.

1.2 g of CF-11 cellulose was added to 50.0 ml of DMEM, and then poured into a 50 ml chromatography column. The column was equilibrated by allowing most of the DMEM to wash out. The pepsin-digested bradyzoites were diluted with 45 ml of DMEM and loaded onto the column. The column was allowed to drip slowly and the flow through was collected. The column was washed with another 50 ml of DMEM and the flow through was again collected. The two 50 ml flow through aliquots were centrifuged at 2,000 rpm for 15 min. The supernatant was carefully removed and the bradyzoite pellet was resuspended in 1 ml of sterile PBS buffer. The number of bradyzoites obtained was determined by counting an aliquot using a hemacytometer.

Bradyzoites prepared as described above were lysed in a PBS, 0.001% Triton X-100 solution by freeze-thawing four times in liquid nitrogen and a 37° C. water bath. The resulting lysate was further treated by sonication for ten, 30 second bursts, while on ice. Following protein determination using a BCA Protein Kit (available from Pierce Biochemicals, Rockford, Ill.), the bradyzoite lysate was mixed with Freunds Complete and Freunds Incomplete Adjuvants for the first and subsequent (booster) injections respectively. The first injection of rabbit #2448 contained 46 mg of soluble protein, and the two following boosts contained 6 ug of soluble protein each. Injections were given subcutaneously at four week intervals, and serum, designated 2448, was collected every three weeks.

Antiserum 2448 was used to isolate nucleic acid molecules herein designated BZ1-2, BZ1-3, BZ1-6, BZ2-3, BZ2-5, BZ3-2, BZ4-3 and BZ4-6 as follows: E. coli Y1090 was infected with approximately $2 \times 10^5$ PFU and then evenly spread on 4 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-rabbit IgG. Of the $2 \times 10^5$ plaques screened in this manner, 8 nucleic acid molecules capable of expressing proteins recognized by antisera 2448 were plaque purified.

Characterization of Immunogenic T. gondii proteins encoded by nucleic acid molecules selected from the T. gondii genomic expression library:

The nucleic acid molecules identified as positive for expression of Toxoplasma stage-specific antigenic proteins by immunoscreening with antisera 2448 were screened for expression of proteins reactive with intestinal secretions from immune cats, as described above. The results of this assay are summarized in Table 5. None of the 8 nucleic acid molecules expressing proteins recognized by antisera 2448 were positive for reactivity to immune cat intestinal secretions in this assay.

erty Laboratories, Liberty Corners, N.J.) was maintained in isolation and allowed to come to term. The kittens (4) were housed with the mother and nursed normally throughout the protocol. At day seven post-partum, one kitten was selected as the control and its intestine harvested as described below. The remaining kittens were infected orally with 5000 mouse brain-derived tissue cysts of the T. gondii strain C, by dripping a solution of the tissue cysts in 1 ml of PBS down the back of their throats. The infected kitten intestines were obtained and processed on day 7 post-infection. The Queen 2 was also infected orally at the same time and in a similar fashion using 100 tissue cysts of T. gondii C strain.

In order to obtain fresh intestine, the following procedure was used for both the control and infected animals. A kitten was first anesthetized by placing it in an inhalation chamber which was flooded with both isoflurane and oxygen until the animal was anesthetized. The kitten was then euthanized with an intravenous injection of commercial pentobarbital euthanasia solution at the recommended dose (88 mg/kg). The animal was immediately dissected to expose the small intestine. This was removed by excisions at the anterior junction with the stomach and the posterior junction with the large intestine. The intestine was opened by a single cut from the anterior to the posterior end, exposing the mucosal surface. The gut was then dipped sequentially into three separate washing baths containing cold HBSS (Hanks buff-

TABLE 5

Nucleic Acid Molecules Selected with Rabbit Sera Specific to Bradyzoites

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | λCRO | IN VITRO | IN VIVO | SERUM | IS |
| 38 | BZ1-2 | ND | ND | ND | ND | ND | ND | ND | ND | ND | – |
| 40 | BZ1-3 | ND | ND | ND | ND | ND | ND | ND | ND | ND | – |
| 42 | BZ1-6 | ND | ND | ND | ND | ND | ND | ND | ND | ND | – |
| 44 | BZ2-3 | ND | ND | ND | ND | ND | ND | ND | ND | ND | – |
| 46 | BZ2-5 | ND | ND | ND | ND | ND | ND | ND | ND | ND | – |
| 48 | BZ3-2 | ND | ND | ND | ND | ND | ND | ND | ND | ND | – |
| 50 | BZ4-3 | ND | ND | ND | ND | ND | ND | ND | ND | ND | – |
| 52 | BZ4-6 | ND | ND | ND | ND | ND | ND | ND | ND | ND | – |

Sequence analysis of nucleic acid molecules selected for expression of proteins recognized by antisera 2448

The nucleic acid molecules selected for expression of proteins recognized by antisera 2448 were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3. Nucleic acid molecule BZ1-2 was sequenced again and some changes found between the first and second sequence. The resequenced nucleic acid molecule is referred to herein as BZ2-1-a.

Example 4

This Example discloses a method of isolation of T. gondii nucleic acid molecules encoding immunogenic T. gondii proteins recognized by rabbit antisera raised against infected cat gut. This Example further discloses recombinant nucleic acid molecules, proteins and cells of the present invention.

Production of rabbit antisera to infected cat gut: A pregnant female cat (designated Queen 2) (available from Libered saline solution) (available from Life Technologies Inc. (Gibco/BRL), Gaithersburg, Md.). The intestine was then placed flat on a chilled laminated sterile surface with the mucosal layer up. A single piece of dry nitrocellulose (BA85, available from Schleicher and Schuell Inc., Keene, N.H.) the length of the intestine, ranging in size from 40 to 70 cm long (this varied with the animal) and 5 mm wide, was carefully placed lengthwise on the mucosal surface of the intestine to obtain an impression smear of the villus epithelial cells. After the nitrocellulose strip became wet (approximately 30 seconds after application), the strip was carefully lifted off and allowed to air dry. The orientation of the anterior and posterior ends of the intestine and strip were noted. Forty biopsy samples, approximately 4 mm by 4 mm sections, were then taken from random positions throughout the length of the intestine, and immediately fixed in either methanol or gluteraldehyde, and maintained for further histological analysis. The intestine was then cut into ten equal sections, and each section placed in a separate bag, labeled and quick frozen in a dry ice and acetone bath. The intestinal sections were maintained at −70° until further processing.

Sections of the cat gut which contained *T. gondii* were identified using PCR analysis of the DNA captured by the nitrocellulose lift with primers specific to the *T. gondii* α-tubulin gene. The presence of *T. gondii* parasite infection was confirmed by histological analysis of the biopsy sections. Portions of *T. gondii*-positive cat gut sections were then prepared as follows for subsequent injections into rabbits to produce antibody directed toward major epitopes from *T. gondii* gametogenic stages. The same methods were also used to produce antibody in cats to infected cat gut preparations, as herein described (in Example 5). A piece of intestine approximately 2 mm by 20 mm was cut from five frozen sections of infected cat gut material. The pieces were maintained at 4° C., laid flat and the mucosal layer carefully scraped from the intestine wall and muscle layers using a razor blade. This material was then minced and placed in 5 ml of sterile PBS containing 1% nystatin, 10 μg/ml gentamicin, and 1% penicillin/streptomycin in a conical centrifuge tube. The mixture was brought through 4 cycles of a freeze-thaw treatment using liquid nitrogen and a 37° C. waterbath. The sample was vortexed between each cycle. The sample was placed on ice and then sonicated using a microtip for 20 seconds followed by 20 seconds on ice. This was repeated four times. The suspension was divided among four Eppendorf tubes and centrifuged (Eppendorf 5415 C centrifuge, available from Brinkmann Instruments Inc., Westbury, N.Y.) at maximum speed for 30 minutes at 4° C. The supernatant was then put through a 0.22 micron filter and a protein determination performed using the BCA Protein Determination Kit (available from Pierce Chemical Co., Rockford, Ill.) according to the manufacturer's protocol. The sample was stored as small aliquots at −70° C. until used.

Polyclonal antisera against infected cat gut (ICG) antigens (also herein referred to as anti-ICG antiserum, or anti-ICG antibody) were prepared by immunization of New Zealand White rabbits with infected cat gut tissue protein as follows. Six rabbits were injected with the solubilized cat gut material; two rabbits (designated #4603 and #8049) were injected with solubilized material from uninfected cat gut, and 4 rabbits (designated #4604, #4499, #8050, and #8051) were injected with solubilized material from infected cat gut material. For the first injection, 0.5 mg of soluble protein, prepared as described above, was brought to 0.5 ml and mixed with an equal volume of Freunds Complete Adjuvant. This solution was delivered sub-cutaneously (SQ). The second injection, two weeks later, was identical to the first, except Freunds Incomplete Adjuvant was used. A third injection, twelve weeks after the first injection, was similar to prior injections except that the total amount of protein injected was 1.5 mg. The animals were pre-bled prior to the first immunization and were bled at approximately monthly intervals to monitor antibody responses. The blood was allowed to clot at room temperature and serum obtained by centrifugation. The sera were evaluated for the presence of antibody specific to *T. gondii* by both Western blot analysis using tachyzoite lysates and by indirect immunofluorescent antibody assay (section IFA) using histological sections obtained from infected cat intestine.

The rabbit antisera were preabsorbed to uninfected cat gut material prior to use in immunoscreening, either by absorbing the antisera to Sepharose beads to which solubilized uninfected cat gut material had been covalently linked, or by absorbing the antisera to nitrocellulose sheets to which uninfected cat gut protein was bound. Western analysis demonstrated that greater than 98% of the serum reactivity to uninfected cat gut was removed by preabsorption to the column. The remaining (unabsorbed) sera showed reactivity towards *T. gondii* tachyzoite lysates. The unabsorbed sera were used to screen the Toxoplasma genomic library.

Antisera 4604 was used to isolate nucleic acid molecules herein designated 4604-2, 4604-3, 4604-5, 4604-10, 4604-17, 4604-54, 4604-62, 4604-63 and 4604-69 as follows: Two separate immunoscreens were performed with this antisera, and Toxoplasma-specific nucleic acid molecules were isolated form each screen. In the first screen, *E. coli* Y1090 was infected with approximately $5\times10^4$ PFU and then evenly spread on 10 LB-amp agarose culture plates. In the second screen, *E. coli* Y1090 was infected with approximately $1.5\times10^6$ PFU and then evenly spread on 12 LB-amp agarose culture plates. The rest of the screening procedure was as described for immunoscreening with antisera Q4-1959 (Example 2), with the following exceptions: the primary antibody was used at a 1:500 dilution, and the secondary antibody was a 1:500 dilution of AP-conjugated goat anti-rabbit IgG. Of the approximately $1.5\times10^6$ plaques screened in this manner, 15 nucleic acid molecules capable of expressing proteins recognized by antisera 4604 were plaque purified.

Antisera 4499 was used to isolate nucleic acid molecule 4499-9 as follows: *E. coli* Y1090 was infected with approximately $5\times10^4$ PFU and then evenly spread on 10 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:500 dilution of AP-conjugated goat anti-rabbit IgG. Of the $5\times10^4$ plaques screened in this manner, 2 nucleic acid molecules capable of expressing proteins recognized by antisera 4499 were plaque purified.

Antisera R8050 (rabbit antisera raised against infected cat gut) was used to isolate nucleic acid molecules herein designated R8050-2, R8050-5, and R8050-6 as follows: *E. coli* Y1090 was infected with approximately $5\times10^6$ PFU and then evenly spread on 10 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-rabbit IgG (available from Kirkegaard Perry Laboratories). Of the $5\times10^6$ plaques screened in this manner, 4 nucleic acid molecules capable of expressing proteins recognized by antisera R8050 were plaque purified.

Selected nucleic acid molecules identified by screening for the expression of proteins recognized by rabbit anti-ICG antisera were subcloned and sequenced as described in Example 2. The results of assays to characterize the isolated nucleic acid molecules are summarized in Table 6.

TABLE 6

Nucleic Acid Molecules Selected with Rabbit Sera Specific to Infected Cat Gut

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | λCRO | IN VITRO | IN VIVO | SERUM | IS |
| 19 | BZ1-2 | + | − | + | + | ND | + | ND | ND | + | + |
| 21 | 4604-2 | + | − | + | + | ND | + | ND | ND | ND | − |
| 23 | 4604-3 | + | − | + | − | ND | + | ND | ND | ND | − |
| 25 | 4604-5 | − | − | + | + | ND | − | ND | ND | ND | − |
| 26 | 4604-10 | − | − | + | + | ND | − | ND | ND | ND | − |
| 28 | 4604-17 | + | − | + | + | ND | − | ND | ND | ND | − |
| 30 | 4604-54 | + | − | − | 2+ | ND | + | ND | ND | ND | − |
| 32 | 4604-62 | + | − | + | + | + | ND | ND | ND | ND | − |
| 34 | 4604-63 | + | − | + | + | − | ND | ND | ND | ND | − |
| 36 | 4604-69 | + | − | 2+ | + | ND | + | ND | ND | ND | − |
| 103 | R8050-2 | + | − | 2+ | + | + | ND | ND | ND | ND | − |
| 105 | R8050-5 | − | − | + | − | + | ND | ND | ND | ND | − |
| 107 | R8050-6 | + | − | 2+ | − | − | ND | ND | ND | ND | − |

Table 6 Legend: See Legend for Table 2.

Sequence analysis of nucleic acid molecules selected for expression of proteins recognized by rabbit anti-ICG antisera 4604, 4499 and R8050:

Nucleic acid molecules 4604-2, 4604-3, 4604-5, 4604-10, 4604-17, 4604-54, 4604-62, 4604-6, 4604-69, R8050-2, R8050-5, and R8050-6 were sequenced as described above. These nucleic acid molecules were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3., as described above. The results of these searches are summarized in Table 3.

The sequence data described above were used to design unique primers specific to each nucleic acid molecule of the present invention. These primer sequences are listed in Table 4. The unique primers listed in Table 4 were used in reverse transcriptase-polymerase chain reaction (RT-PCR) assays to assess the expression of the particular nucleic acid sequence in ICG, bradyzoites and tachyzoites. The results of these assays are summarized in Table 6.

*T. gondii* nucleic acid molecules encoding immunogenic *T. gondii* proteins isolated by immunoscreening with rabbit anti-ICG antiserum were subcloned into either or both of two expression vectors: pTrcHisB (as described above) or Prcro/T2ori/RSET-B (described below). Expression of the fusion proteins from these vectors, and purification of their expressed fusion proteins, were as described above. The results of assays for the expression of recombinant immunogenic *T. gondii* proteins from these expression vectors is summarized in Table 6.

Recombinant nucleic acid molecules and protein molecules including sequences encoding *T. gondii* antigenic proteins and sequences from the vector Prcro/T2ori/RSET-B: Recombinant molecules containing *T. gondii* nucleic acid molecules operatively linked to lambda phage transcriptional control sequences and to a fusion sequence encoding a poly-histidine segment, were produced in the following manner. *T. gondii* DNA fragments in λ gt11 were PCR amplified from nucleic acid molecules herein designated 4499-9, 4604-2, 4604-3, 4604-5, 4604-10, 4604-17, 4604-54, and 4604-69, using the λgt11 forward and reverse primers herein described. Recombinant molecules were produced by digesting the PCR product with EcoR I, gel purifying the resulting fragment, and subcloning into expression vector PRcro/T2ori/RSET-B (also referred to herein as λ CRO) that had been cleaved with EcoR I and gel purified. Expression vector PRcro/T2ori/RSET-B contains the following nucleotide segments: An about 1990-bp Pvu II to Aat II fragment from pUC19 containing the ampicillin resistance gene and *E. coli* of replication; an about 1000-bp Pvu II to Bgl II fragment from pRK248cIts (available from American Type Culture Collection, Rockville, Md.) containing lambda transcriptional regulatory regions (including the gene encoding cI$^{ts}$, the promoter P$_R$, and a sequence encoding 22 amino acids of the cro protein); an about 60-bp BgI II to Xha I fragment from pGEMEX-1 (available from Promega Corp.) which contains the T7 promoter; an about 166-bp Xba I to EcoR I fragment from pRSET-B (available from Invitrogen, San Diego Calif.) which contains sequences encoding the T7-S10 translational enhancer, the His$_6$ fusion, the 14-amino acid S10 leader fusion, and an enterokinase cleavage site as well as the multiple cloning site; and an about 210-bp EcoR I to Aat II fragment containing synthetic translational and transcription termination signals including the T$_1$, translation terminators in all three reading frames, an RNA stabilization sequence from *Bacillus thurengiensis* crystal protein and the T$_2$ rho-independent transcription terminator from the trpA operon. Expression vector PRcro/T2ori/RSET-B contains the following nucleotide segments. An about 1990-bp PvuII to AatII fragment from pUC19 containing the ampicillin resistance gene and *E. coli* of replication; an about 1000-bp PvuII to Bg/II fragment from pRK248cIts (available from American Type Culture Collection, Rockville, Md.) containing lambda transcriptional regulatory regions (including the gene encoding cI$^{ts}$, the promoter p$_R$, and a sequence encoding 22 amino acids of the cro protein); an about 60-bp Bg/II to XbaI fragment from pGEMEX-1 (available from Promega Corp., Madison Wis.) which contains the T7 promoter; an about 166-bp XbaI to EcoRI fragment from pRSET-B (available from Invitrogen Corp., San Diego Calif.) which contains sequences encoding the T7-S10 translational enhancer, the His$_6$ fusion, the 14-amino acid S10 leader fusion, and an enterokinase cleavage site as well as the multiple cloning site; and an about 210-bp EcoRI to AatII fragment containing synthetic translational and transcription termination signals including the T$_1$ translation terminators in all three reading frames, an RNA stabilization sequence from *Bacillus thurengiensis* crystal protein and the T$_2$rho-independent transcription terminator from the trpA operon.

The resulting recombinant molecules were transformed into E. coli to form recombinant cells, using standard techniques as disclosed in Sambrook et al., ibid.

The recombinant cells were cultured in shake flasks containing an enriched bacterial growth medium containing 0.1 mg/ml ampicillin and 1% glucose at about 32° C. When the cells reached an $OD_{600}$ of about 0.6, expression of the Toxoplasma antigen was induced by quickly adjusting the temperature to 42° C. and continuing cultivation of the cells for about 2 hours. Protein production was monitored by SDS PAGE of recombinant cell lysates, followed by immunoblot analysis using standard techniques as described herein and as known in the art. The results of these assays are summarized in Table 6.

The antisera used to originally isolate each Toxoplasma-specific nucleic acid molecule (i.e., either antiserum 4604, or antiserum 4499) was used to identify recombinant proteins in E. coli extracts as follows. The material in crude extracts from E. coli were separated by running 5 μg protein per lane on a 12-well 10% Tris-glycine SDS-PAGE gel at 200 volts for 1 hour, and then transferred to nitrocellulose membranes by standard methods. After transfer, the membranes were blocked in 5% (w/v) dry milk for 1 hr at 37° C. The membranes were then incubated with a 1:200 dilution in Tris buffered saline of the sera originally used to select the nucleic acid molecule encoding Toxoplasma-specific portion of the fusion protein. After 1 hr incubation at room temperature, the blots were washed, and antibody binding resolved using a secondary antibody bound to a substrate for a color indicator. Using the original selecting antibody, immunoblot analysis of E. coli lysates identified fusions proteins at or near the predicted molecular weight of the recombinant fusion protein. The results of these assays are summarized in Table 6.

Histidine tagged fusion proteins were purified from cell lysates as follows. Cell cultures containing nucleic acid molecules of the present invention inserted into either pTrcHisB or λ CRO were grown to an $OD_{600}$ of approximately 0.4 to 0.5. The cultures were induced with IPTG, and the cells harvested 4 hours later. Ten ml of cell culture was centrifuged at 3000 rpm on a table top centrifuge and the protein isolated according to the manufacturer's instructions using a Ni-NTA Spin Kit (available from Qiagen Inc.). Protein purification was monitored by SDS PAGE followed by Coomassie Blue staining of the column eluate fractions. Recombinant cells including recombinant molecules 4499-9, 4604-2, 4604-3, 4604-54, and 4604-69 produced proteins that were able to bind to a T7 tag monoclonal antibody (available from Novagen Inc., Madison, Wis.) directed against the fusion portion of the recombinant fusion protein.

Recombinant nucleic acid molecules and protein molecules including sequences encoding T. gondii antigenic proteins and sequences from the vector pTrcHisB:

Recombinant nucleic acid molecules including sequences encoding T. gondii antigenic proteins and sequences from the vector pTrcHisB were produced as described in Example 2. In brief, T. gondii DNA fragments in λ gt11 were PCR amplified from nucleic acid molecules herein designated 4604-62, 4604-63, R8050-2, R8050-5, and R8050-6, using the λ gt11 forward and reverse primers herein described. The resulting recombinant molecules were transformed into *E. coli* to form recombinant cells 4604-62, 4604-63, R8050-2, R8050-5, and R8050-6. Immunoblot analysis of the recombinant cell lysates using a T7 tag monoclonal antibody (available from Novagen Inc., Madison, Wis.) directed against the fusion portion of the recombinant Toxoplasma fusion protein was used to confirm the expression of the fusion proteins and to identify their size. Of the six nucleic acid molecules selected by immunoscreening with rabbit anti-ICG antiserum that were subcloned into the expression vector pTrcHisB, 15(4604-62, R8050-2, and R8050-5) were positive by this immunoblot assay. The results of these assays are summarized in Table 6.

Example 5

This Example discloses a method of isolation of *T. gondii* nucleic acid molecules encoding immunogenic *T. gondii* proteins recognized by cat antisera raised against infected cat gut. This Example further discloses recombinant nucleic acid molecules, proteins and cells of the present invention.

Preparation of cat antibody against infected cat gut: Preparation of infected cat gut material and production of anti-ICG antisera in cats was performed essentially as herein described for production of rabbit anti-ICG antiserum. Polyclonal cat antisera against infected cat gut (ICG) antigens (also herein referred to as anti-ICG antiserum or antisera, or anti-ICG antibody) were prepared by immunization of cats as follows. Three cats were injected with cat gut material. One cat (#AME5) was injected with material from uninfected cat gut material and two cats (#AMI4, #AMX1) were injected with material from infected cat gut preparations. The same injection, boost and bleed regimen and antigen preparation were used for cats as was used for rabbits, described above. Like the rabbit antisera, the cat antisera were preabsorbed to uninfected cat gut material prior to use in immunoscreening.

Anti-sera AMI was used to isolate nucleic acid molecules herein designated AMI-23, AMI-24, AMI-28, and AMI-47 as follows: *E. coli* Y1090 was infected with approximately $5\times10^6$ PFU and then evenly spread on 10 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-cat IgG. Of the $5\times10^6$ plaques screened in this manner, 6 nucleic acid molecules capable of expressing proteins recognized by antisera AMI were plaque purified.

Anti-sera AMX/I was used to isolate nucleic acid molecules herein designated AMX/I-5, AMX/I-6, AMX/I-7, AMX/I-9, and AMX/I-10 as follows: *E. coli* Y1090 was infected with approximately $5\times10^6$ PFU and then evenly spread on 12 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-cat IgG. Of the $5\times10^6$ plaques screened in this manner, 6 nucleic acid molecules capable of expressing proteins recognized by antisera AMX/I were plaque purified. The results of this immunoscreen are summarized in Table 7.

TABLE 7

Nucleic Acid Molecules Selected by Cat Serum Specific to Infected Cat Gut

| | ORIGINAL | DETECTION | | | | EXPRESSION | | pDVAC | | REACTIVITY | |
|---|---|---|---|---|---|---|---|---|---|---|---|
| SEQ ID NO | DESIGNATION | ICG | UCG | TZ | BZ | pTrCHIS | λCRO | IN VITRO | IN VIVO | SERUM | IS |
| 54 | AMX/I-5  | +  | − | +  | + | +  | +  | ND | ND | ND | + |
| 55 | AMX/I-6  | 2+ | − | 2+ | + | ND | +  | ND | ND | ND | − |
| 57 | AMX/I-7  | 2+ | − | −  | + | ND | +  | ND | ND | ND | − |
| 59 | AMX/I-9  | 2+ | − | +  | + | +  | ND | ND | ND | ND | − |
| 61 | AMX/I-10 | +  | + | −  | − |    | +  | ND | ND | ND | − |
| 63 | AMI-23   | +  | + | −  | − | ND | ND | ND | ND | ND | − |
| 65 | AMI-24   | +  | − | +  | 2+ | + | ND | ND | ND | ND | − |
| 67 | AMI-28   | +  | − | +  | 2+ | ND | ND | ND | ND | ND | − |
| 68 | AMI-47   | −  | − | +  | − | +  | ND | ND | ND | ND | − |

Table 7 Legend: See Legend for Table 2.

Selected nucleic acid molecules identified by screening for the expression of proteins recognized by cat anti-ICG antisera were subcloned and sequenced as described in Example 2.

Sequence analysis of nucleic acid molecules selected for expression of proteins recognized by cat anti-ICG antisera AMI and AMX/I:

The nucleic acid molecules isolated using antisera AMI or AMX/I were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3.

The sequence data described above were used to design unique primers specific to each nucleic acid molecule of the present invention. These primer sequences are listed in Table 4. The unique primers listed in Table 4 were used in reverse transcriptase-polymerase chain reaction (RT-PCR) assays to assess the expression of the particular nucleic acid sequence in ICG, bradyzoites and tachyzoites. The results of these assays are summarized in Table 7.

T. gondii nucleic acid molecules encoding immunogenic T. gondii proteins isolated by immunoscreening with cat anti-ICG antiserum (antiserum AMI or AMX/I) were subcloned into either or both of two expression vectors: pTrcHisB or Prcro/T2ori/RSET-B (as described above). Expression of the fusion proteins from these vectors, and purification of their expressed fusion proteins, were as described above.

Recombinant nucleic acid molecules, protein molecules and cells including sequences encoding T. gondii antigenic proteins and sequences from the vector Prcro/T2ori/RSET-B:

Recombinant molecules containing T. gondii nucleic acid molecules operatively linked to lambda phage transcriptional control sequences and to a fusion sequence encoding a poly-histidine segment in the vector Prcro/T2ori/RSET-B, were produced essentially as described above, resulting in the production of recombinant molecules. The resulting recombinant molecules were transformed into E. coli to form recombinant cells using standard techniques as disclosed in Sambrook et al., ibid. Assays for the expression of an immunogenic T. gondii fusion protein by these cells were performed as described above, and the results are summarized in Table 7.

Recombinant nucleic acid molecules, protein molecules and cells including sequences encoding T. gondii antigenic proteins and sequences from the vector pTrcHisB:

Recombinant nucleic acid molecules including sequences encoding T. gondii antigenic proteins and sequences from the vector pTrcHisB were produced as described in Example 2. In brief, T. gondii DNA fragments in λ gt11 were PCR amplified from nucleic acid molecules herein designated AMX/I-5, AMX/I-9, AMI-24 and AMI-47 using the λ gt11 forward and reverse primers herein described. The resulting recombinant molecules were transformed into E. coli to form recombinant cells AMX/I-5, AMX/I-9, AMI-24 and AMI-47. Immunoblot analysis of the recombinant cell lysates using a T7 tag monoclonal antibody (available from Novagen Inc., Madison, Wis.) directed against the fusion portion of the recombinant Toxoplasma fusion protein was used to confirm the expression of the fusion proteins and to identify their size. The results of this immunoblot analysis are summarized in Table 7.

Example 6

This Example discloses a method of isolation of T. gondii nucleic acid molecules encoding immunogenic T gondii proteins recognized by cat immune sera. This Example further discloses recombinant nucleic acid molecules, proteins and cells of the present invention.

Production of cat immune sera:

Eight specific-pathogen free (SPF) cats (available from Liberty Laboratories, Liberty Corners, N.J.), ages 8–10 months, were randomly assigned to two groups; Group 1, n=5 and Group 2, n=3 (the uninfected control group). Before the initiation of any studies with these animals, serum samples were taken from each and tested for reactivity to solubilized tachyzoites. Each animal was seronegative for T. gondii by standard Western and ELISA analysis using solubilized tachyzoites as the antigen. This serum also served as the pre-bleed in subsequent studies. Feces from each animal were analyzed for the presence of shed T. gondii oocysts using flotation by sugar solution centrifugation followed by microscopic examination. Food was removed from both groups fourteen hours prior to Day 0, and on the day prior to all sample collections. On Day 0 the cats in Group 1 were orally inoculated by syringe at the back of the throat with 1000 mouse brain derived T. gondii tissue cysts of the Mozart strain. This strain represents an isolate from a cat which presented with Toxoplasmosis at the Veterinary Teaching Hospital, Colorado State University, in 1992. The Group 2 cats were not infected.

The Group 1 cats were housed in individual stainless steel cages in an infectious disease isolation unit. The feces from each animal were collected every day for the first fourteen days post infection (PI) and weekly thereafter until parasite challenge. The feces were analyzed for the presence of shed *T. gondii* oocysts. Five milliliters of whole blood was collected from each animal by jugular venipuncture on the following days post primary infection: 3, 7, 10, 14, 21, 28, 42, 56, 70, 84, 112, 140, 143, 147, 154, 161, 168, and 182.

On day 140 post primary infection, all Group 1 cats were orally challenged with 1000 mouse brain-derived tissue cysts of the Mozart strain. Fecal samples were collected and monitored for the excretion of oocysts for thirty days post challenge (PC). The cats were then bled as before on days: 3, 7, 14, 21, 28, and 42 post challenge.

In addition to the serum samples collected on the bleed dates, both salivary secretions and intestinal secretions were obtained at weeks 0, 1, 2, 4, 8, 10, 16, 20, 21, 22, 23, 24, and 26. These samples were obtained by first anesthetizing each animal with an injection of thiobarbiturate, then intubating the animals and maintaining them with halothane and oxygen. Approximately 0.1 ml of saliva was collected into an equal volume of 0.1 M EDTA. The intestinal secretions were obtained from the upper portion of the small intestine using an endoscope fitted with medical tubing which allowed suction of intestinal fluid. Intestinal secretions were diluted 1:1 with sterile 0.9% NaCl and centrifuged at 10,000×g for 5 minutes in an Eppendorf centrifuge. The secretions were stored at −70° C. until use. Pooled secretions included equal aliquots from all five immune animals from week 20 through 26 post infection. These pooled secretions were used to test the reactivity of intestinal secretions from immune cats to proteins expressed by nucleic acid molecules of the present invention.

All Group 1 animals shed oocysts in their feces during the primary infection and all seroconverted as assessed by Western blot analysis using tachyzoite lysates as the antigen. None of these animals shed oocysts when challenged, and were therefore considered immune. The sera from the immune animals was pooled, and is referred to herein as Mozart II antiserum or antisera, or as immune antiserum or antisera.

Mozart II antisera was used to isolate nucleic acid molecules herein designated 4CQA-7, 4CQA-11, 4CQA-19, 4CQA-21, 4CQA-22, 4CQA-24, 4CQA-25, 4CQA-26, 4CQA-27, and 4CQA29 as follows: *E. coli* Y1090 was infected with approximately $8.3 \times 10^5$ PFU and then evenly spread on 13 LB-amp agarose culture plates. The rest of the screening procedure was as described for immunoscreening with antisera Q4-1959 (Example 2), with the following exceptions: the primary antibody was used at a 1:80 dilution, and the secondary antibody was a 1:50 dilution of monoclonal mouse anti-cat α chain (available from Serotec, Oxford, England) and the tertiary antibody was a 1:1000 dilution of AP-conjugated goat anti-mouse IgG (Kirkegaard Perry Laboratories). Of the $8.3 \times 10^5$ plaques screened in this manner, 13 nucleic acid molecules capable of expressing proteins recognized by Mozart II antisera were plaque purified. The results of assays to characterize these nucleic acid molecules are summarized in Table 8.

TABLE 8

Nucleic Acid Molecules Selected with Immune Cat Sera in Screens II and III

| SEQ ID NO | ORIGINAL DESIGNATION | DETECTION | | | | EXPRESSION | | pDVAC | | REACTIVITY | |
|---|---|---|---|---|---|---|---|---|---|---|---|
| | | ICG | UCG | TZ | BZ | pTrCHIS | ICRO | IN VITRO | IN VIVO | SERUM | IS |
| 1 | Tg-41 | 2+ | − | + | 3+ | + | ND | + | + | + | − |
| 3 | Tg-45 | + | − | 2+ | + | + | ND | + | + | + | + |
| 5 | Tg-50 | + | − | + | + | + | ND | ND | ND | + | + |
| 82 | 4CQA-7 | ND | ND | ND | ND | ND | ND | ND | ND | + | − |
| 85 | 4CQA-11 | 2+ | − | + | 2+ | − | ND | + | ND | + | + |
| 87 | 4CQA-19 | + | − | + | + | − | ND | ND | ND | + | − |
| 89 | 4CQA-21 | 3+ | − | 3+ | + | + | ND | ND | ND | + | − |
| 91 | 4CQA-22 | + | − | 3+ | 2+ | − | ND | ND | ND | + | − |
| 93 | 4CQA-24 | + | − | 2+ | 3+ | − | ND | ND | ND | + | − |
| 95 | 4CQA-25 | + | − | 2+ | 3+ | − | ND | ND | ND | + | − |
| 97 | 4CQA-26 | + | + | + | + | − | ND | ND | ND | + | − |
| 99 | 4CQA-27 | + | − | + | + | + | ND | ND | ND | + | − |
| 101 | 4CQA-29 | + | − | + | 2+ | − | ND | ND | ND | + | − |
| 109 | M2A-1 | + | − | + | + | ND | ND | ND | ND | + | + |
| 111 | M2A-2 | ND | ND | ND | ND | ND | ND | ND | ND | + | − |
| 113 | M2A-3 | − | − | − | − | ND | ND | ND | ND | + | − |
| 115 | M2A-4 | + | − | + | + | ND | ND | ND | ND | + | − |
| 117 | M2A-5 | + | − | ND | ND | ND | ND | ND | ND | + | − |
| 119 | M2A-6 | − | − | − | − | ND | ND | ND | ND | + | − |
| 121 | M2A-7 | + | − | + | + | ND | ND | ND | ND | + | − |
| 123 | M2A-11 | + | − | + | + | ND | ND | ND | ND | + | − |
| 125 | M2A-16 | + | − | ND | ND | ND | ND | ND | ND | + | − |
| 127 | M2A-18 | + | − | + | + | ND | ND | ND | ND | + | − |
| 129 | M2A-19 | + | + | − | + | ND | ND | ND | ND | + | − |
| 131 | M2A-20 | + | − | + | + | ND | ND | ND | ND | + | − |
| 132 | M2A-21 | − | − | − | − | ND | ND | ND | ND | + | − |
| 134 | M2A-22 | + | − | + | + | ND | ND | ND | ND | + | − |
| 136 | M2A-23 | − | − | − | − | ND | ND | ND | ND | + | − |
| 139 | M2A-24 | − | − | − | − | ND | ND | ND | ND | + | − |
| 141 | M2A-25 | + | − | + | + | ND | ND | ND | ND | + | − |
| 143 | M2A-29 | + | − | + | + | ND | ND | ND | ND | + | − |

Table 8 Legend: See Legend for Table 2.

In addition to the immunoscreen described above, Mozart II antisera was used in another immunoscreen to isolate nucleic acid molecules herein designated M2A1, M2A2, M2A3, M2A4, M2A5, M2A6, M2A7, M2A11, M2A16, M2A18, M2A19, M2A20, M2A21, M2A22, M2A23, M2A24, M2A25, and M2A29 as follows: *E. coli* Y1090 was infected with approximately 1×10$^6$ PFU and then evenly spread on 10 LB-amp agarose culture plates. The rest of the screening procedure was as described for immunoscreening with antisera Q4-1959 (Example 2), with the following exceptions: the primary antibody was used at a 1:50 dilution, and the secondary antibody was a 1:200 dilution of AP-conjugated goat anti-cat IgA (available from Bethyl Laboratories Inc., Montgomery, Tex.). Of the 1×10$^6$ plaques screened in this manner, 18 nucleic acid molecules capable of expressing proteins recognized by Mozart II antisera were plaque purified. The results of assays to characterize these nucleic acid molecules are summarized in Table 8.

Mozart II antisera was also used in yet another immunoscreen to isolate nucleic acid molecules herein designated Tg-41, Tg-45, and Tg-50 as follows: *E. coli* Y1090 was infected with approximately 1×10$^6$ PFU and then evenly spread on 12 LB-amp agarose culture plates. The rest of the screening procedure was as described for immunoscreening with antisera Q4-1959 (Example 2), with the following exceptions: the primary antibody was used at a 1:50 dilution, and the secondary antibody was a 1:200 dilution of AP-conjugated goat anti-cat IgA Fc. Of the 1×10$^6$ plaques screened in this manner, 4 nucleic acid molecules capable of expressing proteins recognized by Mozart II antisera were plaque purified. The results of assays to characterize these nucleic acid molecules are summarized in Table 8.

Selected nucleic acid molecules identified by screening for the expression of proteins recognized by Mozart II (immune) antiserum were subcloned and sequenced as described in Example 2.

Sequence analysis of nucleic acid molecules selected for expression of proteins recognized by Mozart II (immune) antiserum:

The nucleic acid molecules isolated using Mozart II (immune) serum were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3. Nucleic acid molecule M2A3 was sequenced again and some changes found between the first and second sequence. The resequenced nucleic acid molecule is referred to herein as M2A3-a. In addition, nucleic acid molecule M2A18 was sequenced again and some changes found between the first and second sequence. The resequenced nucleic acid molecule is referred to herein as M2A18-a.

The sequence data described above were used to design unique primers specific to each nucleic acid molecule of the present invention. These primer sequences are listed in Table 4. The unique primers listed in Table 4 were used in reverse transcriptase-polymerase chain reaction (RT-PCR) assays to assess the expression of the particular nucleic acid sequence in ICG, bradyzoites and tachyzoites. The results of these assays are summarized in Table 8.

Recombinant nucleic acid molecules, protein molecules and cells including sequences encoding *T. gondii* antigenic proteins and sequences from the vector pTrcHisB:

Recombinant nucleic acid molecules including sequences encoding *T. gondii* antigenic proteins and sequences from the vector pTrcHisB were produced as described in Example 2. In brief, *T. gondii* DNA fragments in λ gt11 were PCR amplified from nucleic acid molecules herein designated 4CQA-11, 4CQA-19, 4CQA-21, 4CQA-22, 4CQA-24, 4CQA-25, 4CQA-26, 4CQA-27, 4CQA-29, Tg-41, Tg-45, and Tg-50 using the λ gt11 forward and reverse primers herein described. The resulting recombinant molecules were transformed into *E. coli* to form recombinant cells. Immunoblot analysis of the recombinant cell lysates using a T7 tag monoclonal antibody (available from Novagen Inc., Madison, Wis.) directed against the fusion portion of the recombinant Toxoplasma fusion protein was used to confirm the expression of the fusion proteins and to identify their size. The results of this immunoblot analysis are summarized in Table 8.

Example 7

This Example discloses a method of isolation of *T. gondii* nucleic acid molecules encoding immunogenic *T. gondii* proteins recognized by cat immune sera enriched for antibodies to gametogenic stages (herein referred to as absorbed immune sera or serum). This Example further discloses recombinant nucleic acid molecules, proteins and cells of the present invention.

Production of cat immune sera enriched for antibodies to gametogenic stages:

Sera from cats which were infected and then subsequently challenged with mouse brain-derived tissue cysts were tested for reactivity to extracts of infected cat gut material by Western blot analysis. Sera from one specific cat, designated Queen 2, demonstrated reactivity to particular ICG sections in which the presence of *T. gondii* had been shown by immunofluorescence assay. Queen 2 was originally infected with 100 mouse brain-derived tissue cysts, did not shed oocysts, and seroconverted to positive for tachyzoite antigens by day 39 post-infection. This sera was highly reactive to the asexual stage, tachyzoites. Therefore, to enhance the utility of this sera as a reagent for detection of gametogenic proteins, this sera was used in conjunction with a western blot of infected cat intestinal cell lysates to obtain a fraction enriched in antibody reactive to the gametogenic proteins. The enrichment of the Queen 2 sera (also referred to herein as Q2 sera) was performed as follows:

A 12% SDS-PAGE gel was prepared according to standard methods (Laemmli, 1970, Nature 227, 680–685). 1000 µg of solubilized ICG protein, prepared as described above, was loaded on 20×20×0.1 cm gel and run at 8 V/cm for 5 hours. Toxoplasma tachyzoite (TZ) antigen, prepared from solubilized tachyzoites, was used as a control. Separated proteins were transferred to nitrocellulose according to standard procedures for western blotting. After transfer, the nitrocellulose filter was blocked with 4% (w/v) dry milk powder in PBS (pH 7.5), and incubated with a 1:200 dilution of immune cat (Queen 2) antiserum at room temperature for 5 hours with gentle shaking. The filter was then washed with PBS (pH 7.5). After washing, a 0.5 cm strip was cut off the end of the filter and incubated with a 1:1000 dilution of alkaline phosphatase labeled goat anti-cat IgG antibody at room temperature for 1 hour. The strip was stained with 5-bromo-4-chloro-3-indolylphosphate p-toluene salt/ nitroblue tetrazolium chloride substrates (BCIP/NBT) (available from Gibco/BRL). The areas of the gel that stained with BCIP/NBT substrates represented ICG protein bands which were recognized by IgG antibodies in immune cat serum.

The regions of interest that were visualized on the BCIP/ NBT-stained end strip were cut from the remainder of the filter, and the bound antibody eluted with 0.1 M glycine (pH 2.8), 1 mM EDTA at room temperature for 10 minutes. The antibody in glycine was neutralized with 10 mM Tris (pH 9.0), 0.02% $NaN_3$ was added, and the solution was stored at 4° C. The purified antibody was analyzed by Western blot of ICG to monitor successful recovery of the eluted antibody, verifying recovery of antibody that reacted with the appropriate molecular weight region of the ICG western blot. This antibody preparation is referred to herein as absorbed immune serum or sera.

The absorbed immune serum was used to isolate nucleic acid molecules herein designated Q2-4, Q2-9, Q2-10, and Q2-11 as follows: *E. coli* Y1090 was infected with approximately $3.2 \times 10^5$ PFU and then evenly spread on 8 LB-amp agarose culture plates. The rest of the screening procedure was as described for immunoscreening with antisera Q4-1959 (Example 2), with the following exceptions: the primary antibody was used at a 1:200 dilution, and the secondary antibody was a 1:1000 dilution of AP-conjugated goat anti-cat IgG. Of the $3.2 \times 10^5$ plaques screened in this manner, 4 nucleic acid molecules capable of expressing proteins recognized by absorbed immune serum were plaque purified. The results of assays to characterize these nucleic acid molecules are summarized in Table 9.

Recombinant molecules containing *T. gondii* nucleic acid molecule operatively linked to lambda phage transcriptional control sequences and to a fusion sequence encoding a poly-histidine segment in the vector Prcro/T2ori/RSET-B, were produced essentially as described above, resulting in the production of recombinant molecule. The resulting recombinant molecules were transformed into *E. coli* to form recombinant cells using standard techniques as disclosed in Sambrook et al., ibid. Immunoblot analysis of expression of immunogenic *T. gondii* proteins by these recombinant cells is summarized in Table 9.

Example 8

This Example describes the construction of several cDNA expression libraries of the present invention.

A *T. gondii* tachyzoite cDNA expression library, a *T. gondii* infected cat gut (ICG) cDNA library (constructed from seven day post infection infected cat gut material, which is a mix of both cat intestinal cDNA and *T. gondii* gametogenic cDNA), and an uninfected cat gut (UCG) cDNA expression library were from total RNAs as follows:

Isolation of Total RNA From Tachyzoites: Total RNA from tachyzoites was prepared using Tri-Reagent™ (available from Molecular Research Center, Inc, Cincinnati,

TABLE 9

Nucleic Acid Molecules Selected with Absorbed Immune Sera

| ORIGINAL | | DETECTION | | | | EXPRESSION | | pDVAC | | REACTIVITY | |
|---|---|---|---|---|---|---|---|---|---|---|---|
| SEQ ID NO | DESIGNATION | ICG | UCG | TZ | BZ | pTrCHIS | λCRO | IN VITRO | IN VIVO | SERUM | IS |
| 9 | Q2-4 | 2+ | − | + | 2+ | ND | + | ND | ND | + | − |
| 13 | Q2-9 | + | − | + | + | − | − | ND | ND | + | − |
| 15 | Q2-10 | + | − | + | + | ND | + | ND | ND | + | − |
| 17 | Q2-11 | − | − | + | + | ND | + | ND | ND | + | − |

Table 9 Legend: See Legend for Table 2.

Selected nucleic acid molecules identified by screening for the expression of proteins recognized by absorbed immune serum were subcloned and sequenced as described in Example 2.

Sequence analysis of nucleic acid molecules selected for expression of proteins recognized by absorbed immune serum:

The nucleic acid molecules selected for expression of proteins recognized by absorbed immune serum were sequenced as described above. BLASTn and BLASTp homology searches were performed on these sequences using the NCBI GenBank™ non-redundant (nr) nucleotide (n) and amino acid (p) databases, and the dbEST (est) database as described above. The results of these searches are summarized in Table 3. Nucleic acid molecule Q2-9 was sequenced again and some changes found between the first and second sequence. The resequenced nucleic acid molecule is referred to herein as Q2-9-a.

The sequence data described above were used to design unique primers specific to each nucleic acid molecule of the present invention. These primer sequences are listed in Table 4. The unique primers listed in Table 4 were used in reverse transcriptase-polymerase chain reaction (RT-PCR) assays to assess the expression of the particular nucleic acid sequence in ICG, bradyzoites and tachyzoites. The results of these assays are summarized in Table 9.

Recombinant nucleic acid molecules, protein molecules and cells including sequences encoding *T. gondii* antigenic proteins and sequences from the vector Prcro/T2ori/RSET-B:

Ohio) according to the manufacturer's directions. Briefly, $4 \times 10^9$ tachyzoites were resuspended in 6 ml of TriReagent with a syringe and 18 gauge needle. Successive triturations were made with 20 gauge and 22 gauge needles. A volume of $CHCl_3$ equal to one-fifth the original volume of TriReagent® was added and the mixtures were shaken for 15 seconds. The aqueous and organic phases were then separated by centrifugation. Total RNA was recovered from the aqueous phase by precipitation in isopropanol.

PolyA+ RNA was isolated from total RNA using Pharmacia mRNA purification kit (available from Pharmacia Biotech Inc., Piscataway, N.J.).

Isolation of Total RNA from Other Sources: The method of isolation of total RNA from various tissues was the same for all tissues. The only variable was the starting material. For example, to obtain RNA from infected cat gut (ICG) or uninfected cat gut (UCG), the epithelial layer of a fifteen square centimeter section of gut was scraped into 6 ml of Tri-Reagent and processed as described above. RNA from mouse was obtained from 1 gm of mouse brain and treated with Tri-Reagent as described above. RNA from bradyzoites was obtained from 7,000 tissue cysts propagated in mouse brain, obtained as described, and treated with Tri-Reagent as described above.

PolyA+ mRNA was isolated from total RNA using Pharmacia mRNA purification kit (available from Pharmacia Biotech Inc., Piscataway, N.J.).

Preparation of λ cDNA libraries:

The ZAP-cDNA® synthesis kit (available from Stratagene) was used according to manufacturer's instructions to synthesize cDNA. Briefly, 5 or 10 µg of PolyA+ mRNA (prepared as described above) was reverse transcribed using Superscript® reverse transcriptase and 0.6 mM dGTP, dATP, dTTP, and 0.3 mM 5-methyl dCTP and 1.4 µg of oligo dT linker primer supplied with the ZAP-cDNA® Synthesis Kit. The second strand was made by digesting the RNA template with RNaseH and priming second strand synthesis with DNA polymerase I. The cDNA was then ligated into the Uni-ZAP® XR lambda insertion vector (available from Stratagene), packaged and amplified to produce tachyzoite and ICG cDNA libraries.

5 µg of polyA+ RNA was used to prepare the ICG cDNA library, and 10 µg of polyA+RNA was used to prepare the tachyzoite cDNA library. For each library, 100 ng of double stranded cDNA was ligated and packaged and gave approximately $1.5 \times 10^6$ unique nucleic acid molecules. The average size of the cloned inserts was 1.9 Kb in the tachyzoite cDNA library, and 2.1 Kb in the ICG cDNA library.

Example 9

This Example describes the construction and identification of cDNA sequences encoding near full-length *T. gondii* nucleic acid molecules encoding immunogenic *T. gondii* proteins.

Two of the molecular libraries described above were used to isolate near full-length *T. gondii* nucleic acid molecules encoding immunogenic *T. gondii* proteins: the tachyzoite cDNA library and the ICG cDNA library constructed from seven day post infection infected cat gut material.

The general approach to isolating nucleic acid sequences representing full length, or near full-length cDNA sequences was as follows: First, the MacVector DNA analysis program was used to design DNA primers for each of the Toxoplasma sequences cloned in an expression vector as herein described. These primers were then used in a PCR reaction in which the template was either of the Toxoplasma cDNA libraries herein described. The presence of a positive band on an agarose gel following PCR was diagnostic of the presence in the cDNA library of a nucleic acid molecule with homology to the primers. A near full-length cDNA molecule having sequence homology with the genomic DNA sequence designated Q2-4 was obtained by a direct hybridization screen of the libraries using radiolabeled clone-specific PCR fragments as templates. The isolation of one of these near full-length sequences is herein described in detail as representative of the methods used to isolate all of the near full-length sequences identified by this strategy.

A cDNA sequence representing a near full-length gene having homology to a nucleic acid sequence herein designated Q2-4 (isolated from the Toxoplasma genomic DNA library) was isolated from the infected cat gut (ICG) cDNA library by hybridization screening as follows: *E. coli* Y1090 was infected with approximately $1 \times 10^6$ PFU of the Toxoplasma ICG cDNA library and then plated at a density of about 50,000 plaques per 150 mm agar plate. The resulting plaques were transferred to nitrocellulose filters. The filters were then soaked in denaturing solution (1.5 M NaCl, 0.5 M NaOH) for two minutes, neutralization solution (1.5 M NaCl, 0.5 M Tris, pH 8) for five minutes, and then rinsed several times in 2×SSC (150 mM NaCl, 15 mM Na citrate, pH 7). The DNA bound to the filters was crosslinked using a Stratalinker® UV crosslinker (available from Stratagene) according to the manufacturer's directions.

A radioactive hybridization probe was made by incorporating $^{32}$p into clone-specific template DNA using a Prime-It® II random primer labeling kit (available from Stratagene) following the manufacturers directions. The template was a PCR fragment generated by using two primers specific for Q2-4. For each 100 µl reaction, 30 ng of Toxoplasma genomic DNA was PCR amplified using 200 mM of each dCTP, dGTP, dTTP, dATP, 200 nM of each specific primer, 2.5 mM MgCl$_2$, 20 mM Tris pH 8.4, 50 mM KCl, and 2.5 units Taq DNA polymerase (available from The Perkin Elmer Corp.) for thirty-five cycles in a Perkin-Elmer Gene Amp PCR System (available from The Perkin Elmer Corp.).

The nitrocellulose filters containing crosslinked DNA were hybridized in 2×PIPES buffer (10 mM piperazine-N, N'-bis[2-ethanesulfonic acid] (pH 6.5), 400 mM NaCl), 50% formamide, 0.5% SDS, 100 mg/ml denatured salmon sperm DNA and $10^7$ cpm/ml of the radioactive hybridization probe. The filters were incubated with this hybridization solution overnight at 42° C. The next day the filters were washed in 0.1×SSC, 0.1% SDS and then exposed to X-ray film (available from Kodak, Rochester, N.Y.) in order to visualize positive plaques.

Plaques in the area corresponding to the positive signals were picked into SM buffer (50 mM Tris, pH 7.5, 100 mM NaCl, 8 mM MgSO$_4$, and 0.01% gelatin) and the phage replated at a lower density. The same screening procedure was repeated three or four times until a pure plaque corresponding to a full length cDNA nucleic acid sequence representing Q2-4 was isolated.

After plaque purification, the nucleic acid molecules were mapped and the areas of interest sequenced using primers specific to the original clone, long fragment PCR, and cycle sequencing of the large fragments.

Example 10

This Example describes the expression in a eucaryotic cell of nucleic acid molecules encoding immunogenic *T. gondii* proteins, and DNA vaccination with nucleic acid molecules encoding immunogenic *T. gondii* proteins.

Cloning into a eucaryotic expression vector(pDVacI):

Inserts from eight clones (OC-2, OC-13, OC-14, OC-22, Tg-41, Tg-45, Tg-50, 4CQA-11) were ligated into the pDVacI expression vector. This vector contained a eucaryotic promoter from cytomegalovirus (CMV), followed by the start codon and signal sequence for a mouse kappa immunoglobulin gene. An EcoR I site was inserted in frame downstream to the signal sequence. This allowed the insertion of Eco RI fragments directly from the original lambda phage. The nucleic acid molecules produced by insertion of nucleic acid molecules encoding immunogenic *T. gondii* proteins into pDVacI are referred to herein as pDVacI:Toxoplasma nucleic acid molecules. If the EcoR I inserts represent nucleic acid sequence that is entirely open reading frame, then the protein product expressed from these inserts may be in frame with a C-terminal fusion consisting of both a poly histidine track and amino acid sequence representing an epitope from the human myc gene as a reporter sequence. The N-terminal fusion adds 49 amino acids, or about 5.4 kD to the protein encoded by the *T. gondii nucleic acid molecule, and the C-terminal fusion adds* 38 amino acids, or about 4.2 kD, to the fusion protein.

Expression in vitro:

Direct sequencing of the inserts in each plasmid confirmed the production of eight different pDVacI:Toxoplasma nucleic acid molecules. DNA from these molecules was then tested for eukaryotic expression of antigenic *T. gondii* proteins by transfecting BHK cells in vitro with DNA isolated from the pDVacI:Toxoplasma nucleic acid molecules. Analysis of the eukaryotic expression products of the pDVacI:Toxoplasma nucleic acid molecules was done by western blot on cell lysates and on supernatants from the transformed BHK cells. Either a monoclonal reactive with the myc epitope or antibody specific to each clone was used as the primary antibody. Seven out of the eight plasmid constructs expressed a protein in vitro. See Table 10.

TABLE 10

Analysis of Clones in Eucaryotic Expression Vector and DNA Vaccination

| Clone | Size (KD) Expressed in pDVac | EU/ug DNA* | Expression in vitro Pellet | Super | Sero-conversion (# of Mice)** |
|---|---|---|---|---|---|
| OC-2 | 40 | 0.3/0.4 | + | + | 5/5/5 |
| OC-13 | 38 | 0/0.23 | + | + | 0/0/4 |
| OC-14 | 32 | 7.7/3.8 | − | − | *** |
| OC-22 | 40 | 0.5/0.44 | + | + | 4/5/5 |
| Tg-41 | 33 | 23/1.8 | + | + | 0/1/5 |
| Tg-45 | 26 | 0/0 | + | + | 3/5/5 |
| Tg-50 | 55 | 4.0/4.0 | + | + | 5/5/5 |
| 4cqa-11 | 25 | 0.95/5.3 | + | + | 0/0/0 |

Table 10 legend:
*The first and second numbers represent the endotoxin units (EU)/ug of DNA for the first and second immunizations respectively.
**The numbers represent the # of mice that sero-converted at the 4, 7, and 9 week bleeds, respectively, out of the group of five that were injected.
***Antigen for Nt4 protein was not available to analyze for these sera samples.

Expression in vivo 100 ug of each pDVacI:Toxoplasma nucleic acid molecule was injected intradermally into five mice. The administrations were at day zero and week five; bleeds were collected at weeks four, seven and nine. The mouse sera were used to determine if the DNA vaccination with each clone elicited a serological response to the cloned fusion protein. This was measured by western blot analysis with the protein expressed in the BHK lysates. Six of the eight clones induced antibodies in mice by week nine, see Table 10.

Reactivity of antibody raised against recombinant OC-1 protein:

Purified recombinant protein expressed by an expression vector containing the nucleic acid sequence referred to as OC-1 (SEQ ID NO:70) was used to immunize mice and rabbits by methods well known in the art. The animals were bled, and serum collected used in immunofluorescence assays against infected and uninfected cat gut tissue. The results of these assays showed that antibody raised, in mice and rabbits, to recombinant OC-1 protein bound to most of the enteroepithelial stages in the infected cat gut. The antiserum did not react with uninfected cat gut.

Example 11

This example describes the construction of a *Toxoplasma gondii* EMBL3 genomic library from tachyzoites grown in tissue culture. This Example further describes isolation of near full-length nucleic acid molecules encoding stage specific *T. gondii* antigenic proteins.

An EMBL3 library of Toxoplasma genomic DNA was constructed using standard molecular cloning methods, well known to those skilled in the art of cloning (see, for example, Sambrook, et al., ibid.). In brief, Toxoplasma genomic DNA, prepared from tachyzoites as herein described, was partially digested with Sau3A I, using a series of different ratios of units of enzyme to μg of DNA. Digestions were incubated at 37° C. for one hour. Ratios of 0.06, 0.03, and 0.015 units of enzyme per μg of DNA produced high molecular weight DNA fragments which were then run on a preparative agarose gel. The fraction of the gel corresponding to DNA in a size range of between 15 and 20 Kb was excised. The DNA fragments were extracted from the gel, and the amount of extracted DNA quantitated. The EMBL3 library was then constructed using this DNA and the Lambda EMBL3/BamH I Vector Kit (available from Stratagene). The manufacturer's instructions were followed for all cloning steps, and the resulting ligated DNA was packaged using the Gigapack® II XL Packaging Extract (available from Stratagene). Packaging and amplification followed the manufacturer's specifications. The resulting library is referred to herein as the EMBL3:Toxoplasma genomic library.

The EMBL3:Toxoplasma genomic library was plated at a density of 50,000 plaques per 150 mM agar plate and the plaques transferred to a nitrocellulose filter. The filters were soaked in denaturing solution (1.5 M NaCl, 0.5 M NaOH) for two minutes, neutralization solution (1.5 M NaCl, 0.5 M Tris, pH 8) for five minutes, rinsed several times in 2×SSC (150 mM NaCl, 15 mM Na citrate, pH 7), and the DNA crosslinked using a Stratalinker® UV crosslinker (available from Stratagene) according to the manufacturer's instructions.

The EMBL3:Toxoplasma genomic library was screened with probes made from PCR amplified nucleic acid molecules isolated by immunoscreening the λ gt11:Toxoplasma genomic library. The primers used to generate these probes were derived using the MacVector Sequence Analysis program and the sequences of nucleic acid molecules encoding *T. gondii* antigenic proteins isolated from the λ gt11:Toxoplasma genomic library.

The filters were hybridized in 2×PIPES buffer (10 mM piperazine-N,N'-bis[2-ethanesulfonic acid] (pH 6.5), 400 mM NaCl), 50% formamide, 0.5% SDS, 100 μg/ml denatured salmon sperm DNA (available from Sigma) and $10^7$ cpm/ml of radioactive hybridization probe. The filters were hybridized overnight at 42° C. The next day the filters were washed in 0.1×SSC, 0.1% SDS, and then exposed to X-ray film (Kodak).

Plaques in the area corresponding to the positive signals were picked into SM buffer (50 mM Tris, pH 7.5, 100 mM NaCl, 8 mM $MgSO_4$, and 0.01% gelatin) and the phage replated at a lower density. The same screening procedure was repeated three or four times until a pure plaque hybridizing with a nucleic acid molecule isolated by immunoscreening the λ gt11:Toxoplasma genomic library was isolated. After plaque purification, the nucleic acid molecules were mapped and the areas of interest sequenced using primers specific to the original clone, long fragment PCR, and cycle sequencing of the large fragments.

Long fragment PCR was done with a Perkin-Elmer XL PCR kit (available from The Perkin-Elmer Corp., Foster City, Calif.) as follows: A 100 μl reaction was separated into two layers with a wax bead so one would have a hot-start reaction. The lower layer contained 1×XL PCR buffer supplied with the kit, 40 pM each of the forward and reverse primers, SC1011 and SC1002, (supplied by the manufacturer with the XL PCR kit, 2.5 mM each dNTP, 1.1 mM $Mg(OAc)_2$. The upper layer contained 1×XL buffer, 4 units of rTth DNA polymerase (available from The Perkin-Elmer Corp.) and about 5 ng of the plaque purified EMBL3 :Toxoplasma genomic DNA as the template. The reaction was done in a Hybaid thermocycler (available from Hybaid Ltd., Middlesex, UK), and the reaction products were resolved on a 0.6% agarose gel.

Example 12

This Example describes the detection of *T. gondii* oocysts in cat feces by PCR amplification of nucleic acid sequences homologous to nucleic acid sequences encoding immunogenic *T. gondii* proteins of the present invention. Specifically, this example describes a rapid PCR dipstick method for the detection of oocysts in feces.

Naive cats were infected per os by 1000 mouse-brain derived tissue cysts of *T. gondii* strain C at day zero. Feces from each animal were collected, if available, on a daily basis starting at day zero and each day for 19 days post infection (PI). A portion of the feces was treated by the standard sugar floatation method (Dubey, J. P., Swan, G. V., and Frenkel, J. K. 1972, Journal of Parasitology. 58: 1005–1006) and the oocysts visualized using a microscope and counted on a haemacytometer. A portion of each feces was also suspended in PBS, vortexed and a small sample obtained by dipping an IsoCodeJ™ dipstick (available from Schleicher & Schuell, Keene, N.H.) into the fecal solution. The dipstick was allowed to air dry and then washed in 500 μl of distilled water by vortexing the stick end and water in a tube for 10 seconds. Material adhering to the filter was then eluted in 50 μl of fresh distilled water by heating to 95° C. for 30 minutes. The remaining supernatant was then used for standard hot start PCR, according to methods well known in the art, using primers representing DNA sequences from nucleic acid molecules encoding *T. gondii* antigenic proteins. The results of an experiment in which primers derived from nucleic acid molecule OC-2 were used are shown in Table 11. The results of this experiment demonstrated that the PCR detection method was at least as sensitive at detecting oocysts in fecal matter as the conventional floatation method.

A series of additional experiments was performed in order to investigate further the PCR dipstick method for the detection of oocyts in feces. In this set of experiments, the following methods were used to produce *T. gondii* infected cats, and to detect oocysts in the feces of the infected cats. *T. gondii* C-strain tissue cysts were obtained by orally infecting 6–8 week old Swiss Webster mice with a sub-lethal dose of mouse brain derived tissue cysts. At six weeks post infection, the animals were euthanized with $CO_2$ and the brains were removed and placed in 30% Dextran in HBSS (Gibco/BRL). The brains were then homogenized with a Tissuemizer (Tekmar Co., Cincinnati Ohio) and centrifuged at 5,000×g's for 10 min at 4° C. The pellet was resuspended in HBSS and the tissue cysts were counted. The tissue cysts were diluted with PBS to the appropriate concentration for oral administration to cats at the back of the throat using a 1 ml syringe. A total of twenty cats was used in this study: seventeen were experimentally infected with 1000 tissue cysts and three were used as uninfected controls. All cats were housed in separate cages and feces were collected at the day of infection and daily for the next 21 days. On average there were approximately twelve samples per cat. The fecal samples were stored at 4° C. until tested, which was within two weeks of collection.

Conventional quantification of oocysts in feces was based on the sugar flotation method of Dubey and Beattie, 1988, and is described in full as follows. Each fecal sample was weighed and then 2 grams of feces were mixed with 15 ml of sugar solution (53 gm sugar, 100 ml of water). Following solubilization with a tongue depressor, the mixture was passed through two layers of gauze. The filtrate was poured into a 15 ml conical tube and centrifuged at 1,200×g for 10 minutes. The top 3 ml of the sample was added to 13 ml of sugar solution and centrifuged as above. The top 3 ml of the second flotation was added to 13 ml of water and centrifuged at 1,200×g for 10 minutes. The resulting oocyst pellet was resuspended in 1 ml of water and the oocysts counted using a hemacytometer. Alternatively, the entire fecal sample was

TABLE 11

PCR Analysis of Cat Feces

| #3528-U | | | #3512-I | | | #3515-I | | |
| --- | --- | --- | --- | --- | --- | --- | --- | --- |
| Day PI | Oocysts/gm Float | PCR Dipstick Oc2 | Day PI | Oocysts/gm Float | PCR Dipstick Oc2 | Day PI | Oocysts/gm Float | PCR Dipstick Oc2 |
| 0 | 0 | − | 0 | 0 | − | 0 | 0 | − |
| 1 | 0 | − | 1 | 0 | − | 1 | 0 | − |
| 2 | 0 | − | 2 | 0 | − | 2 | 0 | − |
| 3 | 0 | − | 3 | 0 | − | 3 | 0 | − |
| 4 | 0 | − | 4 | | | 4 | 1 × 10e6 | + |
| 5 | 0 | − | 5 | 1 × 10e4 | + | 5 | 5 × 10e6 | + |
| 6 | | | 6 | 3 × 10e5 | + | 6 | 1 × 10e6 | + |
| 7 | 0 | − | 7 | 1 × 10e6 | + | 7 | | |
| 8 | | | 8 | 1 × 10e6 | + | 8 | 2 × 10e5 | + |
| 9 | 0 | − | 9 | 1 × 10e6 | + | 9 | 7 × 10e4 | + |
| 10 | 0 | − | 10 | 1 × 10e5 | + | 10 | 0 | + |
| 11 | 0 | − | 11 | 1 × 10e5 | + | 11 | 0 | − |
| 12 | | | 12 | 0 | + | 12 | 0 | − |
| 13 | | | 13 | 0 | − | 13 | 0 | − |
| 14 | | | 14 | 0 | − | 14 | 0 | − |
| 15 | 0 | − | 15 | 0 | − | 15 | 0 | − |
| 16 | | | 16 | | | 16 | 0 | − |
| 17 | | | 17 | | | 17 | 0 | − |
| 18 | | | 18 | 0 | − | 18 | 0 | − |
| 19 | 0 | − | 19 | 0 | − | 19 | 0 | − | solubilized in PBS by adding five ml of PBS per gram of the pre-weighed feces in a 250 ml plastic beaker. After one hour at room temperature, a tongue depressor was used to thoroughly suspend the feces. Five ml of the fecal slurry was added to a 15 ml tube containing 5 ml of 2× sugar solution and inverted several times. The tube was then centrifuged at 1,200×g for 10 minutes. The top 3 ml of the sample was subjected to a second sugar flotation, resuspended, and counted as described above.

Analysis of the fecal samples by the PCR dipstick method was performed as follows. One ml aliquots were taken, prior to further processing for floatation, from each of the initial fecal slurries described above. Samples were collected directly onto dipsticks, either by spotting 10 ul onto each dipstick filter or by directly dipping the dipstick into the fecal slurry. The filters were then dried at room temperature and the filter portion of the dipstick was cut off into a sterile 1.5 ml centrifuge tube. The filter was washed with 500 ul of sterile distilled water by vortexing for 8 seconds. The wash was removed and 50 ul of sterile water was added to the tube and adherent oocyst DNA eluted by heating at 95° C. for 1 hour. The filter was removed with a sterile tip and the sample stored (also referred to as the dipstick eluate) at −20° C.

Primers specific to two *T. gondii* genes, B1 and OC-2, were used in the amplification reactions. The primers for the B1 gene (Burg, et al., 1989, *Journal of Clinical Microbiology*, 27: 1787–1792) were B1 forward (5'-GGA ACT GCA TCC GTT CAT GAG-3', herein referred to as SEQ ID NO:332), B1 reverse (5'-TCT TAA AGC GTT CGT GGT C-3', herein referred to as SEQ ID NO:333), and a B1 internal primer (5'-GGC GAC CAA TCT GCG AAT ACA CC-3', herein referred to as SEQ ID NO:334). The *T. gondii* OC-2 was isolated as herein described. The OC-2-derived primers were OC-2 forward (5'-GCA TCC TTG GAG ACA GAG CTT GAG-3', herein referred to as SEQ ID NO:335), OC-2 reverse (5'-GGG TTC TCT TCT CGC TCA TCT TTC-3', herein referred to as SEQ ID NO:336), and an OC-2 internal primer (5'-AGT CAG AAG CAG TCA AGG C-3' herein referred to as SEQ ID NO:337). The PCR mixture contained 1×PCR buffer (10 mM Tris-HCl$_2$, 1.5 mM MgCl$_2$, 50 mM KCl), 0.2 mM deoxynucleoside triphosphates (Perkin-Elmer Cetus Corp., Norwalk, Conn.), 0.8 uM of each primer, 0.5 U of Gold AmpliTaq™ DNA polymerase (Available from Perkin-Elmer Corp.), and 1 ul DNA template in a total volume of 25 ul. The reaction mixture was denatured at 95° C. for 10 minutes, amplified for 42 cycles including a denaturation step at 95° C. for 30 seconds, annealing at 58° C. for 30 seconds, extension at 72° C. for 40 seconds, and a final extension for 5 minutes at 75 ° C. on an automated DNA thermal cycler (Model 9700, Perkin-Elmer, Foster City, Calif.). PCR products were analyzed by electrophoresis on a 1.5 % agarose gel, stained with ethidium bromide (0.5 ug/ml), and photographed on a UV transilluminator.

Following electrophoresis, the DNA products were denatured in 0.5 N NaOH and 1.5 M NaCl buffer for 30 minutes, transferred to a nylon membrane (Maximum Strength Nytran Plus, available from Schleicher & Schuell) overnight and cross-linked by exposure to UV light (UV Stratalinker 1800, available from Stratagene). The filters were incubated in prehybridization buffer (5×SSC, 1× Denhardt's reagent, 0.2% SDS, 1 mg/ml sheared DNA) at 42° C. for 2 hours and then in hybridization buffer (5×SSC, 1× Denhardt's reagent, 0.2% SDS, 1 mg/ml sheared DNA) containing 5'γ-$^{32}$P labeled oligonucleotide probe at 42° C. overnight. After overnight incubation, membranes were washed twice in 2×SSC, 0.1% SDS for 15 minutes at room temperature, and then washed twice in 0.2×SSC, 0.1% SDS at 55° C. for 1 hour. The filters were autoradiographed at −70° C. with Kodak XRR film.

Ethidium bromide-stained agarose gel and Southern hybridization analysis of PCR amplified products from oocyst-seeded fecal samples was performed in order to determine whether the dipstick method described herein resulted in a reduction of inhibition of PCR amplification of *T. gondii*-specific DNA in fecal slurries as compared with fecal slurries alone. Two sets of solutions, PBS and PBS/Feces (1:4 gm/ml), were seeded with four concentrations of oocysts, 2×10$^6$, 5×10$^5$, 5×10$^4$, and 5×10$^3$. Using the dipstick technique described above, this resulted in an estimated maximum number of oocysts in the PCR amplification tube to be 400, 100, 10, and 1 as indicated for the PBS solution and for the PBS/Feces solution respectively. Southern hybridization was performed using the OC-2 gene internal primer as the probe. Southern hybridization results and the ethidium bromide stained gel demonstrated that inhibition of PCR amplification of the exogenously added DNA was dramatically reduced (as compared with fecal extract alone) in samples prepared as per the dipstick assay as described above.

Three different paper supports were tested for their ability to support the PCR dipstick assay: IsoCodeJ™ Stix, S&S® #903™ (available from Schleicher and Schuell) and Nobuto Blood Filter Strips (available from Advantec, Pleasantville, Calif.). First, IsoCodeJ™ Stix were tested for the ability to bind oocysts. Oocysts were diluted into either PBS or a suspension of uninfected feces and PBS. The fecal dipstick procedure as described above was used to sample and elute DNA for PCR analysis. The concentration of oocysts per reaction was adjusted so that theoretical maximum could be 1, 10, 100, and 400 oocysts respectively. The amplification products were run on an agarose gel and stained as described above. According to this assay, oocysts diluted into PBS alone could be readily detected at 10 oocysts per ul of dipstick eluate with primers directed to the *T. gondii* OC-2 gene. In addition, oocysts in a suspension of feces and PBS could be detected when present at a concentration of between 10 and 100 oocysts per ul. This experiment demonstrates that the oocysts are bound to the IsoCodeJ™ Stix in the presence of feces, are eluted by heat, and following a wash and heat elution step are sufficiently free from inhibitors to be detected by PCR amplification.

Under these conditions, detecting 10 oocysts per ul of eluate from the IsoCodeJ™ Stix is equivalent to detecting oocysts at a concentration of 2.5×10$^5$ oocysts/gram of feces. Several parameters were tested for their ability to increase the sensitivity of this test. First, two additional paper supports, S&S®#903™ and Nobuto Blood Filter Strips, were tested for both the ability to bind oocysts in the presence of solubilized feces, and the ability to support subsequent PCR detection of oocyst DNA. Each of these filter papers bound *T. gondii* oocysts, and subsequent PCR amplification with OC-2 primers detected the presence of *T. gondii* DNA. However, the sensitivity of detection for each of these papers was somewhat less than the sensitivity of the assay when using IsoCodeJ Stix™. All three paper supports were also tested for binding of oocysts in the presence of feces over a range of pH from 4 to 9. The S&S®#903™ and Nobuto Blood Filter Strips were most effective at pH 7. Binding of oocysts to the IsoCodeJ Stix™ was significantly increased at pH 9. All subsequent assays described below used IsoCodeJ Stix™ and pH 9 for binding of oocysts to dipsticks.

Another approach to increasing the sensitivity of the assay was to use primers from the B1 gene during the PCR amplification reaction. The B1 gene is a multicopy gene that is present at approximately 35 copies per *T. gondii* genome. Using a B1-specific primer resulted in a ten-fold increase in sensitivity, and produced an assay in which 1 oocyst/ul could routinely be detected. This level of sensitivity of the assay correlated with the ability to detect approximately $1 \times 10^4$ oocysts/gram of feces.

The sensitivity and specificity of the PCR detection method was tested in experimentally infected animals using flotation and visualization of oocysts as the standard for quantification of oocysts. SPF cats were infected with mouse brain-derived tissue cysts and feces were collected from the cats for twenty-one days. Each sample was analyzed by both direct visualization and the dipstick PCR technique. Following gel electrophoresis of the products from PCR amplification, the results were scored as either positive or negative depending on the presence or absence of the correct gene-specific PCR product. Table 12 shows the results of PCR detection using both the B1 and OC-2 DNA primers for each individual fecal sample. The positive and negative predicative values were 93.2% and 97.2% respectively using the B1 gene DNA primers and 80.2% and 95.8% respectively using the OC-2 DNA primers.

TABLE 12

Sensitivity, specificity and predicative values for the PCR detection of oocysts in experimentally infected cat feces.

| Method | Total Samples +/− | f/n[a] | f/p[b] | Sensitivity % | Specificity % | Predictive Value % +/− |
|---|---|---|---|---|---|---|
| Microscopy PCR | 69/176 | 0 | 0 | 100 | 100 | 100/100 |
| B1 Primers | 64/171 | 5 | 5 | 94.7 | 96.7 | 93.2/97.2 |
| OC-2 Primers | 61/161 | 7 | 16 | 89.7 | 96.4 | 80.2/95.8 |

[a]false negative
[b]false positive

Example 13

A PCR ELISA was developed for the detection and quantification of PCR amplification products from the PCR dipstick method. In general, digoxigenin-labeled amplified product produced by the PCR dipstick detection method were detected by hybridization to an internal biotinylated B1 gene primer bound to microtiter wells. The concentration of PCR labeled digoxigenin fragment was determined using an alkaline phosphatase-linked anti-digoxigenin antibody (available from Boehringer Mannheim Biochemica Gmbh). The alkaline phosphatase activity level was then determined using a standard ELISA reader. This quantitative PCR ELISA method detected oocysts at a lower limit of $1 \times 10^4$ oocysts/gram when tested with uninfected cat feces seeded with known concentrations of *T. gondii* oocysts. The method is described in detail as follows.

PCR amplification using B1 gene-specific primers was performed on eluates from the fecal dipstick method herein described. Amplification products were labeled by incorporation of digoxigenin-11-dUTP (DIG-11-dUTP) present in the reaction mix at 2.5 uM. The concentration of dTTP in this reaction mix was reduced to 22.5 uM. The resulting labeled fragment was detected using reagents from the PCR ELISA (DIG Detection) kit (available from Boehringer Mannheim Biochemica Gmbh, Mannheim, Germany). The procedure was as follows. Four ul of the primary amplification reaction product was added to 16 ul of denaturation buffer and incubated at room temperature for 10 minutes. This was mixed with 200 ul hybridization buffer that contained 20 pmol/ml of the biotinylated B1 gene probe. One-half of the hybridization reaction mixture was transferred to a well in a streptavidin-coated microtiter plate and incubated at 50° C. for 3 hours with shaking. The plate was washed with washing buffer five times at room temperature and incubated with 100 ul of anti-digoxigenin Fab conjugated with peroxidase at 37° C. for 45 minutes. Following five washes, 100 ul of ABTS substrate solution (available from Boehringer Marnheim Biochemica) was added to each well and the color was developed at room temperature for 45 minutes. The optical densities (OD) at 405 nm were read in a spectrophotometer (SpectraMAX 250, available from Molecular Devices Inc., Sunnyvale, Calif.) and analyzed with Soft Max Pro™ software (available from Molecular Devices Inc.).

Quantification of oocysts in feces by the PCR ELISA technique was compared with quantification by the microscopic analysis. Individual feces from six different cats were collected (as available) at various days post infection. Oocysts were then quantified for each sample by two separate techniques, microscopy and PCR ELISA. The results from each of these two methods were in good agreement. Standard regression analysis produced a correlation coefficient of 0.91.

Example 14

This example describes the detection of *Cryptosporidium parvum* oocysts and *Giardia lamblia* cysts in feces using the PCR dipstick detection method described above. Oocysts and cysts from *C. parvum* and *G. lamblia* respectively were detected by the dipstick PCR detection method, thereby demonstrating the usefulness of this method for the detection of cysts or oocysts from unrelated species.

Feline fecal samples from SPF cats were seeded with either *C. parvum* oocysts or *G. lamblia* cysts and used in the PCR detection method described herein. The primers used to detect *C. parvum* were specific for the *C. parvum* AWA gene, while the primers used to detect *G. lamblia* were specific for the *G. lamblia* ABB gene (Rochelle, et al., 1997, *Applied and Environmental Microbiology* 63:106–114).

In order to demonstrate binding of *C. parvum* oocysts to a dipstick in the presence of feline fecal slurry, aliquots of feline fecal slurry (1:4, mg/ml) were seeded with between $5 \times 10^2$ and $5 \times 10^6$ *C. parvum* oocysts/ml. These samples were then tested for binding of the oocysts and subsequent PCR analysis according to the PCR detection methods described herein. The primers used in the PCR amplification were specific for the *C. parvum* AWA gene. The PCR amplified products were run on and agarose gel and stained with ethidium bromide. The *C. parvum*-specific primer primed amplification of a DNA product of the predicted mobility, in an oocyst concentration-dependent manner, from the dipstick eluate as described above. The results of this experiment demonstrated that *C. parvum* oocysts bound to a dipstick in the presence of feline fecal slurry, and that about $5 \times 10^2$ *C. parvum* oocysts/ml were detectable by the PCR detection method after binding to the dipstick under these conditions. Because $5 \times 10^2$ oocysts/ml was the lowest concentration tested, and the products were easily observable, the concentration of cysts detectable by this method is likely to be lower than $5 \times 10^2$ oocysts/ml.

In order to demonstrate binding of Giardia cysts to a dipstick in the presence of feline fecal slurry, aliquots of feline fecal slurry (1:4, mg/ml) were seeded with between $5 \times 10^2$ and $5 \times 10^5$ G. lamblia cysts/ml. These samples were then tested for binding of the cysts and subsequent PCR analysis according to the PCR detection methods described herein. The primers used in PCR amplification were specific for the G. lamblia ABB gene. The PCR amplified products were run on and agarose gel and stained with ethidium bromide. The G. lamblia-specific primer primed amplification of a DNA product of the predicted mobility, in a cyst concentration-dependent manner, from the dipstick eluate as described above. The results of this experiment demonstrated that G. lamblia cysts bound to a dipstick in the presence of feline fecal slurry, and that about $5 \times 10^2$ G. lamblia cysts/ml were detectable by the PCR detection method after binding to the dipstick under these conditions. Because $5 \times 10^2$ cysts/ml was the lowest concentration tested, and the products were easily observable, the concentration of cysts detectable by this method is likely to be lower than $5 \times 10^2$ cysts/ml.

Example 15

This Example discloses a method of isolation of T. gondii nucleic acid molecules encoding immunogenic T. gondii proteins recognized by intestinal secretions from infected cats. This Example further discloses recombinant nucleic acid molecules and proteins of the present invention.

The production of intestinal secretions and from infected cats and the use of these secretions for screening for nucleic acid molecules encoding immunogenic *T. gondii* proteins are described herein in Example 6. Intestinal secretions collected from a single cat that had been previously infected with *T. gondii* were pooled and preabsorbed to remove antibodies directed against UCG and *E. coli.* The pooled, preabsorbed intestinal secretions are also referred to herein as MGIS antiserum. MGIS antiserum was used to immune screen an ICG cDNA library in order to identify and isolate nucleic acid molecules encoding immunogenic *T. gondii* proteins recognized by intestinal secretions from infected cats. Six nucleic acid molecules encoding immunogenic *T. gondii* proteins recognized by intestinal secretions from infected cats were identified and isolated using the following methods. These six nucleic acid molecules are referred to herein as MGIS4-2 (also herein referred to as SEQ ID NO:282 and SEQ ID NO:284, representing the coding strand and its reverse complement, respectively), MGIS4-4 (also herein referred to as SEQ ID NO:292 and SEQ ID NO:294), MGIS4-8 (also herein referred to as SEQ ID NO:306 and SEQ ID NO:308), MGIS6-5 (also herein referred to as SEQ ID NO:311 and SEQ ID NO:313), MGIS6-2 (also herein referred to as SEQ ID NO:326 and SEQ ID NO:328), and MGIS1-3 (also herein referred to as SEQ ID NO:329 and SEQ ID NO:331).

Absorption of MGIS Antibody

MGIS antiserum was collected, as previously described, from the cat intestine on weeks 6, 10, and 13 after infection, and on weeks 0, 1, 2, 3, 4, and 5 after challenge. Both pools of antisera were combined and used to screen the cDNA library, and are herein referred to as MGIS antiserum.

To remove anti-cat intestinal and anti-*E. coli* tissue reactive antibodies, the MGIS pools were absorbed to nitrocellulose (NC) filters coated with either cat intestinal proteins or *E.coli* proteins. Cat intestinal proteins used to coat the nitrocellulose filters were generated as follow. The epithelial layer of uninfected cat intestine was scraped on dry ice and the cells subsequently passed through several different gauge needles (No. 18, 21, and 23) 10 times each. The sample was frozen and thawed 3 times, and then sonicated on ice for 10 minutes. The protein extract was diluted to 400 ug/ml in PBS and immersed with the nitrocellulose at room temperature for 1 hour, and was then blocked with 4% milk in PBS for 30 minutes. Similarly, XL-1 blue *E.coli* cells were resuspended in PBS and bacterial protein extracts prepared similar to the cat intestinal proteins. The bacterial extract was diluted to a final concentration of 2.3 mg/ml in PBS and bound to the filter in a manner similar as the cat intestinal extract.

MGIS antiserum was diluted 1:20 with 4% milk in PBS and absorbed sequentially to both the cat intestinal and bacterial protein coated filters at room temperature for 1 hour. To demonstrate that all UCG and *E. coli*-reactive antibody had been removed from the MGIS antiserum preparation, the MGIS antiserum subjected to Western blot analysis which showed that the absorbed antibody had no reactivity to either the cat intestinal proteins or to the bacterial extract.

Immune Screening of *T. gondii* cDNA Phage Library

The ICG cDNA library was constructed from infected cat intestinal mRNA, and the cDNA product cloned into the EcoRI/XhoI sites of the Uni-Zap XR vector. Toxoplasma-specific nucleic acid molecules represented approximately 10% of the library. The ICG cDNA phage library was plated to approximately $2–5\times10^{e4-5}$ pfu per 135 mm plates with XL-1Blue MRF' cells (available from Stratagene). Ten plates were treated in the following manner after the phage were pinhead in size. Nitrocellulose filters that had been previously treated with IPTG were overlaid on top of the phage and incubated at 37° C. for 5 hours. The filters were marked, washed with TBS, pH 8.0, blocked with 4% milk in TBS, and incubated with MGIS antiserum at room temperature overnight. After washing three times with TBS, horseradish peroxidase (HRP)-labeled goat anti-cat IgA antibody (Bethyl Lab. Inc.) was diluted 1:350, and incubated with the filters at room temperature for 2 hours. The color indicator was developed with 4-chloro-1-naphthol substrate and $H_2O_2$. Forty-one positive clones were selected for further screening.

Hybridization Screening and Clone Purification

Selected clones were replated on NZYM plates, and forty-eight individual plaques randomly picked and resuspended in 100 ul of SM buffer. Insert DNAs were PCR amplified in a final volume of 12.5 ul containing 1 ul of template DNA, 50 mM KCL, 10 mM Tris-HCL (pH 8.3), 2 mM $MgCl_2$, 0.2 mM each dNTP, 0.2 mM each of T3 and T7 vector specific oligonucleotide primers, and 0.3 units of Taq polymerase. Amplification was performed by 1 cycle of 95° C. for 3 min., 35 cycles of 95° C. for 30 sec., 50° C. for 30 sec., and 72° C. for 2 min., followed by 75° C. for 5 min. on a Perkin Elmer 9600 thermocycler. The PCR amplified products were analyzed on a 1% agarose TBE gel, and the DNA transferred to a nylon membrane.

A hundred nanograms of *T. gondii* genomic DNA was labeled using the Megaprime DNA labeling systems (available from Amersham International) and used as a probe to analyze the PCR amplified DNA fragments on the nylon membrane. The membrane was pre-hybridized in 5×SSPE (1×SSPE: 0.18M NaCl, 10 mM $NaH_2PO_4$, and 1 mM EDTA pH 7.7), 0.5% SDS, 5×Denhardt's solution, and 0.1 1 mg/ml single stranded salmon sperm DNA at 65° C. for 3 hours. Membranes were then hybridized overnight at 65° C., and then washed with 2×SSPE, 0.1% SDS at room temperature for 10 min., twice, and 0.2×SSPE, 0.5% SDS at 65° C. for 1 hour, twice. The membrane was exposed to film at −70° C. overnight. Twenty-three clones were thus shown to contain *T. gondii*-specific DNA, with an insert size of 1–2 Kb in length.

Clone Identification by Phage Drop Test

Each of the twenty-three *T. gondii*-specific clones were rescreened to confirm reactivity with MGIS antiserum. Phage clones were diluted 1:10e7 from the SM buffer stock, and 3 ul of this dilution (~5–50 phage) was spotted onto a NZYM/XL-1Blue MRF' agar plate, and incubated at 37° C. for 5 hours. Afterwards, an IPTG pre-treated nitrocellulose filter was overlaid onto the agar surface and incubated for another 5 hours. The filter was marked, washed with TBS buffer (pH 8.0) at room temperature for 15 minutes, and blocked with 4% milk in PBS for 30 minutes. Pre-absorbed MGIS antiserum was added to the filter and allowed to react at room temperature overnight. The filter was subsequently washed in TBS at room temperature for 10 minutes, three times. Goat anti-cat IgA polyclonal antibody labeled with HRP (available from Bethyl Laboratories, Inc.) was diluted 1:300 in TBS buffer and incubated with the filter at room temperature for 2 hours. The filter was washed and developed using 4-chloro-1-naphthol substrate and $H_2O_2$. Thirteen of the 23 clones were identified as positive for expressing antigen recognized by IgA in the MGIS antiserum.

DNA Sequencing

The DNA inserts in the thirteen clones identified as positive were subcloned into the TA vector using the TA cloning kit (available from Invitrogen). Individual clones were PCR amplified using the T3 and T7 vector-specific primers. The DNA fragments produced by PCR amplification were gel electrophoresed on a 1% agarose gel, and gel purified using a Qiagen Gel Purification kit (available from Qiagen). Plasmid DNA was purified using the 5 prime 3 prime Perfect Plasmid DNA Preparation kit (available from 5 Prime 3 Prime Inc., Boulder, Colo.). DNA sequencing was carried out on six of the *T. gondii*-specific DNA inserts using a Prizm dideoxy termination kit (available from Perkin Elmer) on an ABI 377 DNA sequencer (available from Applied Biosystems). TA sense and TA antisense oligonucleotide primers were used for DNA sequencing, and insert-specific oligonucleotide primers were used to generate internal fragment sequences. The only variation from this general protocol was in the case of MGIS4-4, where the Erase a Base system (available from Promega) was used to generate plasmids containing deleted fragments in order to facilitate sequencing. The primers used for sequencing each of the inserts were the following:

The primers used in sequencing MGIS4-2 are herein referred to as SEQ ID NO:275, SEQ ID NO:276, SEQ ID NO:277, SEQ ID NO:278, SEQ ID NO:279, SEQ ID NO:280, and SEQ ID NO:281. The primers used in sequencing MGIS4-4 are herein referred to as SEQ ID NO:285, SEQ ID NO:286, SEQ ID NO:287, SEQ ID NO:288, SEQ ID NO:289, SEQ ID NO:290, and SEQ ID NO:291. The primers used in sequencing MGIS4-8 are herein referred to as SEQ ID NO:295, SEQ ID NO:296, SEQ ID NO:297, SEQ ID NO:298, SEQ ID NO:209, SEQ ID NO:300, SEQ ID NO:301, SEQ ID NO:302, SEQ ID NO:303, SEQ ID NO:304, and SEQ ID NO:305. The primers used in sequencing MGIS6-5 are herein referred to as SEQ ID NO:309 and SEQ ID NO:310. The primers used in sequencing MGIS6-2 are herein referred to as SEQ ID NO:314, SEQ ID NO:315, SEQ ID NO:316, SEQ ID NO:317, SEQ ID NO:318, SEQ ID NO:319, SEQ ID NO:320, SEQ ID NO:321, SEQ ID NO:322, SEQ ID NO:323, SEQ ID NO:324, and SEQ ID NO:325. And the primers used in sequencing MGIS1-3 are herein referred to as SEQ ID NO:314, SEQ ID NO:315, SEQ ID NO:316, SEQ ID NO:317, SEQ ID NO:318, SEQ ID NO:319, SEQ ID NO:320, SEQ ID NO:321, SEQ ID NO:322, SEQ ID NO:323, SEQ ID NO:324, and SEQ ID NO:325 (note that the same primers were used for sequencing MGIS6-2 and MGIS1-3).

PCR Amplification of Feline and *T. gondii* DNA With Clone-specific Primers

The IgA selected MGIS clones were shown to be Toxoplasma specific by PCR amplification analysis. The following different cDNA samples were tested for the presence of DNA representing each of the six different IgA-selected nucleic acid molecules: a) uninfected cat gut (UCG); b) infected cat gut (ICG); c) *T. gondii* tachyzoite (TgTz); d) Toxoplasma bradyzoite (TgBz); and e) Toxoplasma genomic DNA (TgTz DNA). The preparation of UCG, ICG, Toxoplasma tachyzoite and bradyzoite cDNA was as described above. Toxoplasma genomic DNA was isolated from tachyzoites by phenol/chloroform/isoamylalcohol pH 8.0 extraction. Oligonucleotide sense and anti-sense primers specific to each of five MGIS-selected nucleic acid molecules were synthesized and used as primers in the PCR amplification reactions. The reaction condition were: 95° C. for 10 min., followed by 35 cycles of 95° C. for 30 sec., 58° C. for 30 sec., 72° C. for 40 sec; this was followed by 75° C. for 5 min. afterwards to complete the reaction. The amount of the different templates used in the PCR reactions (~3–30 ng of DNA), was empirically determined by comparison with a PCR amplified Toxoplasma tubulin gene product standard generated with each template. The oligonucleotide primers and the size of the expected products are listed in Table 13, below.

TABLE 13

| MGIS Clone | Sense Primer Position: Sequence | Anti-Sense Primer Position: Sequence | Product Size (bp) |
|---|---|---|---|
| 1-3 | 1513: SEQ ID NO: 319 | 1858: SEQ ID NO: 320 | 346 |
| 4-2 | 168: SEQ ID NO: 276 | 594: SEQ ID NO: 279 | 427 |
| 4-4 | 455: SEQ ID NO: 285 | 775: SEQ ID NO: 290 | 331 |
| 4-8 | 2018: SEQ ID NO: 300 | 2310: SEQ ID NO: 301 | 293 |
| 6-2 | 1301: SEQ ID NO: 319 | 1646: SEQ ID NO: 320 | 346 |

The oligonucleotide primers specific for each of the five MGIS-selected nucleic acid molecules PCR amplified products only when the template DNA contained Toxoplasma DNA. There were no PCR amplified products in this assay when the template DNA was UCG cDNA. These results confirm the *T. gondii* origin of the MGIS-selected nucleic acid molecules.

Sequence Analysis

Homology searches of a non-redundant protein database were performed on all six MGIS-selected nucleic acid molecules, translated into all six reading frames, using the BLASTX program available through the BLAST™ network of the National Center for Biotechnology Information (NCBI) (National Library of Medicine, National Institute of Health, Baltimore, Md.). This database includes SwissProt+ PIR+SPupdate+GenPept+GPUpdate+PDB databases. In addition, BLASTN homology searches were performed on these sequences using the NCBI databases including the non-redundant database of GenBank EST, and genembl. In all cases, the default parameters for the homology programs were used.

The highest scoring match of the homology search (BLASTX) of translation products of the nucleic acid sequence SEQ ID NO:282 (MGIS4-2) was to GenBank™

Accession No. prf 2208369A, a *Homo sapiens* signal peptidase 12 kD subunit protein. The protein encoded by nucleic acid residues 742–945 of MGIS4-2 (SEQ ID NO:282) showed about 44% identity to amino acid residues 12 to 79 of the protein represented by GenBank™ Accession No. prf 2208369A. At the nucleotide level, SEQ ID NO:282 showed 97% identity over 353 nt with te sequence represented by GenBank™ Accession No. W0680 (TgESTzy81e12.rl), an EST fragment isolated from *T. gondii* tachyzoite cDNA. The homology spans the region from nt 748 to nt 1097 of SEQ ID NO:282, and nt 15 to 365 of GenBank™ Accession No. W0680. There were no other significant homology matches to SEQ ID NO:282 nucleic acid sequence.

The highest scoring matches of the homology search (BLASTX) of translation products of the nucleic acid sequence SEQ ID NO:292 (MGIS4-4) were to proteins described as elongation factor 1-gamma, with the highest match to the sequence represented by GenBank™ Accession No. gi 2160158, described as "a protein similar to elongation factor" The protein encoded by residues 47–1222 of SEQ ID NO:292 showed about 37% identity to amino acid residues 5–414 of the protein represented by GenBank™ Accession No. gi 2160158. At the nucleotide level SEQ ID NO:292 showed 94% identity over 413 nt with an EST fragment, GenBank™ Accession No. N81326 (TgESTzy40a12.rl), an EST fragment isolated from *T. gondii* cDNA. The homology spans the region from nt 420 to nt 832 of SEQ ID NO:292, and nt 15 to 427 of GenBank™ Accession No.N81326. In addition, SEQ ID NO:292 showed 99% identity over 187 nt with an EST fragrnent, GenBank™ Accession No. W05869 (TgESTzy85a09.rl), an EST fragment isolated from *T. gondii* cDNA clone. The homology spans the region from nt 757 to nt 943 of SEQ ID NO:292, and nt 62 to 248 of GenBank™ Accession No.W05869.

The highest scoring match of the homology search (BLASTX in the genembl database) of translation products of the nucleic acid sequence SEQ ID NO:329 (MGIS1-3) was to Herpesvirus Saimiri complete genome, represented by GenBank™ Accession No. X64346. The amino acid residues 777 to 1432 of the protein encoded by reading frame +2 of SEQ ID NO:329 showed about 36% identity to amino acid residues 106974 to 106517 of the protein represented by GenBank™ Accession No. X64346. At the nucleotide level, SEQ ID NO:329 showed 94% identity over 578 nt with an EST fragment, GenBank™ Accession No. AA520348 (TgESTzz69d04.rl), an EST fragment isolated from *T. gondii* bradyzoite cDNA. The homology spans the region from nt 1334 to 1910 of SEQ ID NO:329, and nt 5 to 571 of GenBank™ Accession No. AA520348.

The highest scoring match of the homology search (BLASTN of the non-redundant databases, GenBank+EMBL+DDBJ+PDB) of SEQ ID NO:311 (MGIS6-5) was to a *T. gondii* lactate dehydrogenase gene, represented by GenBank™ Accession No. TGU35118. SEQ ID NO:311 showed 99% identity over 1619 nt.

The highest scoring match of the homology search (BLASTX in the genembl database) of translation products of the nucleic acid sequence SEQ ID NO:326 (MGIS6-2) was to Herpesvirus Saimiri complete genome, represented by GenBank™ Accession No. X64346. Amino acid residues 751 to 1206 encoded by SEQ ID NO:326 showed about 36% identity to amino acid residues 106972 to 106517 of the protein represented by GenBank™ Accession No. X64346. At the nucleotide level, SEQ ID NO:326 showed 96% identity over 247 nucleotides with an EST fragment, GenBank™ Accession No. AA520348 (TgESTzz69d04.rl), an EST fragment isolated from *T. gondii* bradyzoite cDNA. The homology spans the region from nt 890 toll36 of SEQ ID NO:326, and nt 144 to 390 of GenBank™ Accession No. AA520348.

The highest scoring match of the homology search (BLASTX of the non-redundant GenBank CDS database including Translations+PDB+SwissProt+SPupdate+PIR) of translation products of the nucleic acid sequence SEQ ID NO:306 (MGIS4-8) was to a rice 26S protease regulatory subunit 4 homolog (TAT-binding protein homolog 2), represented by GenBank™ Accession No. P46466. 26S protease regulatory subunit 4 homologs representing other species also have high homology to a translation product of SEQ ID NO:306. The protein encoded by nucleic acid residues 465 to 1565 of SEQ ID NO:306 showed about 72% identity to amino acid residues 35 to 448 of the protein represented by GenBank™ Accession No. X64346. It should be noted a gap of 42 amino acids was required in the amino acid sequence encoded by SEQ ID NO:306 in order to achieve the sequence fit resulting in this high homology. At the nucleotide level, SEQ ID NO:306 showed 98% identity over 269 nucleotides with an EST fragment, GenBank™ Accession No. W35531 (TgESTzy90g01.rl), an EST fragment isolated from *T. gondii* cDNA. The homology spans the region from nt 668 to nt 936 of SEQ ID NO:326, and nt 23 to nt 291 of GenBank™ Accession No. W3553 1.

Example 16

This Example discloses the isolation and sequence analysis of a 1397 bp *T. gondii* nucleic acid molecule composed of four fragments isolated by subtractive selection from an infected cat gut cDNA library. Also described is an additional nucleic acid molecule representing the genomic DNA sequence immediately upstream (5') of, and overlapping, the genomic DNA sequence encoding the cDNA sequence.

A 1397 bp *T. gondii* nucleic acid molecule, denoted $nTG_{1397}$ (the coding strand of which is herein referred to as SEQ ID NO:343, and the reverse complement of which is herein referred to as SEQ ID NO:345), is a composite of four overlapping PCR amplified products isolated from an infected cat gut (ICG) cDNA library. Specifically, a first 424 bp fragment (representing nucleotide positions 709–1132 of SEQ ID NO:343), was isolated after two rounds of selection using the PCR-Select™ Subtraction kit (available from Clontech, Palo Alto, Calif.), using day eight, RsaI restriction enzyme digested ICG cDNA as tester, and similarly digested uninfected cat gut cDNA as driver DNA. Fragments enriched by the PCR-Select™ Subtraction selection process were digested with the restriction enzyme SmaI and cloned into SmaI site in the commercially available positive selection vector, QuanTox™ (available from Quantum Biotechnologies Inc., Laval, Quebec, Canada). The cloned inserts were subsequently sequenced using the oligonucleotide primers, T7 (TAATACGACTCACTATAGGG, herein referred to as SEQ ID NO:348) and T3 (ATTAACCCTCACTAAAGGGA, herein referred to as SEQ ID NO:347). A 424 bp *T. gondii* nucleic acid molecule, referred to herein as $nTG_{424}$, was isolated, cloned and sequenced by this method.

The orientation of $nTG_{424}$, as well as additional nucleic acid sequence representing cDNA sequence occurring downstream (3') of $nTG_{424}$ was determined as follows. A 689 bp fragment including the 3'-end of the gene comprising $nTG_{424}$ was generated by PCR amplification of an ICG cDNA library constructed in the Uni-Zap XR insertion vector (available from Stratagene). The two primers used for this amplification reaction are represented by SEQ ID NO:358 ($^{709}$ACAACGACCACGACATCAACTAC$^{731}$, derived from the sequence of $nTG_{424}$, also referred to as pRay8), and an adaptor oligonucleotide primer that hybridized to the cDNA poly A tail (GGCCACGCGTCGACTACT$_{17}$ from BRL/GIBCO, Gaithersburg, Md., herein referred to as SEQ ID NO:364). The superscript numbers at the beginning and end of the primer sequences described herein represent the location of the primer sequence relative to $nTG_{1397}$ (SEQ ID NO:343). A resulting 689bp *T. gondii* nucleic acid molecule (also referred to as $nTG_{689}$) was cloned into PCR2.1 (available from Invitrogen, Carlsbad, Calif.), and sequenced using the M13 reverse oligonucleotide primers (CAGGAAACAGCTATGACC, herein referred to as SEQ ID NO:346) and the T7 oligonucleotide primer (SEQ ID NO:348). The sequence of $nTG_{689}$ revealed 266 bp of additional cDNA sequence (from 1133–1397 bp, relative to SEQ ID NO:343), with an overlap with $nTG_{424}$ from 709–1132 bp (relative to SEQ ID NO:343). There were three nucleotide differences between the sequence data for $nTG_{424}$ and the sequence data for $nTG_{689}$. Instead of a "T", "C" and "T" nucleotide at positions 1159, 1166, and 1169 respectively, the sequence data for $nTG_{689}$ revealed a "C", "T", and "A" at those positions.

The remainder of the nucleic acid sequence of $nTG_{1397}$ was determined in two PCR amplification steps using the ICG cDNA library as the template. The primers for the first PCR amplification were: a) an anti-sense oligonucleotide primer specific for $nTG_{424}$, having the sequence $^{929}$GTTGTCGTAGATGTCGTTGTAGTT$^{906}$, and herein referred to as SEQ ID NO:359; and b) a Uni-Zap XR insertion vector-specific oligonucleotide primer (available from Stratagene, and referred to as Tp277) having the sequence, GGGAACAAAAGCTGGAGCTCCACC, and herein referred to as SEQ ID NO:354. In the first PCR amplification step, SEQ ID NO:359 and SEQ ID NO:354 were used to generate an 884 bp nucleic acid molecule, (825 bp of which was $nTG_{1397}$-specific DNA sequence), that was then cloned into PCR2.1. The *T. gondii*-specific nucleic acid molecule is herein referred to as $nTG_{825}$. $nTG_{825}$ was sequenced using a TA sense oligonucleotide primer (having the sequence, CGAGCTCGGATCCACTAG, herein referred to as SEQ ID NO:350), and a TA anti-sense oligonucleotide primer (having the sequence, GCCAGTGTGATGGATATCTGCAG, herein referred to as SEQ ID NO:349), as well as a $nTG_{1397}$-specific internal oligonucleotide primer having the sequence, $^{564}$GAGGAGATCGAACTTTGCTTGTGC$^{541}$, herein referred to as SEQ ID NO:361. Sequencing revealed that $nTG_{825}$ added an additional 604 bp to the sequence of $nTG_{1397}$, from nucleotides 105–708 (relative to SEQ ID NO:343). $nTG_{825}$ overlapped with $nTG_{424}$ and $nTG_{689}$ from base 709–939 (relative to SEQ ID NO:343).

The primers for the second PCR amplification step were: a) an oligonucleotide primer specific for $nTG_{424}$, having the sequence $^{225}$AGAAGCGCCTTTGCGTTTCTACGT$^{202}$, herein referred to as SEQ ID NO:360; and b) Tp277. These two primers were used to generate a 225 bp *T. gondii* DNA fragment, referred to as $nTG_{225}$.$nTG_{225}$ cloned into PCR2.1, and nucleotide sequenced with the TA oligonucleotide primers as above, thereby generating the sequence from nucleotides 1–104 of SEQ ID NO:343. Sequence analysis revealed that $nTG_{225}$ overlapped with previously isolated $nTG_{825}$ DNA sequence from base105–225, relative to SEQ ID NO:343.

The contiguous cDNA sequence of the overlapping fragments representing $nTG_{1397}$ was determined (and referred to herein as SEQ ID NO:343), and sequence analysis of the composite molecule revealed an 867 bp coding region (referred to as $nTG_{867}$), assuming an initiation codon at position 238–240, and a stop codon at position 1102–1104 (relative to SEQ ID NO: 343). The coding strand of $nTG_{867}$ is herein referred to as SEQ ID NO:340, and the reverse complement is herein referred to as SEQ ID NO:342. Translation of the coding region of $nTG_{867}$ yields a 288 amino acid protein herein referred to as $PTg_{288}$, the amino acid sequence of which is herein referred to as SEQ ID NO:341.

To confirm the DNA sequence in the predicted coding region of $nTG_{1397}$, a PCR amplified fragment containing nucleotides 238 to 1271 was generated using an oligonucleotide primer having the sequence, AAGGATAGGCGGC-CGCAGGTACC$^{238}$ATGGCAGGAAGGCAGGCGGCGTT$^{260}$, herein referred to as SEQ ID NO:362, and an oligonucleotide primer having the sequence, ACCGCTCGAGAAGCTT$^{1271}$GAAGCCAAGACATCCCTTCGTGCA$^{1248}$, herein referred to as SEQ ID NO:363. The nucleotides in italics represent non-$nTG_{1397}$ nucleotide sequence, and were present to attach convenient restriction sites to the PCR product. The resulting PCR fragment was cloned into a eukaryotic expression vector, referred to as pDVacIII, and sequenced using two vector-specific oligonucleotide primers: a) Tp244, having the sequence, GGATGCAATGAAGAGAGGGCTC, and herein referred to as SEQ ID NO:352; and b) Tp245, having the sequence, AACTAGAAGGCACAGTCGAGGCTG, and herein referred to as SEQ ID NO:353. The PCR fragment thus generated contained two nucleotide differences as compared with the previously determined cDNA sequence of $nTG_{1397}$. Instead of an "A" at position 643, a "G" residue was found, and in place of a "T" at position 1187, a "C" residue was found. The resulting nucleotide change at position 643 altered the predicted encoded amino acid from an arginine to a glycine residue. The change at position 1187 did not change the predicted amino acid sequence of $nTG_{1397}$.

Genomic DNA sequence upstream of the gene comprising $nTG_{1397}$ was determined by generating a 747 bp fragment by PCR amplification of the λ-EMBL-3 Sau3A partial Toxoplasma genomic library herein described. The primers used were SEQ ID NO:360 (representing nucleotides 202–225 in $nTGI_{397}$) and a λ-EMBL-3-specific primer having the sequence, GGTTCTCTCCAGAGGTTCATTAC, and herein referred to as SEQ ID NO:351. The resulting DNA fragment was cloned in PCR2.1 and sequenced with TA oligonucleotide primers (SEQ ID NO:349, and SEQ ID NO:350) and two gene specific oligonucleotide primers, Tp310 ($^{365}$CGGACGTTGCATGTCAGTGGACA$^{343}$, herein referred to as SEQ ID NO:355) and Tp311 ($^{243}$CACGAAGCTGCATGTTCCAGCTAG$^{265}$, herein referred to as SEQ ID NO:356). The sequence of the PCR fragment revealed a 647 bp DNA fragment, $nTG_{647}$, (herein referred to as SEQ ID NO:338, the reverse complement is herein referred to as SEQ ID NO:339) including 421 nucleotides of new genomic DNA sequence upstream of the 5' end of the cDNA sequence of $Tg_{1397}$. The fragment contained 327 bp of genomic DNA sequence that overlapped with the cDNA sequence, SEQ ID NO:343 (in other words, bases 422–647 of the genomic DNA sequence, SEQ ID NO:338, overlap with bases 1–225 of the cDNA sequence, SEQ ID NO:343). There was a single nucleotide difference between the genomic and the cDNA sequences at position 118 of the cDNA sequence (SEQ ID NO:343), where there is a "G" in the genomic DNA sequence and an "A" at the equivalent position in the cDNA sequence.

SEQ ID NO:343 was shown to be *T. gondii* specific by PCR amplification analysis of various DNAs, using nTG$_{1397}$-specific DNA primers to drive the reaction. The following cDNA samples were tested for the presence of nTG$_{1397}$ DNA: a) uninfected cat gut (UCG), b) infected cat gut (ICG), c) *T. gondii* tachyzoite (TgTz), and d) Toxoplasma bradyzoite (TgBz). To generate UCG and ICG RNA, gut tissue samples from an uninfected cat and a cat 7 days post infection with *T. gondii* tissue cysts (1000 cysts) were processed by scraping and collecting the epithelial layer of gut cells on dry ice. Cells from UCG, ICG, and *T. gondii* tachyzoites and bradyzoites were solubilized by homogenization in TRI-reagent (available from Molecular Research Center Inc., Cincinnati, Ohio), and the homogenate passed through a 18/20/and 22 gauge needle 10 times each sequentially. After standing at room temperature for 5 min., 100 ul of bromochloropropane (available from Molecular Research Center Inc.)/ml of TRI reagent was added, and the homogenate vortexed for 15 seconds. The sample was centrifuged at 14,000 rpm for 15 min. at 4° C., the aqueous layer collected, and RNA precipitated with one half volume of isopropanol. Contaminating genomic DNA was removed by digestion with 10 units of RNase free DNaseI (available from Boehringer Mannheim Corp.) at 37° C. for 30 min. The sample was then extracted with phenol/chloroform/isoamylalcohol, pH 6.0. The RNA was precipitated from the aqueous layer with ethanol and resuspended in diethylpyrocarbonate (available from Sigma) treated water. cDNA was generated from total RNA using a commercially available RT-PCR kit (available from Stratagene).

Two nTG$_{1397}$-specific oligonucleotide primers were used in the reaction: SEQ ID NO:358, having the sequence, $^{709}$ACAACGACCACGACATCAACTAC$^{731}$, and SEQ ID NO:357, having the sequence, $^{1114}$ACACTTTGGTCTAATCGAGGGTAG$^{1091}$. The reaction conditions were: 95° C. 12 min., followed by 3 cycles of 94° C. 30 sec., 70° C. 30 sec., 72° C. 60 sec., 3 cycles of 94° C. 30 sec., 67° C. 30 sec., 72° C. 60 sec., 3 cycles of 94° C. 30 sec., 65° C. 30 sec., 72° C. 60 sec., 6 cycles of 94° C. 30 sec., 63° C. 30 sec., 72° C. 60 sec., 25 cycles of 94° C. 30 sec., 59° C. 30 sec., 72° C. 60 sec., and a seven minute extension at 75° C. to complete the reaction. The amount of template used in each PCR reaction (~3–30 ng of DNA), was empirically determined by comparison with a PCR amplified Toxoplasma tubulin gene product standard generated with each template. The PCR amplification reaction generated a 406 bp product only in the reactions containing tachyzoite and ICG cDNA template DNA, thereby confirming the *T. gondii*-specificity of SEQ ID NO:343.

Sequence Analysis

Homology searches of a non-redundant protein database were performed on SEQ ID NO:340 (representing the coding region of nTG$_{1397}$, translated in frame 1, using the BLASTP program available through the BLAST™ network of the National Center for Biotechnology Information (NCBI) (National Library of Medicine, National Institute of Health, Baltimore, Md.). This database searched was PIR. In addition, a BLASTP homology search was performed on SEQ ID NO:341 (representing the amino acid sequence encoded by SEQ ID NO:340) using the NCBI database SwissProt. In all cases, the default parameters for the homology programs were used. Another homology search was run on SEQ ID NO:343 using the BLASTN search program and the database genembl.

When run against the PIR database, the highest scoring match of the homology search of translation products of the nucleic acid sequence SEQ ID NO:340 (the coding strand of the coding sequence) was to GenBank™ accession number A60095, a Drosophila larval glue protein precursor. Other significant homologies included homology to an African clawed frog mucin, and a promastigote surface antigen-2. When analyzed by the GCG program, using BESTFIT and default parameters, amino acid residues 145 to 281 of the protein encoded by SEQ ID NO:340 showed about 70% identity to amino acid residues 42 to 178 of the protein represented by GenBank™ accession number A60095. In addition, amino acid residues 153 to 282 of the protein encoded by SEQ ID NO:340 showed about 73% identity to amino acid residues 394 to 523 of the protein represented by GenBank™ accession number A45155 (African clawed frog mucin). When compared with the SwissProt database, the highest scoring match of the homology search of the amino acid sequence SEQ ID NO:341 (the protein encoded by SEQ ID NO:340) was to GenBank™ accession number Q05049, the African clawed frog mucin. These two amino acid sequences showed a 73% identity from amino acid 153 to 282 of SEQ ID NO:341 and amino acid 394 10 523 of the amino acid sequence represented by GenBank™ accession number Q05049. A comparison of SEQ ID NO:343 (the cDNA coding strand) using the BLASTN search program and the database genembl revealed a 76% nucleic acid sequence identity to a *D. discoideum* protein kinase, GenBank™ accession number M38703. This identity was between nt 765 to 1058 of SEQ ID NO:343 and nt 772 to 1065 of the sequence represented by GenBank™ accession number M38703. In addition, a BLASTN comparison SEQ ID NO:343 with the non-redundant GenBank™ database including GenBank EMBL+DDBJ+PDB revealed an 89% identity between nucleic acid residues 779 to 902 of SEQ ID NO:343 and nt 2150 to nt 2273 of the nucleic acid sequence represented by GenBank™ accession number DDDU86962.

Example 17

This example describes the induction of humoral and cellular responses in cats by proteins expressed by the *T. gondii* nucleic acid molecules of the present invention. Protein immunization with *T. gondii* recombinant protein and several different adjuvants induced both antibodies and T cell proliferative responses in cats. DNA immunization of cats with plasmid constructs expressing *T. gondii* immunogenic proteins of the present invention also induced antibody responses.

Protein Immunization

Protein immunization of cats was carried out with three primary subcutaneous immunizations at intervals of four weeks (prime at week 0 and boosts at weeks 4 and 8) using 50 μg protein per injection in adjuvant. The primary antigen was OC-22, which was purified as a HIS fusion protein from *E. coli*. The experimental groups were as follows: two cats were immunized with OC-22 protein in alum, two cats were immunized with OC-22 protein in polyphosphazine (PCPP), and two cats were immunized with OC-22 protein in BAYER1005 (Stunkel, K. G., et al., in *Cellular Basis of Immune Modulation*, 1989, pp. 575–579, incorporated herein by reference in its entirety). One cat was injected with two different antigens in BAYER1005:50 ug of OC-22 and 12 ug of protein 4499-9. One control cat was injected with saline.

Whole blood was collected from all of the animals at intervals before and after the immunizations. Mononuclear cells were selected from the blood for T cell proliferation analysis (see blow) and the remaining plasma processed for detection of humoral responses. The presence of antibody was determined by western blot analysis and by ELISA using recombinant purified antigens. The western blot analysis was more sensitive at detecting a positive or negative response, while the ELISA provided a more quantitative comparison of the cat's responses to the immunogenic proteins.

Western blot analysis was performed on Recombinant purified OC-22 protein was loaded at 2 μg per lane and blotted to nitrocellulose. Samples were from pre-immune cats and cats at 1, 3, and 5 weeks after immunization. Recombinant purified OC-22 protein was loaded at 2 μg per lane and blotted to nitrocellulose. Analysis of the sera collected at three weeks following the first immunization demonstrated that all seven cats responded positively to OC-22 protein. Both anti-cat IgG and anti-cat IgA were used as secondary antibodies (on separate blots). The westerns showed that OC-22 protein elicited both IgA and IgG responses, although the IgA response was not as strong as the IgG response. The ELISA titers were monitored throughout the immunization regimen. The sera collected at week eight and a half, immediately following the second boost had detectable ELISA titers equal to or greater than 1:10,000 for all seven cats. These analyses did not demonstrate any apparent differences between the cats immunized with different adjuvants. The single cat immunized with 12 ug of 4499-9 protein was not positive to 4499-9 protein by either western blot analysis or ELISA, although the same cat demonstrated immune responses to OC-22 that were comparable to the other cats in the study.

Cellular responses to the recombinant *T. gondii* OC-22 protein were tested by in vitro proliferation of isolated peripheral blood mononuclear cells (PBMC) to purified protein at concentrations ranging from 0.5 to 8 μg/ml. At higher concentrations of protein, non-specific stimulation was evident, making interpretation difficult, but at lower concentrations of antigen, distinct differences were seen between cats. One week after the first boost, T cells from all of the cats in either the PCPP or BAY R1005 adjuvant groups demonstrated stimulation indices (SI) greater than 3. Cells from the PBS control and two alum group cats did not show any proliferative responses. Peak proliferative responses were seen one week after each boost, with the highest responses observed after the first boost. The cats immunized with protein in PCPP had the highest responses, followed by the cats immunized with protein in BAY R1005. The responses observed at 0.5 μg antigen per ml were lower than the responses observed at higher doses, but correlated well with the results observed at 2 ug/ml (data not shown). All of the immunized cats responded to antigen, at some point during the experiment, with an SI level above 3.

DNA Immunization

Cats were immunized with the recombinant eukaryotic expression vector, pDVac II, encoding *T. gondii* nucleic acid molecules encoding the immunogenic proteins OC-2, OC-22, and Tg-50. The pDVacII vector contains the CMV promoter and intron A sequences. The protein expressed by this vector includes the *T. gondii* antigen of interest, fused at the 5 prime end to the tissue plasminogen activator signal sequence and fused at the three prime end with both a stretch of poly histidines and an amino acid epitope from the mammalian myc gene. Fifteen cats were divided into four experimental groups: three cats received saline (cats 1, 8, and 16), four cats received DNA encoding OC-2 (cats 2, 5, 9, and 15), four cats received DNA encoding OC-22 (cats 3, 6, 10, and 12), and four cats received a combination of DNA encoding OC-2, OC-22, and Tg-50 (cats 4, 7, 13, and 14). Each cat was injected intramuscularly with a total 300 ug of DNA at two sites per immunization. The combined formulation included 300 ug of each plasmid per injection. The cats were given one injection and then at eight weeks received a boost.

The serum samples collected at six weeks after the primary immunization were analyzed. Two out of eight cats immunized with OC-2 DNA were shown to sero convert to antibody positive to OC-2 protein by western blot analysis. None of the sera collected at this time from the cats immunized with OC-22 or Tg-50 DNA were positive by western blot analysis to OC-22 or Tg-50 protein respectively. When sera collected one week following the boost (week 9) were analyzed by western blots, seven of eight cats immunized with OC-2 were positive to OC-2, six of eight cats immunized with OC-22 were positive to OC-22, and one of four cats immunized with Tg-50 were positive to Tg-50. Similar to the western blot analysis for the protein immunogenicity study described above, faint IgA responses from all of the OC-22 sero-positive animals could be observed. ELISA analysis of sera taken one week after the boost indicated that four out of eight cats immunized with OC-2 and four of eight cats immunized with OC-22 had midpoint titers greater then 1:1000.

The T cell analysis demonstrated positive proliferative responses to several antigens, however the data were difficult to interpret. Cells isolated from two cats immunized with the OC-22 gene and one cat immunized with the OC-2 gene each demonstrated significant SI responses. However, the same cells from each of these cats were also stimulated by the other recombinant antigen; i.e. cells from OC-22-injected cats responded to OC-2 protein and cells from OC-2-injected cats responded to OC-22 protein. Sera from these animals did not react with the poly histidine or myc fusions on other control fusion proteins. This inability to demonstrate strong proliferative responses in PBMC is consistent with other results observed while exploring the induction of proliferative responses in T cells from DNA immunized cats. Cat peripheral blood is a poor source of responsive T cells.

Analysis of Oocvst Shedding in Protein an DNA immunized cats

Analysis of oocysts shed following tissue cyst challenge of cats in both the protein and DNA immunogenicity studies showed no significant difference in oocyst shedding between any of the test groups and the control within each study. However, the number of animals in these studies varied between two and four per group, and thus this result is statistically meaningless. However, significant reduction, i.e., greater than several logs of total oocysts, was not observed in this experiment.

Example 18

This example describes immunization of cats with nucleic acid molecules encoding immunogenic *T. gondii* proteins, and subsequent challenge of the immunized cats.

Immunization Protocol

The following set of conditions were used for the delivery of DNA-coated gold particles to cats: 1.25 ug of DNA was delivered per shot by Gene Gun (available from Biorad). 1.6 micron gold particles were used in the presence of 0.05 mg/ml PVP (polyvinyl pyrrolidine, 360 kD). The microcarrier loading quantity was 0.5 mg DNA/cartridge, while the DNA loading ratio was 2.5 ug DNA/mg gold. The animals were anesthetized and shaved at the points of contact with the gun. A total of six shots were delivered to the animal for each immunization: three shots to the inner thigh at 300 psi and three shots to the lower side of the abdomen at 600 psi. The immunization regimen consisted of one prime and two boosts at six week intervals. Tissue cyst challenge was performed two weeks following the second boost. The challenge was with 1000 mouse brain-derived tissue cysts.

The plasmid containing the human growth hormone (hGH) gene was used in the control groups and as a marker in the other groups in all studies. In most control groups, the hGH plasmid was diluted to a concentration similar to that in the test groups. Humoral immune responses to the gene product were measured with an ELISA assay, and cellular responses were measured using hGH protein.

First immunogenicity study: The first immunization was followed by a challenge of 1000 mouse brain derived tissue cysts fourteen weeks later. Sample collection was terminated three weeks after that. There were four groups of five animals per group, as follows: Group 1: Control, hGH (0.125 ug/shot), pDVacIII (1.125 ug/shot) This group received one prime and two boosts, at 0, 6 and 12 weeks, respectively. Group 2: OC-22 in pDVacIII (1.25 ug/shot). This group received one prime and two boosts, at 0, 6 and 12 weeks, respectively. Group 3: hGH (0.125 ug/shot), 9 Toxoplasma nucleic acid molecules OC-2, OC-22, OC-13, OC-14, Tg-41, Tg-45, Tg-50, 4604-3, and 4CQA11 (0.125 ug/shot). This group received one prime and two boosts, at 0, 6 and 12 weeks, respectively. Group 4:hGH (0.125 ug/shot), the same DNA as in Group 3 (9 Toxoplasma nucleic acid molecules), but this group received one prime and one boost, at 6 and 12 weeks, respectively. ELISA analysis for hGH sero conversion using sera collected throughout the study demonstrated that five of five cats in Group 1 were positive (i.e., demonstrated an end point titer>1,000). Three of five animals in Group 3 were sero-positive to hGH. ELISA analysis for sero conversion to OC-22 protein using sera from Group 2 and Group 3 indicated that three of five and zero of five cats were positive respectively. These data suggest that competition from the other plasmids reduced the rate of sero conversion to an individual plasmid. In all cases positive titers did not occur until after the first boost. Specific-T cell proliferative responses using PBMC from animals in each group were not observed. Using the B1 gene-based PCR ELISA herein described, the average number of oocysts shed for each group was: Group 1, 1.03e8; Group 2, 1.11e8; Group 3, 5.79e7 and Group 4, 8.83e7. Statistical analysis of the data indicated no significant difference between the test groups and the control.

Second immunogenicity study

The first immunization for this study was followed by a challenge of 1000 mouse brain derived tissue cysts fourteen weeks later. Sample collection was terrninated three weeks after that. There were four groups of five animals per group, and all animals received one prime and two boosts. Group 2 consisted of DNA representing 18 nucleic acid molecules of the present invention. Group 3 represent 14 additional nucleic acid molecules of the present invention. Group 4 was a combination of both of these groups. The specific nucleic acid molecules and concentrations used in the immunizations were as follows: Group 1: Control, hGH (0.083 ug/shot), pDVacIII (1.125 ug/shot). Group 2:hGH (0.070 ug/shot), 18 Toxoplasma nucleic acid molecules (BZ1-2, 4604-2, 4604-62, 4CQA27, 4CQA29, 4CQA21, 4CQA27, 4604-62, Q2-4, R8050-6,Tg5O, M2A1, M2A5, M2A7, M2A11, M2A19, M2A22, M2A29) (0.070 ug/shot). Group 3:hGH(0.083 ug/shot), 14 Toxoplasma nucleic acid molecules (M2A3, M2A21, M2A18, M2A20, M2A24, M2A6, Q2-9, Q2-10, Q2-11, 4604-63, 4604-17, 4604-69, 4604-54, 4CQA19) (0.083 ug/shot). Group 4:hGH (0.040 ug/shot), 32 Toxoplasma nucleic acid molecules (BZ1-2, 4604-2, 4604-62, 4CQA27, 4CQA29, 4CQA21, 4CQA27, 4604-62, Q2-4, R8050-6,Tg-50, M2A1, M2A5, M2A7, M2Al1, M2Al9, M2A22, M2A29,M2A3, M2A21, M2A18, M2A20, M2A24, M2A6, Q2-9, Q2-10, Q2-11, 4604-63, 4604-17, 4604-69, 4604-54, 4CQAl9) (0.040 ug/shot).

The ELISA analysis of antibody to hGH protein demonstrated that two of five, three of five, zero of five, and two of five animals seroconverted in Groups 1, 2, 3, and 4 respectively. Using low amounts of hGHplasmid in the presence of eighteen or thirty-two additional plasmids containing nucleic acid molecules of the present invention still induced sero conversion in several animals per group. This observation suggests that there is not a strict reduction in the production of antibodies when a gene is injected with several other constructs.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to detect an encysted stage of a parasite in feces, said encysted stage selected from the group consisting of a cyst and an oocyst, said method comprising:
   (a) contacting a sample of feces with a solid support capable of binding said encysted parasites;
   (b) allowing the sample to dry onto the solid support;
   (c) washing the sample on the solid support with an aqueous wash solution;
   (d) adding an aqueous elution solution to the sample and eluting DNA from the sample into the aqueous elution solution by heating;
   (e) PCR amplifying encysted parasite-specific DNA with primers specific to the encysted parasite being detected; and
   (f) detecting the presence of a PCR amplification product resulting from amplification of encysted parasite-specific DNA in the sample, wherein the presence of said product indicates the presence of encysted parasite in said feces; and
   wherein said method is conducted in the absence of a step to remove or inhibit inhibitors of PCR amplification.

2. A method according to claim 1, wherein the sample of feces is solubilized in an aqueous solution before contacting the sample with a solid support capable of binding said encysted parasite.

3. A method according to claim 1; wherein the aqueous wash solution comprises distilled water.

4. A method according to claim 1, wherein the aqueous elution solution comprises distilled water.

5. A method according to claim 1, wherein the heating step comprises heating to approximately 95° C.

6. A method according to claim 1, wherein the solid support capable of binding said encysted parasite comprises paper.

7. The method of claim 1, wherein the encysted parasite are enteric apicomplexa oocysts.

8. The method of claim 7, wherein the enteric apicomplexa oocysts are selected from the group consisting of Cryptosporidium oocysts and Toxoplasma oocysts.

9. The method of claim 1, wherein said encysted parasites are Giardia cysts.

10. A method to detect an encysted stage of a parasite in feces, said encysted stage selected from the group consisting of a cyst and an oocyst, said method comprising:
    (a) contacting a sample of feces with a solid support capable of binding said encysted parasites;
    (b) allowing the sample to dry onto the solid support;
    (c) washing the sample on the solid support with an aqueous wash solution;
    (d) adding an aqueous elution solution to the sample and eluting DNA from the sample into the aqueous elution solution by heating;
    (e) PCR amplifying encysted parasite-specific DNA with primers specific to the encysted parasite being detected; and
    (f) detecting the presence of a PCR amplification product resulting from amplification of encysted parasite-specific DNA in the sample, wherein the presence of said product indicates the presence of encysted parasite in said feces;
    wherein said sample of feces has not been treated to concentrate said encysted parasite; and
    wherein said method is conducted in the absence of a step to remove or inhibit inhibitors of PCT amplification.

11. A method according to claim 10, wherein the sample of feces is suspended in an aqueous solution before contacting the sample with a solid support capable of binding said encysted parasite.

12. A method according to claim 10, wherein the aqueous wash solution comprises distilled water.

13. A method according to claim 10, wherein the aqueous elution solution comprises distilled water.

14. A method according to claim 10, wherein the heating step comprises heating to approximately 95° C.

15. A method according to claim 10, wherein the solid support capable of binding said encysted parasite comprises paper.

16. The method of claim 10, wherein the encysted parasites are Giardia cysts.

17. The method of claim 10, wherein said encysted parasites are selected from the group consisting of Cryptosporidium oocysts and Toxoplasma oocysts.

18. A method to detect an encysted stage of a parasite in feces, said encysted stage selected from the group consisting of a cyst and an oocyst, said method consisting of:
    (a) suspending a sample of feces in an aqueous solution;
    (b) contacting said suspended feces with a solid support capable of binding said encysted parasite;
    (c) allowing the sample to dry onto the solid support;
    (d) washing the sample on the solid support with an aqueous wash solution;
    (e) adding an aqueous elution solution to the sample and eluting DNA from the sample into the aqueous elution solution by heating;
    (f) PCR amplifying encysted parasite-specific DNA with primers specific to the encysted parasite being detected; and
    (g) detecting the presence of a PCT amplification product resulting from amplification of encysted parasite-specific DNA in the sample, wherein the presence of said product indicates the presence of said encysted parasite in said feces.

* * * * *

UNITED STATES PATENT AND TRADEMARK OFFICE
CERTIFICATE OF CORRECTION

PATENT NO. : 6,514,694 B2
DATED : February 4, 2003
INVENTOR(S) : Michael James Milhausen It is certified that error appears in the above-identified patent and that said Letters Patent is hereby corrected as shown below:

<u>Column 368,</u>
Lines 13 and 49, please delete "PCT" and replace with -- PCR --.

Signed and Sealed this

Twenty-ninth Day of June, 2004

JON W. DUDAS
*Acting Director of the United States Patent and Trademark Office*